(12) United States Patent
Mundhada et al.

(10) Patent No.: US 11,407,976 B2
(45) Date of Patent: *Aug. 9, 2022

(54) GENETICALLY MODIFIED MICROORGANISMS HAVING IMPROVED TOLERANCE TOWARDS L-SERINE

(71) Applicant: CysBio ApS, Hørsholm (DK)

(72) Inventors: Hemanshu Mundhada, Kgs. Lyngby (DK); Alex Toftgaard Nielsen, Rungsted Kyst (DK)

(73) Assignee: CysBio ApS, Hørsholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/064,203

(22) Filed: Oct. 6, 2020

(65) Prior Publication Data

US 2021/0095245 A1    Apr. 1, 2021

Related U.S. Application Data

(63) Continuation of application No. 15/545,563, filed as application No. PCT/EP2016/051728 on Jan. 27, 2016, now Pat. No. 10,793,826.

(30) Foreign Application Priority Data

Jan. 27, 2015 (EP) .................................... 15152643

(51) Int. Cl.

| | | |
|---|---|---|
| *C12N 1/36* | (2006.01) | |
| *C12N 1/20* | (2006.01) | |
| *C12P 13/06* | (2006.01) | |
| *C12N 9/04* | (2006.01) | |
| *C12N 9/10* | (2006.01) | |
| *C12N 9/12* | (2006.01) | |
| *C12N 9/16* | (2006.01) | |
| *C12N 9/88* | (2006.01) | |
| *C12N 15/52* | (2006.01) | |
| *C12P 13/00* | (2006.01) | |
| *C12N 9/90* | (2006.01) | |
| *C12P 17/16* | (2006.01) | |
| *C12P 13/22* | (2006.01) | |
| *C12N 15/01* | (2006.01) | |
| *C12P 13/12* | (2006.01) | |
| *C07K 14/245* | (2006.01) | |
| *C12N 9/00* | (2006.01) | |
| *C07K 14/32* | (2006.01) | |

(52) U.S. Cl.
CPC ............. *C12N 1/36* (2013.01); *C07K 14/245* (2013.01); *C07K 14/32* (2013.01); *C12N 1/20* (2013.01); *C12N 9/0006* (2013.01); *C12N 9/1014* (2013.01); *C12N 9/1096* (2013.01); *C12N 9/1205* (2013.01); *C12N 9/1217* (2013.01); *C12N 9/1247* (2013.01); *C12N 9/16* (2013.01); *C12N 9/88* (2013.01); *C12N 9/90* (2013.01); *C12N 9/93* (2013.01); *C12N 15/01* (2013.01); *C12N 15/52* (2013.01); *C12P 13/001* (2013.01); *C12P 13/06* (2013.01); *C12P 13/12* (2013.01); *C12P 13/22* (2013.01); *C12P 17/165* (2013.01); *C12P 17/167* (2013.01); *C12Y 101/01003* (2013.01); *C12Y 101/01095* (2013.01); *C12Y 201/02001* (2013.01); *C12Y 206/01052* (2013.01); *C12Y 207/02003* (2013.01); *C12Y 301/03003* (2013.01); *C12Y 403/01017* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 5,175,107 A | 12/1992 | Debabov et al. |
| 6,303,383 B1 | 10/2001 | Nakamura et al. |

FOREIGN PATENT DOCUMENTS

| | | |
|---|---|---|
| CN | 102703371 A | 10/2012 |
| WO | WO 95/34672 A1 | 12/1995 |
| WO | WO 2007/144018 A1 | 12/2007 |

OTHER PUBLICATIONS

Al-Rabiee, Regina et al., "The Mechanism of Velocity Modulated Allosteric Regulation in D-3-Phosphoglycerate Dehydrogenase" The Journal of Biological Chemistry, Sep. 1996, pp. 23235-23238, vol. 271, No. 38.

Baba, Tomoya et al., "Construction of *Escherichia coli* K-12 in-frame, single-gene knockout mutants: the Keio collection" Molecular Systems Biology, 2006, Article No. 2006.0008.

(Continued)

*Primary Examiner* — Richard G Hutson
(74) *Attorney, Agent, or Firm* — Knobbe Martens Olson & Bear LLP

(57) ABSTRACT

The present invention generally relates to the microbiological industry, and specifically to the production of L-serine or L-serine derivatives using genetically modified bacteria. The present invention provides genetically modified microorganisms, such as bacteria, wherein the expression of genes encoding for enzymes involved in the degradation of L-serine is attenuated, such as by inactivation, which makes them particularly suitable for the production of L-serine at higher yield. The present invention also provides means by which the microorganism, and more particularly a bacterium, can be made tolerant towards higher concentrations of serine. The present invention also provides methods for the production of L-serine or L-serine derivative using such genetically modified microorganisms.

13 Claims, 23 Drawing Sheets

Specification includes a Sequence Listing.

(56) References Cited

OTHER PUBLICATIONS

Blazeck et al., Promoter engineering: Recent advances in controlling transcription at the most fundamental level, *Biotechnology Journal*, Jan. 2013, 8, 46-58.

Burgard, Anthony P. et al., "Probing the Performance Limits of the *Escherichia coli* Metabolic Network Subject to Gene Additions or Deletions" Biotechnology and Bioengineering, Sep. 2001, pp. 364-375, vol. 74, No. 5.

Chowdhury, Anupam et al., "k-OptForce: Integrating Kinetics with Flux Balance Analysis for Strain Design" PLOS Computational Biology, Feb. 2014, pp. 1-18, vol. 10, Issue No. 2, e1003487.

Datsenko, Kirill A. et al., "One-step inactivation of chromosomal genes in *Escherichia coli* K-12 using PCR products" PNAS, Jun. 6, 2000, pp. 6640-6645, vol. 97, No. 12.

Deatherage, Daniel E. et al., "Identification of Mutations in Laboratory-Evolved Microbes from Next-Generation Sequencing Data Using breseq" Methods in Molecular Biology (Engineering and Analyzing Multicellular Systems: Methods and Protocols), 2014, pp. 165-188, vol. 1151.

Freddolino, Peter L. et al., "Newly Identified Genetic Variations in Common *Escherichia coli* MG1655 Stock Cultures" Journal of Bacteriology, Nov. 2011, pp. 303-306.

Gu, Pengfei et al., "Construction of an L-serine producing *Escherichia coli* via metabolic engineering" J Ind Microbiol Biotechnol, 2014, pp. 1443-1450, vol. 41.

Hagishita, Tairo et al., "Efficient L-Serine Production from Methanol and Glycine by Resting Cells of *Methylobacterium* sp. Strain MN43" Biosci. Biotech. Biochem., 1996, pp. 1604-1607, vol. 60, No. 10.

Hama, Hiroko et al., "Target of Serine Inhibition in *Escherichia coli*" Biochemical and Biophysical Research Communications, May 16, 1990, pp. 1211-1216, vol. 168.

Iwashima, Akio et al., "Incorporation of Glycine in Pyrimidine and Thiazole Moieties of Thiamine in *Escherichia coli*" Biochim. Biophys. Acta, 1971, pp. 235-238, vol. 252.

Kamp, Axel Von et al., "Enumeration of Smallest Intervention Strategies in Genome-Scale Metabolic Networks" PLOS Computational Biology, Jan. 2014, pp. 1-13, vol. 10, Issue 1, e1003378.

Kildegaard, Kanchana R. et al., "Evolution reveals a glutathione-dependent mechanism of 3-hydroxypropionic acid tolerance" Metabolic Engineering, 2014, pp. 57-66, vol. 26.

Kwon, Dong H. et al., "Frameshift mutations in rdxA and metronidazole resistance in North American Helicobacter pylori isolates" Journal of Antimicrobial Chemotherapy, 2000, pp. 793-796, vol. 46.

Langmead, Ben et al., "Fast gapped-read alignment with Bowtie 2" Nature Methods, Apr. 2012, pp. 357-360, vol. 9, No. 4.

Lennen, Rebecca M. et al., "Transient overexpression of DNA adenine methylase enables efficient and mobile genome engineering with reduced off-target effects" Nucleic Acids Research, 2016, pp. 1-14, vol. 44, No. 4, e36.

Leuchtenberger, Wolfgang et al., "Biotechnological production of amino acids and derivatives: current status and prospects" Appl Microbiol Biotechnol, 2005, pp. 1-8, vol. 69.

Li, Yu et al., "Construction of *Escherichia coli* strains producing L-serine from glucose" Biotechnol Lett, 2012, pp. 1525-1530, vol. 34.

Lorenzo, Victor DE et al., "Chemical reactivity drives spatiotemporal organisation of bacterial metabolism" FEMS Microbiol Rev, 2014, pp. 1-29.

Maier, Thomas P. "Semisynthetic production of unnatural L-α-amino acids by metabolic engineering of the cysteine-biosynthetic pathway" Nature Biotechnology, Apr. 2003, pp. 422-427, vol. 21.

Mertens, Nico et al., "Tight Transcriptional Control Mechanism Ensures Stable High-Level Expression from T7 Promoter-Based Expression Plasmids" Bio/Technology, Feb. 1995, pp. 175-179, vol. 13.

Ngo et al. in The Protein Folding Problem and Tertiary Structure Prediction, 1994, Merz et al. (ed.), Birkhauser, Boston, MA, pp. 433 and 492-495.

Omori et al., J of Bacteriology vol. 175, No. 3, pp. 785-794, 1993.

Pereira, Brian et al., "Engineering a Novel Biosynthetic Pathway in *Escherichia coli* for Production of Renewable Ethylene Glycol" Biotechnology and Bioengineering, Feb. 2016, pp. 376-383, vol. 113, No. 2.

Peters-Wendich, Petra et al., "Metabolic Engineering of Corynebacterium glutamicum for L-Serine Production" Applied and Environmental Microbiology, Nov. 2005, pp. 7139-7144, vol. 71, No. 11.

Qiu, Zhihao et al., "The *Escherichia coli* polB Locus Is Identical to dinA, the Structural Gene for DNA Polymerase II" The Journal of Biological Chemistry, Mar. 1997, pp. 8611-8617, vol. 272, No. 13.

Sawers, Gary "The anaerobic degradation of L-serine and L-threonine in enterobacteria: networks of pathways and regulatory signals" Arch Microbiol, 1998 pp. 1-5, vol. 171.

Sawitzke, James A. et al., "Recombineering: Using Drug Cassettes to Knock out Genes in vivo" Methods in Enzymology, 2013, pp. 79-102, vol. 533.

Shujuan, Lai et al., "Metabolic engineering and flux analysis of Corynebacterium glutamicum for L-serine production" Science China—Life Science, Apr. 2012, pp. 283-290, vol. 55, No. 4.

Stolz, Michael et al., "Reduced Folate Supply as a Key to Enhanced L-Serine Production by Corynebacterium glutamicum" Applied and Environmental Microbiology, Feb. 2007, pp. 750-755, vol. 73, No. 3.

St-Pierre, François et al., "One-Step Cloning and Chromosomal Integration of DNA" ACS Synth. Biol., 2013, pp. 537-541, vol. 2.

Thomason, Lynn C. et al., "*E. coli* Genome Manipulation by P1 Transduction" Current Protocols in Molecular Biology, Jul. 2007, pp. 1.17.1-1.17.8, Supplement 79.

Wang, Harris H. et al., "Programming cells by multiplex genome engineering and accelerated evolution" Nature, Aug. 2009, pp. 894-899, vol. 460.

Wang, Harris H. et al., "Multiplexed Genome Engineering and Genotyping Methods: Applications for Synthetic Biology and Metabolic Engineering" Methods in Enzymology, 2011, pp. 409-426, vol. 498.

Yu, Daiguan et al., "An efficient recombination system for chromosome engineering in *Escherichia coli*" PNAS, May 2000, pp. 5978-5983, vol. 97, No. 11.

Zhang, Xiao et al., "Deficiency in L-serine deaminase results in abnormal growth and cell division of *Escherichia coli* K-12" Molecular Microbiology, 2008, pp. 870-881, vol. 69, No. 4.

International Search Report for PCT/EP2016/051728 dated Apr. 15, 2016.

10A.

10B.

11A.

11B.

11C.

12A.

12B.

12C.

14A.

14B.

14C.

GENETICALLY MODIFIED MICROORGANISMS HAVING IMPROVED TOLERANCE TOWARDS L-SERINE

CROSS-REFERENCE TO RELATED APPLICATIONS

This application is a Continuation of and claims the benefit and priority to U.S. patent application Ser. No. 15/545,563, filed on Jul. 21, 2017, which is a U.S. National Phase Application of PCT International Application Number PCT/EP2016/051728, filed on Jan. 27, 2016, designating the United States of America and published in the English language, which is an International Application of and claims the benefit of priority to European Patent Application No. 15152643.1, filed on Jan. 27, 2015. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 37 U.S.C. § 1.52(e). The name of the ASCII text file for the Sequence Listing is SeqList-ZACCO188-004C1.txt, the date of creation of the ASCII text file is Oct. 6, 2020, and the size of the ASCII text file is 129 KB.

TECHNICAL FIELD OF THE INVENTION

The present invention generally relates to the microbiological industry, and specifically to the production of L-serine using genetically modified bacteria. The present invention provides genetically modified microorganisms, such as bacteria, wherein the expression of genes encoding for enzymes involved in the degradation of L-serine is attenuated, such as by inactivation, which makes them particularly suitable for the production of L-serine at higher yield. The present invention also provides means by which the microorganism, and more particularly a bacterium, can be made tolerant towards higher concentrations of serine. The present invention also provides methods for the production of L-serine or L-serine derivative using such genetically modified microorganisms.

BACKGROUND OF THE INVENTION

L-serine is an amino acid that currently is used in the cosmetics, pharmaceutical and medical industry. The estimated annual production of serine is between 300-1000 tons (Leuchtenberger et al., 2005). The compound has also been identified as one of the top 30 most interesting biochemicals because of its potential use as a building block biochemical.

Serine is a key amino acid which is used as a precursor in the cell to produce many other amino acids such as glycine, cysteine, methionine and tryptophan (Sawers 1998). Apart from these amino acids serine has been also used to produce intermediates such as O-Acetyl serine (Maier 2003) or heterologous compounds such as ethylene glycol (Pereira et al. 2016). Ethanolamine can be produced from L-serine by expressing a serine decarboxylase as described previously (Pereira et al 2016). Ethylene glycol can furthermore be produced from ethanolamine by deamination (Pereira et al 2016). Glycine is derived from L-serine intracellularly. High flux of glycine is desirable for production a range of compounds such as thimine (Iwashima et al 1971).

The current production is based on conversion of glycine and methanol using resting cells (Hagishita et al., 1996), where methylotrophs convert methanol to formaldehyde and transfer the $CH_2$—OH unit of the molecule to glycine using serine hydroxymethyltransferase (glyA). This fermentation process is time consuming and glycine is an expensive starting material. Developing a method for producing serine at low cost directly from glucose is therefore attractive.

Serine has the potential to be made from glucose by fermentation with a very high theoretical yield (Burgard and Maranas, 2001). However, several challenges need to be addressed in order to increase the yield, the most crucial one being degradation of serine in the production organism. Serine has two key degradation pathways in E. coli. Serine to pyruvate catabolism is in E. coli catalyzed by three deaminases namely sdaA, sdaB and tdcG, while C. glutamicum only has one deaminase (sdaA) with activity towards serine. In both organisms, the conversion of serine to glycine is encoded by glyA. Serine production by knocking out only deaminases has been attempted in E. coli (Li et al., 2012) and C. glutamicum (Peters-Wendisch et al., 2005). In E. coli transient accumulation of 3.8 mg/L from 1 g/L glucose was observed when only one of the pathway gene (serA) was overexpressed. Deletion of the deaminase on C. glutamicum lead to marginal and transient increase in the serine titer. In recent studies, E. coli was engineered to enhance the flux of 3-phosphoglycerate by perturbing the TCA-cycle and glyoxylate shunt (Gu et al., 2014). The resulting strain, where only one deaminase, was removed (sdaA) was reported to produce 8.45 g/L serine from 75 g/L glucose (11.2% yield).

Down regulation of glyA (Peters-Wendisch et al., 2005) in C. glutamicum resulted in the production of 9 g/L serine from 40 g/L glucose but lead to an unstable strain. glyA is an important enzyme that converts serine to glycine and in this step transfers one carbon unit to tetra hydrofolate (THF), which is used as cofactor. Removal of the folic acid pathway and supplementation of folic acid lead to a stable C. glutamicum, and a production of 36 g/L serine, however with a relatively low yield (Stolz et al, 2007).

Deletion of both of the major serine degradation pathways (serine to pyruvate and serine to glycine) has not been previously been achieved. It is furthermore known that serine becomes toxic even at low concentrations in strains that lack the pyruvate degradation pathway (Zhang and Newman, 2008). It is expected that serine may inhibit the production of branched amino acids in E. coli Hama et al., 1990), and the conversion of serine to hydroxypyruvate and acrylates, which is toxic to the cell (de Lorenzo, 2014). For efficient production of L-serine or a derivative thereof, it is therefore necessary to both remove the serine degradation pathways and address the problems associated with toxicity of serine.

SUMMARY OF THE INVENTION

The object of the present invention is to provide means allowing a more efficient production of L-serine. More particularly, it is an object of the present invention to provide means allowing the production of L-serine at higher nominal yield and improved mass yield.

This is achieved by the finding that the production of L-serine can be enhanced by, e.g., inactivation of genes encoding enzymes involved in the degradation of L-serine, notably the genes sdaA, sdaB, tdcG and glyA.

The present invention thus provides in a first aspect a bacterium, especially a bacterium having an ability to produce L-serine, wherein said bacterium has been modified to attenuate expression of at least one gene coding for a polypeptide having serine deaminase activity and/or to attenuate expression of a gene coding for a polypeptide having serine hydroxymethyltransferase activity.

More particularly, the present invention provides a bacterium which has been modified to attenuate the expression of the genes sdaA, sdaB, tdcG and/or glyA, e.g., by inactivation of these genes.

The present invention provides in a second aspect a method for producing L-serine comprising: cultivating the bacterium as described above in a medium.

The present invention provides in a further aspect a (isolated) nucleic acid molecule, such a vector, comprising a nucleotide sequence encoding a polypeptide having an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 11 which comprises an amino acid substitution at position Y356, S357 and/or S359.

The present invention provides in a further aspect a (isolated) polypeptide having an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 11 which comprises an amino acid substitution at position Y356, S357 and/or S359. The (isolated) polypeptide may be one expressed by (and isolated from) a bacterium of the invention.

The present invention provides in a further aspect a bacterium which expresses an aspartate kinase I/homoserine dehydrogenase I (ThrA) mutant having one or more amino acid substitutions which increase tolerance towards L-serine.

The present invention may be summarized by the following items:

1. A bacterium which has been modified to attenuate expression of at least one gene coding for a polypeptide having serine deaminase activity and/or to attenuate expression of a gene coding for a polypeptide having serine hydroxymethyltransferase activity.

2. The bacterium according to item 1, wherein the bacterium has been modified to attenuate the expression of at least one gene coding for a polypeptide having serine deaminase activity.

3. The bacterium according to item 1 or 2, wherein the bacterium has been modified to attenuate expression of at least two genes coding for polypeptides having serine deaminase activity.

4. The bacterium according to any one of items 1 to 3, wherein the bacterium has been modified to attenuate expression of at least three genes coding for polypeptides having serine deaminase activity.

5. The bacterium according to any one of items 1 to 4, wherein the at least one gene coding for a polypeptide having serine deaminase activity is selected from the group consisting of sdaA, sdaB and tdcG.

6. The bacterium according to any one of items 1 to 4, wherein the bacterium has been modified to attenuate expression of at least the gene sdaA.

7. The bacterium according to any one of items 1 to 6, wherein the bacterium has been modified to attenuate expression of at least the gene sdaB.

8. The bacterium according to any one of items 1 to 7, wherein the bacterium has been modified to attenuate expression of at least the gene tdcG.

9. The bacterium according to any one of claims 1 to 8, wherein the bacterium has been modified to attenuate the expression of a gene coding for a polypeptide having serine hydroxymethyltransferase activity.

10. The bacterium according to item 9, wherein the gene coding for a polypeptide having serine hydroxymethyltransferase activity is glyA.

11. The bacterium according to any one of items 1 to 10, wherein the bacterium has been modified to attenuate expression of the genes sdaA, sdaB, tdcG and glyA.

12. The bacterium according to any one of items 1 to 10, wherein the bacterium has been modified to attenuate expression of at most three of the genes sdaA, sdaB, tdcG and glyA.

13. The bacterium according to any one of items 1 to 12, wherein the expression of the gene or genes is attenuated by inactivation of the gene or genes.

14. The bacterium according to any one of items 1 to 13, wherein at least one gene coding for a polypeptide having serine deaminase activity is inactivated.

15. The bacterium according to any one of items 1 to 14, wherein at least two genes coding for polypeptides having serine deaminase activity are inactivated.

16. The bacterium according to any one of items 1 to 15, wherein at least three genes coding for polypeptides having serine deaminase activity are inactivated.

17. The bacterium according to any one of items 1 to 16, wherein at least one gene selected from the group consisting of sdaA, sdaB and tdcG is inactivated.

18. The bacterium according to any one of items 1 to 17, wherein the gene sdaA is inactivated.

19. The bacterium according to any one of items 1 to 18, wherein the gene sdaB is inactivated.

20. The bacterium according to any one of items 1 to 19, wherein the gene tdcG is inactivated.

21. The bacterium according to any one of claims 1 to 20, wherein a gene coding for a polypeptide having serine hydroxymethyltransferase activity is inactivated.

22. The bacterium according to item 9, wherein the gene coding for a polypeptide having serine hydroxymethyltransferase activity is glyA.

23. The bacterium according to any one of items 1 to 22, wherein the genes sdaA, sdaB, tdcG and glyA are inactivated.

24. The bacterium according to any one of items 1 to 22, wherein at most three of the genes sdaA, sdaB, tdcG and glyA are inactivated.

25. The bacterium according to any one of items 1 to 24, wherein said bacterium has been further modified to overexpress a 3-phosphoglycerate dehydrogenase, a phosphoserine phosphatase and a phosphoserine aminotransferase.

26. The bacterium according to any one of claims 1 to 25, wherein said bacterium comprises an exogenous nucleic acid molecule comprising a nucleotide sequence encoding a 3-phosphoglycerate dehydrogenase.

27. The bacterium according to any one of items 1 to 26, wherein said bacterium comprises an exogenous nucleic acid molecule comprising a nucleotide sequence encoding a 3-phosphoserine aminotransferase.

28. The bacterium according to any one of items 1 to 27, wherein said bacterium comprises an exogenous nucleic acid molecule comprising a nucleotide sequence encoding a phosphoserine phosphatase.

29. The bacterium according to any one of items 26 to 28, wherein the exogenous nucleic acid molecule(s) is an expression vector.

30. The bacterium according to any one of items 26 to 28, wherein the exogenous nucleic acid is stably integrated into the genome of the bacterium.

31. The bacterium according to any one of items 1 to 30, wherein said bacterium is capable of growing in a minimal culture medium comprising L-serine at a concentration of at least about 6.25 g/L.

32. The bacterium according to any one of items 1 to 31, wherein said bacterium is capable of growing in a minimal culture medium comprising L-serine at a concentration of at least about 6.25 g/L at a growth rate of at least 0.1 $hr^{-1}$ during exponential growth.

33. The bacterium according to any one of items 1 to 32, wherein said bacterium comprises within the thrA gene one or more nucleotide substitutions resulting in one or more amino acid substitutions which increase tolerance towards L-serine.

34. The bacterium according to any one of items 1 to 33, wherein said bacterium expresses a aspartate kinase I/homoserine dehydrogenase I (ThrA) mutant having one or more amino acid substitutions which increase tolerance towards L-serine.

35. The bacterium according to any one of items 1 to 34, wherein said bacterium comprises within the thrA gene one or more nucleotide substitutions resulting in one or more amino acid substitutions in the encoded polypeptide at a position selected from the group consisting of Y356, S357 and S359.

36. The bacterium according to any one of items 1 to 35, wherein said bacterium expresses a aspartate kinase I/homoserine dehydrogenase I (ThrA) mutant having one or more amino acid substitutions at a position selected from the group consisting of Y356, S357 and S359.

37. The bacterium according to any one of items 1 to 36, wherein said bacterium comprises within the thrA gene one or more nucleotide substitutions resulting in an amino acid substitution in the encoded polypeptide at position Y356, one or more nucleotide substitutions resulting in an amino acid substitution in the encoded polypeptide at position S357 and/or one or more nucleotide substitutions resulting in an amino acid substitution in the encoded polypeptide at position S359; wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L; the substitution at position S357 is selected from the group consisting of S357R, S357V, S357P, S357G, S357L, S357Y, S357A, S357N, S357F, S357H, S357K, S357I and S357M; and the substitution at position S359 is selected from the group consisting of S359R, S359G, S359M, S359F, S359T, S359P, S359V, S359Q, S359A, S359C, S359K, S359E and S359L.

38. The bacterium according to any one of items 1 to 37, wherein said bacterium expresses a aspartate kinase I/homoserine dehydrogenase I (ThrA) mutant having an amino acid substitution at position Y356, wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L.

39. The bacterium according to any one of items 1 to 38, wherein said bacterium comprises within the thrA gene one or more nucleotide substitutions resulting in an amino acid substitution in the encoded polypeptide at position S357, wherein the substitution at position S357 is selected from the group consisting of S357R, S357V, S357P, S357G, S357L, S357Y, S357A, S357N, S357F, S357H, S357K, S357I and S357M.

40. The bacterium according to any one of items 1 to 29, wherein said bacterium expresses a aspartate kinase I/homoserine dehydrogenase I (ThrA) mutant having an amino acid substitution at position S357, wherein the substitution at position S357 is selected from the group consisting of S357R, S357V, S357P, S357G, S357L, S357Y, S357A, S357N, S357F, S357H, S357K, S357I and S357M.

41. The bacterium according to any one of items 1 to 40, wherein said bacterium comprises within the thrA gene one or more nucleotide substitutions resulting in an amino acid substitution in the encoded polypeptide at position S359, wherein the substitution at position S359 is selected from the group consisting of S359R, S359G, S359M, S359F, S359T, S359P, S359V, S359Q, S359A, S359C, S359K, S359E and S359L.

42. The bacterium according to any one of items 1 to 42, wherein said bacterium expresses a aspartate kinase I/homoserine dehydrogenase I (ThrA) mutant having an amino acid substitution at position S359, wherein the substitution at position S359 is selected from the group consisting of S359R, S359G, S359M, S359F, S359T, S359P, S359V, S359Q, S359A, S359C, S359K, S359E and S359L.

43. The bacterium according to any one of items 1 to 42, wherein said bacterium comprises within the thrA gene one or more nucleotide substitutions resulting in one or more amino acid substitutions selected from the group consisting of Y356C, S357R and S359R.

44. The bacterium according to any one of items 1 to 43, wherein said bacterium expresses a aspartate kinase I/homoserine dehydrogenase I (ThrA) mutant having one or more amino acid substitutions selected from the group consisting of Y356C, S357R and S359R.

45. The bacterium according to any one of items 1 to 44, wherein said bacterium has been further modified to overexpress the gene ydeD.

46. The bacterium according to any one of items 1 to 45, wherein said bacterium comprises an exogenous nucleic acid molecule comprising a nucleotide sequence encoding the protein product of the gene ydeD.

47. The bacterium according to item 46, wherein the exogenous nucleic acid molecule is an expression vector.

48. The bacterium according to item 46, wherein the exogenous nucleic acid is stably integrated into the genome of the bacterium.

49. The bacterium according to any one of items 1 to 48, wherein said bacterium comprises within the lrp gene one or more nucleotide substitutions resulting in an amino acid substitution, such as non-conservative amino acid substitution, at position D143, such as the amino acid substitution D143G, in the encoded polypeptide.

50. The bacterium according to any one of items 1 to 49, wherein said bacterium comprises within the rho gene one or more nucleotide substitutions resulting in an amino acid substitution, such as non-conservative amino acid substitution, at position R87, such as the amino acid substitution R87L, in the encoded polypeptide.

51. The bacterium according to any one of items 1 to 50, wherein said bacterium comprises within the eno gene one or more nucleotide substitutions resulting in an amino acid substitution, such as non-conservative amino acid substitution, at position V164, such as the amino acid substitution V164L, in the encoded polypeptide.

52. The bacterium according to any one of items 1 to 51 wherein said bacterium comprises within the argP gene one or more nucleotide substitutions resulting in an amino acid substitution, such as non-conservative amino acid substitution, at position Q132, such as the amino acid substitution Q132K, in the encoded polypeptide.

53. The bacterium according to any one of items 1 to 52, wherein said bacterium comprises within the tufA gene one or more nucleotide substitutions resulting in an amino acid substitution, such as non-conservative amino acid substitution, at position G19, such as the amino acid substitution G19V, in the encoded polypeptide.

54. The bacterium according to any one of items 1 to 53, wherein said bacterium comprises within the cycA gene one or more nucleotide substitutions resulting in an amino acid substitution, such as non-conservative amino acid substitution, at position I220, such as the amino acid substitution I220V, in the encoded polypeptide.

55. The bacterium according to any one of items 1 to 54, wherein said bacterium comprises within the rpe gene one or more nucleotide substitutions resulting in an amino acid substitution, such as non-conservative amino acid substitution, at position I202, such as the amino acid substitution I202T, in the encoded polypeptide.

56. The bacterium according to any one of items 1 to 55, wherein said bacterium comprises within the yojI gene one or more nucleotide substitutions resulting in an amino acid substitution, such as non-conservative amino acid substitution, at position D334, such as the amino acid substitution D334H, in the encoded polypeptide.

57. The bacterium according to any one of items 1 to 56, wherein said bacterium comprises within the hyaF gene one or more nucleotide substitutions resulting in an amino acid substitution, such as non-conservative amino acid substitution, at position V120, such as the amino acid subsitution V120G, in the encoded polypeptide.

58. The bacterium according to any one of items 1 to 57, wherein said bacterium has been further modified to attenuate expression of the gene pykF (e.g., by inactivation of the gene).

59. The bacterium according to any one of items 1 to 58, wherein the gene pykF is inactivated.

60. The bacterium according to any one of items 1 to 59, wherein said bacterium has been further modified to attenuate expression of the gene malT (e.g., by inactivation of the gene).

61. The bacterium according to any one of items 1 to 60, wherein the gene malT is inactivated.

62. The bacterium according to any one of items 1 to 61, wherein said bacterium comprises within the rpoB gene one or more nucleotide substitutions resulting in an amino acid substitution, such as non-conservative amino acid substitution, at position P520, such as the amino acid substitution P520L, in the encoded polypeptide.

63. The bacterium according to any one of items 1 to 62, wherein said bacterium comprises within the fumB gene one or more nucleotide substitutions resulting in an amino acid substitution, such as non-conservative amino acid substitution, at position T218, such as the amino acid substitution T218P, in the encoded polypeptide.

64. The bacterium according to any one of items 1 to 63, wherein said bacterium comprises within the gshA gene one or more nucleotide substitutions resulting in an amino acid substitution, such as non-conservative amino acid substitution, at position A178, such as the amino acid substitution A178V, in the encoded polypeptide.

65. The bacterium according to any one of items 1 to 64, wherein said bacterium has been further modified to attenuate expression of the gene lamB (e.g., by inactivation of the gene).

66. The bacterium according to any one of items 1 to 65, wherein the gene lamB is inactivated.

67. The bacterium according to any one of items 1 to 66, wherein said bacterium comprises within its genome a deletion of about 2854 bp from a location which corresponds to location 850092 in the *E. coli* K12 MG1655 reference genome deposited under NCBI accession number NC_000913.2.

68. The bacterium according to any one of items 1 to 67, wherein the bacterium comprises within its genome an insertion of an 768 bp long insertion sequence element IS1 in the lagging strand at a location which corresponds to location 3966174 in the *E. coli* K12 MG1655 reference genome deposited under NCBI accession number NC_000913.2.

69. The bacterium according to any one of items 1 to 68, wherein the bacterium comprises within its genome an insertion of 1 bp at a location which corresponds to location 2942629 in the *E. coli* K12 MG1655 reference genome deposited under NCBI accession number NC_000913.2.

70. The bacterium according to any one of items 1 to 69, wherein the bacterium comprises within its genome an insertion of a 1342 bp long insertion sequence element 154 at a location which corresponds to location 2942878 in the *E. coli* K12 MG1655 reference genome deposited under NCBI accession number NC_000913.2.

71. The bacterium according to any one of items 1 to 70, the bacterium comprises within its genome an insertion of 1 bp at a location which corresponds to location 2599854 in the *E. coli* K12 MG1655 reference genome deposited under NCBI accession number NC_000913.2.

72. The bacterium according to any one of items 1 to 71, wherein the bacterium comprises within its genome an insertion of an 768 bp long insertion sequence element IS1 in the lagging strand at a location which corresponds to location 2492323 in the *E. coli* K12 MG1655 reference genome deposited under NCBI accession number NC_000913.2.

73. The bacterium according to any one of items 1 to 72, wherein the bacterium comprises within its genome an insertion of an 1195 bp long insertion sequence element IS5 at a location which corresponds to location 121518 in the *E. coli* K12 MG1655 reference genome deposited under NCBI accession number NC_000913.2.

74. The bacterium according to any one of items 1 to 73, wherein the bacterium comprises within its genome an insertion of an 768 bp long insertion sequence element IS1 in the lagging strand at a location which corresponds to location 1673670 in the *E. coli* K12 MG1655 reference genome deposited under NCBI accession number NC_000913.2.

75. The bacterium according to any one of items 1 to 74, wherein said bacterium has been modified to attenuate expression of a gene coding for a polypeptide having Glucose 6-phosphate-1-dehydrogenase (G6PDH) activity.

76. The bacterium according to item 75, wherein the expression of the zwf gene is attenuated.

77. The bacterium according to item 75 or 76, wherein the expression of the gene is attenuated by inactivation of the gene.

78. The bacterium according to any one of items 75 to 77, wherein the gene zwf is inactivated.

79. The bacterium according to any one of items 1 to 78, wherein said bacterium expresses a polypeptide encoded by the brnQ gene, wherein said polypeptide terminates after position 308 or any position upstream thereof.

80. The bacterium according to any one of items 1 to 79, wherein said bacterium has been further modified to attenuate expression of the gene brnQ (e.g., by inactivation of the gene).

81. The bacterium according to any one of items 1 to 80, wherein the gene brnQ is inactivated.

82. The bacterium according to any one of items 1 to 81, wherein said bacterium belongs to the Enterobacteriaceae family.

83. The bacterium according to any one of items 1 to 82, wherein said bacterium belongs to a genus selected from the group consisting of *Escherichia, Arsenophonus, Biostraticola, Brenneria, Buchnera, Budvicia, Buttiauxella, Cedecea, Citrobacter, Cosenzaea, Cronobacter, Dickeya, Edwardsiella, Enterobacter, Erwinia, Ewingella, Gibbsiella, Hafnia, Klebsiella, Leclercia, Leminorella, Lonsdalea, Mangrovibacter, Moellerella, Morganella, Obesumbacterium, Pantoea, Pectobacterium, Phaseolibacter, Photorhabdus, Plesiomonas, Proteus, Rahnella, Raoultella, Saccharobacter, Salmonella, Samsonia, Serratia, Shimwellia, Sodalis, Tatumella, Thorsellia, Trabulsiella, Wigglesworthia, Yersinia* and *Yokenella.*

84. The bacterium according to any one of items 1 to 83, wherein said bacterium belongs to the genus *Escherichia.*

85. The bacterium according to any one of items 1 to 84, wherein said bacterium is *Escherichia coli.*

86. A method for producing L-serine or a L-serine derivative, the method comprises cultivating a bacterium according to any one of items 1 to 85 in a culture medium.

87. The method according to item 86, wherein the method is for producing L-serine.

88. The method according to item 86, wherein the method is for producing an L-serine derivative.

89. The method according to item 88, wherein the L-serine derivative is selected from the group consisting of L-cysteine, L-methionine, L-glycine, O-acetylserine, L-tryptophan, thiamine, ethanolamine and ethylene glycol.

90. The method according to item 86, wherein the method is for producing L-cysteine.

91. The method according to item 86, wherein the method is for producing L-methionine.

92. The method according to item 86, wherein the method is for producing L-glycine.

93. The method according to item 86, wherein the method is for producing 0-acetylserine.

94. The method according to item 86, wherein the method is for producing L-tryptophan.

95. The method according to item 86, wherein the method is for producing thiamine.

96. The method according to item 86, wherein the method is for producing ethanolamine.

96. The method according to item 86, wherein the method is for producing ethylene glycol.

97. The method according to any one of items 86 to 96, the method further comprises collecting L-serine or the L-serine derivative from the culture medium.

98. A (isolated) nucleic acid molecule, such a vector, comprising a nucleotide sequence encoding a polypeptide having an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 11 which comprises an amino acid substitution at position Y356, S357 and/or S359.

99. The (isolated) nucleic acid molecule according to item 98, wherein the polypeptide has the amino acid sequence set forth in SEQ ID NO: 11 which comprises an amino acid substitution at position Y356, S357 and/or S359.

100. The (isolated) nucleic acid molecule according to item 98 or 99, wherein the amino acid substitution is at position Y356.

101. The (isolated) nucleic acid molecule according to any one of items 98 to 100 wherein the amino acid substitution is at position S357.

102. The (isolated) nucleic acid molecule according to any one of items 98 to 101, wherein the amino acid substitution is at position S359.

103. The (isolated) nucleic acid molecule according to any one of items 98 to 102, wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L; the substitution at position S357 is selected from the group consisting of S357R, S357V, S357P, S357G, S357L, S357Y, S357A, S357N, S357F, S357H, S357K, S357I and S357M; and the substitution at position S359 is selected from the group consisting of S359R, S359G, S359M, S359F, S359T, S359P, S359V, S359Q, S359A, S359C, S359K, S359E and S359L.

104. A (isolated) polypeptide having an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 11 which comprises an amino acid substitution at position Y356, S357 and/or S359.

105. The (isolated) polypeptide according to item 104, where the polypeptide has the amino acid sequence set forth in SEQ ID NO: 11 which comprises an amino acid substitution at position Y356, 5357 and/or S359.

106. The (isolated) polypeptide according to any one of items 104 or 105, wherein the amino acid substitution is at position Y356.

107. The (isolated) polypeptide according to any one of items 104 to 106, wherein the amino acid substitution is at position S357.

108. The (isolated) polypeptide according to any one of items 104 to 107, wherein the amino acid substitution is at position S359.

109. The (isolated) polypeptide according to any one of items 104 to 108, wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L; the substitution at position S357 is selected from the group consisting of S357R, S357V, S357P, S357G, S357L, S357Y, S357A, S357N, S357F, S357H, S357K, S357I and S357M; and the substitution at position S359 is selected from the group consisting of S359R, S359G, S359M, S359F, S359T, S359P, S359V, S359Q, S359A, S359C, S359K, S359E and S359L.

110. A bacterium comprising the nucleic acid molecule according to any one of items 98 to 103.

111. A bacterium comprising the polypeptide according to any one of items 104 to 109.

112. A bacterium which expresses an aspartate kinase I/homoserine dehydrogenase I (ThrA) mutant having one or more amino acid substitutions which increase tolerance towards L-serine.

113. The bacterium according to item 112, wherein said bacterium comprises within the thrA gene one or more nucleotide substitutions resulting in one or more amino acid substitutions in the encoded polypeptide at a position selected from the group consisting of Y356, S357 and S359.

114. The bacterium according to item 112 or 113, wherein said bacterium expresses an aspartate kinase I/homoserine dehydrogenase I (ThrA) mutant having one or more amino acid substitutions at a position selected from the group consisting of Y356, S357 and S359.

115. The bacterium according to any one of items 112 to 114, wherein said bacterium comprises within the thrA gene one or more nucleotide substitutions resulting in an amino acid substitution in the encoded polypeptide at position Y356, one or more nucleotide substitutions resulting in an amino acid substitution in the encoded polypeptide at position S357 and/or one or more nucleotide substitutions resulting in an amino acid substitution in the encoded polypeptide at position S359; wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L; the substitution at position S357 is selected from the group consisting of S357R, S357V, S357P, S357G, S357L, S357Y, S357A, S357N, S357F, S357H, S357K, S357I and S357M; and the substitution at position S359 is selected from the group consisting of S359R, S359G, S359M, S359F, S359T, S359P, S359V, S359Q, S359A, S359C, S359K, S359E and S359L.

116. The bacterium according to any one of items 112 to 115, wherein said bacterium expresses a aspartate kinase I/homoserine dehydrogenase I (ThrA) mutant having an amino acid substitution at position Y356, wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L.

117. The bacterium according to any one of items 112 to 116, wherein said bacterium comprises within the thrA gene one or more nucleotide substitutions resulting in an amino acid substitution in the encoded polypeptide at position S357, wherein the substitution at position S357 is selected from the group consisting of S357R, S357V, S357P, S357G, S357L, S357Y, S357A, S357N, S357F, S357H, S357K, S357I and S357M.

118. The bacterium according to any one of items 112 to 117, wherein said bacterium expresses a aspartate kinase I/homoserine dehydrogenase I (ThrA) mutant having an amino acid substitution at position S357, wherein the substitution at position S357 is selected from the group consisting of S357R, S357V, S357P, S357G, S357L, S357Y, S357A, S357N, S357F, S357H, S357K, S357I and S357M.

119. The bacterium according to any one of items 112 to 118, wherein said bacterium comprises within the thrA gene one or more nucleotide substitutions resulting in an amino acid substitution in the encoded polypeptide at position S359, wherein the substitution at position S359 is selected from the group consisting of S359R, S359G, S359M, S359F, S359T, S359P, S359V, S359Q, S359A, S359C, S359K, S359E and S359L.

120. The bacterium according to any one of items 112 to 119, wherein said bacterium expresses an aspartate kinase I/homoserine dehydrogenase I (ThrA) mutant having an amino acid substitution at position S359, wherein the substitution at position S359 is selected from the group consisting of S359R, S359G, S359M, S359F, S359I, S359P, S359V, S359Q, S359A, S359C, S359K, S359E and S359L.

121. The bacterium according to any one of items 112 to 120, wherein said bacterium comprises within the thrA gene one or more nucleotide substitutions resulting in one or more amino acid substitutions selected from the group consisting of Y356C, S357R and S359R.

122. The bacterium according to any one of items 112 to 121, wherein said bacterium comprises an exogenous nucleic acid molecule comprising a nucleotide sequence encoding a polypeptide having an amino acid sequence which has at least about 90% sequence identity to the amino acid sequence set forth in SEQ ID NO: 11 which comprises an amino acid substitution at position Y356, S357 and/or S359.

123. The bacterium according to claim 122, wherein the substitution at position Y356 is selected from the group consisting of Y356C, Y356T, Y356V, Y356S, Y356W, Y356A, Y356G, Y356N, Y356D, Y356E, Y356F, Y356A, Y356I, Y356P, Y356H, Y356R and Y356L; the substitution at position S357 is selected from the group consisting of S357R, S357V, S357P, S357G, S357L, S357Y, S357A, S357N, S357F, S357H, S357K, S357I and S357M; and the substitution at position S359 is selected from the group consisting of S359R, S359G, S359M, S359F, S359T, S359P, S359V, S359Q, S359A, S359C, S359K, S359E and S359L.

124. The bacterium according to any one of items 112 to 123, wherein said bacterium comprises an exogenous nucleic acid molecule comprising a nucleotide sequence encoding a polypeptide having an amino acid sequence which has at least about 90% sequence identity to the amino acid sequence set forth in SEQ ID NO: 11 which comprises an amino acid substitution at position Y356.

125. The bacterium according to item 124, wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R, Y356L.

126. The bacterium according to any one of items 112 to 125, wherein said bacterium comprises an exogenous nucleic acid molecule comprising a nucleotide sequence encoding a polypeptide having an amino acid sequence which has at least about 90% sequence identity to the amino acid sequence set forth in SEQ ID NO: 11 which comprises an amino acid substitution at position S357.

127. The bacterium according to item 126, wherein the substitution at position S357 is selected from the group consisting of S357R, S357V, S357P, S357G, S357L, S357Y, S357A, S357N, S357F, S357H, S357K, S357I and S357M.

128. The bacterium according to any one of items 112 to 127, wherein said bacterium comprises an exogenous nucleic acid molecule comprising a nucleotide sequence encoding a polypeptide having an amino acid sequence which has at least about 90% sequence identity to the amino acid sequence set forth in SEQ ID NO: 11 which comprises an amino acid substitution at position S359.

129. The bacterium according to item 128, wherein the substitution at position S359 is selected from the group consisting of S359R, S359G, S359M, S359F, S359T, S359P, S359V, S359Q, S359A, S359C, S359K, S359E and S359L.

BRIEF DESCRIPTION OF THE FIGURES

FIG. 6A Growth rates during the evolution experiment. FIG. 6B Improved growth of evolved strains in the presence of high concentrations of serine. FIG. 6C Growth profile of serine tolerant strains and parent Q1 in M9-50 g/l serine.

FIG. 9A Serine production and cell density (OD 600 nm) measured at different time points during fed batch fermentation of the Q1(DE3) and Q3(DE3) strains. FIG. 9B Production of serine from the glucose fed to the fermentor. The slope of the curve indicates the mass yield during the fermentation.

Figure 1:
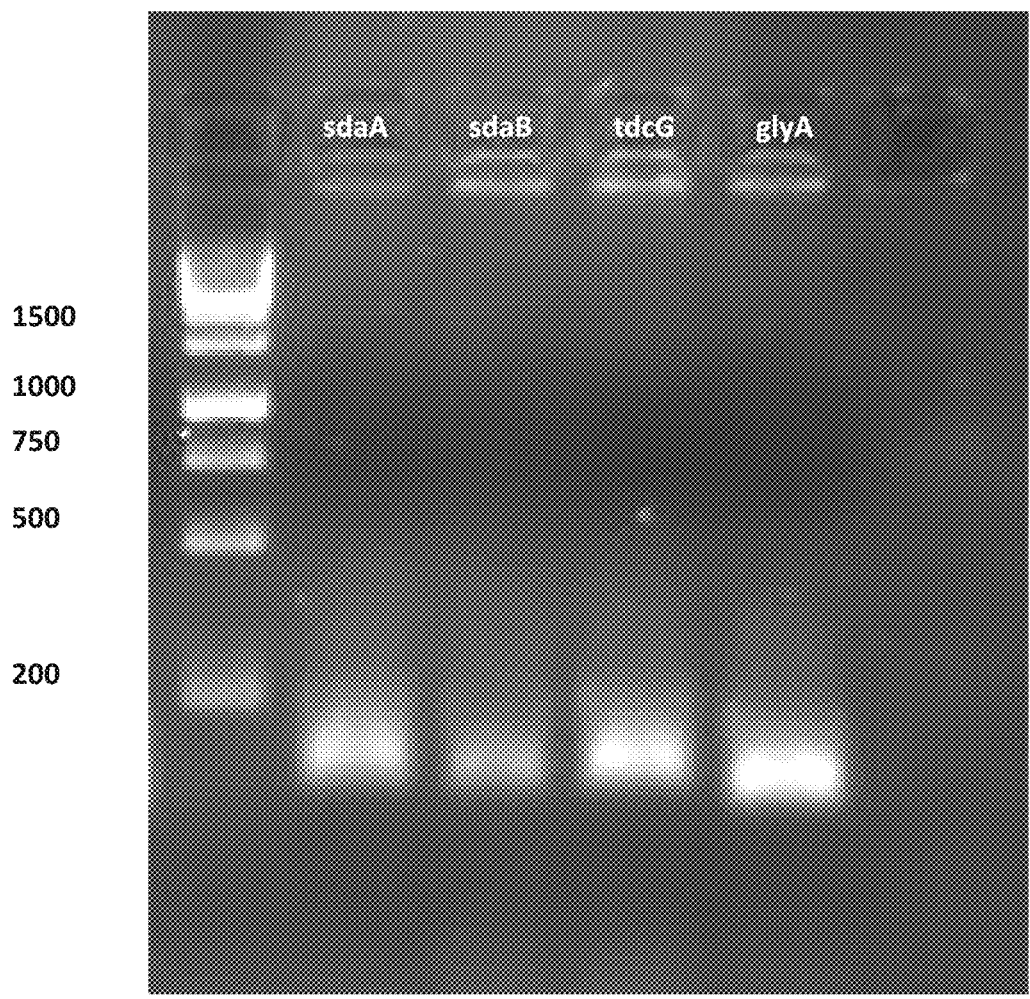
FIG. 1: Deletion of the main genes involved in serine degradation, sdaA, sdaB, tdcG and glyA in *E. coli*. The removal of the four genes was demonstrated using PCR with primers specific to the relevant genes.

The present invention is now described in more detail below.

DETAILED DESCRIPTION OF THE INVENTION

Unless specifically defined herein, all technical and scientific terms used have the same meaning as commonly understood by a skilled artisan in the fields of biochemistry, genetics, and microbiology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, and recombinant DNA, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

Bacterium of the Invention

As indicated above, the present invention is inter alia based on the finding that the production of L-serine can be enhanced by, e.g., inactivation of genes encoding enzymes involved in the degradation of L-serine, notably the genes sdaA, sdaB, tdcG and glyA.

Accordingly, the present invention provides a bacterium, especially a bacterium having an ability to produce L-serine, wherein said bacterium has been modified to attenuate expression of at least one gene coding for a polypeptide having serine deaminase activity and/or to attenuate expression of a gene coding for a polypeptide having serine hydroxymethyltransferase activity.

According to certain embodiments, a bacterium of the invention has been modified to attenuate the expression of at least one gene coding for a polypeptide having serine deaminase activity, such as at least one gene selected from the group consisting of sdaA, sdaB and tdcG.

According to certain embodiments, a bacterium of the invention has been modified to attenuate expression of at least two genes coding for polypeptides having serine deaminase activity, such as at least two genes selected from the group consisting of sdaA, sdaB and tdcG.

According to certain embodiments, a bacterium of the invention has been modified to attenuate expression of at least three genes coding for polypeptides having serine deaminase activity, such as the genes sdaA, sdaB and tdcG.

According to certain embodiments, a bacterium of the invention has been modified to attenuate the expression of a gene coding for a polypeptide having serine hydroxymethyltransferase activity, such as the gene glyA.

According to certain embodiments, a bacterium of the invention has been modified to attenuate expression of genes coding for polypeptides having serine deaminase activity and to attenuate expression of a gene coding for a polypeptide having serine hydroxymethyltransferase activity.

According to certain embodiments, a bacterium of the invention has been modified to attenuate expression of at least one gene coding for polypeptides having serine deaminase activity, but has not been modified to attenuate expression of a gene coding for a polypeptide having serine hydroxymethyltransferase activity.

The genes sdaA, sdaB and tdcG encode L-serine deaminase I (SdaA), L-serine deaminase II (SdaB) and L-serine deaminase III (TdcG), respectively, which are the three enzymes carrying out the sole step in the pathway of L-serine degradation, converting serine into the basic cellular building block, pyruvate. Further information regarding sdaA, sdaB and tdcG of, e.g., *Escherichia coli* is available at EcoCyc (www.biocyc.org) under Accession numbers EG10930, EG11623 and G7624, respectively. Representative nucleotide sequences of sdaA, sdaB and tdcG are set forth in SEQ ID NOs: 1 to 3, respectively.

The gene glyA encodes serine hydroxymethyltransferase (GlyA) which converts serine to glycine, transferring a methyl group to tetrahydrofolate, thus forming 5,10-methylene-tetrahydrofolate (5,10-mTHF). 5,10-mTHF is the major source of C1 units in the cell, making GlyA a key enzyme in the biosynthesis of purines, thymidine, methionine, choline and lipids. Further information regarding glyA of, e.g., *Escherichia coli* is available at EcoCyc (www.biocyc.org) under Accession number EG10408. A representative nucleotide sequence of glyA is set forth in SEQ ID NO: 4.

According to certain embodiments, a bacterium of the invention has been modified to attenuate expression of the gene sdaA. According to certain embodiments, a bacterium of the invention has been modified to attenuate expression of the gene sdaB. According to certain embodiments, a bacterium of the invention has been modified to attenuate expression of the gene tdcG. According to certain embodiments, a bacterium of the invention has been modified to attenuate expression of the gene glyA.

According to certain embodiments, a bacterium of the invention has been modified to attenuate expression of the genes sdaA and sdaB. According to certain embodiments, a bacterium of the invention has been modified to attenuate expression of the genes sdaA and tdcG. According to certain embodiments, a bacterium of the invention has been modified to attenuate expression of the genes sdaA and glyA. According to certain embodiments, a bacterium of the invention has been modified to attenuate expression of the genes sdaB and tdcG. According to certain embodiments, a bacterium of the invention has been modified to attenuate expression of the genes sdaB and glyA. According to certain embodiments, a bacterium of the invention has been modified to attenuate expression of the genes tdcG and glyA.

According to certain embodiments, a bacterium of the invention has been modified to attenuate expression of the genes sdaA, sdaB and tdcG. According to certain embodiments, a bacterium of the invention has been modified to attenuate expression of the genes sdaA, sdaB and glyA. According to certain embodiments, a bacterium of the invention has been modified to attenuate expression of the genes sdaB, tdcG and glyA.

According to certain embodiments, a bacterium of the invention has been modified to attenuate the expression of the genes sdaA, sdaB, tdcG and glyA.

According to certain embodiments, a bacterium of the invention has been modified to attenuate expression of at most three of the genes sdaA, sdaB, tdcG and glyA. More specifically, a bacterium of the invention may thus be a bacterium which has not been modified to attenuate expression of all the genes sdaA, sdaB, tdcG and glyA.

According to certain embodiments, a bacterium of the invention has been modified to attenuate expression of the genes sdaA, sdaB and glyA, but has not been modified to attenuate expression of the gene tdcG.

According to certain embodiments, a bacterium of the invention has been modified to attenuate expression of the genes sdaA, tdcG and glyA, but has not been modified to attenuate expression of the gene sdaB.

According to certain embodiments, a bacterium of the invention has been modified to attenuate expression of the genes sdaB, tdcG and glyA, but has not been modified to attenuate expression of the gene sdaA.

According to certain embodiments, a bacterium of the invention has been modified to attenuate the expression of at least one gene selected from sdaA, sdaB and tdcG, but has not been modified to attenuate expression of the gene glyA.

The expression of the gene or genes may be attenuated by inactivation of the gene or genes. Thus, a bacterium according to the invention may be a bacterium which has been modified to inactivate at least one gene coding for polypeptides having serine deaminase activity and/or to inactive a gene coding for a polypeptide having serine hydroxymethyltransferase activity. Accordingly, a bacterium of the invention may be a bacterium wherein at least one gene coding for polypeptides having serine deaminase activity and/or a gene coding for a polypeptide having serine hydroxymethyltransferase activity is inactivated.

According to certain embodiments, the expression of at least one gene selected from the genes sdaA, sdaB and tdcG is attenuated by inactivation of the gene(s). Thus, a bacterium is provided wherein at least one gene selected from the genes sdaA, sdaB and tdcG is inactivated. According to certain embodiments, the expression of at least two genes selected from the genes sdaA, sdaB and tdcG is attenuated by inactivation of the genes. Thus, a bacterium is provided wherein at least two genes selected from the genes sdaA, sdaB and tdcG are inactivated. According to certain embodiments, the expression of the genes sdaA, sdaB and tdcG is attenuated by inactivation of the genes. Thus, a bacterium is provided wherein the genes sdaA, sdaB and tdcG are inactivated. According to certain embodiments, the expression of glyA is attenuated by inactivation of the gene. Thus, a bacterium is provided wherein the gene glyA is inactivated. According to certain embodiments, the expression of at least one gene selected from the genes sdaA, sdaB and tdcG, and the expression of glyA is attenuated by inactivation of the genes. Thus, a bacterium is provided wherein at least one gene selected from the genes sdaA, sdaB and tdcG, and the gene glyA are inactivated. According to particular embodiments, the expression of the genes sdaA, sdaB, tdcG and glyA is attenuated by inactivation of these genes. Thus, a bacterium is provided wherein the genes sdaA, sdaB, tdcG and glyA are inactivated.

According to certain embodiments, a bacterium of the invention has been modified to inactivate at least one gene selected from sdaA, sdaB, tdcG and glyA. Thus, a bacterium is provided wherein at least one gene selected from sdaA, sdaB, tdcG and glyA is inactivated. According to certain embodiments, a bacterium of the invention has been modified to inactivate at least two genes selected from sdaA, sdaB, tdcG and glyA. Thus, a bacterium is provided wherein at least two genes selected from sdaA, sdaB, tdcG and glyA are inactivated. According to certain embodiments, a bacterium of the invention has been modified to inactivate at least three genes selected from sdaA, sdaB, tdcG and glyA.

Thus, a bacterium is provided wherein at least three genes selected from the sdaA, sdaB, tdcG and glyA are inactivated.

According to certain embodiments, a bacterium of the invention has been modified to inactivate at least one gene selected from sdaA, sdaB and tdcG. Thus, a bacterium is provided wherein at least one gene selected from sdaA, sdaB and tdcG is inactivated.

According to certain embodiments, a bacterium of the invention has been modified to inactivate at least two genes selected from sdaA, sdaB and tdcG. Thus, a bacterium is provided wherein at least two genes selected from sdaA, sdaB and tdcG are inactivated.

According to certain embodiments, a bacterium of the invention has been modified to inactivate at least the gene sdaA. Thus, a bacterium is provided wherein at least the gene sdaA is inactivated. According to certain embodiments, a bacterium of the invention has been modified to inactivate at least the gene sdaB. Thus, a bacterium is provided wherein at least the gene sdaB is inactivated. According to certain embodiments, a bacterium of the invention has been modified to inactivate at least the gene tdcG. Thus, a bacterium is provided wherein at least the gene tdcG is inactivated. According to certain embodiments, a bacterium of the invention has been modified to inactivate the gene glyA. Thus, a bacterium is provided wherein at least the gene glyA is inactivated.

According to certain embodiments, a bacterium of the invention has been modified to inactivate at least the genes sdaA and sdaB. Thus, a bacterium is provided wherein at least the genes sdaA and sdaB are inactivated. According to certain embodiments, a bacterium of the invention has been modified to inactivate at least the genes sdaA and tdcG. Thus, a bacterium is provided wherein at least the genes sdaA and tdcG are inactivated. According to certain embodiments, a bacterium of the invention has been modified to inactivate at least the genes sdaA and glyA. Thus, a bacterium is provided wherein at least the genes sdaA and glyA are inactivated. According to certain embodiments, a bacterium of the invention has been modified to inactivate at least the genes sdaB and tdcG. Thus, a bacterium is provided wherein at least the genes sdaB and tdcG are inactivated. According to certain embodiments, a bacterium of the invention has been modified to inactivate at least the genes sdaB and glyA. Thus, a bacterium is provided wherein at least the genes sdaB and glyA are inactivated. According to certain embodiments, a bacterium of the invention has been modified to inactivate at least the genes tdcG and glyA. Thus, a bacterium is provided wherein at least the genes tdcG and glyA are inactivated.

According to certain embodiments, a bacterium of the invention has been modified to inactivate at least the genes sdaA, sdaB and tdcG. Thus, a bacterium is provided wherein at least the genes sdaA, sdaB and tdcG are inactivated. According to certain embodiments, a bacterium of the invention has been modified to inactivate at least the genes sdaA, sdaB and glyA. Thus, a bacterium is provided wherein at least the genes sdaA, sdaB and glyA are inactivated. According to certain embodiments, a bacterium of the invention has been modified to inactivate at least the genes sdaB, tdcG and glyA. Thus, a bacterium is provided wherein at least the genes sdaB, tdcG and glyA are inactivated. According to certain embodiments, a bacterium of the invention has been modified to inactivate the genes sdaA, sdaB, tdcG and glyA. Thus, a bacterium is provided wherein the genes sdaA, sdaB, tdcG and glyA are inactivated.

According to certain embodiments, a bacterium of the invention has been modified to inactivate at most three of the genes sdaA, sdaB, tdcG and glyA. Thus, a bacterium is provided wherein at most three of the genes sdaA, sdaB, tdcG and glyA are inactivated. More specifically, a bacterium of the invention may thus be a bacterium wherein one, two or three, but not all, of the genes sdaA, sdaB, tdcG and glyA are inactivated.

According to certain embodiments, a bacterium of the invention has been modified to inactivate the genes sdaA, sdaB and glyA, but has not been modified to inactivate the gene tdcG. Thus, a bacterium is provided wherein the genes sdaA, sdaB and glyA are inactivated, but not the gene tdcG.

According to certain embodiments, a bacterium of the invention has been modified to inactivate the genes sdaA, tdcG and glyA, but has not been modified to inactivate the gene sdaB. Thus, a bacterium is provided wherein the genes sdaA, tdcG and glyA are inactivated, but not the gene sdaB.

According to certain embodiments, a bacterium of the invention has been modified to inactivate the genes sdaB, tdcG and glyA, but has not been modified to inactivate the gene sdaA. Thus, a bacterium is provided wherein the genes sdaB, tdcG and glyA are inactivated, but not the gene sdaA.

According to certain embodiments, a bacterium of the invention has been modified to inactivate at least one gene selected from sdaA, sdaB and tdcG, but has not been modified to inactivate the gene glyA. Thus, a bacterium is provided wherein the genes sdaA, sdaB and tdcG are inactivated, but not the gene glyA.

Expression of a gene can be attenuated by introducing a mutation into the gene on the chromosome so that the intracellular activity of the protein encoded by the gene is decreased as compared to an unmodified strain. Mutations which result in attenuation of expression of the gene include the replacement of one nucleotide or more to cause an amino acid substitution in the protein encoded by the gene (missense mutation), introduction of a stop codon (nonsense mutation), deletion or insertion of nucleotides to cause a frame shift, insertion of a drug-resistance gene, or deletion of a part of the gene or the entire gene (Qiu and Goodman, 1997; Kwon et al., 2000). Expression can also be attenuated by modifying an expression regulating sequence such as the promoter, the Shine-Dalgarno (SD) sequence, etc. (WO95/34672).

For example, the following methods may be employed to introduce a mutation by gene recombination. A mutant gene encoding a mutant protein with decreased activity can be prepared, and the bacterium to be modified can be transformed with a DNA fragment containing the mutant gene. Then, the native gene on the chromosome is replaced with the mutant gene by homologous recombination, and the resulting strain can be selected. Gene replacement using homologous recombination can be conducted by employing a linear DNA, which is known as "lambda-red mediated gene replacement" (Datsenko and Wanner, 2000), or by employing a plasmid containing a temperature-sensitive replication origin (U.S. Pat. No. 6,303,383 or JP 05-007491 A). Furthermore, site-specific mutation by gene substitution can also be incorporated using homologous recombination such as set forth above using a plasmid which is unable to replicate in the host.

Expression of the gene can also be attenuated by inserting a transposon or an IS factor into the coding region of the gene (U.S. Pat. No. 5,175,107), or by conventional methods, such as by mutagenesis with UV irradiation or nitrosoguanidine (N-methyl-N'-nitro-N-n itrosoguanidine), site-directed mutagenesis, gene disruption using homologous recombination, and/or gene replacement (Yu et al., 2000; and Datsenko and Wanner, 2000), such as the "lambda-red mediated gene replacement". The lambda-red mediated gene replacement is a particularly suitable method to inactive one or more genes as described herein. Hence, according to particular embodiments, expression of genes is attenuated by inactivation of the genes using lambda-red mediated gene replacement.

The inactivation of at least one of sdaA, sdaB, tdcG and glyA results in an increase in specific productivity and yield of L-serine from glucose.

Figure 3:
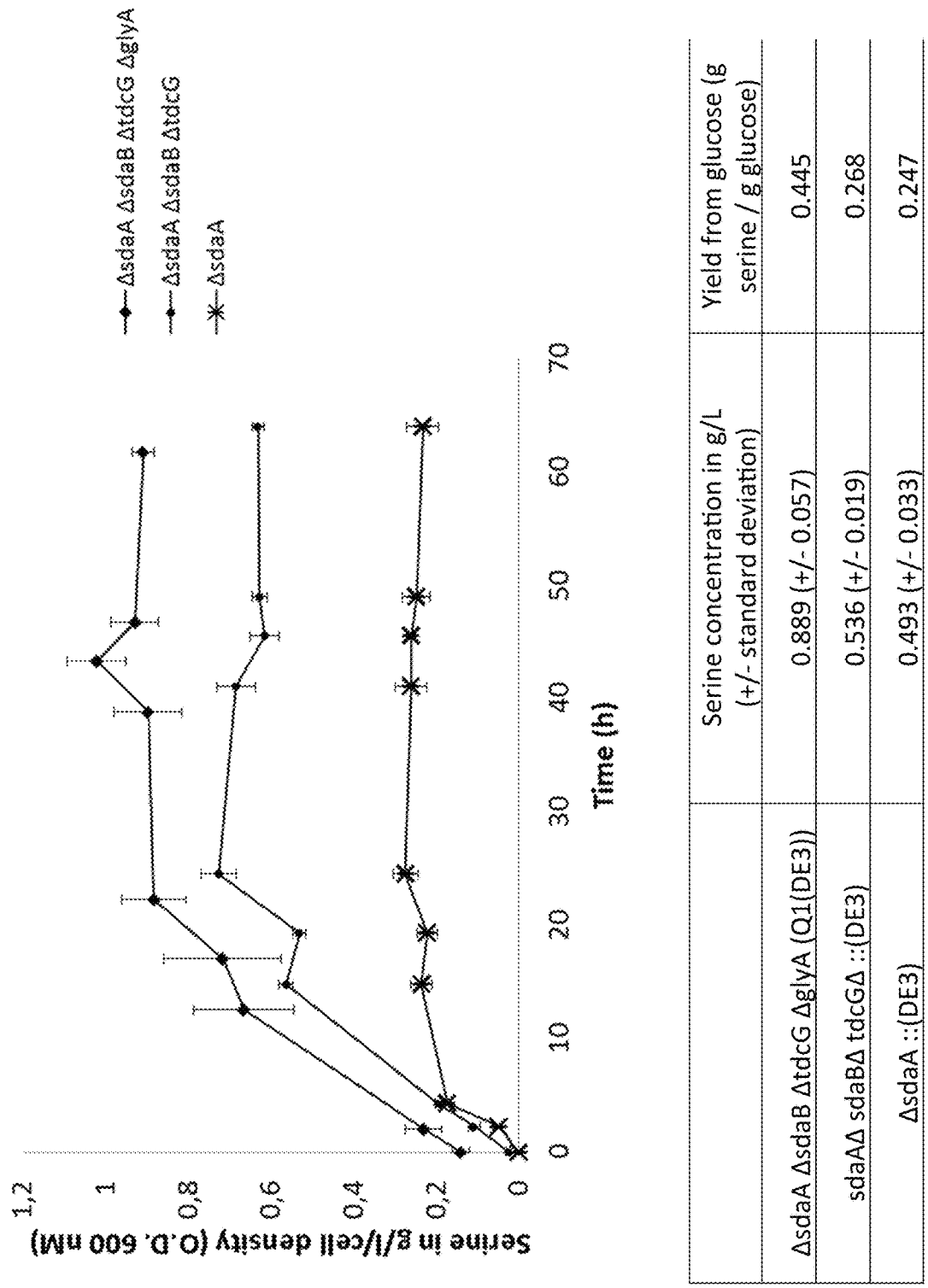
FIG. 3: Serine production during batch fermentation in shake flasks.

As shown in FIG. 3, the inactivation of all four genes (sdaA, sdaB, tdcG and glyA) involved in serine degradation results in the highest specific productivity and the highest yield from glucose compared to inactivation of only the three genes involved in L-serine degradation via the serine to pyruvate pathway (sdaA, sdaB, and tdcG).

Serine is produced from glyceraldehyde-3-phosphate using three enzymes encoded by the genes serA (encoding a 3-phosphoglycerate dehydrogenase), serB (encoding a phosphoserine phosphatase) and serC (encoding a phosphoserine aminotransferase). In order to increase production of L-serine, these genes may be overexpressed. Relevant information regarding serA, serB and serC of, e.g., *Escherichia coli* is available at EcoCyc (www.biocyc.org) under Accession numbers EG10944, EG10945 and EG10946, respectively.

Therefore, according to certain embodiments, the bacterium has been modified to overexpress a 3-phosphoglycerate dehydrogenase, a phosphoserine phosphatase and a phosphoserine aminotransferase. More particularly, the bacterium has been further modified to overexpress the genes serA, serB and serC. This may be achieved by introducing into the bacterium one or more (such as two or three) exogenous nucleic acid molecules, such as one or more vectors, comprising a nucleotide sequence encoding a 3-phosphoglycerate dehydrogenase, a nucleotide sequence encoding a phosphoserine phosphatase and/or a nucleotide sequence encoding a phosphoserine aminotransferase.

The 3-phosphoglycerate dehydrogenase may be derived from the same species as the bacterium in which it is overexpressed or may be derived from a species different to the one in which it is overexpressed (i.e. it is heterologous). According to certain embodiments, the 3-phosphoglycerate dehydrogenase is derived from the same species as the bacterium in which it is overexpressed. According to certain other embodiments, the 3-phosphoglycerate dehydrogenase is derived from a species different to the one in which it is overexpressed (i.e. it is heterologous).

According to certain embodiments, the bacterium comprises an exogenous nucleic acid molecule comprising a nucleotide sequence encoding a 3-phosphoglycerate dehydrogenase. The exogenous nucleic acid molecule may comprise a nucleotide sequence encoding a polypeptide comprising an amino acid sequence set forth in SEQ ID NO: 5. The exogenous nucleic acid molecule may comprise a nucleotide sequence encoding a polypeptide comprising an amino acid sequence set which has at least about 90%, at least about 93%, at least about 95%, at least about 96%, at least about 97%, at least about 98%, or at least about 99%, sequence identity to the amino acid sequence set forth in SEQ ID NO: 5. Preferably, the polypeptide has 3-phosphoglycerate dehydrogenase activity. More preferably, the polypeptide has 3-phosphoglycerate dehydrogenase activity similar to that of the polypeptide comprising an amino acid sequence set forth in SEQ ID NO: 5. The exogenous nucleic acid molecule may comprise a nucleotide sequence encoding a polypeptide comprising an amino acid sequence set which has at least about 95%, such as at least about 96%, at least about 97%, at least about 98%, or at least about 99%, sequence identity to the amino acid sequence set forth in SEQ ID NO: 5. Preferably, the polypeptide has 3-phosphoglycerate dehydrogenase activity. More, preferably, the polypeptide has 3-phosphoglycerate dehydrogenase activity similar to that of the polypeptide comprising an amino acid sequence set forth in SEQ ID NO: 5. The exogenous nucleic acid molecule may comprise a nucleotide sequence encoding a polypeptide comprising an amino acid sequence set forth in SEQ ID NO: 5, wherein 1 or more, such as about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted, and/or inserted. Preferably, the polypeptide has 3-phosphoglycerate dehydrogenase activity.

More preferably, the polypeptide has 3-phosphoglycerate dehydrogenase activity similar to that of the polypeptide comprising an amino acid sequence set forth in SEQ ID NO: 5. The exogenous nucleic acid molecule may comprise a nucleotide sequence encoding a polypeptide comprising an amino acid sequence set forth in SEQ ID NO: 5, wherein about 1 to about 5, such as about 1 to about 3, amino acid residues are substituted, deleted, and/or inserted. Preferably, the polypeptide has 3-phosphoglycerate dehydrogenase activity. More preferably, the polypeptide has 3-phosphoglycerate dehydrogenase activity similar to that of the polypeptide comprising an amino acid sequence set forth in SEQ ID NO: 5.

It is further beneficial to overexpress a mutant serA gene which encodes a 3-phosphoglycerate dehydrogenase being resistant towards feedback inhibition of serine. This may, for example, be achieved by deleting the last four C-terminal residues of the wild type 3-phosphoglycerate dehydrogenase (SerA). Alternatively, feedback inhibition of SerA can be removed by mutating the three residues H344, N346 and N364 to alanine. A representative amino acid sequence of such 3-phosphoglycerate dehydrogenase mutant is set forth in SEQ ID NO: 6. Therefore, according to particular embodiments, the bacterium comprises an exogenous nucleic acid molecule comprising a nucleotide sequence encoding a 3-phosphoglycerate dehydrogenase being resistant towards feedback inhibition of serine. The exogenous nucleic acid molecule may comprise a nucleotide sequence encoding a polypeptide comprising an amino acid sequence set forth in SEQ ID NO: 6. The exogenous nucleic acid molecule may comprise a nucleotide sequence encoding a polypeptide comprising an amino acid sequence set which has at least about 90%, at least about 93%, at least about 95%, at least about 96%, at least about 97%, at least about 98%, or at least about 99%, sequence identity to the amino acid sequence set forth in SEQ ID NO: 6. Preferably, the polypeptide has 3-phosphoglycerate dehydrogenase activity. More preferably, the polypeptide has 3-phosphoglycerate dehydrogenase activity similar to that of the polypeptide comprising an amino acid sequence set forth in SEQ ID NO: 6. The exogenous nucleic acid molecule may comprise a nucleotide sequence encoding a polypeptide comprising an amino acid sequence set which has at least about 95%, such as at least about 96%, at least about 97%, at least about 98%, or at least about 99%, sequence identity to the amino acid sequence set forth in SEQ ID NO: 6. Preferably, the polypeptide has 3-phosphoglycerate dehydrogenase activity. More preferably, the polypeptide has 3-phosphoglycerate dehydrogenase activity similar to that of the polypeptide comprising an amino acid sequence set forth in SEQ ID NO: 6. The exogenous nucleic acid molecule may comprise a nucleotide sequence encoding a polypeptide comprising an amino acid sequence set forth in SEQ ID NO: 6, wherein 1 or more, such as about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted, and/or inserted. Preferably, the polypeptide has 3-phosphoglycerate dehydrogenase activity. More preferably, the polypeptide has 3-phosphoglycerate dehydrogenase activity similar to that of the polypeptide comprising an amino acid sequence set forth in SEQ ID NO: 6. The exogenous nucleic acid molecule may comprise a nucleotide sequence encoding a polypeptide comprising an amino acid sequence set forth in SEQ ID NO: 6, wherein about 1 to about 5, such as about 1 to about 3, amino acid residues are substituted, deleted, and/or inserted. Preferably, the polypeptide has 3-phosphoglycerate dehydrogenase activity. More preferably, the polypeptide has 3-phosphoglycerate dehydrogenase activity similar to that of the polypeptide comprising an amino acid sequence set forth in SEQ ID NO: 6.

The phosphoserine phosphatase may be derived from the same species as the bacterium in which it is overexpressed or may be derived from a species different to the one in which it is overexpressed (i.e. it is heterologous). According to certain embodiments, the phosphoserine phosphatase is derived from the same species as the bacterium in which it is overexpressed. According to certain other embodiments, the phosphoserine phosphatase is derived from a species different to the one in which it is overexpressed (i.e. it is heterologous).

According to certain embodiments, the bacterium comprises an exogenous nucleic acid molecule comprising a nucleotide sequence encoding a phosphoserine phosphatase. The exogenous nucleic acid molecule may comprise a nucleotide sequence encoding a polypeptide comprising an amino acid sequence set forth in SEQ ID NO: 7. The exogenous nucleic acid molecule may comprise a nucleotide sequence encoding a polypeptide comprising an amino acid sequence set which has at least about 90%, at least about 93%, at least about 95%, at least about 96%, at least about 97%, at least about 98%, or at least about 99%, sequence identity to the amino acid sequence set forth in SEQ ID NO: 7. Preferably, the polypeptide has phosphoserine phosphatase activity. More preferably, the polypeptide has phosphoserine phosphatase activity similar to that of the polypeptide comprising an amino acid sequence set forth in SEQ ID NO: 7. The exogenous nucleic acid molecule may comprise a nucleotide sequence encoding a polypeptide comprising an amino acid sequence set which has at least about 95%, such as at least about 96%, at least about 97%, at least about 98%, or at least about 99%, sequence identity to the amino acid sequence set forth in SEQ ID NO: 7. Preferably, the polypeptide has phosphoserine phosphatase activity. More preferably, the polypeptide has phosphoserine phosphatase activity similar to that of the polypeptide comprising an amino acid sequence set forth in SEQ ID NO: 7. The exogenous nucleic acid molecule may comprise a nucleotide sequence encoding a polypeptide comprising an amino acid sequence set forth in SEQ ID NO: 7, wherein 1 or more, such as about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted, and/or inserted. Preferably, the polypeptide has phosphoserine phosphatase activity. More preferably, the polypeptide has phosphoserine phosphatase activity similar to that of the polypeptide comprising an amino acid sequence set forth in SEQ ID NO: 7. The exogenous nucleic acid molecule may comprise a nucleotide sequence encoding a polypeptide comprising an amino acid sequence set forth in SEQ ID NO: 7, wherein about 1 to about 5, such as about 1 to about 3, amino acid residues are substituted, deleted, and/or inserted. Preferably, the polypeptide has phosphoserine phosphatase activity. More preferably, the polypeptide has phosphoserine phosphatase activity similar to that of the polypeptide comprising an amino acid sequence set forth in SEQ ID NO: 7.

The phosphoserine aminotransferase may be derived from the same species as the bacterium in which it is overexpressed or may be derived from a species different to the one in which it is overexpressed (i.e. it is heterologous). According to certain embodiments, the phosphoserine aminotransferase is derived from the same species as the bacterium in which it is overexpressed. According to certain other embodiments, the phosphoserine aminotransferase is derived from a species different to the one in which it is overexpressed (i.e. it is heterologous).

According to certain embodiments, the bacterium comprises an exogenous nucleic acid molecule comprising a nucleotide sequence encoding a phosphoserine aminotransferase. The exogenous nucleic acid molecule may comprise a nucleotide sequence encoding a polypeptide comprising an amino acid sequence set forth in SEQ ID NO: 8. The exogenous nucleic acid molecule may comprise a nucleotide sequence encoding a polypeptide comprising an amino acid sequence set which has at least about 90%, at least about 93%, at least about 95%, at least about 96%, at least about 97%, at least about 98%, or at least about 99%, sequence identity to the amino acid sequence set forth in SEQ ID NO: 8. Preferably the polypeptide has phosphoserine aminotransferase activity. More preferably, the polypeptide has phosphoserine aminotransferase activity similar to that of the polypeptide comprising an amino acid sequence set forth in SEQ ID NO: 8. The exogenous nucleic acid molecule may comprise a nucleotide sequence encoding a polypeptide comprising an amino acid sequence set which has at least about 95%, such as at least about 96%, at least about 97%, at least about 98%, or at least about 99%, sequence identity to the amino acid sequence set forth in SEQ ID NO: 8. Preferably, the polypeptide has phosphoserine aminotransferase activity. More preferably, the polypeptide has phosphoserine aminotransferase activity similar to that of the polypeptide comprising an amino acid sequence set forth in SEQ ID NO: 8. The exogenous nucleic acid molecule may comprise a nucleotide sequence encoding a polypeptide comprising an amino acid sequence set forth in SEQ ID NO: 8, wherein 1 or more, such as about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted, and/or inserted. Preferably, the polypeptide has phosphoserine aminotransferase activity. More preferably, the polypeptide has phosphoserine aminotransferase activity similar to that of the polypeptide comprising an amino acid sequence set forth in SEQ ID NO: 8. The exogenous nucleic acid molecule may comprise a nucleotide sequence encoding a polypeptide comprising an amino acid sequence set forth in SEQ ID NO: 8, wherein about 1 to about 5, such as about 1 to about 3, amino acid residues are substituted, deleted, and/or inserted. Preferably, the polypeptide has phosphoserine aminotransferase activity. More preferably, the polypeptide has phosphoserine aminotransferase activity similar to that of the polypeptide comprising an amino acid sequence set forth in SEQ ID NO: 8.

A bacterium, such as *Escherichia coli*, which has been modified to attenuate expression of genes coding for polypeptides having serine deaminase activity and/or to attenuate expression of a gene coding for a polypeptide having serine hydroxymethyltransferase (e.g., by inactivation of the genes), may show a low tolerance towards serine. Therefore, it would be desirable to provide a bacterium which shows increased tolerance towards serine.

In this respect, the present inventors have found that product toxicity can be reduced by overexpression of novel exporters, by evolving bacterial strains by random mutagenesis, and by adaptive evolution. As a result, bacteria having increased tolerance towards serine are provided. "Increased tolerance" as used herein means that a bacterium is capable of growing in a minimal culture medium (such as M9 minimal medium) comprising L-serine at a concentration of at least about 6.25 g/L.

According to certain embodiments, a bacterium of the present invention is capable of growing in a minimal culture medium (such as M9 minimal medium) comprising L-serine at a concentration of at least about 6.25 g/L (such as at least about 12.5 g/L). According to particular embodiments, the bacterium is capable of growing in a minimal culture medium (such as M9 minimal medium) comprising L-serine at a concentration of at least about 12.5 g/L (such as at least about 25 g/L). According to particular embodiments, the bacterium is capable of growing in a minimal culture medium (such as M9 minimal medium) comprising L-serine at a concentration of at least about 25 g/L (such as at least about 40 g/L). According to particular embodiments, the bacterium is capable of growing in a minimal culture medium (such as M9 minimal medium) comprising L-serine at a concentration of at least about 40 g/L (such as at least about 50 g/L). According to particular embodiments, the bacterium is capable of growing in a minimal culture medium (such as M9 minimal medium) comprising L-serine at a concentration of at least about 50 g/L (such as at least about 75 g/L). According to particular embodiments, the bacterium is capable of growing in a minimal culture medium (such as M9 minimal medium) comprising L-serine at a concentration of at least about 75 g/L (such as at least about 100 g/L. According to particular embodiments, the bacterium is capable of growing in a minimal culture medium (such as M9 minimal medium) comprising L-serine at a concentration of at least about 100 g/L.

Preferably, the minimal culture medium, such as M9 minimal medium, is supplemented with 2 mM glycine and 2 g/L glucose. The bacterium is generally cultivated using adequate aeration at about 37° C. for a period of about 24 to about 40 hours.

According to certain embodiments, a bacterium of the present invention is capable of growing in a minimal culture medium (such as M9 minimal medium) comprising L-serine at a concentration of at least about 6.25 g/L (such as at least about 12.5 g/L) at a growth rate of at least about 0.1 hr$^{-1}$ during exponential growth. According to particular embodiments, a bacterium of the invention is capable of growing in a minimal culture medium (such as M9 minimal medium) comprising L-serine at a concentration of at least about 12.5 g/L (such as at least about 25 g/L) at a growth rate of at least about 0.1 hr$^{-1}$ during exponential growth. According to particular embodiments, a bacterium of the invention is capable of growing in a minimal culture medium (such as M9 minimal medium) comprising L-serine at a concentration of at least about 25 g/L (such as at least about 50 g/L) at a growth rate of at least about 0.1 hr$^{-1}$ during exponential growth.

Preferably, the minimal culture medium, such as M9 minimal medium, is supplemented with 2 mM glycine and 2 g/L glucose. The bacterium is generally cultivated using adequate aeration at about 37° C. for a period of about 24 to about 40 hours.

According to certain embodiments, a bacterium is provided which contains at least one mutation which leads to an at least 20% increase in growth rate compared to an otherwise identical bacterium not carrying said mutation.

One novel exporter which when overexpressed in a bacterium improved tolerance towards serine is the O-acetylserine/cysteine export protein encoded by the gene ydeD. Further information regarding ydeD of, e.g., *Escherichia coli* is available at EcoCyc (www.biocyc.org) under Accession numbers EG11639. A representative amino acid sequence of such exporter protein is set forth in SEQ ID NO: 9. Therefore, the present invention provides a bacterium which has been modified to overexpress the gene ydeD.

According to certain embodiments, a bacterium of the invention comprises an exogenous nucleic acid molecule, such as an expression vector, comprising a nucleotide sequence encoding the protein product of the gene ydeD. According to particular embodiments, the bacterium comprises an exogenous nucleic acid molecule comprising a nucleotide sequence encoding a polypeptide comprising an amino acid sequence set forth in SEQ ID NO: 9. The exogenous nucleic acid molecule may comprise a nucleotide sequence encoding a polypeptide comprising an amino acid sequence set which has at least about 90%, at least about 93%, at least about 95%, at least about 96%, at least about 97%, at least about 98%, or at least about 99%, sequence identity to the amino acid sequence set forth in SEQ ID NO: 9. Preferably, the polypeptide has 0-acetylserine and/or cysteine transporter activity. More preferably, the polypeptide has O-acetylserine and/or cysteine transporter activity similar to that of the polypeptide comprising an amino acid sequence set forth in SEQ ID NO: 9. The exogenous nucleic acid molecule may comprise a nucleotide sequence encoding a polypeptide comprising an amino acid sequence set which has at least about 95%, such as at least about 96%, at least about 97%, at least about 98%, or at least about 99%, sequence identity to the amino acid sequence set forth in SEQ ID NO: 9. Preferably, the polypeptide has O-acetylserine and/or cysteine transporter activity. More preferably, the polypeptide has O-acetylserine and/or cysteine transporter activity similar to that of the polypeptide comprising an amino acid sequence set forth in SEQ ID NO: 9. The exogenous nucleic acid molecule may comprise a nucleotide sequence encoding a polypeptide comprising an amino acid sequence set forth in SEQ ID NO: 9, wherein 1 or more, such as about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted, and/or inserted. Preferably, the polypeptide has 0-acetylserine and/or cysteine transporter activity. More preferably, the polypeptide has 0-acetylserine and/or cysteine transporter activity similar to that of the polypeptide comprising an amino acid sequence set forth in SEQ ID NO: 9. The exogenous nucleic acid molecule may comprise a nucleotide sequence encoding a polypeptide comprising an amino acid sequence set forth in SEQ ID NO: 9, wherein about 1 to about 5, such as about 1 to about 3, amino acid residues are substituted, deleted, and/or inserted. Preferably, the polypeptide has 0-acetylserine and/or cysteine transporter activity. More preferably, the polypeptide has 0-acetylserine and/or cysteine transporter activity similar to that of the polypeptide comprising an amino acid sequence set forth in SEQ ID NO: 9.

A modified YdeD polypeptide containing an additional stretch of 6 histidine residues at the C-terminus is set forth in SEQ ID NO: 10. According to particular embodiments, the bacterium comprises an exogenous nucleic acid molecule comprising a nucleotide sequence encoding a polypeptide comprising an amino acid sequence set forth in SEQ ID NO: 10. The exogenous nucleic acid molecule may comprise a nucleotide sequence encoding a polypeptide comprising an amino acid sequence set which has at least about 90%, at least about 93%, at least about 95%, at least about 96%, at least about 97%, at least about 98%, or at least about 99%, sequence identity to the amino acid sequence set forth in SEQ ID NO: 10. Preferably, the polypeptide has 0-acetylserine and/or cysteine transporter activity. More preferably, the polypeptide has 0-acetylserine and/or cysteine transporter activity similar to that of the polypeptide comprising an amino acid sequence set forth in SEQ ID NO: 10. The exogenous nucleic acid molecule may comprise a nucleotide sequence encoding a polypeptide comprising an amino acid sequence set which has at least about 95%, such as at least about 96%, at least about 97%, at least about 98%, or at least about 99%, sequence identity to the amino acid sequence set forth in SEQ ID NO: 10. Preferably, the polypeptide has 0-acetylserine and/or cysteine transporter activity. More preferably, the polypeptide has 0-acetylserine and/or cysteine transporter activity similar to that of the polypeptide comprising an amino acid sequence set forth in SEQ ID NO: 10. The exogenous nucleic acid molecule may comprise a nucleotide sequence encoding a polypeptide comprising an amino acid sequence set forth in SEQ ID NO: 10, wherein 1 or more, such as about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted, and/or inserted. Preferably, the polypeptide has 0-acetylserine and/or cysteine transporter activity. More preferably, the polypeptide has 0-acetylserine and/or cysteine transporter activity similar to that of the polypeptide comprising an amino acid sequence set forth in SEQ ID NO: 10. The exogenous nucleic acid molecule may comprise a nucleotide sequence encoding a polypeptide comprising an amino acid sequence set forth in SEQ ID NO: 10, wherein about 1 to about 5, such as about 1 to about 3, amino acid residues are substituted, deleted, and/or inserted. Preferably, the polypeptide has 0-acetylserine and/or cysteine transporter activity. More preferably, the polypeptide has 0-acetylserine and/or cysteine transporter activity similar to that of the polypeptide comprising an amino acid sequence set forth in SEQ ID NO: 10.

Figure 4:
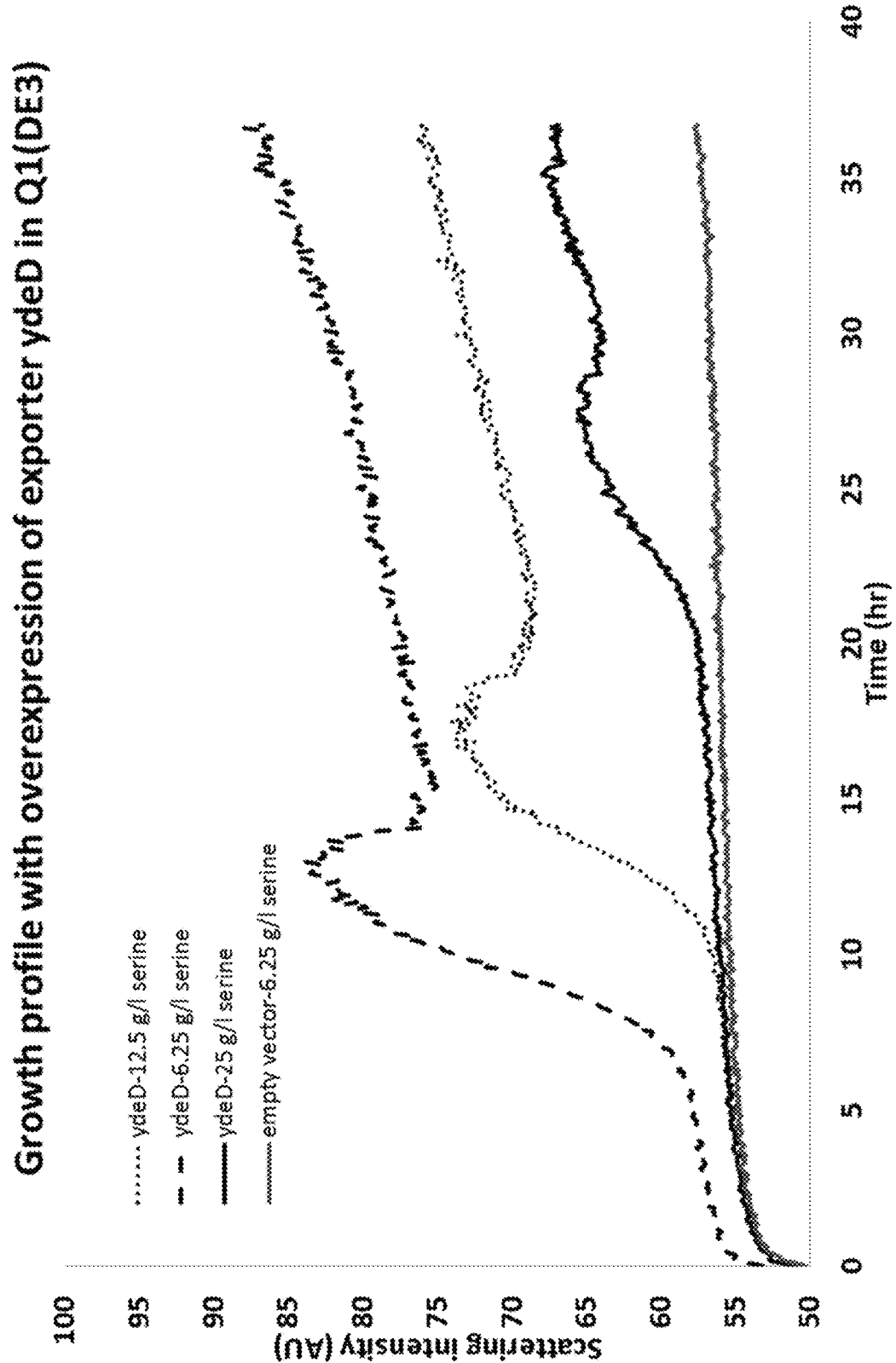
FIG. 4: Increased tolerance towards serine can be achieved by overexpression of ydeD, a potential serine transporter. The figure shows the growth of the cells in the presence of various concentrations of serine.

As shown in FIG. 4, growth of a bacterium, such as *E. coli*, lacking the main serine degradation pathways is severely growth inhibited in the presence of even low concentrations of serine. Upon overexpression of ydeD, the tolerance towards serine is increased substantially, suggesting that YdeD may potentially transport serine out of the cell.

A bacterium of the invention having improved tolerance towards serine, such as one capable of growing in a minimal culture medium comprising L-serine at a concentration of at least about 6.25 g/L as mentioned above, can be obtained by random mutagenesis or by adaptive evolution. Respective details are provided in Examples 4 and 5, respectively.

Adaptive evolution may, for example, be achieved by carrying out the following method: Prior to the start of the experiment, suitable tubes are filled with 25 ml of culture media which are kept at 37° C. in a heat block. Controlled aeration is obtained using magnetic tumble stirrers placed inside the tubes and spinning at 1,800 rpm. At the start of the experiment, a single colony (of the starter strain) is grown overnight in one of the tubes, and 100 µL aliquots are used to inoculate a new tube containing 25 ml of fresh culture media. As the bacteria grow, multiple OD measurements at 600 nm are performed. Growth rates are calculated by taking the slope of a least-square linear regression line fit to the logarithm of the OD measurements. Once reaching a target OD of 0.4, 100 µl of culture are used to inoculate a new tube containing 25 ml of culture media. This way, cultures are serially passed (2-3 times per day) to tubes with fresh media after reaching the targeted cell density such that stationary phase is never reached. The experiment is initiated with an L-serine concentration of 3 g/L serine, followed by an increase to 6 g/L of L-Serine after the desired growth rate has been reached. Once the populations achieved a stable phenotype (i.e. growth rate), the L-Serine concentration is increased to 12 g/L. This process is repeated iteratively using 24, 50, 75, and 100 g/L of L-serine. The final population may then be plated on the LB-agar for further cultivation and selection of an L-serine tolerant strain. The foregoing method may be performed manually or by using an automated system enable the propagation of evolving populations over the course of many days while monitoring their growth rates.

As further demonstrate herein, the present inventors have identified beneficial mutations in a number of genes which confer tolerance towards L-serine. Respective genes and mutations are depicted in Table 55.

Figure 7:
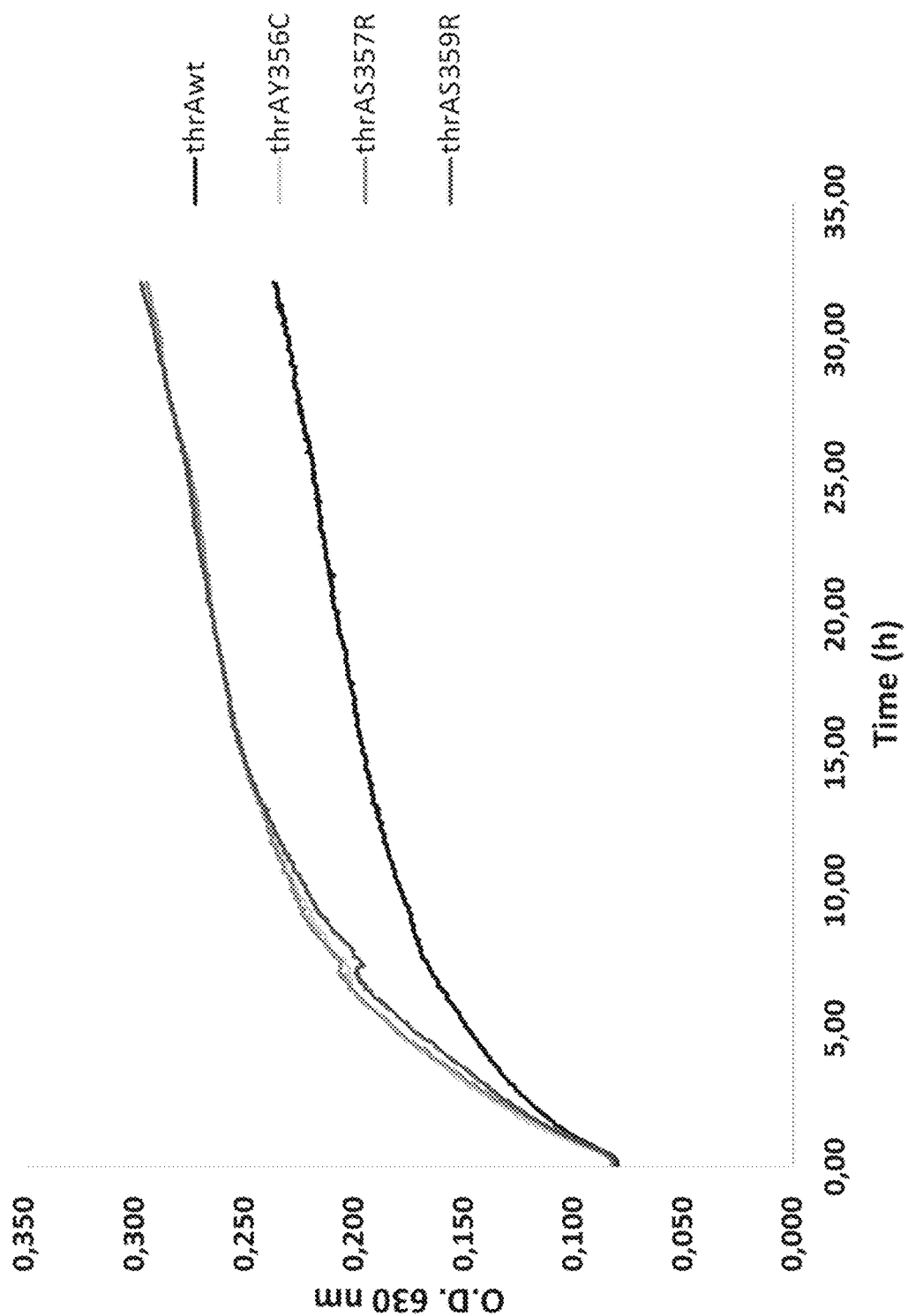
FIG. 7: The effect of mutations in thrA on tolerance towards serine. Three specific mutations of thrA (Y356C, S357R, S359R) were introduced into the Q1 background and the growth of the clones was compared to the growth of the Q1 strain in the presence of 6.25 g/L of serine.
Figure 11:
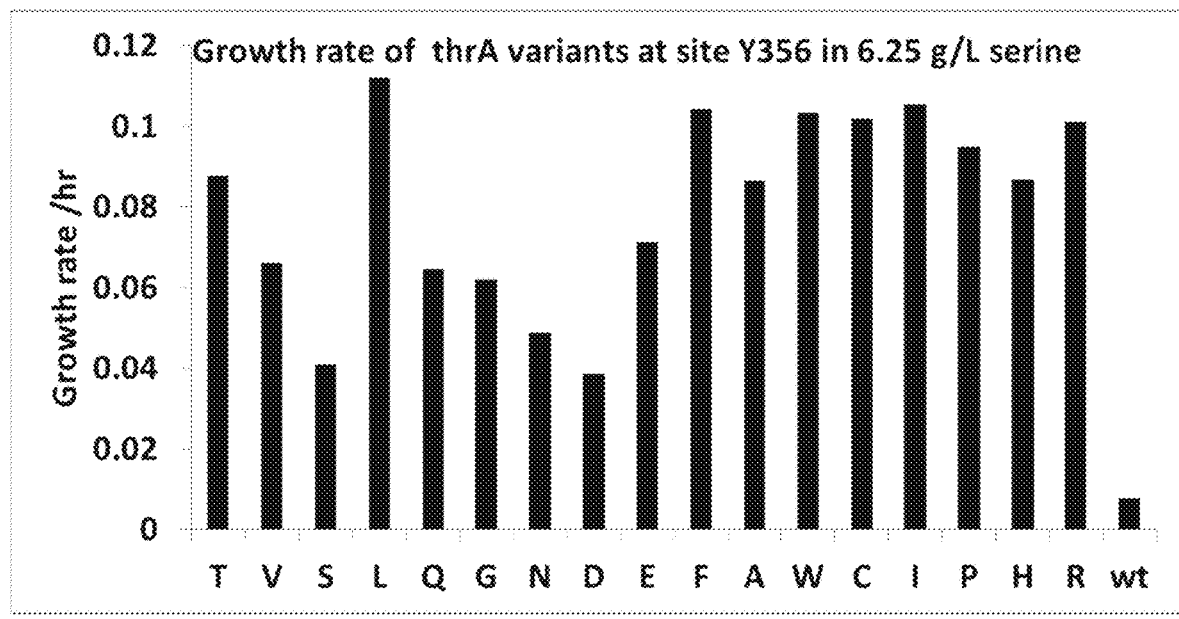
FIG. 11: Growth rate of mutant *E. coli* strains having different amino acid substitutions observed at positions 356 (11A), 357 (11B) and 359 (11C) of ThrA, respectively (the amino acid substitution is denoted by the respective one-letter code). The growth rate of *E. coli* carrying the wild type thrA gene is denoted "wt".
Figure 11:
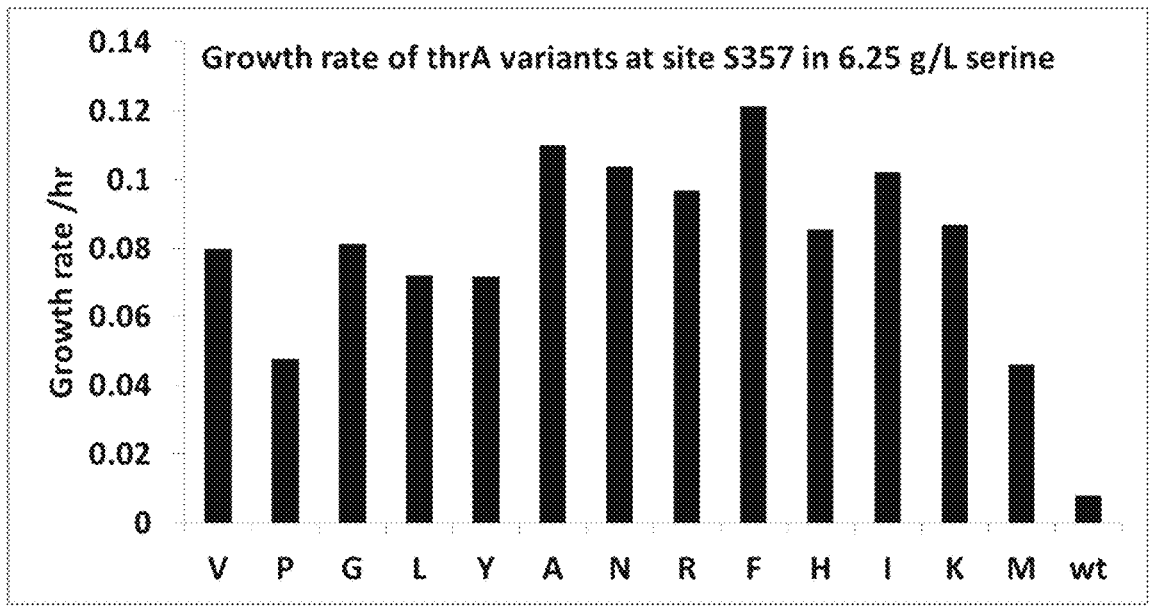
Figure 11:
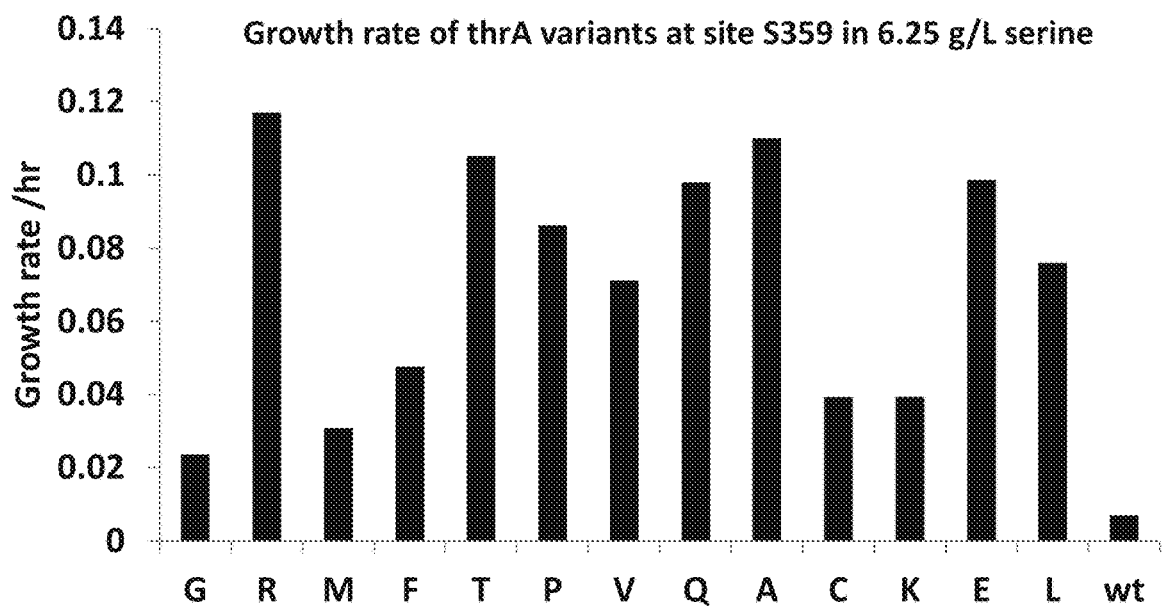

One such gene is thrA which encodes an aspartate kinase I/homoserine dehydrogenase I (ThrA). Further information regarding thrA of, e.g., *Escherichia coli* is available at EcoCyc (www.biocyc.org) under Accession numbers EG10998. A representative amino acid sequence of a wild type Aspartate kinase I/homoserine dehydrogenase I (ThrA) is set forth in SEQ ID NO: 11. As demonstrated in Example 6 and 10, introducing certain mutation within the amino acid sequence of the aspartate kinase I/homoserine dehydrogenase results in a very significant increase in tolerance towards serine (FIGS. 7 and 11). Particularly, the following mutations have been shown to be beneficial: Y356C, S357R and S359R.

As further demonstrated in Example 14, expressing an aspartate kinase I/homoserine dehydrogenase I (ThrA) mutant as detailed herein also results in an increased tolerance towards L-serine of a bacterium wherein none of the genes sdaA, sdaB, tdcG and glyA have been inactivated. This means that the increased tolerance towards L-serine seen with such ThrA mutants is independent from whether or not genes encoding enzymes involved in the degradation of L-serine, notably the genes sdaA, sdaB, tdcG and glyA, are inactivated.

Therefore, a bacterium of the invention may be a bacterium which expresses an aspartate kinase/homoserine dehydrogenase I (ThrA) mutant having one or more amino acid substitutions which increase tolerance towards L-serine.

According to certain embodiments, the present invention provides a bacterium which expresses an aspartate kinase I/homoserine dehydrogenase I (ThrA) mutant which is not inhibited by L-serine.

According to certain embodiments, the present invention provides a bacterium which comprises within the thrA gene one or more nucleotide substitutions resulting in one or more amino acid substitutions which increase tolerance towards L-serine. More particularly, a bacterium is provided which comprises within the thrA gene one or more nucleotide substitutions resulting in one or more amino acid substitutions in the encoded polypeptide at a position selected from the group consisting of Y356, S357 and S359. A bacterium of the invention may thus express an aspartate kinase I/homoserine dehydrogenase I (ThrA) having one or more amino acid substitutions at a position selected from the group consisting of Y356, S357 and S359. More particularly, a bacterium of the invention may express a polypeptide having the amino acid sequence set forth in SEQ ID NO: 11 which comprises one or more amino acid substitutions at a position selected from the group consisting of Y356, S357 and S359. Preferably, the one or more amino acid substitutions are non-conservative substitutions.

According to certain embodiments, the present invention provides a bacterium which comprises within the thrA gene one or more nucleotide substitutions resulting in an amino acid substitution in the encoded polypeptide at position Y356. A bacterium of the invention may thus express a polypeptide encoded by the thrA gene, wherein said polypeptide comprises an amino acid substitution at position Y356. According to particular embodiments, the amino acid substitution is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R, and Y356L. According to other particular embodiments, the amino acid substitution is selected from the group consisting of Y356C, Y356T, Y356V, Y356W, Y356Q, Y356G, Y356E, Y356F, Y356A, Y356I, Y356P, Y356H, Y356R, and Y356L. According to more particular embodiments, the amino acid substitution is selected from the group consisting of Y356C, Y356T, Y356W, Y356F, Y356A, Y356I, Y356P, Y356H, Y356R, and Y356L. According to other more particular embodiments, the amino acid substitution is selected from the group consisting of Y356C, Y356W, Y356F, Y356I, Y356P, Y356R, and Y356L.

According to certain embodiments, the bacterium comprises within the thrA gene one or more nucleotide substitutions resulting in a Y356C substitution in the encoded polypeptide. A bacterium of the invention may thus express a polypeptide encoded by the thrA gene, wherein said polypeptide comprises a Y356C substitution. According to certain embodiments, the bacterium comprises within the thrA gene one or more nucleotide substitutions resulting in a Y356T substitution in the encoded polypeptide. A bacterium of the invention may thus express a polypeptide encoded by the thrA gene, wherein said polypeptide comprises a Y356T substitution.

According to certain embodiments, the bacterium comprises within the thrA gene one or more nucleotide substitutions resulting in a Y356V substitution in the encoded polypeptide. A bacterium of the invention may thus express a polypeptide encoded by the thrA gene, wherein said polypeptide comprises a Y356V substitution. According to certain embodiments, the bacterium comprises within the thrA gene one or more nucleotide substitutions resulting in a Y356S substitution in the encoded polypeptide. A bacterium of the invention may thus express a polypeptide encoded by the thrA gene, wherein said polypeptide comprises a Y356S substitution. According to certain embodiments, the bacterium comprises within the thrA gene one or more nucleotide substitutions resulting in a Y356W substitution in the encoded polypeptide. A bacterium of the invention may thus express a polypeptide encoded by the thrA gene, wherein said polypeptide comprises a Y356W substitution. According to certain embodiments, the bacterium comprises within the thrA gene one or more nucleotide substitutions resulting in a Y356G substitution in the encoded polypeptide. A bacterium of the invention may thus express a polypeptide encoded by the thrA gene, wherein said polypeptide comprises a Y356G substitution. According to certain embodiments, the bacterium comprises within the thrA gene one or more nucleotide substitutions resulting in a Y356N substitution in the encoded polypeptide. A bacterium of the invention may thus express a polypeptide encoded by the thrA gene, wherein said polypeptide comprises a Y356N substitution. According to certain embodiments, the bacterium comprises within the thrA gene one or more nucleotide substitutions resulting in a Y356D substitution in the encoded polypeptide. A bacterium of the invention may thus express a polypeptide encoded by the thrA gene, wherein said polypeptide comprises a Y356D substitution. According to certain embodiments, the bacterium comprises within the thrA gene one or more nucleotide substitutions resulting in a Y356E substitution in the encoded polypeptide. A bacterium of the invention may thus express a polypeptide encoded by the thrA gene, wherein said polypeptide comprises a Y356E substitution. According to certain embodiments, the bacterium comprises within the thrA gene one or more nucleotide substitutions resulting in a Y356F substitution in the encoded polypeptide. A bacterium of the invention may thus express a polypeptide encoded by the thrA gene, wherein said polypeptide comprises a Y356F substitution. According to certain embodiments, the bacterium comprises within the thrA gene one or more nucleotide substitutions resulting in a Y356A substitution in the encoded polypeptide. A bacterium of the invention may thus express a polypeptide encoded by the thrA gene, wherein said polypeptide comprises a Y356I substitution. According to certain embodiments, the bacterium comprises within the thrA gene one or more nucleotide substitutions resulting in a Y356A substitution in the encoded polypeptide. A bacterium of the invention may thus express a polypeptide encoded by the thrA gene, wherein said polypeptide comprises a Y356I substitution. According to certain embodiments, the bacterium comprises within the thrA gene one or more nucleotide substitutions resulting in a Y356P substitution in the encoded polypeptide. A bacterium of the invention may thus express a polypeptide encoded by the thrA gene, wherein said polypeptide comprises a Y356P substitution. According to certain embodiments, the bacterium comprises within the thrA gene one or more nucleotide substitutions resulting in a Y356H substitution in the encoded polypeptide. A bacterium of the invention may thus express a polypeptide encoded by the thrA gene, wherein said polypeptide comprises a Y356H substitution. According to certain embodiments, the bacterium comprises within the thrA gene one or more nucleotide substitutions resulting in a Y356R substitution in the encoded polypeptide. A bacterium of the invention may thus express a polypeptide encoded by the thrA gene, wherein said polypeptide comprises a Y356R substitution. According to certain embodiments, the bacterium comprises within the thrA gene one or more nucleotide substitutions resulting in a Y356L substitution in the encoded polypeptide. A bacterium of the invention may thus express a polypeptide encoded by the thrA gene, wherein said polypeptide comprises a Y356L substitution.

According to certain embodiments, the present invention provides a bacterium which comprises within the thrA gene one or more nucleotide substitutions resulting in an amino acid substitution in the encoded polypeptide at position S357. A bacterium of the invention may thus express a polypeptide encoded by the thrA gene, wherein said polypeptide comprises an amino acid substitution at position S357. According to particular embodiments, the amino acid substitution is selected from the group consisting of S357R, S357V, S357P, S357G, S357L, S357Y, S357A, S357N, S357F, S357H, S357K, S357I and S357M. According to other particular embodiments, the amino acid substitution is selected from the group consisting of S357R, S357V, S357G, S357L, S357Y, S357A, S357N, S357F and S357H. According to more particular embodiments, the amino acid substitution is selected from the group consisting of S357R, S357A, S357N and S357F. According to other more particular embodiments, the amino acid substitution is selected from the group consisting of S357A and S357F.

According to certain embodiments, the bacterium comprises within the thrA gene one or more nucleotide substitutions resulting in a S357R substitution in the encoded polypeptide. A bacterium of the invention may thus express a polypeptide encoded by the thrA gene, wherein said polypeptide comprises a S357R substitution. According to certain embodiments, the bacterium comprises within the thrA gene one or more nucleotide substitutions resulting in a S357V substitution in the encoded polypeptide. A bacterium of the invention may thus express a polypeptide encoded by the thrA gene, wherein said polypeptide comprises a S357V substitution. According to certain embodiments, the bacterium comprises within the thrA gene one or more nucleotide substitutions resulting in a S357P substitution in the encoded polypeptide. A bacterium of the invention may thus express a polypeptide encoded by the thrA gene, wherein said polypeptide comprises a S357P substitution. According to certain embodiments, the bacterium comprises within the thrA gene one or more nucleotide substitutions resulting in a S357G substitution in the encoded polypeptide. A bacterium of the invention may thus express a polypeptide encoded by the thrA gene, wherein said polypeptide comprises a S357G substitution. According to certain embodiments, the bacterium comprises within the thrA gene one or more nucleotide substitutions resulting in a S357L substitution in the encoded polypeptide. A bacterium of the invention may thus express a polypeptide encoded by the thrA gene, wherein said polypeptide comprises a S357L substitution. According to certain embodiments, the bacterium comprises within the thrA gene one or more nucleotide substitutions resulting in a S357Y substitution in the encoded polypeptide. A bacterium of the invention may thus express a polypeptide encoded by the thrA gene, wherein said polypeptide comprises a S357Y substitution. According to certain embodiments, the bacterium comprises within the thrA gene one or more nucleotide substitutions resulting in a S357A substitution in the encoded polypeptide. A bacterium of the invention may thus express a polypeptide encoded by the thrA gene, wherein said polypeptide comprises a S357A substitution. According to certain embodiments, the bacterium comprises within the thrA gene one or more nucleotide substitutions resulting in a S357N substitution in the encoded polypeptide. A bacterium of the invention may thus express a polypeptide encoded by the thrA gene, wherein said polypeptide comprises a S357N substitution. According to certain embodiments, the bacterium comprises within the thrA gene one or more nucleotide substitutions resulting in a S357F substitution in the encoded polypeptide. A bacterium of the invention may thus express a polypeptide encoded by the thrA gene, wherein said polypeptide comprises a S357F substitution. According to certain embodiments, the bacterium comprises within the thrA gene one or more nucleotide substitutions resulting in a S357H substitution in the encoded polypeptide. A bacterium of the invention may thus express a polypeptide encoded by the thrA gene, wherein said polypeptide comprises a S357H substitution. According to certain embodiments, the bacterium comprises within the thrA gene one or more nucleotide substitutions resulting in a S357K substitution in the encoded polypeptide. A bacterium of the invention may thus express a polypeptide encoded by the thrA gene, wherein said polypeptide comprises a S357K substitution. According to certain embodiments, the bacterium comprises within the thrA gene one or more nucleotide substitutions resulting in a S357I substitution in the encoded polypeptide. A bacterium of the invention may thus express a polypeptide encoded by the thrA gene, wherein said polypeptide comprises a S357I substitution. According to certain embodiments, the bacterium comprises within the thrA gene one or more nucleotide substitutions resulting in a S357M substitution in the encoded polypeptide. A bacterium of the invention may thus express a polypeptide encoded by the thrA gene, wherein said polypeptide comprises a S357M substitution.

According to certain embodiments, the present invention provides a bacterium which comprises within the thrA gene one or more nucleotide substitutions resulting in an amino acid substitution in the encoded polypeptide at position S359. A bacterium of the invention may thus express a polypeptide encoded by the thrA gene, wherein said polypeptide comprises an amino acid substitution at position S359. According to particular embodiments, the amino acid substitution is selected from the group consisting of S359R, S359G, S359M, S359F, S359I, S359P, S359V, S359Q, S359A, S359C, S359K, S359E and S359L. According to other particular embodiments, the amino acid substitution is selected from the group consisting of S359R, S359F, S359T, S359P, S359V, S359Q, S359A, S359C, S359K, S359E and S359L. According to more particular embodiments, the amino acid substitution is selected from the group consisting of S359R, S359I, S359P, S359V, S359Q, S359A, S359E and S359L. According to other more particular embodiments, the amino acid substitution is selected from the group consisting of S359R, S359T, S359P, S359Q, S359A, S359E and S359L. According to other more particular embodiments, the amino acid substitution is selected from the group consisting of S359R, S359T, S359Q, S359A and S359E. According to other more particular embodiments, the amino acid substitution is selected from the group consisting of S359R, S359T and S359A. According to other more particular embodiments, the amino acid substitution is selected from the group consisting of S359R and S359A.

According to certain embodiments, the bacterium comprises within the thrA gene one or more nucleotide substitutions resulting in a S359R substitution in the encoded polypeptide. A bacterium of the invention may thus express a polypeptide encoded by the thrA gene, wherein said polypeptide comprises a S359R substitution. According to certain embodiments, the bacterium comprises within the thrA gene one or more nucleotide substitutions resulting in a S359G substitution in the encoded polypeptide. A bacterium of the invention may thus express a polypeptide encoded by the thrA gene, wherein said polypeptide comprises a S359G substitution. According to certain embodiments, the bacterium comprises within the thrA gene one or more nucleotide substitutions resulting in a S359M substitution in the encoded polypeptide. A bacterium of the invention may thus express a polypeptide encoded by the thrA gene, wherein said polypeptide comprises a S359M substitution. According to certain embodiments, the bacterium comprises within the thrA gene one or more nucleotide substitutions resulting in a S359F substitution in the encoded polypeptide. A bacterium of the invention may thus express a polypeptide encoded by the thrA gene, wherein said polypeptide comprises a S359F substitution. According to certain embodiments, the bacterium comprises within the thrA gene one or more nucleotide substitutions resulting in a S359T substitution in the encoded polypeptide. A bacterium of the invention may thus express a polypeptide encoded by the thrA gene, wherein said polypeptide comprises a S359T substitution. According to certain embodiments, the bacterium comprises within the thrA gene one or more nucleotide substitutions resulting in a S359P substitution in the encoded polypeptide. A bacterium of the invention may thus express a polypeptide encoded by the thrA gene, wherein said polypeptide comprises a S359P substitution. According to certain embodiments, the bacterium comprises within the thrA gene one or more nucleotide substitutions resulting in a S359V substitution in the encoded polypeptide. A bacterium of the invention may thus express a polypeptide encoded by the thrA gene, wherein said polypeptide comprises a S359V substitution. According to certain embodiments, the bacterium comprises within the thrA gene one or more nucleotide substitutions resulting in a S359Q substitution in the encoded polypeptide. A bacterium of the invention may thus express a polypeptide encoded by the thrA gene, wherein said polypeptide comprises a S359Q substitution. According to certain embodiments, the bacterium comprises within the thrA gene one or more nucleotide substitutions resulting in a S359A substitution in the encoded polypeptide. A bacterium of the invention may thus express a polypeptide encoded by the thrA gene, wherein said polypeptide comprises a S359A substitution. According to certain embodiments, the bacterium comprises within the thrA gene one or more nucleotide substitutions resulting in a S359C substitution in the encoded polypeptide. A bacterium of the invention may thus express a polypeptide encoded by the thrA gene, wherein said polypeptide comprises a S359C substitution. According to certain embodiments, the bacterium comprises within the thrA gene one or more nucleotide substitutions resulting in a S359K substitution in the encoded polypeptide. A bacterium of the invention may thus express a polypeptide encoded by the thrA gene, wherein said polypeptide comprises a S359K substitution. According to certain embodiments, the bacterium comprises within the thrA gene one or more nucleotide substitutions resulting in a S359E substitution in the encoded polypeptide. A bacterium of the invention may thus express a polypeptide encoded by the thrA gene, wherein said polypeptide comprises a S359E substitution. According to certain embodiments, the bacterium comprises within the thrA gene one or more nucleotide substitutions resulting in a S359L substitution in the encoded polypeptide. A bacterium of the invention may thus express a polypeptide encoded by the thrA gene, wherein said polypeptide comprises a S359L substitution.

According to certain embodiments, the present invention provides a bacterium which comprises within the thrA gene one or more nucleotide substitutions resulting in an amino acid substitution in the encoded polypeptide at position Y356, one or more nucleotide substitutions resulting in an amino acid substitution in the encoded polypeptide at position S357 and/or one or more nucleotide substitutions resulting in an amino acid substitution in the encoded polypeptide at position S359; wherein the substitution at position Y356 is selected from the group consisting of Y356C, Y356I, Y356V, Y356S, Y356W, Y356Q, Y356G, Y356N, Y356D, Y356E, Y356F, Y356A, Y356I, Y356P, Y356H, Y356R and Y356L; the substitution at position S357 is selected from the group consisting of S357R, S357V, S357P, S357G, S357L, S357Y, S357A, S357N, S357F, S357H, S357K, S357I and S357M; and the substitution at position S359 is selected from the group consisting of S359R, S359G, S359M, S359F, S359T, S359P, S359V, S359Q, S359A, S359C, S359K, S359E and S359L.

According to certain embodiments, the present invention provides a bacterium which comprises within the thrA gene one or more nucleotide substitutions resulting in an amino acid substitution in the encoded polypeptide at position Y356 and/or one or more nucleotide substitutions resulting in an amino acid substitution in the encoded polypeptide at position S357; wherein the substitution at position Y356 is selected from the group consisting of Y356C, Y356T, Y356V, Y356S, Y356W, Y3560, Y356G, Y356N, Y356D, Y356E, Y356F, Y356A, Y356I, Y356P, Y356H, Y356R and Y356L; and the substitution at position S357 is selected from the group consisting of S357R, S357V, S357P, S357G, S357L, S357Y, S357A, S357N, S357F, S357H, S357K, S357I and S357M.

According to certain embodiments, the present invention provides a bacterium which comprises within the thrA gene one or more nucleotide substitutions resulting in an amino acid substitution in the encoded polypeptide at position Y356 and/or one or more nucleotide substitutions resulting in an amino acid substitution in the encoded polypeptide at position S359, wherein the substitution at position Y356 is selected from the group consisting of Y356C, Y356T, Y356V, Y356S, Y356W, Y356G, Y356G, Y356N, Y3560, Y356E, Y356F, Y356A, Y356I, Y356P, Y356H, Y356R and Y356L; and the substitution at position S359 is selected from the group consisting of S359R, S359G, S359M, S359F, S359T, S359P, S359V, S359Q, S359A, S359C, S359K, S359E and S359L.

According to certain embodiments, the present invention provides a bacterium which comprises within the thrA gene one or more nucleotide substitutions resulting in an amino acid substitution in the encoded polypeptide at position S357 and/or one or more nucleotide substitutions resulting in an amino acid substitution in the encoded polypeptide at position S359; wherein the substitution at position S357 is selected from the group consisting of S357R, S357V, S357P, S357G, S357L, S357Y, S357A, S357N, S357F, S357H, S357K, S357I and S357M; and the substitution at position S359 is selected from the group consisting of S359R, S359G, S359M, S359F, S359T, S359P, S359V, S359Q, S359A, S359C, S359K, S359E and S359L.

According to certain embodiments, the present invention provides a bacterium which comprises within the thrA gene one or more nucleotide substitutions resulting in an amino acid substitution in the encoded polypeptide at position Y356, one or more nucleotide substitutions resulting in an amino acid substitution in the encoded polypeptide at position S357 and one or more nucleotide substitutions resulting in an amino acid substitution in the encoded polypeptide at position S359; wherein the substitution at position Y356 is selected from the group consisting of Y356C, Y356T, Y356V, Y356S, Y356W, Y3560, Y356G, Y356N, Y356D, Y356E, Y356F, Y356A, Y356I, Y356P, Y356H, Y356R and Y356L; the substitution at position S357 is selected from the group consisting of S357R, S357V, S357P, S357G, S357L, S357Y, S357A, S357N, S357F, S357H, S357K, S357I and S357M; and the substitution at position S359 is selected from the group consisting of S359R, S359G, S359M, S359F, S359T, S359P, S359V, S359Q, S359A, S359C, S359K, S359E and S359L.

According to certain embodiments, the present invention provides a bacterium which comprises within the thrA gene one or more nucleotide substitutions resulting in an amino acid substitution in the encoded polypeptide at position Y356 and one or more nucleotide substitutions resulting in an amino acid substitution in the encoded polypeptide at position S357; wherein the substitution at position Y356 is selected from the group consisting of Y356C, Y356T, Y356V, Y356S, Y356W, Y356A, Y356G, Y356N, Y356D, Y356E, Y356F, Y356A, Y356I, Y356P, Y356H, Y356R and Y356L; and the substitution at position S357 is selected from the group consisting of S357R, S357V, S357P, S357G, S357L, S357Y, S357A, S357N, S357F, S357H, S357K, S357I and S357M.

According to certain embodiments, the present invention provides a bacterium which comprises within the thrA gene one or more nucleotide substitutions resulting in an amino acid substitution in the encoded polypeptide at position Y356 and one or more nucleotide substitutions resulting in an amino acid substitution in the encoded polypeptide at position S359; wherein the substitution at position Y356 is selected from the group consisting of Y356C, Y356T, Y356V, Y356S, Y356W, Y356Q, Y356G, Y356N, Y356D, Y356E, Y356F and Y356A; and the substitution at position S359 is selected from the group consisting of S359R, S359G, S359M, S359F, S359T, S359P, S359V, S359Q, S359A, S359C, S359K, S359E and S359L.

According to certain embodiments, the present invention provides a bacterium which comprises within the thrA gene one or more nucleotide substitutions resulting in an amino acid substitution in the encoded polypeptide at position S357 and one or more nucleotide substitutions resulting in an amino acid substitution in the encoded polypeptide at position S359; wherein the substitution at position S357 is selected from the group consisting of S357R, S357V, S357P, S357G, S357L, S357Y, S357A, S357N, S357F, S357H, S357K, S357I and S357M; and the substitution at position S359 is selected from the group consisting of S359R, S359G, S359M, S359F, S3591, S359P, S359V, S359Q, S359A, S359C, S359K, S359E and S359L.

According to certain embodiments, a bacterium of the invention express a polypeptide having the amino acid sequence set forth in SEQ ID NO: 11 which comprises an amino acid substitution at position Y356, S357 and/or S359, wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L; the substitution at position S357 is selected from the group consisting of S357R, S357V, S357P, S357G, S357L, S357Y, S357A, S357N, S357F, S357H, S357K, S357I and S357M; and the substitution at position S359 is selected from the group consisting of S359R, S359G, S359M, S359F, S359T, S359P, S359V, S359Q, S359A, S359C, S359K, S359E and S359L.

According to certain embodiments, a bacterium of the invention express a polypeptide having the amino acid sequence set forth in SEQ ID NO: 11 which comprises an amino acid substitution at position Y356 and/or S357, wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L; and the substitution at position S357 is selected from the group consisting of S357R, S357V, S357P, S357G, S357L, S357Y, S357A, S357N, S357F, S357H, S357K, S357I and S357M.

According to certain embodiments, a bacterium of the invention express a polypeptide having the amino acid sequence set forth in SEQ ID NO: 11 which comprises an amino acid substitution at position Y356 and/or S359, wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L; and the substitution at position S359 is selected from the group consisting of S359R, S359G, S359M, S359F, S359T, S359P, S359V, S359Q, S359A, S359C, S359K, S359E and S359L.

According to certain embodiments, a bacterium of the invention express a polypeptide having the amino acid sequence set forth in SEQ ID NO: 11 which comprises an amino acid substitution at position S357 and/or S359, wherein the substitution at position S357 is selected from the group consisting of S357R, S357V, S357P, S357G, S357L, S357Y, S357A, S357N, S357F, S357H, S357K, S357I and S357M; and the substitution at position S359 is selected from the group consisting of S359R, S359G, S359M, S359F, S359T, S359P, S359V, S359Q, S359A, S359C, S359K, S359E and S359L.

According to certain embodiments, a bacterium of the invention express a polypeptide having the amino acid sequence set forth in SEQ ID NO: 11 which comprises an amino acid substitution at position Y356, wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L.

According to certain embodiments, a bacterium of the invention express a polypeptide having the amino acid sequence set forth in SEQ ID NO: 11 which comprises an amino acid substitution at position S357, wherein the substitution at position S357 is selected from the group consisting of S357R, S357V, S357P, S357G, S357L, S357Y, S357A, S357N, S357F, S357H, S357K, S357I and S357M; and the substitution at position S359 is selected from the group consisting of S359R, S359G, S359M, S359F, S359T, S359P, S359V, S359A, S359A, S359C, S359K, S359E and S359L.

According to certain embodiments, a bacterium of the invention express a polypeptide having the amino acid sequence set forth in SEQ ID NO: 11 which comprises an amino acid substitution at position S359, wherein the substitution at position S359 is selected from the group consisting of S359R, S359G, S359M, S359F, S359T, S359P, S359V, S359Q, S359A, S359C, S359K, S359E and S359L.

According to certain embodiments, a bacterium of the invention express a polypeptide having the amino acid sequence set forth in SEQ ID NO: 11 which comprises an amino acid substitution at position Y356 and S357, wherein the substitution at position Y356 is selected from the group consisting of Y356C, Y356T, Y356V, Y356S, Y356W, Y356Q, Y356G, Y356N, Y356D, Y356E, Y356F and Y356A; and the substitution at position S357 is selected from the group consisting of S357R, S357V, S357P, S357G, S357L, S357Y, S357A, S357N, S357F, S357H, S357K, S357I and S357M.

According to certain embodiments, a bacterium of the invention express a polypeptide having the amino acid sequence set forth in SEQ ID NO: 11 which comprises an amino acid substitution at position Y356 and S359, wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L; and the substitution at position S359 is selected from the group consisting of S359R, S359G, S359M, S359F, S359T, S359P, S359V, S359Q, S359A, S359C, S359K, S359E and S359L.

According to certain embodiments, a bacterium of the invention express a polypeptide having the amino acid sequence set forth in SEQ ID NO: 11 which comprises an amino acid substitution at position S357 and S359, wherein the substitution at position S357 is selected from the group consisting of S357R, S357V, S357P, S357G, S357L, S357Y, S357A, S357N, S357F, S357H, S357K, S357I and S357M; and the substitution at position S359 is selected from the group consisting of S359R, S359G, S359M, S359F, S359T, S359P, S359V, S359Q, S359A, S359C, S359K, S359E and S359L.

According to certain embodiments, a bacterium of the invention express a polypeptide having the amino acid sequence set forth in SEQ ID NO: 11 which comprises an amino acid substitution at position Y356, S357 and S359, wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L; the substitution at position S357 is selected from the group consisting of S357R, S357V, S357P, S357G, S357L, S357Y, S357A, S357N, S357F, S357H, S357K, S357I and S357M; and the substitution at position S359 is selected from the group consisting of S359R, S359G, S359M, S359F, S359T, S359P, S359V, S359Q, S359A, S359C, S359K, S359E and S359L.

According to certain embodiments, a bacterium of the invention expresses a polypeptide having the amino acid sequence set forth in SEQ ID NO: 11, wherein at position 356 tyrosine is replaced by cysteine. According to certain embodiments, a bacterium of the invention expresses a polypeptide having the amino acid sequence set forth in SEQ ID NO: 11, wherein at position 356 tyrosine is replaced by threonine. According to certain embodiments, a bacterium of the invention expresses a polypeptide having the amino acid sequence set forth in SEQ ID NO: 11, wherein at position 356 tyrosine is replaced by valine. According to certain embodiments, a bacterium of the invention expresses a polypeptide having the amino acid sequence set forth in SEQ ID NO: 11, wherein at position 356 tyrosine is replaced by serine. According to certain embodiments, a bacterium of the invention expresses a polypeptide having the amino acid sequence set forth in SEQ ID NO: 11, wherein at position 356 tyrosine is replaced by tryptophan. According to certain embodiments, a bacterium of the invention expresses a polypeptide having the amino acid sequence set forth in SEQ ID NO: 11, wherein at position 356 tyrosine is replaced by glutamine. According to certain embodiments, a bacterium of the invention expresses a polypeptide having the amino acid sequence set forth in SEQ ID NO: 11, wherein at position 356 tyrosine is replaced by glycine. According to certain embodiments, a bacterium of the invention expresses a polypeptide having the amino acid sequence set forth in SEQ ID NO: 11, wherein at position 356 tyrosine is replaced by asparagine. According to certain embodiments, a bacterium of the invention expresses a polypeptide having the amino acid sequence set forth in SEQ ID NO: 11, wherein at position 356 tyrosine is replaced by aspartic acid. According to certain embodiments, a bacterium of the invention expresses a polypeptide having the amino acid sequence set forth in SEQ ID NO: 11, wherein at position 356 tyrosine is replaced by glutamic acid. According to certain embodiments, a bacterium of the invention expresses a polypeptide having the amino acid sequence set forth in SEQ ID NO: 11, wherein at position 356 tyrosine is replaced by phenylalanine. According to certain embodiments, a bacterium of the invention expresses a polypeptide having the amino acid sequence set forth in SEQ ID NO: 11, wherein at position 356 tyrosine is replaced by alanine. According to certain embodiments, a bacterium of the invention expresses a polypeptide having the amino acid sequence set forth in SEQ ID NO: 11, wherein at position 356 tyrosine is replaced by isoleucine. According to certain embodiments, a bacterium of the invention expresses a polypeptide having the amino acid sequence set forth in SEQ ID NO: 11, wherein at position 356 tyrosine is replaced by proline. According to certain embodiments, a bacterium of the invention expresses a polypeptide having the amino acid sequence set forth in SEQ ID NO: 11, wherein at position 356 tyrosine is replaced by histidine. According to certain embodiments, a bacterium of the invention expresses a polypeptide having the amino acid sequence set forth in SEQ ID NO: 11, wherein at position 356 tyrosine is replaced by arginine. According to certain embodiments, a bacterium of the invention expresses a polypeptide having the amino acid sequence set forth in SEQ ID NO: 11, wherein at position 356 tyrosine is replaced by leucine.

According to certain embodiments, a bacterium of the invention expresses a polypeptide having the amino acid sequence set forth in SEQ ID NO: 11, wherein at position 357 serine is replaced by arginine. According to certain embodiments, a bacterium of the invention expresses a polypeptide having the amino acid sequence set forth in SEQ ID NO: 11, wherein at position 357 serine is replaced by valine. According to certain embodiments, a bacterium of the invention expresses a polypeptide having the amino acid sequence set forth in SEQ ID NO: 11, wherein at position 357 serine is replaced by proline. According to certain embodiments, a bacterium of the invention expresses a polypeptide having the amino acid sequence set forth in SEQ ID NO: 11, wherein at position 357 serine is replaced by glycine. According to certain embodiments, a bacterium of the invention expresses a polypeptide having the amino acid sequence set forth in SEQ ID NO: 11, wherein at position 357 serine is replaced by leucine. According to certain embodiments, a bacterium of the invention expresses a polypeptide having the amino acid sequence set forth in SEQ ID NO: 11, wherein at position 357 serine is replaced by tyrosine. According to certain embodiments, a bacterium of the invention expresses a polypeptide having the amino acid sequence set forth in SEQ ID NO: 11, wherein at position 357 serine is replaced by alanine. According to certain embodiments, a bacterium of the invention expresses a polypeptide having the amino acid sequence set forth in SEQ ID NO: 11, wherein at position 357 serine is replaced by asparagine. According to certain embodiments, a bacterium of the invention expresses a polypeptide having the amino acid sequence set forth in SEQ ID NO: 11, wherein at position 357 serine is replaced by phenylalanine. According to certain embodiments, a bacterium of the invention expresses a polypeptide having the amino acid sequence set forth in SEQ ID NO: 11, wherein at position 357 serine is replaced by histidine.

According to certain embodiments, a bacterium of the invention expresses a polypeptide having the amino acid sequence set forth in SEQ ID NO: 11, wherein at position 357 serine is replaced by lysine. According to certain embodiments, a bacterium of the invention expresses a polypeptide having the amino acid sequence set forth in SEQ ID NO: 11, wherein at position 357 serine is replaced by isoleucine. According to certain embodiments, a bacterium of the invention expresses a polypeptide having the amino acid sequence set forth in SEQ ID NO: 11, wherein at position 357 serine is replaced by methionine.

According to certain embodiments, a bacterium of the invention expresses a polypeptide having the amino acid sequence set forth in SEQ ID NO: 11, wherein at position 359 serine is replaced by arginine. According to certain embodiments, a bacterium of the invention expresses a polypeptide having the amino acid sequence set forth in SEQ ID NO: 11, wherein at position 359 serine is replaced by glycine. According to certain embodiments, a bacterium of the invention expresses a polypeptide having the amino acid sequence set forth in SEQ ID NO: 11, wherein at position 359 serine is replaced by methionine. According to certain embodiments, a bacterium of the invention expresses a polypeptide having the amino acid sequence set forth in SEQ ID NO: 11, wherein at position 359 serine is replaced by phenylalanine. According to certain embodiments, a bacterium of the invention expresses a polypeptide having the amino acid sequence set forth in SEQ ID NO: 11, wherein at position 359 serine is replaced by threonine. According to certain embodiments, a bacterium of the invention expresses a polypeptide having the amino acid sequence set forth in SEQ ID NO: 11, wherein at position 359 serine is replaced by proline. According to certain embodiments, a bacterium of the invention expresses a polypeptide having the amino acid sequence set forth in SEQ ID NO: 11, wherein at position 359 serine is replaced by valine. According to certain embodiments, a bacterium of the invention expresses a polypeptide having the amino acid sequence set forth in SEQ ID NO: 11, wherein at position 359 serine is replaced by glutamine. According to certain embodiments, a bacterium of the invention expresses a polypeptide having the amino acid sequence set forth in SEQ ID NO: 11, wherein at position 359 serine is replaced by alanine. According to certain embodiments, a bacterium of the invention expresses a polypeptide having the amino acid sequence set forth in SEQ ID NO: 11, wherein at position 359 serine is replaced by cysteine. According to certain embodiments, a bacterium of the invention expresses a polypeptide having the amino acid sequence set forth in SEQ ID NO: 11, wherein at position 359 serine is replaced by lysine. According to certain embodiments, a bacterium of the invention expresses a polypeptide having the amino acid sequence set forth in SEQ ID NO: 11, wherein at position 359 serine is replaced by glutamic acid. According to certain embodiments, a bacterium of the invention expresses a polypeptide having the amino acid sequence set forth in SEQ ID NO: 11, wherein at position 359 serine is replaced by leucine.

According to certain embodiments, a bacterium of the invention expresses a polypeptide having an amino acid sequence which has at least about 90%, such at least about 93%, at least about 95%, at least about 96%, at least about 97%, at least about 98%, or at least about 99%, sequence identity to the amino acid sequence set forth in SEQ ID NO: 11 which comprises an amino acid substitution at position Y356, S357 and/or S359, wherein the substitution at position Y356 is selected from the group consisting of Y356C, Y356T, Y356V, Y356S, Y356W, Y356Q, Y356G, Y356N, Y356D, Y356E, Y356F, Y3S6A, Y356I, Y356P, Y356H, Y356R and Y356L; the substitution at position S357 is selected from the group consisting of S357R, S357V, S357P, S357G, S357L, S357Y, S357A, S357N, S357F, S357H, S357K, S357I and S357M; and the substitution at position S359 is selected from the group consisting of S359R, S359G, S359M, S359F, S359T, S359P, S359V, S359A, S359A, S359C, S359K, S359E and S359L.

According to certain embodiments, a bacterium of the invention expresses a polypeptide having an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 11 which comprises an amino acid substitution at position Y356 and/or S357, wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L; and the substitution at position S357 is selected from the group consisting of S357R, S357V, S357P, S357G, S357L, S357Y, S357A, S357N, S357F, S357H, S357K, S357I and S357M.

According to certain embodiments, a bacterium of the invention expresses a polypeptide having an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 11 which comprises an amino acid substitution at position Y356 and/or S359, wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L; and the substitution at position S359 is selected from the group consisting of S359R, S359G, S359M, S359F, S359T, S359P, S359V, S359A, S359A, S359C, S359K, S359E and S359L.

According to certain embodiments, a bacterium of the invention expresses a polypeptide having an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 11 which comprises an amino acid substitution at position S357 and/or S359, wherein the substitution at position S357 is selected from the group consisting of S357R, S357V, S357P, S357G, S357L, S357Y, S357A, S357N, S357F, S357H, S357K, S357I and S357M; and the substitution at position S359 is selected from the group consisting of S359R, S359G, S359M, S359F, S359I, S359P, S359V, S359Q, S359A, S359C, S359K, S359E and S359L.

According to certain embodiments, a bacterium of the invention expresses a polypeptide having an amino acid sequence which has at least about 90%, such at least about 93%, at least about 95%, at least about 96%, at least about 97%, at least about 98%, or at least about 99%, sequence identity to the amino acid sequence set forth in SEQ ID NO: 11 which comprises an amino acid substitution at position Y356, wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L.

According to certain embodiments, a bacterium of the invention expresses a polypeptide having an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 11 which comprises an amino acid substitution at position S357, wherein the substitution at position S357 is selected from the group consisting of S357R, S357V, S357P, S357G, S357L, S357Y, S357A, S357N, S357F, S357H, S357K, S357I and S357M.

According to certain embodiments, a bacterium of the invention expresses a polypeptide having an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 11 which comprises an amino acid substitution at position S359, wherein the substitution at position S359 is selected from the group consisting of S359R, S359G, S359M, S359F, S359T, S359P, S359V, S359Q, S359A, S359C, S359K, S359E and S359L.

According to certain embodiments, a bacterium of the invention expresses a polypeptide having an amino acid sequence which has at least about 93%, such as at least about 95%, at least about 96%, at least about 97%, at least about 98%, or at least about 99%, sequence identity to the amino acid sequence set forth in SEQ ID NO: 11 which comprises an amino acid substitution at position Y356, wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L.

According to certain embodiments, a bacterium of the invention expresses a polypeptide having an amino acid sequence which has at least about 93%, such as at least about 95%, at least about 96%, at least about 97%, at least about 98%, or at least about 99%, sequence identity to the amino acid sequence set forth in SEQ ID NO: 11 which comprises an amino acid substitution at position S357, wherein the substitution at position S357 is selected from the group consisting of S357R, S357V, S357P, S357G, S357L, S357Y, S357A, S357N, S357F, S357H, S357K, S357I and S357M.

According to certain embodiments, a bacterium of the invention expresses a polypeptide having an amino acid sequence which has at least about 93%, such as at least about 95%, at least about 96%, at least about 97%, at least about 98%, or at least about 99%, sequence identity to the amino acid sequence set forth in SEQ ID NO: 11 which comprises an amino acid substitution at position S359, wherein the substitution at position S359 is selected from the group consisting of S359R, S359G, S359M, S359F, S359T, S359P, S359V, S359Q, S359A, S359C, S359K, S359E and S359L.

According to certain embodiments, a bacterium of the invention expresses a polypeptide having an amino acid sequence which has at least about 95%, such as at least about 96%, at least about 97%, at least about 98%, or at least about 99%, sequence identity to the amino acid sequence set forth in SEQ ID NO: 11 which comprises an amino acid substitution at position Y356, wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L.

According to certain embodiments, a bacterium of the invention expresses a polypeptide having an amino acid sequence which has at least about 95%, such as at least about 96%, at least about 97%, at least about 98%, or at least about 99%, sequence identity to the amino acid sequence set forth in SEQ ID NO: 11 which comprises an amino acid substitution at position S357, wherein the substitution at position S357 is selected from the group consisting of S357R, S357V, S357P, S357G, S357L, S357Y, S357A, S357N, S357F, S357H, S357K, S357I and S357M.

According to certain embodiments, a bacterium of the invention expresses a polypeptide having an amino acid sequence which has at least about 95%, such as at least about 96%, at least about 97%, at least about 98%, or at least about 99%, sequence identity to the amino acid sequence set forth in SEQ ID NO: 11 which comprises an amino acid substitution at position S359, wherein the substitution at position S359 is selected from the group consisting of S359R, S359G, S359M, S359F, S359T, S359P, S359V, S359Q, S359A, S359C, S359K, S359E and S359L.

According to certain embodiments, a bacterium of the invention expresses a polypeptide having an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 11 which comprises an amino acid substitution at position Y356, S357 and S359, wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L; the substitution at position S357 is selected from the group consisting of S357R, S357V, S357P, S357G, S357L, S357Y, S357A, S357N, S357F, S357H, S357K, S357I and S357M; and the substitution at position S359 is selected from the group consisting of S359R, S359G, S359M, S359F, S359T, S359P, S359V, S359Q, S359A, S359C, S359K, S359E and S359L.

According to certain embodiments, a bacterium of the invention expresses a polypeptide having an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 11 which comprises an amino acid substitution at position Y356 and S357, wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L; and the substitution at position S357 is selected from the group consisting of S357R, S357V, S357P, S357G, S357L, S357Y, S357A, S357N, S357F, S357H, S357K, S357I and S357M.

According to certain embodiments, a bacterium of the invention expresses a polypeptide having an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 11 which comprises an amino acid substitution at position Y356 and S359, wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L; and the substitution at position S359 is selected from the group consisting of S359R, S359G, S359M, S359F, S359T, S359P, S359V, S359A, S359A, S359C, S359K, S359E and S359L.

According to certain embodiments, a bacterium of the invention expresses a polypeptide having an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 11 which comprises an amino acid substitution at position S357 and S359, wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L; the substitution at position S357 is selected from the group consisting of S357R, S357V, S357P, S357G, S357L, S357Y, S357A, S357N, S357F, S357H, S357K, S357I and S357M; and the substitution at position S359 is selected from the group consisting of S359R, S359G, S359M, S359F, S359T, S359P, S359V, S359Q, S359A, S359C, S359K, S359E and S359L.

According to certain embodiments, a bacterium of the invention expresses a polypeptide having an amino acid sequence set forth in SEQ ID NO: 11 which comprises an amino acid substitution at position Y356, S357 and/or S359, wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L; the substitution at position S357 is selected from the group consisting of S357R, S357V, S357P, S357G, S357L, S357Y, S357A, S357N, S357F, S357H, S357K, S357I and S357M; and the substitution at position S359 is selected from the group consisting of S359R, S359G, S359M, S359F, S359T, S359P, S359V, S359Q, S359A, S359C, S359K, S359E and S359L; and wherein 1 or more, such as about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, further amino acid residues are substituted, deleted, and/or inserted.

The bacterium may express a polypeptide having an amino acid sequence set forth in SEQ ID NO: 11 which comprises an amino acid substitution at position Y356, S357 and/or S359, wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L; the substitution at position S357 is selected from the group consisting of S357R, S357V, S357P, S357G, S357L, S357Y, S357A, S357N, S357F, S357H, S357K, S357I and S357M; and the substitution at position S359 is selected from the group consisting of S359R, S359G, S359M, S359F, S359T, S359P, S359V, S359Q, S359A, S359C, S359K, S359E and S359L; and wherein about 1 to about 5, such as about 1 to about 3, further amino acid residues are substituted, deleted, and/or inserted.

According to certain embodiments, the present invention provides a bacterium which comprises within the thrA gene one or more nucleotide substitutions resulting in one or more amino acid substitutions in the encoded polypeptide selected from the group consisting of Y356C, S357R and S359R. A bacterium of the invention may thus express a polypeptide encoded by the thrA gene, wherein said polypeptide comprises one or more (such as two or three) amino acid substitutions selected from the group consisting of Y356C, S357R and S359R. According to certain embodiments, a bacterium of the invention comprises within the thrA gene one or more nucleotide substitutions resulting in one or more (such as two) amino acid substitutions in the encoded polypeptide selected from the group consisting of Y356C and S357R. A bacterium of the invention may thus express a polypeptide encoded by the thrA gene, wherein said polypeptide comprises one or more (such as two) amino acid substitutions in the encoded polypeptide selected from the group consisting of Y356C and S357R. According to certain embodiments, a bacterium of the invention comprises within the thrA gene one or more nucleotide substitutions resulting in one or more (such as two) amino acid substitutions in the encoded polypeptide selected from the group consisting of Y356C and S359R. A bacterium of the invention may thus express a polypeptide encoded by the thrA gene, wherein said polypeptide comprises one or more (such as two) amino acid substitutions in the encoded polypeptide selected from the group consisting of Y356C and S359R. According to certain embodiments, a bacterium of the invention comprises within the thrA gene one or more nucleotide substitutions resulting in one or more (such as two) amino acid substitutions in the encoded polypeptide selected from the group consisting of S357R and S359R. A bacterium of the invention may thus express a polypeptide encoded by the thrA gene, wherein said polypeptide comprises one or more (such as two) amino acid substitutions in the encoded polypeptide selected from the group consisting of S357R and S359R.

According the certain embodiments, the bacterium comprises within the thrA gene one or more nucleotide substitutions resulting in a Y356C substitution in the encoded polypeptide. A bacterium of the invention may thus express a polypeptide encoded by the thrA gene, wherein said polypeptide comprises a Y356C substitution. According the certain embodiments, the bacterium comprises within the thrA gene one or more nucleotide substitutions resulting in a S357R substitution in the encoded polypeptide. A bacterium of the invention may thus express a polypeptide encoded by the thrA gene, wherein said polypeptide comprises a S357R substitution. According the certain embodiments, the bacterium comprises within the thrA gene one or more nucleotide substitutions resulting in a S359R substitution in the encoded polypeptide. A bacterium of the invention may thus express a polypeptide encoded by the thrA gene, wherein said polypeptide comprises a S359R substitution.

A bacterium of the invention may thus express an aspartate kinase I/homoserine dehydrogenase I (ThrA) having one or more amino acid substitutions selected from the group consisting of Y356C, S357R and S359R. More particularly, a bacterium of the invention may express a polypeptide having the amino acid sequence set forth in SEQ ID NO: 11 which comprises one or more amino acid substitutions selected from the group consisting of Y356C, S357R and S359R. According to certain embodiments, the bacterium expresses a polypeptide having the amino acid sequence set forth in SEQ ID NO: 11, wherein at position 356 tyrosine is replaced by cysteine. According to certain embodiments, the bacterium expresses a polypeptide having the amino acid sequence set forth in SEQ ID NO: 11, wherein at position 357 serine is replaced by arginine. According to certain embodiments, the bacterium expresses a polypeptide having the amino acid sequence set forth in SEQ ID NO: 11, wherein at position 359 serine is replaced by arginine.

According to certain embodiments, the bacterium expresses a polypeptide having an amino acid sequence set which has at least about 90%, at least about 93%, at least about 95%, at least about 96%, at least about 97%, at least about 98%, or at least about 99%, sequence identity to the amino acid sequence set forth in SEQ ID NO: 11 which comprises one or more amino acid substitutions selected from the group consisting of Y356C, S357R and S359R.

According to certain embodiments, the bacterium expresses a polypeptide having an amino acid sequence which has at least about 90%, at least about 93%, at least about 95%, at least about 96%, at least about 97%, at least about 98%, or at least about 99%, sequence identity to the amino acid sequence set forth in SEQ ID NO: 11, wherein at position 356 tyrosine is replaced by cysteine. According to particular embodiments, the bacterium expresses a polypeptide having an amino acid sequence which has at least about 95%, such as at least about 96%, at least about 97%, at least about 98%, or at least about 99%, sequence identity to the amino acid sequence set forth in SEQ ID NO: 11, wherein at position 356 tyrosine is replaced by cysteine.

According to certain embodiments, the bacterium expresses a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 11, wherein at position 357 serine is replaced by arginine. According to particular embodiments, the bacterium expresses a polypeptide having the amino acid sequence which has at least about 95%, such as at least about 96%, at least about 97%, at least about 98%, or at least about 99%, sequence identity to the amino acid sequence set forth in SEQ ID NO: 11, wherein at position 357 serine is replaced by arginine.

According to certain embodiments, the bacterium expresses a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 11, wherein at position 359 serine is replaced by arginine. According to particular embodiments, the bacterium expresses a polypeptide having the amino acid sequence which has at least about 95%, at least about 96%, at least about 97%, at least about 98%, or at least about 99%, sequence identity to the amino acid sequence set forth in SEQ ID NO: 11, wherein at position 359 serine is replaced by arginine.

According to certain embodiments, the bacterium expresses a polypeptide having an amino acid sequence set forth in SEQ ID NO: 11 which comprises one or more amino acid substitutions selected from the group consisting of Y356C, S357R and S359R, wherein 1 or more, such as about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, further amino acid residues are substituted, deleted, and/or inserted. The bacterium may express a polypeptide having an amino acid sequence set forth in SEQ ID NO: 11 which comprises one or more amino acid substitutions selected from the group consisting of Y356C, S357R and S359R, wherein about 1 to about 5, or about 1 to about 3, further amino acid residues are substituted, deleted, and/or inserted.

The ThrA polypeptide mutant(s) described above may be (over-)expressed by the bacterium by way of an exogenous nucleic acid molecule, such as an expression vector, which has been introduced into the bacterium. Therefore, according to certain embodiments, the bacterium of the invention comprises an exogenous nucleic acid molecule comprising a nucleotide sequence encoding a aspartate kinase I/homoserine dehydrogenase I (ThrA) polypeptide mutant as described above.

For example, a bacterium of the invention may comprise an exogenous nucleic acid molecule, such as an expression vector, comprising a nucleotide sequence encoding a polypeptide having the amino acid sequence set forth in SEQ ID NO: 11 which comprises an amino acid substitution at position Y356, S357 and/or S359. According to certain embodiments, a bacterium of the invention thus comprises an exogenous nucleic acid molecule comprising a nucleotide sequence encoding a polypeptide having the amino acid sequence set forth in SEQ ID NO: 11 which comprises an amino acid substitution at position Y356, S357 and/or S359, wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L; the substitution at position S357 is selected from the group consisting of S357R, S357V, S357P, S357G, S357L, S357Y, S357A, S357N, S357F, S357H, S357K, S357I and S357M; and the substitution at position S359 is selected from the group consisting of S359R, S359G, S359M, S359F, S359T, S359P, S359V, S359Q, S359A, S359C, S359K, S359E and S359L.

According to certain embodiments, a bacterium of the invention comprises an exogenous nucleic acid molecule comprising a nucleotide sequence encoding a polypeptide having an amino acid sequence which has at least about 90%, such at least about 93%, at least about 95%, at least about 96%, at least about 97%, at least about 98%, or at least about 99%, sequence identity to the amino acid sequence set forth in SEQ ID NO: 11 which comprises an amino acid substitution at position Y356, S357 and/or S359. According to certain embodiments, a bacterium of the invention comprises an exogenous nucleic acid molecule comprising a nucleotide sequence encoding a polypeptide having an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 11 which comprises an amino acid substitution at position Y356, S357 and/or S359, wherein the substitution at position Y356 is selected from the group consisting of Y356C, Y356I, Y356V, Y356S, Y356W, Y356Q, Y356G, Y356N, Y356D, Y356E, Y356F, Y356A, Y356I, Y356P, Y356H, Y356R and Y356L; the substitution at position S357 is selected from the group consisting of S357R, S357V, S357P, S357G, S357L, S357Y, S357A, S357N, S357F, S357H, S357K, S357I and S357M; and the substitution at position S359 is selected from the group consisting of S359R, S359G, S359M, S359F, S359T, S359P, S359V, S359Q, S359A, S359C, S359K, S359E and S359L.

According to certain embodiments, a bacterium of the invention comprises an exogenous nucleic acid molecule comprising a nucleotide sequence encoding a polypeptide having an amino acid sequence which has at least about 93%, at least about 95%, at least about 96%, at least about 97%, at least about 98%, or at least about 99%, sequence identity to the amino acid sequence set forth in SEQ ID NO: 11 which comprises an amino acid substitution at position Y356, S357 and/or S359. According to certain embodiments, a bacterium of the invention comprises an exogenous nucleic acid molecule comprising a nucleotide sequence encoding a polypeptide having an amino acid sequence which has at least about 93%, at least about 95%, at least about 96%, at least about 97%, at least about 98%, or at least about 99%, sequence identity to the amino acid sequence set forth in SEQ ID NO: 11 which comprises an amino acid substitution at position Y356, S357 and/or S359, wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L; the substitution at position S357 is selected from the group consisting of S357R, S357V, S357P, S357G, S357L, S357Y, S357A, S357N, S357F, S357H, S357K, S357I and S357M; and the substitution at position S359 is selected from the group consisting of S359R, S359G, S359M, S359F, S359T, S359P, S359V, S359Q, S359A, S359C, S359K, S359E and S359L.

According to certain embodiments, a bacterium of the invention comprises an exogenous nucleic acid molecule comprising a nucleotide sequence encoding a polypeptide having an amino acid sequence which has at least about 95%, at least about 96%, at least about 97%, at least about 98%, or at least about 99%, sequence identity to the amino acid sequence set forth in SEQ ID NO: 11 which comprises an amino acid substitution at position Y356, S357 and/or S359. According to certain embodiments, a bacterium of the invention comprises an exogenous nucleic acid molecule comprising a nucleotide sequence encoding a polypeptide having an amino acid sequence which has at least about 95%, at least about 96%, at least about 97%, at least about 98%, or at least about 99%, sequence identity to the amino acid sequence set forth in SEQ ID NO: 11 which comprises an amino acid substitution at position Y356, S357 and/or S359, wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L; the substitution at position S357 is selected from the group consisting of S357R, S357V, S357P, S357G, S357L, S357Y, S357A, S357N, S357F, S357H, S357K, S357I and S357M; and the substitution at position S359 is selected from the group consisting of S359R, S359G, S359M, S359F, S359T, S359P, S359V, S359Q, S359A, S359C, S359K, S359E and S359L.

In this connection, the present invention further provides a (isolated) nucleic acid molecule, such an expression vector, comprising a nucleotide sequence encoding a ThrA mutant as described above. Such nucleic acid may be introduced into the bacterium of the invention. According to certain embodiments, the nucleic acid molecule comprises a nucleotide sequence encoding a polypeptide having an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 11 which comprises an amino acid substitution at position Y356, S357 and/or S359. According to certain embodiments, the nucleic acid molecule comprises a nucleotide sequence encoding a polypeptide having an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 11 which comprises an amino acid substitution at position Y356, S357 and/or S359; wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L; the substitution at position S357 is selected from the group consisting of S357R, S357V, S357P, S357G, S357L, S357Y, S357A, S357N, S357F, S357H, S357K, S357I and S357M; and the substitution at position S359 is selected from the group consisting of S359R, S359G, S359M, S359F, S359T, S359P, S359V, S359Q, S359A, S359C, S359K, S359E and S359L.

According to certain embodiments, the nucleic acid molecule comprising a nucleotide sequence encoding a polypeptide having the amino acid sequence set forth in SEQ ID NO: 11 which comprises an amino acid substitution at position Y356, S357 and/or S359. According to certain embodiments, the nucleic acid molecule comprising a nucleotide sequence encoding a polypeptide having the amino acid sequence set forth in SEQ ID NO: 11 which comprises an amino acid substitution at position Y356, S357 and/or S359, wherein the substitution at position Y356 is selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L; the substitution at position S357 is selected from the group consisting of S357R, S357V, S357P, S357G, S357L, S357Y, S357A, S357N, S357F, S357H, S357K, S357I and S357M; and the substitution at position S359 is selected from the group consisting of S359R, S359G, S359M, S359F, S359T, S359P, S359V, S359Q, S359A, S359C, S359K, S359E and S359L.

The (isolated) nucleic acid molecule may be the exogenous nucleic acid as detailed above. The (isolated) nucleic acid molecule may comprise suitable regulatory elements such as a promoter that is functional in the bacterial cell to cause the production of an mRNA molecule and that is operably linked to the nucleotide sequence encoding said polypeptide. Further details on suitable regulatory elements are provided below with respect to an "exogenous" nucleic acid molecule, and apply mutatis mutandis.

The present invention also provides a bacterium which comprises within the lrp gene one or more nucleotide substitutions resulting in the amino acid substitution D143G in the encoded polypeptide. Further information regarding lrp of, e.g., *Escherichia coli* is available at EcoCyc (www.biocyc.org) under Accession number EG10547. According to certain embodiments, a bacterium of the invention expresses a polypeptide encoded by the lrp gene, wherein in said polypeptide at position 143 D is replaced by G. A representative amino acid sequence of a polypeptide encoded by the lrp gene is set forth in SEQ ID NO: 12. According to particular embodiments, a bacterium of the invention expresses a polypeptide having the amino acid sequence set forth in SEQ ID NO: 12 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 12, wherein in said amino acid sequence at position 143 D is replaced by G.

According to certain embodiments, the present invention provides a bacterium which comprises within the lrp gene one or more nucleotide substitutions resulting in one or more amino acid substitutions which increase tolerance towards L-serine. More particularly, a bacterium is provided which comprises within the lrp gene one or more nucleotide substitutions resulting in an amino acid substitution in the encoded polypeptide at position D143. According to particular embodiments, a bacterium of the invention expresses a polypeptide having the amino acid sequence set forth in SEQ ID NO: 12 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 12, wherein in said amino acid sequence at position 143 D is replaced by another amino acid. Preferably, the one or more amino acid substitutions are non-conservative substitutions.

The present invention also provides a bacterium which comprises within the rho gene one or more nucleotide substitutions resulting in the amino acid substitution R87L in the encoded polypeptide. Further information regarding rho of, e.g., *Escherichia coli* such as nucleotide sequence of the gene or amino acid sequence of the encoded polypeptide is available at EcoCyc (www.biocyc.org) under Accession number EG10845. According to certain embodiments, a bacterium of the invention expresses a polypeptide encoded by the rho gene, wherein in said polypeptide at position 87 R is replaced by L. A representative amino acid sequence of a polypeptide encoded by the rho gene is set forth in SEQ ID NO: 13. According to particular embodiments, a bacterium of the invention expresses a polypeptide having the amino acid sequence set forth in SEQ ID NO: 13 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 13, wherein in said amino acid sequence at position 87 R is replaced by L.

According to certain embodiments, the present invention provides a bacterium which comprises within the rho gene one or more nucleotide substitutions resulting in one or more amino acid substitutions which increase tolerance towards L-serine. More particularly, a bacterium is provided which comprises within the rho gene one or more nucleotide substitutions resulting in an amino acid substitution in the encoded polypeptide at position R87. According to particular embodiments, a bacterium of the invention expresses a polypeptide having the amino acid sequence set forth in SEQ ID NO: 13 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 13, wherein in said amino acid sequence at position 87 R is replaced by another amino acid. Preferably, the one or more amino acid substitutions are non-conservative substitutions.

The present invention also provides a bacterium which comprises within the eno gene one or more nucleotide substitutions resulting in the amino acid substitution V164L in the encoded polypeptide. Further information regarding eno of, e.g., *Escherichia coli* is available at EcoCyc (www.biocyc.org) under Accession number EG10258. According to certain embodiments, a bacterium of the invention expresses a polypeptide encoded by the eno gene, wherein in said polypeptide at position 164 V is replaced by L. A representative amino acid sequence of a polypeptide encoded by the eno gene is set forth in SEQ ID NO: 14. According to particular embodiments, a bacterium of the invention may thus express a polypeptide having the amino acid sequence set forth in SEQ ID NO: 14 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 14, wherein in said amino acid sequence at position at position 164 V is replaced by L.

According to certain embodiments, the present invention provides a bacterium which comprises within the eno gene one or more nucleotide substitutions resulting in one or more amino acid substitutions which increase tolerance towards L-serine. More particularly, a bacterium is provided which comprises within the eno gene one or more nucleotide substitutions resulting in an amino acid substitution in the encoded polypeptide at position V164. According to particular embodiments, a bacterium of the invention expresses a polypeptide having the amino acid sequence set forth in SEQ ID NO: 14 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 14, wherein in said amino acid sequence at position 164 V is replaced by another amino acid. Preferably, the one or more amino acid substitutions are non-conservative substitutions.

The present invention also provides a bacterium which comprises within the argP gene one or more nucleotide substitutions resulting in the amino acid substitution V164L in the encoded polypeptide. Further information regarding argP of, e.g., *Escherichia coli* is available at EcoCyc (www.biocyc.org) under Accession number EG10490. According to certain embodiments, a bacterium of the invention expresses a polypeptide encoded by the argP gene, wherein in said polypeptide at position 132 Q is replaced by K. A representative amino acid sequence of a polypeptide encoded by the argP gene is set forth in SEQ ID NO: 15. According to particular embodiments, a bacterium of the invention expresses a polypeptide having the amino acid sequence set forth in SEQ ID NO: 15 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 15, wherein in said amino acid sequence at position at position 132 Q is replaced by K.

According to certain embodiments, the present invention provides a bacterium which comprises within the argP gene one or more nucleotide substitutions resulting in one or more amino acid substitutions which increase tolerance towards L-serine. More particularly, a bacterium is provided which comprises within the argP gene one or more nucleotide substitutions resulting in an amino acid substitution in the encoded polypeptide at position Q132. According to particular embodiments, a bacterium of the invention expresses a polypeptide having the amino acid sequence set forth in SEQ ID NO: 15 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 15, wherein in said amino acid sequence at position 132 Q is replaced by another amino acid. Preferably, the one or more amino acid substitutions are non-conservative substitutions.

The present invention also provides a bacterium which comprises within the tufA gene one or more nucleotide substitutions resulting in the amino acid substitution G19V in the encoded polypeptide. Further information regarding tufA of, e.g., *Escherichia coli* is available at EcoCyc (www.biocyc.org) under Accession number EG11036. According to certain embodiments, a bacterium of the invention expresses a polypeptide encoded by the tufA gene, wherein in said polypeptide at position 19 G is replaced by V. A representative amino acid sequence of a polypeptide encoded by the tufA gene is set forth in SEQ ID NO: 16. According to particular embodiments, a bacterium of the invention expresses a polypeptide having the amino acid sequence set forth in SEQ ID NO: 16 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 16, wherein in said amino acid sequence at position at position 19 G is replaced by V.

According to certain embodiments, the present invention provides a bacterium which comprises within the tufA gene one or more nucleotide substitutions resulting in one or more amino acid substitutions which increase tolerance towards L-serine. More particularly, a bacterium is provided which comprises within the tufA gene one or more nucleotide substitutions resulting in an amino acid substitution in the encoded polypeptide at position G19. According to particular embodiments, a bacterium of the invention expresses a polypeptide having the amino acid sequence set forth in SEQ ID NO: 16 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 16, wherein in said amino acid sequence at position 19 G is replaced by another amino acid. Preferably, the one or more amino acid substitutions are non-conservative substitutions.

The present invention also provides a bacterium which comprises within the cycA gene one or more nucleotide substitutions resulting in the amino acid substitution I220V in the encoded polypeptide. Further information regarding cycA of, e.g., *Escherichia coli* is available at EcoCyc (www.biocyc.org) under Accession numbers EG12504. According to certain embodiments, a bacterium of the invention expresses a polypeptide encoded by the cycA gene, wherein in said polypeptide at position 220 I is replaced by V. A representative amino acid sequence of a polypeptide encoded by the cycA gene is set forth in SEQ ID NO: 17. According to particular embodiments, a bacterium of the invention expresses a polypeptide having the amino acid sequence set forth in SEQ ID NO: 17 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 17, wherein in said amino acid sequence at position at position 220 I is replaced by V.

According to certain embodiments, the present invention provides a bacterium which comprises within the cycA gene one or more nucleotide substitutions resulting in one or more amino acid substitutions which increase tolerance towards L-serine. More particularly, a bacterium is provided which comprises within the cycA gene one or more nucleotide substitutions resulting in an amino acid substitution in the encoded polypeptide at position I220. According to particular embodiments, a bacterium of the invention expresses a polypeptide having the amino acid sequence set forth in SEQ ID NO: 17 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 17, wherein in said amino acid sequence at position 220 I is replaced by another amino acid. Preferably, the one or more amino acid substitutions are non-conservative substitutions.

The present invention also provides a bacterium which comprises within the rpe gene one or more nucleotide substitutions resulting in the amino acid substitution I202T in the encoded polypeptide. Further information regarding rpe of, e.g., *Escherichia coli* is available at EcoCyc (www.biocyc.org) under Accession numbers M004. According to certain embodiments, a bacterium of the invention expresses a polypeptide encoded by the rpe gene, wherein in said polypeptide at position 202 I is replaced by T. A representative amino acid sequence of a polypeptide encoded by the rpe gene is set forth in SEQ ID NO: 18. According to particular embodiments, a bacterium of the invention expresses a polypeptide having the amino acid sequence set forth in SEQ ID NO: 18 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 18, wherein in said amino acid sequence at position at position 202 I is replaced by T.

According to certain embodiments, the present invention provides a bacterium which comprises within the rpe gene one or more nucleotide substitutions resulting in one or more amino acid substitutions which increase tolerance towards L-serine. More particularly, a bacterium is provided which comprises within the rpe gene one or more nucleotide substitutions resulting in an amino acid substitution in the encoded polypeptide at position 202I. According to particular embodiments, a bacterium of the invention expresses a polypeptide having the amino acid sequence set forth in SEQ ID NO: 18 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 18, wherein in said amino acid sequence at position 202 I is replaced by another amino acid. Preferably, the one or more amino acid substitutions are non-conservative substitutions.

The present invention also provides a bacterium which comprises within the yojl gene one or more nucleotide substitutions resulting in the amino acid substitution D334H in the encoded polypeptide. Further information regarding yojl of, e.g., *Escherichia coli* is available at EcoCyc (www.biocyc.org) under Accession numbers EG12070. According to certain embodiments, a bacterium of the invention expresses a polypeptide encoded by the yojl gene, wherein in said polypeptide at position 334 D is replaced by H. A representative amino acid sequence of a polypeptide encoded by the yojl gene is set forth in SEQ ID NO: 19. According to particular embodiments, a bacterium of the invention expresses a polypeptide having the amino acid sequence set forth in SEQ ID NO: 19 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 19, wherein in said amino acid sequence at position at position 334 D is replaced by H.

According to certain embodiments, the present invention provides a bacterium which comprises within the yojl gene one or more nucleotide substitutions resulting in one or more amino acid substitutions which increase tolerance towards L-serine. More particularly, a bacterium is provided which comprises within the yojl gene one or more nucleotide substitutions resulting in an amino acid substitution in the encoded polypeptide at position D334. According to particular embodiments, a bacterium of the invention expresses a polypeptide having the amino acid sequence set forth in SEQ ID NO: 19 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 19, wherein in said amino acid sequence at position 334 D is replaced by another amino acid. Preferably, the one or more amino acid substitutions are non-conservative substitutions.

The present invention also provides a bacterium which comprises within the hyaF gene one or more nucleotide substitutions resulting in the amino acid substitution V120G in the encoded polypeptide. Further information regarding hyaF of, e.g., *Escherichia coli* is available at EcoCyc (www.biocyc.org) under Accession numbers EG10473. According to certain embodiments, a bacterium of the invention expresses a polypeptide encoded by the hyaF gene, wherein in said polypeptide at position 120 V is replaced by G. A representative amino acid sequence of a polypeptide encoded by the hyaF gene is set forth in SEQ ID NO: 20. According to particular embodiments, a bacterium of the invention expresses a polypeptide having the amino acid sequence set forth in SEQ ID NO: 20 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 20, wherein in said amino acid sequence at position at position 120 V is replaced by G.

According to certain embodiments, the present invention provides a bacterium which comprises within the hyaF gene one or more nucleotide substitutions resulting in one or more amino acid substitutions which increase tolerance towards L-serine. More particularly, a bacterium is provided which comprises within the hyaF gene one or more nucleotide substitutions resulting in an amino acid substitution in the encoded polypeptide at position V120. According to particular embodiments, a bacterium of the invention expresses a polypeptide having the amino acid sequence set forth in SEQ ID NO: 20 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 20, wherein in said amino acid sequence at position 120 V is replaced by another amino acid. Preferably, the one or more amino acid substitutions are non-conservative substitutions.

The present invention also provides a bacterium which comprises within the pykF gene one or more nucleotide substitutions resulting in the amino acid substitution E250* in the encoded polypeptide, where * designates a stop codon. Alternatively, the pykF gene may comprise one or more nucleotide substitutions resulting in the termination of the encoded polypeptide at a position upstream of position 250. Further information regarding pykF of, e.g., *Escherichia coli* is available at EcoCyc (www.biocyc.org) under Accession numbers EG10804. According to certain embodiments, a bacterium of the invention expresses a polypeptide encoded by the pykF gene, wherein said polypeptide terminates after position 249 or any position upstream thereof. A representative amino acid sequence of a polypeptide encoded by the pykF gene is set forth in SEQ ID NO: 21. According to particular embodiments, a bacterium of the invention expresses a polypeptide having the amino acid sequence set forth in SEQ ID NO: 22 or a polypeptide having the amino acid sequence which has at least about 90%, at least about 93%, at least, about 95%, at least about 96%, at least about 97%, at least about 98%, or at least about 99%, sequence identity to the amino acid sequence set forth in SEQ ID NO: 22.

According to other certain embodiments, a bacterium of the invention has been further modified to attenuate the expression of the pykF gene (e.g., by inactivation of the gene). Attenuation, and more particularly inactivation, of the gene expression can be achieved as described herein above. For example, lambda red mediated gene replacement may be used for inactivating gene expression.

The present invention also provides a bacterium which comprises within the malT gene one or more nucleotide substitutions resulting in the amino acid substitution Q420* in the encoded polypeptide, where * designates a stop codon. Alternatively, the malT gene may comprise one or more nucleotide substitutions resulting in the termination of the encoded polypeptide at a position upstream of position 420. Further information regarding malT of, e.g., *Escherichia coli* is available at EcoCyc (www.biocyc.org) under Accession numbers EG10562. According to certain embodiments, a bacterium of the invention expresses a polypeptide encoded by the malT gene, wherein said polypeptide terminates after position 419 or any position upstream thereof. A representative amino acid sequence of a polypeptide encoded by the malT gene is set forth in SEQ ID NO: 23. According to particular embodiments, a bacterium of the invention expresses a polypeptide having the amino acid sequence set forth in SEQ ID NO: 24 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 24.

According to other certain embodiments, a bacterium of the invention has been further modified to attenuate the expression of the malT gene (e.g., by inactivation of the gene). Attenuation, and more particularly inactivation, of the gene expression can be achieved as described herein above. For example, lambda red mediated gene replacement may be used for inactivating gene expression.

The present invention also provides a bacterium which comprises within the rpoB gene one or more nucleotide substitutions resulting in the amino acid substitution P520L in the encoded polypeptide. Further information regarding rpoB of, e.g., *Escherichia coli* is available at EcoCyc (www.biocyc.org) under Accession numbers EG10894. According to certain embodiments, a bacterium of the invention expresses a polypeptide encoded by the rpoB gene, wherein in said polypeptide at position 520 P is replaced by L. A representative amino acid sequence of a polypeptide encoded by the rpoB gene is set forth in SEQ ID NO: 25. According to particular embodiments, a bacterium of the invention expresses a polypeptide having the amino acid sequence set forth in SEQ ID NO: 25 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 25, wherein in said amino acid sequence at position at position 520 P is replaced by L.

According to certain embodiments, the present invention provides a bacterium which comprises within the rpoB gene one or more nucleotide substitutions resulting in one or more amino acid substitutions which increase tolerance towards L-serine. More particularly, a bacterium is provided which comprises within the rpoB gene one or more nucleotide substitutions resulting in an amino acid substitution in the encoded polypeptide at position P520. According to particular embodiments, a bacterium of the invention expresses a polypeptide having the amino acid sequence set forth in SEQ ID NO: 25 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 25, wherein in said amino acid sequence at position 520 P is replaced by another amino acid. Preferably, the one or more amino acid substitutions are non-conservative substitutions.

The present invention also provides a bacterium which comprises within the fumB gene one or more nucleotide substitutions resulting in the amino acid substitution T218P in the encoded polypeptide. Further information regarding fumB of, e.g., *Escherichia coli* is available at EcoCyc (www.biocyc.org) under Accession numbers EG10357. According to certain embodiments, a bacterium of the invention expresses a polypeptide encoded by the fumB gene, wherein in said polypeptide at position 218 T is replaced by P. A representative amino acid sequence of a polypeptide encoded by the fumB gene is set forth in SEQ ID NO: 26. According to particular embodiments, a bacterium of the invention expresses a polypeptide having the amino acid sequence set forth in SEQ ID NO: 26 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 26, wherein in said amino acid sequence at position at position 218 T is replaced by P.

According to certain embodiments, the present invention provides a bacterium which comprises within the fumB gene one or more nucleotide substitutions resulting in one or more amino acid substitutions which increase tolerance towards L-serine. More particularly, a bacterium is provided which comprises within the fumB gene one or more nucleotide substitutions resulting in an amino acid substitution in the encoded polypeptide at position T218. According to particular embodiments, a bacterium of the invention expresses a polypeptide having the amino acid sequence set forth in SEQ ID NO: 26 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 26, wherein in said amino acid sequence at position 218 T is replaced by another amino acid. Preferably, the one or more amino acid substitutions are non-conservative substitutions.

The present invention also provides a bacterium which comprises within the gshA gene one or more nucleotide substitutions resulting in the amino acid substitution A178V in the encoded polypeptide. Further information regarding gshA of, e.g., Escherichia coli is available at EcoCyc (www.biocyc.org) under Accession numbers EG10418. According to certain embodiments, a bacterium of the invention expresses a polypeptide encoded by the gshA gene, wherein in said polypeptide at position 178 A is replaced by V. A representative amino acid sequence of a polypeptide encoded by the gshA gene is set forth in SEQ ID NO: 27. According to particular embodiments, a bacterium of the invention expresses a polypeptide having the amino acid sequence set forth in SEQ ID NO: 27 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 27, wherein in said amino acid sequence at position at position 178 A is replaced by V.

According to certain embodiments, the present invention provides a bacterium which comprises within the gshA gene one or more nucleotide substitutions resulting in one or more amino acid substitutions which increase tolerance towards L-serine. More particularly, a bacterium is provided which comprises within the gshA gene one or more nucleotide substitutions resulting in an amino acid substitution in the encoded polypeptide at position A178. According to particular embodiments, a bacterium of the invention expresses a polypeptide having the amino acid sequence set forth in SEQ ID NO: 27 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 27, wherein in said amino acid sequence at position 178 A is replaced by another amino acid. Preferably, the one or more amino acid substitutions are non-conservative substitutions.

The present invention also provides a bacterium which comprises within the lamB gene one or more nucleotide substitutions resulting in the amino acid substitution Q112* in the encoded polypeptide, where * designates a stop codon. Alternatively, the lamB gene may comprise one or more nucleotide substitutions resulting in the termination of the encoded polypeptide at a position upstream of position 112. Further information regarding lamB of, e.g., Escherichia coli such as nucleotide sequence of the gene or amino acid sequence of the encoded polypeptide is available at EcoCyc (www.biocyc.org) under Accession numbers EG10528. According to certain embodiments, a bacterium of the invention expresses a polypeptide encoded by the lamB gene, wherein said polypeptide terminates after position 111 or any position upstream thereof. A representative amino acid sequence of a polypeptide encoded by the lamB gene is set forth in SEQ ID NO: 28. According to particular embodiments, a bacterium of the invention expresses a polypeptide having the amino acid sequence set forth in SEQ ID NO: 29 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 29.

According to other certain embodiments, a bacterium of the invention has been further modified to attenuate the expression of the lamB gene (e.g., by inactivation of the gene). Attenuation, and more particularly inactivation, of the gene expression can be achieved as described herein above. For example, lambda red mediated gene replacement may be used for inactivating gene expression.

A bacterium of the present invention may comprise one or more, such as two or more, three or more, four or more, or five or more, gene mutations as mentioned.

For example, the bacterium may comprise one or more (such as two or more) gene mutations selected from the group consisting of: one or more nucleotide substitutions within the lrp gene resulting in an amino acid substitution at position D143 in the encoded polypeptide, one or more nucleotide substitutions within the rho gene resulting in an amino acid substitution at position R87 in the encoded polypeptide, one or more nucleotide substitutions within the eno gene resulting in an amino acid substitution at position V164 in the encoded polypeptide, and one or more nucleotide substitutions within the argP gene resulting in an amino acid substitution at position V164 in the encoded polypeptide.

For example, the bacterium may comprise one or more (such as two or more) gene mutations selected from the group consisting of: one or more nucleotide substitutions within the lrp gene resulting in the amino acid substitution D143G in the encoded polypeptide, one or more nucleotide substitutions within the rho gene resulting in the amino acid substitution R87L in the encoded polypeptide, one or more nucleotide substitutions within the eno gene resulting in the amino acid substitution V164L in the encoded polypeptide, and one or more nucleotide substitutions within the argP gene resulting in the amino acid substitution V164L in the encoded polypeptide.

According to certain embodiments, a bacterium of the invention comprises within the thrA gene one or more nucleotide substitutions resulting in an amino acid substitution in the encoded polypeptide at position Y356, said substitution being selected from the group consisting of Y356C, Y356T, Y356V, Y356S, Y356W, Y356Q, Y356G, Y356N, Y356D, Y356E, Y356F, Y356A, Y356I, Y356P, Y356H, Y356R and Y356L; one or more nucleotide substitutions resulting in an amino acid substitution in the encoded polypeptide at position S357, said substitution being selected from the group consisting of S357R, S357V, S357P, S357G, S357L, S357Y, S357A, S357N, S357F, S357H, S357K, S357I and S357M; and/or one or more nucleotide substitutions resulting in an amino acid substitution in the encoded polypeptide at position S359, said substitution being selected from the group consisting of S359R, S359G, S359M, S359F, S359T, S359P, S359V, S359Q, S359A, S359C, S359K, S359E and S359L; and one or more (such as two or more) gene mutations selected from the group consisting of: one or more nucleotide substitutions within the lrp gene resulting in an amino acid substitution at position D143 (such as D143G) in the encoded polypeptide, one or more nucleotide substitutions within the rho gene resulting in the amino acid substitution at position R87 (such as R87L) in the encoded polypeptide, one or more nucleotide substitutions within the eno gene resulting in the amino acid substitution at position V164 (such as V164L) in the encoded polypeptide, and one or more nucleotide substitutions within the argP gene resulting in an amino acid substitution at position V164 (such as V164L) in the encoded polypeptide.

According to certain embodiments, a bacterium of the present invention comprises one or more nucleotide substitutions within the thrA gene resulting in one or more amino acid substitution in the encoded polypeptide selected from the group consisting of Y356C, S357R and S359R; and one or more (such as two or more) gene mutations selected from the group consisting of: one or more nucleotide substitutions within the lrp gene resulting in the amino acid substitution D143G in the encoded polypeptide, one or more nucleotide substitutions within the rho gene resulting in the amino acid substitution R87L in the encoded polypeptide, one or more nucleotide substitutions within the eno gene resulting in the amino acid substitution V164L in the encoded polypeptide, and one or more nucleotide substitutions within the argP gene resulting in the amino acid substitution V164L in the encoded polypeptide.

According to certain embodiments, a bacterium of the present invention comprises one or more nucleotide substitutions within the thrA gene resulting in the amino acid substitution Y356C in the encoded polypeptide; and one or more (such as two or more) gene mutations selected from the group consisting of: one or more nucleotide substitutions within the lrp gene resulting in the amino acid substitution D143G in the encoded polypeptide, one or more nucleotide substitutions within the rho gene resulting in the amino acid substitution R87L in the encoded polypeptide, one or more nucleotide substitutions within the eno gene resulting in the amino acid substitution V164L in the encoded polypeptide, and one or more nucleotide substitutions within the argP gene resulting in the amino acid substitution V164L in the encoded polypeptide.

According to certain embodiments, a bacterium of the present invention comprises one or more nucleotide substitutions within the thrA gene resulting in the amino acid substitution S357R in the encoded polypeptide; and one or more (such as two or more) gene mutations selected from the group consisting of: one or more nucleotide substitutions within the lrp gene resulting in the amino acid substitution D143G in the encoded polypeptide, one or more nucleotide substitutions within the rho gene resulting in the amino acid substitution R87L in the encoded polypeptide, one or more nucleotide substitutions within the eno gene resulting in the amino acid substitution V164L in the encoded polypeptide, and one or more nucleotide substitutions within the argP gene resulting in the amino acid substitution V164L in the encoded polypeptide.

According to certain embodiments, a bacterium of the present invention comprises one or more nucleotide substitutions within the thrA gene resulting in the substitution S359R in the encoded polypeptide; and one or more (such as two or more) gene mutations selected from the group consisting of: one or more nucleotide substitutions within the lrp gene resulting in the amino acid substitution D143G in the encoded polypeptide, one or more nucleotide substitutions within the rho gene resulting in the amino acid substitution R87L in the encoded polypeptide, one or more nucleotide substitutions within the eno gene resulting in the amino acid substitution V164L in the encoded polypeptide, and one or more nucleotide substitutions within the argP gene resulting in the amino acid substitution V164L in the encoded polypeptide.

According to certain embodiments, a bacterium of the invention comprises within its genome a deletion of the first 5 bp of gene rhtA gene, a complete deletion of genes ompX and ybiP, a deletion of 239 bp of sRNA rybA and a deletion of 77 bp of gene mntS. According to certain embodiments, the bacterium comprises within its genome a deletion of about 2854 bp from a location which corresponds to location 850092 in the genome sequence NC_000913. This deletion results in a deletion of the first 5 bp of gene rhtA gene, a complete deletion of genes ompX and ybiP, a deletion of 239 bp of sRNA rybA and a 77 bp deletion of gene mntS. Such deletion can be achieved by using the lambda-red or cam-sacB-system.

According to certain embodiments, a bacterium of the invention comprises within its genome an insertion of an insertion sequence element 151 (e.g., having a length of about 768 bp) in the intergenic region between genes trxA and rho. According to certain embodiments, the bacterium comprises within its genome an insertion of an insertion sequence element 151 (e.g., having a length of about 768 bp) in the lagging strand at a location which corresponds to location 3966174 in the genome sequence NC_000913. According to particular embodiments, the bacterium further comprises a duplication of around 9 bp upstream and downstream of insertion sequence.

According to certain embodiments, a bacterium of the invention comprises within its genome an insertion of 1 bp in the intergenic region between genes gcvA and ygdl. According to certain embodiments, the bacterium comprises within its genome an insertion of 1 bp at a location which corresponds to location 2942629 in the genome sequence NC_000913.

According to certain embodiments, a bacterium of the invention comprises within its genome an insertion of an insertion sequence element IS4 (e.g., having a length of about 1342 bp) in the intergenic region between genes gcvA and ygdl. According to certain embodiments, the bacterium comprises within its genome an insertion of an insertion sequence element IS4 (e.g., having a length of about 1342 bp) at a location which corresponds to location 2942878 in the genome sequence NC_000913. According to particular embodiments, the bacterium further comprises a duplication of about 13 bp upstream and downstream of insertion sequence.

According to certain embodiments, a bacterium of the invention comprises within its genome an insertion of 1 bp in the intergenic region between genes dapA and gcvR. According to certain embodiments, the bacterium comprises within its genome an insertion of 1 bp at a location which corresponds to location 2599854 in the genome sequence NC_000913.

According to certain embodiments, a bacterium of the invention comprises within its genome an insertion of an insertion sequence element IS1 (e.g., having a length of about 768 bp) which lead to a truncation of gene frc. According to certain embodiments, the bacterium comprises within its genome an insertion sequence element IS1 (e.g., having a length of about 768 bp) in the lagging strand at a location which corresponds to location 2492323 in the genome sequence NC_000913. According to particular embodiments, the bacterium further comprises a duplication of 9 bp upstream and downstream of insertion sequence.

According to other certain embodiments, a bacterium of the invention has been further modified to attenuate the expression of the frc gene (e.g., by inactivation of the gene). Attenuation, and more particularly inactivation, of the gene expression can be achieved as described herein above. For example, lambda red mediated gene replacement may be used for inactivating gene expression.

According to certain embodiments, a bacterium of the invention comprises within its genome an insertion of an insertion sequence element IS5 (e.g., having a length of about 1195 bp) which leads to deletion of the majority of gene aroP. According to certain embodiments, the bacterium comprises within its genome an insertion sequence element IS5 (e.g., having a length of about 1195 bp) at a location which corresponds to location 121518 in the genome sequence NC_000913. According to particular embodiments, the bacterium further comprises a duplication of 4 bp upstream and downstream of insertion sequence.

According to other certain embodiments, a bacterium of the invention has been further modified to attenuate the expression of the aroP gene (e.g., by inactivation of the gene). Attenuation, and more particularly inactivation, of the gene expression can be achieved as described herein above. For example, lambda red mediated gene replacement may be used for inactivating gene expression.

According to certain embodiments, a bacterium of the invention comprises within its genome an insertion of an insertion sequence element 151 (e.g., having a length of about 768 bp) in the intergenic region between genes mdtJ and tqsA. According to certain embodiments, the bacterium comprises within its genome an insertion sequence element 151 (e.g., having a length of about 768 bp) in the lagging strand at a location which corresponds to location 1673670 in the genome sequence NC_000913. According to particular embodiments, the bacterium further comprises a duplication of around 9 bp upstream and downstream of insertion sequence.

According to certain embodiments, a bacterium of the invention comprises within its genome a nucleotide substitution, such as a C→T substitution, within the intergenic region between genes trxB and lrp. According to certain embodiments, the bacterium comprises within its genome a nucleotide substitution, such as a C→T substitution, at a location which corresponds to location 923321 in the genome sequence NC_000913. Such mutation is 271 bp upstream of trx8 and 274 bp upstream of lrp.

According to certain embodiments, a bacterium of the invention comprises within its genome a nucleotide substitution, such as a T→C substitution, within the intergenic region between genes yftB and fklB. According to certain embodiments, the bacterium comprises within its genome a nucleotide substitution, such as a T→C substitution, at a location which corresponds to location 4428871 in the genome sequence NC_000913. Such mutation is 154 bp upstream of of yftB and 64 bp upstream of fklB.

As further demonstrate herein, attenuating (e.g., by inactivating of the gene) the expression of a gene coding for a polypeptide having Glucose 6-phosphate-1-dehydrogenase (G6PDH) activity in a reversed engineered strain resulted in a significantly increased production and yield of L-serine from glucose as shown in Table S9 (Example 8).

Therefore, according to certain embodiments, a bacterium of the invention has been modified to attenuate expression of a gene coding for a polypeptide having glucose 6-phosphate-1-dehydrogenase (G6PDH) activity. More particularly, the present invention provides a bacterium which has been modified to attenuate the expression of the gene zwf. Further information regarding zwf of, e.g., *Escherichia coli* is available at EcoCyc (www.biocyc.org) under Accession numbers EG11221. A representative nucleotide sequence of zwf is set forth in SEQ ID NO: 30.

The gene expression may be attenuated by inactivation of the gene. Thus, a bacterium according to the invention can be one which has been modified to inactivate the gene coding for a polypeptide having Glucose 6-phosphate-1-dehydrogenase (G6PDH) activity (e.g, by inactivation of the gene).

Attenuation, and more particularly inactivation, of the gene expression can be achieved as described herein above. For example, lambda red mediated gene replacement may be used for inactivating gene expression.

According to certain embodiments, a bacterium of the invention expresses a polypeptide encoded by the brnQ gene, wherein said polypeptide terminates after position 308 or any position upstream thereof. According to other certain embodiments, a bacterium of the invention has been further modified to attenuate the expression of the brnQ gene (e.g., by inactivation of the gene). Attenuation, and more particularly inactivation, of the gene expression can be achieved as described herein above. For example, lambda red mediated gene replacement may be used for inactivating gene expression.

According to certain embodiments, a bacterium of the invention has been further modified to attenuate expression of a gene coding for a polypeptide having glucose 6-phosphate-1-dehydrogenase (G6PDH) activity; express a polypeptide encoded by the thrA gene, wherein in said polypeptide at position 357 serine is replaced by arginine; expresses a polypeptide encoded by the rho gene, wherein in said polypeptide at position 87 R is replaced by L; and expresses a polypeptide encoded by the brnQ gene, wherein said polypeptide terminates after position 308 or any position upstream thereof. Alternatively, the bacterium may be modified to attenuate the expression of the brnQ gene (e.g., by inactivation of the gene). Suitable methods for attenuation of gene expression are described above.

Further information regarding brnQ of, e.g., *Escherichia coli* is available at EcoCyc (www.biocyc.org) under Accession numbers EG12168. A representative amino acid sequence of brnQ is set forth in SEQ ID NO: 31.

According to particular embodiments, the bacterium has been further modified to attenuate expression of the gene zwf (e.g, by inactivation of the gene); expresses a polypeptide having the amino acid sequence set forth in SEQ ID NO: 11 or a polypeptide having at least about 90%, at least about 93%, at least about 95%, at least about 96%, at least about 97%, at least about 98%, or at least about 99%, sequence identity to the amino acid sequence set forth in SEQ ID NO: 11, wherein in said amino acid sequence at position 357 serine is replaced by arginine; express a polypeptide having the amino acid sequence set forth in SEQ ID NO: 13 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 13, wherein in said amino acid sequence at position 87 R is replaced by L; and expresses a polypeptide having the amino acid sequence set forth in SEQ ID NO: 32 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 32.

According to particular embodiments, the bacterium has been further modified to attenuate expression of the gene zwf and brnQ (e.g, by inactivation of the genes); and expresses a polypeptide having the amino acid sequence set forth in SEQ ID NO: 11 or a polypeptide having at least about 90%, at least about 93%, at least about 95%, at least about 96%, at least about 97%, at least about 98%, or at least about 99%, sequence identity to the amino acid sequence set forth in SEQ ID NO: 11, wherein in said amino acid sequence at position 357 serine is replaced by arginine; express a polypeptide having the amino acid sequence set forth in SEQ ID NO: 13 or a polypeptide having the amino acid sequence which has at least about 90%, at least about 93%, at least about 95%, at least about 96%, at least about 97%, at least about 98%, or at least about 99%, sequence identity to the amino acid sequence set forth in SEQ ID NO: 13, wherein in said amino acid sequence at position 87 R is replaced by L.

As detailed above, a bacterium of the invention may have been modified to overexpress certain polypeptides as detailed herein, which means that an exogenous nucleic acid molecule, such as a DNA molecule, which comprises a nucleotide sequence encoding said polypeptide has been introduced in the bacterium. Techniques for introducing exogenous nucleic acid molecule, such as a DNA molecule, into a bacterial cells are well-known to those of skill in the art, and include transformation (e.g., heat shock or natural transformation) among others.

In order to facilitate overexpression of a polypeptide in the bacterium, the exogenous nucleic acid molecule may comprise suitable regulatory elements such as a promoter that is functional in the bacterial cell to cause the production of an mRNA molecule and that is operably linked to the nucleotide sequence encoding said polypeptide.

Promoters useful in accordance with the invention are any known promoters that are functional in a given host cell to cause the production of an mRNA molecule. Many such promoters are known to the skilled person. Such promoters include promoters normally associated with other genes, and/or promoters isolated from any bacteria. The use of promoters for protein expression is generally known to those of skilled in the art of molecular biology, for example, see Sambrook et al., Molecular cloning: A Laboratory Manual, Cold Spring Harbor Laboratory, Cold Spring Harbor, N.Y., 1989. The promoter employed may be inducible, such as a temperature inducible promoter (e.g., a pL or pR phage lambda promoters, each of which can be controlled by the temperature-sensitive lambda repressor c1857). The term "inducible" used in the context of a promoter means that the promoter only directs transcription of an operably linked nucleotide sequence if a stimulus is present, such as a change in temperature or the presence of a chemical substance ("chemical inducer"). As used herein, "chemical induction" according to the present invention refers to the physical application of an exogenous or endogenous substance (incl. macromolecules, e.g., proteins or nucleic acids) to a host cell. This has the effect of causing the target promoter present in the host cell to increase the rate of transcription. Alternatively, the promoter employed may be constitutive. The term "constitutive" used in the context of a promoter means that the promoter is capable of directing transcription of an operably linked nucleotide sequence in the absence of stimulus (such as heat shock, chemicals etc.).

Temperature induction systems work, for example, by employing promoters that are repressed by thermolabile repressors. These repressors are active at lower temperatures for example at 30° C., while unable to fold correctly at 37° C. and are therefore inactive. Such circuits therefore can be used to directly regulate the genes of interest (St-Pierre et al. 2013) also by genome integration of the genes along with the repressors. Examples of such as a temperature inducible expression system are based on the pL and/or pR λ phage promoters which are regulated by the thermolabile c1857 repressor. Similar to the genome integrated DE3 system, the expression of the T7 RNA polymerase gene may also be controlled using a temperature controlled promoter system (Mertens et al. 1995), while the expression of the genes of interest can be controlled using a T7 promoter.

Non-limiting examples of promoters functional in bacteria, such as *Escherichia coli*, include both constitutive and inducible promoters such as T7 promoter, the beta-lactamase and lactose promoter systems; alkaline phosphatase (phoA) promoter, a tryptophan (trp) promoter system, tetracycline promoter, lambda-phage promoter, ribosomal protein promoters; and hybrid promoters such as the tac promoter. Other bacterial and synthetic promoters are also suitable.

Besides a promoter, the exogenous nucleic acid molecule may further comprise at least one regulatory element selected from a 5' untranslated region (5'UTR) and 3' untranslated region (3' UTR). Many such 5' UTRs and 3' UTRs derived from prokaryotes and eukaryotes are well known to the skilled person. Such regulatory elements include 5' UTRs and 3' UTRs normally associated with other genes, and/or 5' UTRs and 3' UTRs isolated from any bacteria.

Usually, the 5' UTR contains a ribosome binding site (RBS), also known as the Shine Dalgarno sequence which is usually 3-10 base pairs upstream from the initiation codon.

The exogenous nucleic acid molecule may be a vector or part of a vector, such as an expression vector. Normally, such a vector remains extrachromosomal within the bacterial cell which means that it is found outside of the nucleus or nucleoid region of the bacterium.

It is also contemplated by the present invention that the exogenous nucleic acid molecule is stably integrated into the genome of the bacterium. Means for stable integration into the genome of a host cell, e.g., by homologous recombination, are well known to the skilled person.

A bacterium in accordance with the present invention can be produced from any suitable bacterium, such as a Gram-positive or Gram-negative bacterium.

Examples of bacteria which can be used to derive a bacterium of the invention belong to the Enterobacteriaceae family, such as bacteria belonging to a genus selected from the group consisting of *Escherichia, Arsenophonus, Biostraticola, Brenneria, Buchnera, Budvicia, Buttiauxella, Cedecea, Citrobacter, Cosenzaea, Cronobacter, Dickeya, Edwardsiella, Enterobacter, Erwinia, Ewingella, Gibbsiella, Hafnia, Klebsiella, Leclercia, Leminorella, Lonsdalea, Mangrovibacter, Moellerella, Morganella, Obesumbacte-*

*rium, Pantoea, Pectobacterium, Phaseolibacter, Photorhabdus, Plesiomonas, Proteus, Rahnella, Raoultella, Saccharobacter, Salmonella, Samsonia, Serratia, Shimwellia, Sodalis, Tatumella, Thorsellia, Trabulsiella, Wigglesworthia, Yersinia* and *Yokenella*.

According to certain other embodiments, the bacterium belongs to a genus selected from the group selected from *Escherichia, Bacillus, Lactococcus, Lactobacillus, Clostridium, Corynebacterium, Geobacillus, Streptococcus, Pseudomonas, Streptomyces, Shigella, Acinetobacter, Citrobacter, Salmonella, Klebsiella, Enterobacter, Erwinia, Kluyvera, Serratia, Cedecea, Morganella, Hafnia, Edwardsiella, Providencia, Proteus* and *Yersinia*.

According to particular embodiments, the bacterium belongs to the genus *Escherichia*. According to particular embodiments, the bacterium is *Escherichia coli*. Non-limiting examples of a bacterium belonging to the genus *Escherichia*, which can be used to derive a bacterium of the invention, are *Escherichia coli* K-12 (especially substrain MG1655 or W3110), BL21, W, or Crooks. According to more particular embodiments, the bacterium is *Escherichia coli* K-12.

According to other particular embodiments, the bacterium belongs to the genus *Corynebacterium*. A non-limiting example of a bacterium of the genus *Corynebacterium* is *Corynebacterium glutamicum*. According to more particular embodiments, the bacterium is *Corynebacterium glutamicum*.

According to other particular embodiments, the bacterium belongs to the genus *Bacillus*. Non-limiting examples of a bacterium of the genus *Bacillus* are *Bacillus subtilis, Bacillus amyloliquefaciens, Bacillus licheniformis*, and *Bacillus mojavensis*. According to more particular embodiments, the bacterium is *Bacillus subtilis*. According to other more particular embodiments, the bacterium is *Bacillus licheniformis*.

According to other particular embodiments, the bacterium belongs to the genus *Lactococcus*. A non-limiting example of a bacterium of the genus *Lactococcus* is *Lactococcus lactis*. According to more particular embodiments, the bacterium is *Lactococcus lactis*.

According to other particular embodiments, the bacterium belongs to the genus *Streptomyces*. A non-limiting example of a bacterium of the genus *Streptomyces* are *Streptomyces lividans, Streptomyces coelicolor*, or *Streptomyces griseus*. According to more particular embodiments, the bacterium is *Streptomyces lividans*. According to other more particular embodiments, the bacterium is *Streptomyces coelicolor*. According to other more particular embodiments, the bacterium is *Streptomyces griseus*.

According to other particular embodiments, the bacterium belongs to the genus *Pseudomonas*. A non-limiting example of a bacterium of the genus *Pseudomonas* is *Pseudomonas putida*. According to more particular embodiments, the bacterium is *Pseudomonas putida*.

METHOD OF THE INVENTION

The present invention also provides methods for producing L-serine or a L-serine derivative using a bacterium according to the present invention. Particularly, the present invention provides a method for producing L-serine or a L-serine derivative, said method comprises cultivating a bacterium as detailed herein in a culture medium.

According to certain embodiments, present invention provides a method for producing L-serine. Particularly, the present invention provides a method for producing L-serine, said method comprises cultivating a bacterium as detailed herein in a culture medium. The method may further comprise collecting L-serine from the culture medium.

According to certain embodiments, present invention provides a method for producing a L-serine derivative. Particularly, the present invention provides a method for producing a L-serine derivative, said method comprises cultivating a bacterium as detailed herein in a culture medium. The L-serine derivative may be selected from the group consisting of L-cysteine, L-methionine, L-glycine, O-acetylserine, L-tryptophan, thiamine, ethanolamine and ethylene glycol. The method may further comprise collecting the L-serine derivative from the culture medium.

According to certain embodiments, present invention provides a method for producing L-cysteine. Particularly, the present invention provides a method for producing L-cysteine, said method comprises cultivating a bacterium as detailed herein in a culture medium. The method may further comprise collecting L-cysteine from the culture medium.

According to certain embodiments, present invention provides a method for producing L-methionine. Particularly, the present invention provides a method for producing L-methionine; said method comprises cultivating a bacterium as detailed herein in a culture medium. The method may further comprise collecting L-methionine from the culture medium.

According to certain embodiments, present invention provides a method for producing L-glycine. Particularly, the present invention provides a method for producing L-glycine; said method comprises cultivating a bacterium as detailed herein in a culture medium. The method may further comprise collecting L-glycine from the culture medium.

According to certain embodiments, present invention provides a method for producing L-cysteine. Particularly, the present invention provides a method for producing O-acetylserine, said method comprises cultivating a bacterium as detailed herein in a culture medium. The method may further comprise collecting O-acetylserine from the culture medium.

According to certain embodiments, present invention provides a method for producing L-glycine. Particularly, the present invention provides a method for producing L-tryptophan; said method comprises cultivating a bacterium as detailed herein in a culture medium. The method may further comprise collecting L-tryptophan from the culture medium.

According to certain embodiments, present invention provides a method for producing L-cysteine. Particularly, the present invention provides a method for producing thiamine, said method comprises cultivating a bacterium as detailed herein in a culture medium. The method may further comprise collecting thiamine from the culture medium.

According to certain embodiments, present invention provides a method for producing ethanolamine. Particularly, the present invention provides a method for producing ethanolamine; said method comprises cultivating a bacterium as detailed herein in a culture medium. The method may further comprise collecting ethanolamine from the culture medium.

According to certain embodiments, present invention provides a method for producing ethylene glycol. Particularly, the present invention provides a method for producing ethylene glycol; said method comprises cultivating a bacterium as detailed herein in a culture medium. The method may further comprise collecting ethylene glycol from the culture medium.

The culture medium employed may be any conventional medium suitable for culturing a bacterium cell in question, and may be composed according to the principles of the prior art. The medium will usually contain all nutrients necessary for the growth and survival of the respective bacterium, such as carbon and nitrogen sources and other inorganic salts. Suitable media, e.g. minimal or complex media, are available from commercial suppliers, or may be prepared according to published receipts, e.g. the American Type Culture Collection (ATCC) Catalogue of strains. Non-limiting standard medium well known to the skilled person include Luria Bertani (LB) broth, Sabouraud Dextrose (SD) broth, MS broth, Yeast Peptone Dextrose, BMMY, GMMY, or Yeast Malt Extract (YM) broth, which are all commercially available. A non-limiting example of suitable media for culturing bacterial cells, such as E. coli cells, including minimal media and rich media such as Luria Broth (LB), M9 media, M17 media, SA media, MOPS media, Terrific Broth, YT and others.

In order to further increase the yield of L-serine or L-serine derivative, the culture medium may further be supplemented with L-threonine. The culture medium may generally contain L-threonine at a concentration from about 0.05 to about 10 g/L, such as from about 0.05 to about 5 g/L, from about 0.05 to about 2.5 g/L, from about 0.05 to about 1 g/L or from about 0.05 to about 0.5 g/L. According to certain embodiments, the culture medium contains L-threonine at a concentration from about 0.05 to about 5 g/L. According to certain other embodiments, the culture medium contains L-threonine at a concentration from about 0.05 to about 2.5 g/L. According to certain other embodiments, the culture medium contains L-threonine at a concentration from about 0.05 to about 1 g/L. According to certain other embodiments, the culture medium contains L-threonine at a concentration from about 0.05 to about 0.5 g/L. According to certain other embodiments, the culture medium contains L-threonine at a concentration from about 0.1 to about 1 g/L. According to other embodiments, the culture medium contains L-threonine at a concentration from about 0.2 to about 1 g/L.

The carbon source may be any suitable carbon substrate known in the art, and in particularly any carbon substrate commonly used in the cultivation of bacteria and/or fermentation. Non-limiting examples of suitable fermentable carbon substrates are C5 sugars (such as arabinose or xylose), C6 sugars (such as glucose), acetate, glycerol, plant oils, sucrose, yeast extract, peptone, casaminoacids or mixtures thereof. A carbon source of particular interest is a C6 sugar such as glucose.

As the nitrogen source, various ammonium salts such as ammonia and ammonium sulfate, other nitrogen compounds such as amines, a natural nitrogen source such as peptone, soybean-hydrolysate, and digested fermentative microorganism can be used. As minerals, potassium monophosphate, magnesium sulfate, sodium chloride, ferrous sulfate, manganese sulfate, calcium chloride, and the like can be used.

The cultivation can be preferably performed under aerobic conditions, such as by a shaking culture, and by a stirring culture with aeration, at a temperature of about 20 to about 40° C., such as about 30 to 38° C., preferably about 37° C. The pH of the culture is usually from about 5 and about 9, such as from about 6.5 and 7.5. The pH of the culture can be adjusted with ammonia, calcium carbonate, various acids, various bases, and buffers. Usually, 1 to 5-day cultivation leads to accumulation of L-serine in the culture medium.

After cultivation, solids such as cells can be removed from the culture medium by centrifugation or membrane filtration. L-serine or the L-serine derivative can be collected by conventional method for isolation and purification chemical compounds from a medium. Well-known purification procedures include, but are not limited to, centrifugation or filtration, precipitation, ion exchange, chromatographic methods such as e.g. ion exchange chromatography or gel filtration chromatography, and crystallization methods.

The present invention thus provides L-serine or a L-serine derivative obtainable by a method as detailed herein.

CERTAIN OTHER DEFINITIONS

The term "bacterium having ability to produce L-serine" as used herein means a bacterium which is able to produce and cause accumulation of L-serine in a culture medium, can mean that the bacterium is able to cause accumulation in an amount not less than 0.4 g/L, when cultured in minimal M9 media supplemented with 2 g/L glucose, 2 mM glycine and 1 mM threonine at 37° C. with adequate aeration for 40 hours.

The phrase "bacterium which has been modified to attenuate expression of at least one gene encoding a polypeptide having serine deaminase activity" as used herein means that the bacterium has been modified in such a way that the modified bacterium contains a reduced amount of the at least one polypeptide having serine deaminase activity. More particularly, the phrase means that the bacterium is unable to synthesize the polypeptide(s) having serine deaminase activity. An attenuate expression can be determined by comparing the level of expression of the polypeptide having serine deaminase activity encoded by the at least one gene within the modified bacterium compared to that of an otherwise identical bacterium that does not carry said modification (reference bacterium).

The phrase "bacterium which has been modified to attenuate expression of the gene encoding a polypeptide having serine hydroxymethyltransferase activity" as used herein means that the bacterium has been modified in such a way that the modified bacterium contains a reduced amount of the polypeptide having serine hydroxymethyltransferase activity. More particularly, the phrase means that the bacterium is unable to synthesize a polypeptide having serine hydroxymethyltransferase activity. An attenuate expression can be determined by comparing the level of expression of the polypeptide having serine hydroxymethyltransferase activity encoded by the gene within the modified bacterium compared to that of an otherwise identical bacterium that does not carry said modification (reference bacterium).

The phrase "bacterium which has been modified to attenuate expression of the gene encoding a polypeptide having glucose 6-phosphate-1-dehydrogenase (G6PDH) activity" as used herein means that the bacterium has been modified in such a way that the modified bacterium contains a reduced amount of the polypeptide having glucose 6-phosphate-1-dehydrogenase (G6PDH) activity. More particularly, the phrase means that the bacterium is unable to synthesize a polypeptide having glucose 6-phosphate-1-dehydrogenase (G6PDH) activity. An attenuate expression can be determined by comparing the level of expression of the polypeptide having glucose 6-phosphate-1-dehydrogenase (G6PDH) activity encoded by the gene within the modified bacterium compared to that of an otherwise identical bacterium that does not carry said modification (reference bacterium).

The phrase "bacterium of the invention has been further modified to attenuate the expression of the pykF gene" as used herein means that the bacterium has been modified in such a way that the modified bacterium contains a reduced amount of the polypeptide encoded by the pykF gene. More particularly, the phrase means that the bacterium is unable to synthesize a polypeptide encoded by the pykF gene. An attenuate expression can be determined by comparing the level of expression of the polypeptide encoded by the pykF gene within the modified bacterium compared to that of an otherwise identical bacterium that does not carry said modification (reference bacterium).

The phrase "bacterium of the invention has been further modified to attenuate the expression of the malT gene" as used herein means that the bacterium has been modified in such a way that the modified bacterium contains a reduced amount of the polypeptide encoded by the malT gene. More particularly, the phrase means that the bacterium is unable to synthesize a polypeptide encoded by the malT gene. An attenuate expression can be determined by comparing the level of expression of the polypeptide encoded by the malT gene within the modified bacterium compared to that of an otherwise identical bacterium that does not carry said modification (reference bacterium).

The phrase "bacterium of the invention has been further modified to attenuate the expression of the lamB gene" as used herein means that the bacterium has been modified in such a way that the modified bacterium contains a reduced amount of the polypeptide encoded by the lamB gene. More particularly, the phrase means that the bacterium is unable to synthesize a polypeptide encoded by the lamB gene. An attenuate expression can be determined by comparing the level of expression of the polypeptide encoded by the lamB gene within the modified bacterium compared to that of an otherwise identical bacterium that does not carry said modification (reference bacterium).

The phrase "bacterium of the invention has been further modified to attenuate the expression of the frc gene" as used herein means that the bacterium has been modified in such a way that the modified bacterium contains a reduced amount of the polypeptide encoded by the frc gene. More particularly, the phrase means that the bacterium is unable to synthesize a polypeptide encoded by the frc gene. An attenuate expression can be determined by comparing the level of expression of the polypeptide encoded by the frc gene within the modified bacterium compared to that of an otherwise identical bacterium that does not carry said modification (reference bacterium).

The phrase "bacterium of the invention has been further modified to attenuate the expression of the aroP gene" as used herein means that the bacterium has been modified in such a way that the modified bacterium contains a reduced amount of the polypeptide encoded by the aroP gene. More particularly, the phrase means that the bacterium is unable to synthesize a polypeptide encoded by the aroP gene. An attenuate expression can be determined by comparing the level of expression of the polypeptide encoded by the aroP gene within the modified bacterium compared to that of an otherwise identical bacterium that does not carry said modification (reference bacterium).

The phrase "bacterium of the invention has been further modified to attenuate the expression of the brnQ gene" as used herein means that the bacterium has been modified in such a way that the modified bacterium contains a reduced amount of the polypeptide encoded by the brnQ gene. More particularly, the phrase means that the bacterium is unable to synthesize a polypeptide encoded by the brnQ gene. An attenuate expression can be determined by comparing the level of expression of the polypeptide encoded by the brnQ gene within the modified bacterium compared to that of an otherwise identical bacterium that does not carry said modification (reference bacterium).

The phrase "inactivation of a gene" can mean that the modified gene encodes a completely non-functional protein. It is also possible that the modified DNA region is unable to naturally express the gene due to the deletion of a part of or the entire gene sequence, the shifting of the reading frame of the gene, the introduction of missense/nonsense mutation(s), or the modification of an adjacent region of the gene, including sequences controlling gene expression, such as a promoter, enhancer, attenuator, ribosome-binding site, etc. Preferably, a gene of interest is inactivated by deletion of a part of or the entire gene sequence, such as by gene replacement.

The presence or absence of a gene on the chromosome of a bacterium can be detected by well-known methods, including PCR, Southern blotting, and the like. In addition, the level of gene expression can be estimated by measuring the amount of mRNA transcribed from the gene using various well-known methods, including Northern blotting, quantitative RT-PCR, and the like. The amount of the protein encoded by the gene can be measured by well-known methods, including SDS-PAGE followed by an immunoblotting assay (Western blotting analysis), and the like.

"Polypeptide" and "protein" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

"Nucleic acid" or "polynucleotide" are used interchangeably herein to denote a polymer of at least two nucleic acid monomer units or bases (e.g., adenine, cytosine, guanine, thymine) covalently linked by a phosphodiester bond, regardless of length or base modification.

"Recombinant" or "non-naturally occurring" when used with reference to, e.g., a host cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant host cells expressing genes that are not found within the native (non-recombinant) form of the cell or express native genes that are otherwise expressed at a different level.

"Heterologous" as used herein means that a polypeptide is normally not found in or made (i.e. expressed) by the host organism, but derived from a different species.

"Substitution" or "substituted" refers to modification of the polypeptide by replacing one amino acid residue with another, for instance the replacement of an Serine residue with a Glycine or Alanine residue in a polypeptide sequence is an amino acid substitution. When used with reference to a polynucleotide, "substitution" or "substituted" refers to modification of the polynucleotide by replacing one nucleotide with another, for instance the replacement of a cytosine with a thymine in a polynucleotide sequence is a nucleotide substitution.

"Conservative substitution", when used with reference to a polypeptide, refers to a substitution of an amino acid residue with a different residue having a similar side chain, and thus typically involves substitution of the amino acid in the polypeptide with amino acids within the same or similar class of amino acids. By way of example and not limitation, an amino acid with an aliphatic side chain may be substituted with another aliphatic amino acid, e.g., alanine, valine, leucine, and isoleucine; an amino acid with hydroxyl side chain is substituted with another amino acid with a hydroxyl side chain, e.g., serine and threonine; an amino acid having an aromatic side chain is substituted with another amino acid having an aromatic side chain, e.g., phenylalanine, tyrosine, tryptophan, and histidine; an amino acid with a basic side chain is substituted with another amino acid with a basic side chain, e.g., lysine and arginine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively.

"Non-conservative substitution", when used with reference to a polypeptide, refers to a substitution of an amino acid in a polypeptide with an amino acid with significantly differing side chain properties. Non-conservative substitutions may use amino acids between, rather than within, the defined groups and affects (a) the structure of the peptide backbone in the area of the substitution (e.g., serine for glycine), (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Deletion" or "deleted", when used with reference to a polypeptide, refers to modification of the polypeptide by removal of one or more amino acids in the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the polypeptide while retaining enzymatic activity and/or retaining the improved properties of an engineered enzyme. Deletions can be directed to the internal portions and/or terminal portions of the polypeptide, in various embodiments, the deletion can comprise a continuous segment or can be discontinuous.

"Insertion" or "inserted", when used with reference to a polypeptide, refers to modification of the polypeptide by addition of one or more amino acids to the reference polypeptide. Insertions can comprise addition of 1 or more amino acids, 2 or more amino acids, 5 or more amino acids, 10 or more amino acids, 15 or more amino acids, or 20 or more amino acids. Insertions can be in the internal portions of the polypeptide, or to the carboxy or amino terminus. The insertion can be a contiguous segment of amino acids or separated by one or more of the amino acids in the reference polypeptide.

"Expression" includes any step involved in the production of a polypeptide (e.g., encoded enzyme) including, but not limited to, transcription, post-transcriptional modification, translation, post-translational modification, and secretion.

As used herein, "vector" refers to a nucleic acid molecule capable of transporting another nucleic acid molecule to which it has been linked. One type of vector is a "plasmid", which refers to a circular double stranded nucleic acid loop into which additional nucleic acid segments can be ligated. Certain vectors are capable of directing the expression of genes to which they are operatively linked. Such vectors are referred to herein as "expression vectors". Certain other vectors are capable of facilitating the insertion of an exogenous nucleic acid molecule into a genome of a bacterium. Such vectors are referred to herein as "transformation vectors". In general, vectors of utility in recombinant nucleic acid techniques are often in the form of plasmids. In the present specification, "plasmid" and "vector" can be used interchangeably as the plasmid is the most commonly used form of a vector. Large numbers of suitable vectors are known to those of skill in the art and commercially available.

As used herein, "promoter" refers to a sequence of DNA, usually upstream (5') of the coding region of a structural gene, which controls the expression of the coding region by providing recognition and binding sites for RNA polymerase and other factors which may be required for initiation of transcription. The selection of the promoter will depend upon the nucleic acid sequence of interest. A suitable "promoter" is generally one which is capable of supporting the initiation of transcription in a bacterium of the invention, causing the production of an mRNA molecule.

As used herein, "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequence. A promoter sequence is "operably-linked" to a gene when it is in sufficient proximity to the transcription start site of a gene to regulate transcription of the gene.

"Percentage of sequence identity," "% sequence identity" and "percent identity" are used herein to refer to comparisons between an amino acid sequence and a reference amino acid sequence. The "% sequence identify", as used herein, is calculated from the two amino acid sequences as follows: The sequences are aligned using Version 9 of the Genetic Computing Group's GAP (global alignment program), using the default BLOSUM62 matrix (see below) with a gap open penalty of −12 (for the first null of a gap) and a gap extension penalty of −4 (for each additional null in the gap). After alignment, percentage identity is calculated by expressing the number of matches as a percentage of the number of amino acids in the reference amino acid sequence.

The following BLOSUM62 matrix is used:

| Ala | 4  |    |    |    |    |    |    |    |   |
|-----|----|----|----|----|----|----|----|----|---|
| Arg | −1 | 5  |    |    |    |    |    |    |   |
| Asn | −2 | 0  | 6  |    |    |    |    |    |   |
| Asp | −2 | −2 | 1  | 5  |    |    |    |    |   |
| Cys | 0  | −3 | −3 | −3 | 9  |    |    |    |   |
| Gln | −1 | 1  | 0  | 0  | −3 | 8  |    |    |   |
| Glu | −1 | 0  | 0  | 2  | −4 | 2  | 6  |    |   |
| Gly | 0  | −2 | 0  | −1 | −3 | −2 | −2 | 6  |   |
| His | −2 | 0  | 1  | −1 | −3 | 0  | 0  | −2 | 8 |

-continued

| | Ala | Arg | Asn | Asp | Cys | Gln | Glu | Gly | His | Ile | Leu | Lys | Met | Phe | Pro | Ser | Thr | Trp | Tyr | Val |
|---|---|---|---|---|---|---|---|---|---|---|---|---|---|---|---|---|---|---|---|---|
| Ile | -1 | -3 | -3 | -3 | -1 | -3 | -3 | -4 | -3 | 4 | | | | | | | | | | |
| Leu | -1 | -2 | -3 | -4 | -1 | -2 | -3 | -4 | -3 | 2 | 4 | | | | | | | | | |
| Lys | -1 | 2 | 0 | -1 | -3 | 1 | 1 | -2 | -1 | -3 | -2 | 5 | | | | | | | | |
| Met | -1 | -1 | -2 | -3 | -1 | 0 | -2 | -3 | -2 | 1 | 2 | -1 | 8 | | | | | | | |
| Phe | -2 | -3 | -3 | -3 | -2 | -3 | -3 | -3 | -1 | 0 | 0 | -3 | 0 | 6 | | | | | | |
| Pro | -3 | -2 | -2 | -1 | -3 | -1 | -1 | -2 | -2 | -3 | -3 | -1 | -2 | -4 | 7 | | | | | |
| Ser | 1 | -1 | 1 | 0 | -1 | 0 | 0 | 0 | -1 | -2 | -2 | 0 | -1 | -2 | -1 | 4 | | | | |
| Thr | 0 | -1 | 0 | -1 | -1 | -1 | -1 | -2 | -2 | -1 | -1 | -1 | -1 | -2 | -1 | 1 | 6 | | | |
| Trp | -3 | -3 | -4 | -4 | -2 | -2 | -3 | -2 | -2 | -3 | -2 | -3 | -1 | 1 | -4 | -3 | -2 | 11 | | |
| Tyr | -2 | -2 | -2 | -3 | -2 | -1 | -2 | -3 | 2 | -1 | -1 | -2 | -1 | 3 | -3 | -2 | -2 | 2 | 7 | |
| Val | 0 | -3 | -3 | -3 | -1 | -2 | -2 | -3 | -3 | 3 | 1 | -2 | 1 | -1 | -2 | -2 | 0 | -3 | -1 | 4 |
| | Ala | Arg | Asn | Asp | Cys | Gln | Glu | Gly | His | Ile | Leu | Lys | Met | Phe | Pro | Ser | Thr | Trp | Tyr | Val |

"Reference sequence" or "reference amino acid sequence" refers to a defined sequence to which another sequence is compared. In the context of the present invention a reference amino acid sequence may, for example, be an amino acid sequence set forth in SEQ ID NO: 5 or 6.

As used herein, "L-serine derivative" refers to a compound, such as an amino acid, resulting from reaction of L-serine at the amino group or the carboxy group, or from the replacement of any hydrogen of L-serine by a heteroatom. Non-limiting examples of a "L-serine derivative" include L-cysteine, L-methionine, L-glycine, O-acetylserine, L-tryptophan, thiamine, ethanolamine and ethylene glycol. Further examples of a "L-serine derivative" are described by Chemical Entities of Biological Interest (ChEBI), for example, under ChEBI ID CHEBI:84135.

Where a numerical limit or range is stated herein, the endpoints are included. Also, all values and sub ranges within a numerical limit or range are specifically included as if explicitly written out.

Having generally described this invention, a further understanding can be obtained by reference to certain specific examples, which are provided herein for purposes of illustration only, and are not intended to be limiting unless otherwise specified.

EXAMPLES

For the first time, the present inventors show that a bacterium, such as *E. coli*, lacking all four serine degradation genes (sdaA, sdaB, tdcG and glyA) can be constructed (Example 1). Said strain shows higher serine production yield than single and triple deaminase knock outs, when serine pathway is upregulated (Example 2). However, the resulting strain had a low tolerance towards serine, which has also been reported in an *E. coli* triple deletion strain lacking sdaA, sdaB and tdcG (Zhang and Newman, 2008). The inventors furthermore demonstrate that product toxicity can be reduced by over-expression of novel exporters (Example 3), by evolving strains by random mutagenesis (Example 4), and by adaptive evolution (Example 5). The strain was furthermore reverse engineered in order to identify the causative mutations (Example 6). During fed batch fermentation, the tolerant strain shows improved serine production (12.6 g/L with a mass yield of 36.7% from glucose) when compared to the parental quadruple deletion strain (Example 7). This is the highest serine mass yield reported so far from glucose in any production organism.

The inventors additionally demonstrate that inhibition of the pentose phosphate pathway by deletion of zwf in the presence of other causative mutations leads to a further increase in serine production yield (Example 8).

The inventors further have identified beneficial mutations in ThrA resulting in an increase tolerance of the bacterial strain, including wild type *E. coli* and strains carrying an sdaA deletion, towards L-serine (Examples 10, 12, 13 and 14).

Example 1—Deletion of Key Degradation Pathways

Serine has two key degradation pathways in *E. coli*: Serine to pyruvate, which is encoded by three deaminases namely sdaA, sdaB and tdcG, and conversion of serine to glycine, which is encoded by glyA. The deletion of glyA renders *E. coli* auxotrophic for glycine. Deletion of sdaA, sdaB and tdcG was done sequentially by using the lambda red mediated gene replacement method (Datsenko and Wanner, 2000). The protocol applied for deleting these genes is similar to the protocol described by Sawitzke et al. (2013). Primers used for amplification of the kanamycin cassette are shown in Table S1. The PCR reaction contained 250 nM each of KF and KR primer of the given gene, 250 µM of dNTP mix, 4 Units of Phusion polymerase (Thermoscientific, Waltham, Mass., USA), 40 µl of HF buffer and 10 ng of pKD4 plasmid. The following two-step PCR protocol was used for the PCR amplification: An initial denaturation step at 98° C. for 40 seconds, followed by 5 cycles of denaturation at 98° C. for 10 seconds, annealing at 55° C. for 30 seconds, extension at 72° C. for 90 seconds the cycle, followed by 20 cycles, where the annealing temperature was increased from 55° C. to 65° C. The PCR products were column purified (Macherey Nagel, Durn, Germany) and concentration was measured using a Nanodrop instrument (Thermoscientific, Waltham, Mass., USA) and subjected to overnight DpnI digestion. *E. coli* MG1655 was used as parent strain to make sequential knock outs. The parent strain was transformed with pKD46 were grown in 2YT-amp media at 30° C. and 250 rpm. The expression of exo, beta and gamma proteins were induced by addition of 20 mM arabinose at mid log phase (O.D. 0.4 to 0.5) and the cells were harvested after additional 1 h incubation. Culture was then transferred to 50 ml ice cold falcon tubes and centrifuged at 6500 rpm for 5 min at 4° C. Supernatant was discarded and cells were washed twice with ice cold 10% glycerol. These electro-competent cells were transformed with 200 ng of kanamycin cassette, and transfomants were plated on LB-kan plates. The kanamycin cassette was removed using the plasmid pcp20 encoding flippase gene. Primers for checking the loop out are shown in Table S2. Serine hydroxymethyltransferase encoded by glyA was deleted using the P1 phage system protocol (Thomason et al., 2007). A strain from the Keio collection (Baba et al., 2006) harboring glyA::kan was grown in 5 ml of LB-kan supplemented with 0.2% Glucose, 25 mM CaCl2) and 1 mM Glycine media. At early log phase (O.D. 0.1), culture was transduced with P1 phage lysate. The culture was incubated for three hours at 37° C. and 250 rpm for cell lysis. Lysate was filter sterilized by using 0.45 uM filter. 1 ml of overnight culture of the E. coli strain having sdaA, sdaB and tdcG deleted, was resuspended in 200 μL of P1 salt solution and was incubated with 100 μL of the above lysate for 1 h. Cells were then grown overnight in 2 mL LB media supplemented with 2 mM glycine and 200 mM sodium citrate. Cells were plated on LB-kan plate supplemented with 2 mM glycine and 10 mM sodium citrate. The clones were restreaked onto a new plate in order to remove any phage contamination, and isolated colonies were checked for cassette insertion. The loop out was done using pcp20 plasmid. The resulting quadruple deletion strain (FIG. 1) is referred to as Q1. This example demonstrates that it is possible to delete sdaA, sdaB, tdcG and glyA in E. coli, something that has not previously been achieved, and is thus unexpected.

TABLE S1

Primers used for amplification of kanamycin cassette

| Primer name | Sequence |
|---|---|
| sdaA_KF | GCGCTGTTATTAGTTCGTTACTGGAAGTCCAGTCACCT TGTCAGGAGTATTATCGTGGTGTAGGCTGGAGCTGCTT CG |
| sdaA_KR | CGCCCATCCGTTGCAGATGGGCGAGTAAGAAGTATTAG TCACACTGGACCATATGAATATCCTCCTTAGTTCC |
| sdaB_KF | CGCTTTCGGGCGGCGCTTCCTCCGTTTTAACGCGATGT ATTTCCTATGGTGTAGGCTGGAGCTGCTTCG |
| sdaB_KR | GGCCTCGCAAAACGAGGCCTTTGGAGAGCGATTAATCG CAGGCAACCATATGAATATCCTCCTTAGTTCC |
| tdcG_KF | CGTTCCGCTCCACTTCACTGAACGGCAATCCGAGGGTG TGGATATGGTGTAGGCTGGAGCTGCTTCG |
| tdcG_KR | GTGCACCCAAGGATGAAAGCTGACAGCAATGTCAGCCG CAGACCACCATATGAATATCCTCCTTAGTTCC |
| glyA_KF | GTTAGCTGAGTCAGGAGATGCGGATGTTAAAGCGTGAA ATGAACATTGCCGTGTAGGCTGGAGCTGCTTCG |
| glyA_KR | CAACGAGCACATTGACAGCAAATCACCGTTTCGCTTAT GCGTAAACCGGCATATGAATATCCTCCTTAGTTCC |

TABLE S2

Primers used for checking the deletion of given genes

| Primer name | Sequence |
|---|---|
| sdaA_cF | GCGCTGTTATTAGTTCGTTACTGGAAGTCC |
| sdaA_cR | CGCCCATCCGTTGCAGATGGGC |
| sdaB_cF | CGCTTTCGGGCGGCGCTTCCTC |
| sdaB_cR | GGCCTCGCAAAACGAGGCCTTTGG |
| tdcG_cF | CGTTCCGCTCCACTTCACTGAACGG |
| tdcG_cR | GTGCACCCAAGGATGAAAGCTGACAGC |
| glyA_cF | GTTAGCTGAGTCAGGAGATGCGGATGTT |
| glyA_cR | CAACGAGCACATTGACAGCAAATCACCG |

Example 2—Overexpression of Serine Biosynthesis Pathway for Production of Serine Serine is produced in E. coli from three enzymes encoded by serA, serB and serC. All genes were isolated from E. coli MG1655 using primers with respective gene names (Table 53). The 100 μl PCR mixture contain 250 nM each of forward and reverse primer, 250 μM of dNTP, 2 U of Phusion polymerase, 1×HF buffer, 1 μl of overnight culture. The following two-step PCR protocol was used for the PCR amplification: An initial denaturation step at 98° C. for 40, followed by 5 cycles of denaturation at 98° C. for 10 seconds, annealing at 55° C. for 30 seconds, extension at 72° C. for 90 seconds the cycle, followed by 20 cycles, where the annealing temperature was increased from 55° C. to 65° C. After column purification, the gene products and plasmids were digested using Fast digest enzymes (Thermoscientific, Waltham, Mass., USA). About 500 ng of PCR product or 1 μg of plasmids were subjected to digestion by 1 μl each of the restriction enzymes in 1× fast digest buffer. The reaction was incubated for 3h and then column purified again. serA was subjected to double digestion with NcoI and NotI while serC was digested with NdeI and PacI. pCDF-Duet was first digested with NcoI and NotI for cloning of serA leading to plasmid pCDF-Duet-serA and this plasmid was later used for cloning of serC thus making pCDF-Duet-serA-serC. The gene encoding serB was cloned in pACYC-Duet vector at NcoI and PacI site leading to pACYC-ser8. Typical ligation reaction include 1× T4 ligase buffer 50 ng of plasmid DNA and 100 ng of insert and 0.3 μl/10 μl of T4DNA ligase (Thermoscientific, Waltham, Mass., USA).

Feedback inhibition of serA was removed by mutating three residues H344, N346 and N364 to alanine (Al-Rabiee et al., 1996) by site directed mutagenesis (Table S4). The master mix was used as mentioned above with the only modification that the master mix was divided in two equal aliquots, after which forward and reverse primers were added to each aliquot. A total of 100 ng of pCDF-Duet-serA-serC plasmid was used as a template. The two step PCR program: initial denaturation at 98° C. for 40 sec, denaturation at 98° C. for 10 sec, annealing 60° C. for 30 sec, extension 72° C. for 4 min and 30 sec the cycle was repeated 5 times and then the two aliquots were mixed and redistributed for additional 15 cycles. To enable swapping of vector backbones, the NcoI site inside serC was removed by the same approach using the primers listed in Table S4.

Figure 2:
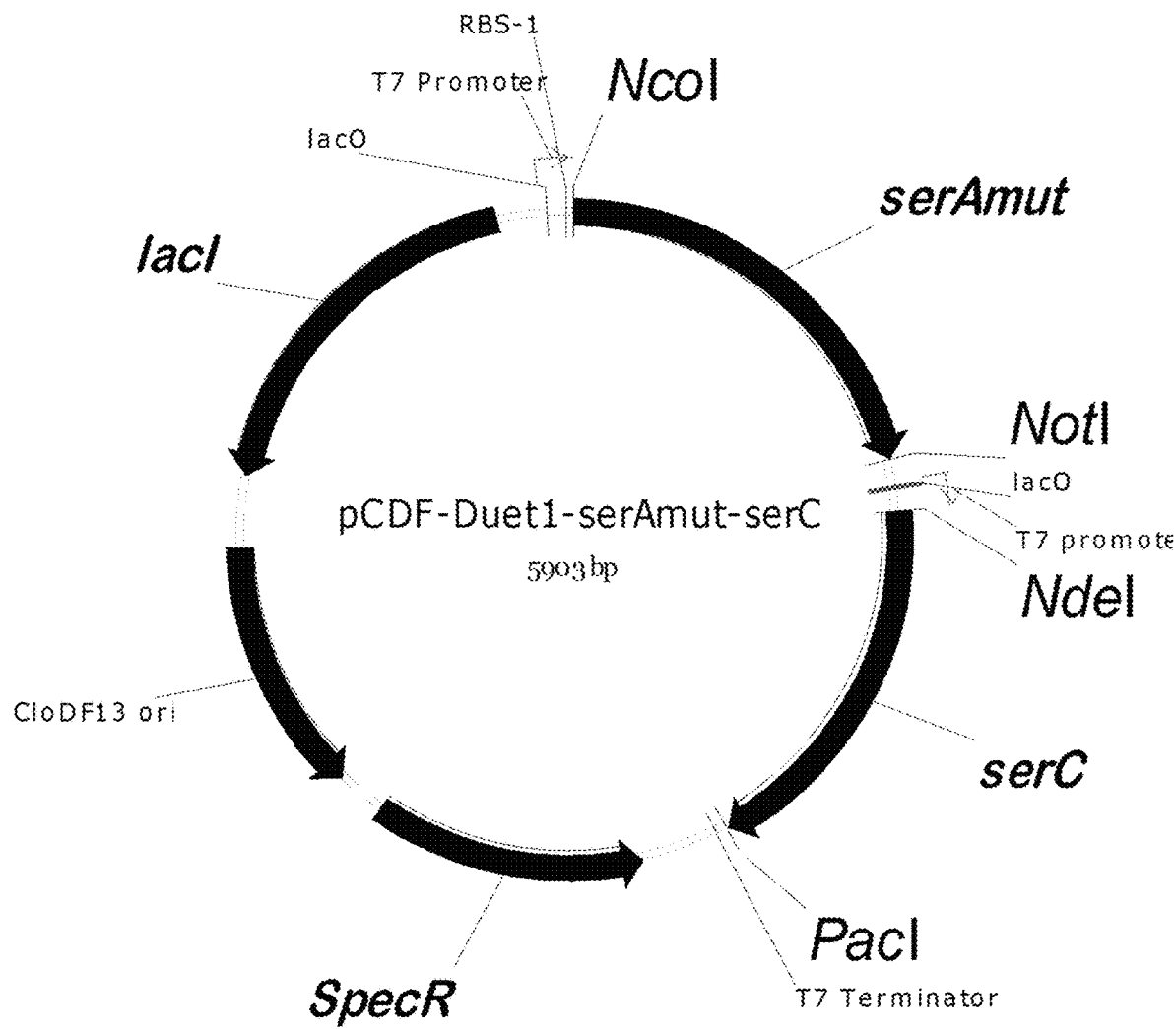
FIG. 2: Vector maps of the constructs (Example 2)
Figure 2:
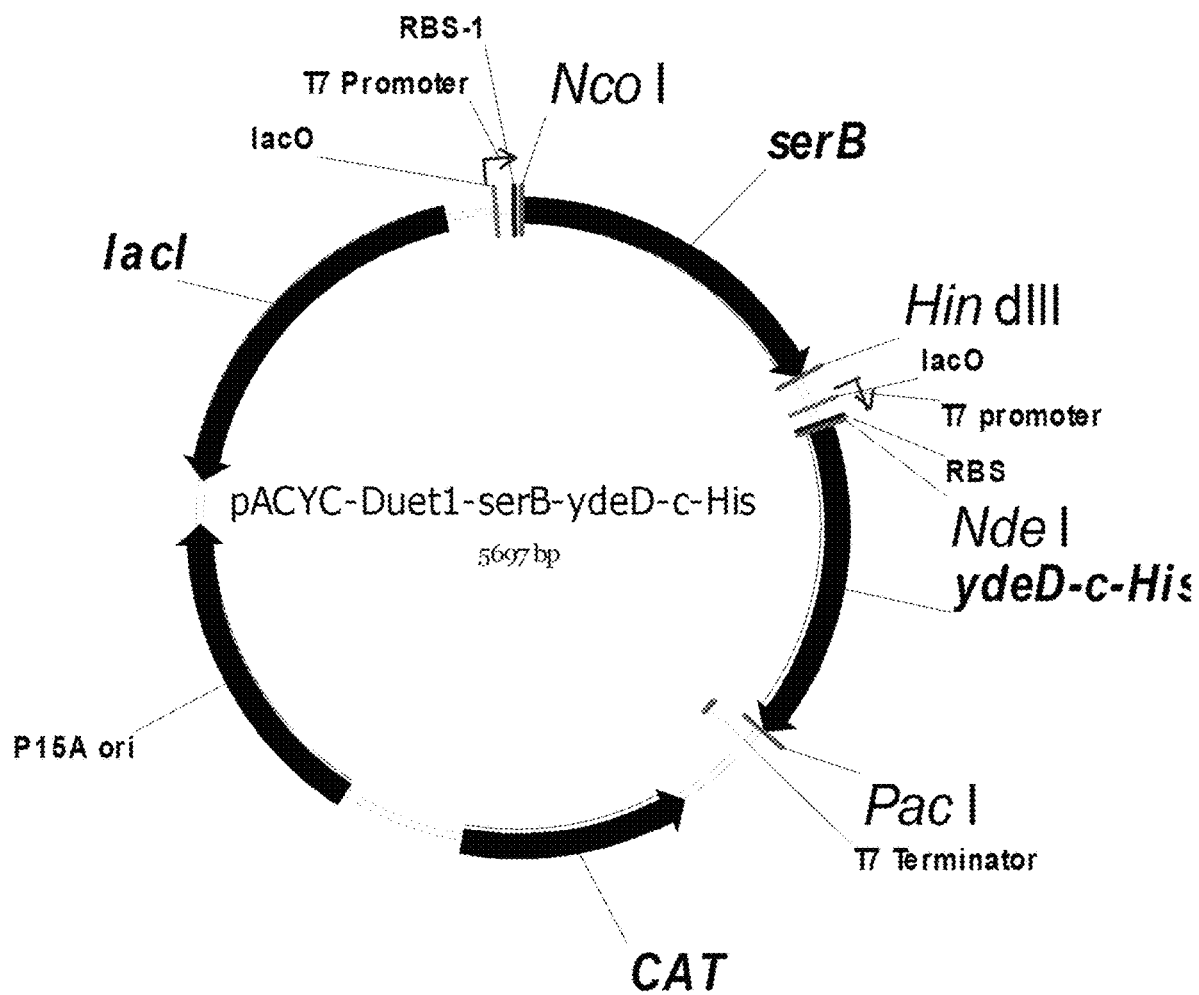
Figure 2:
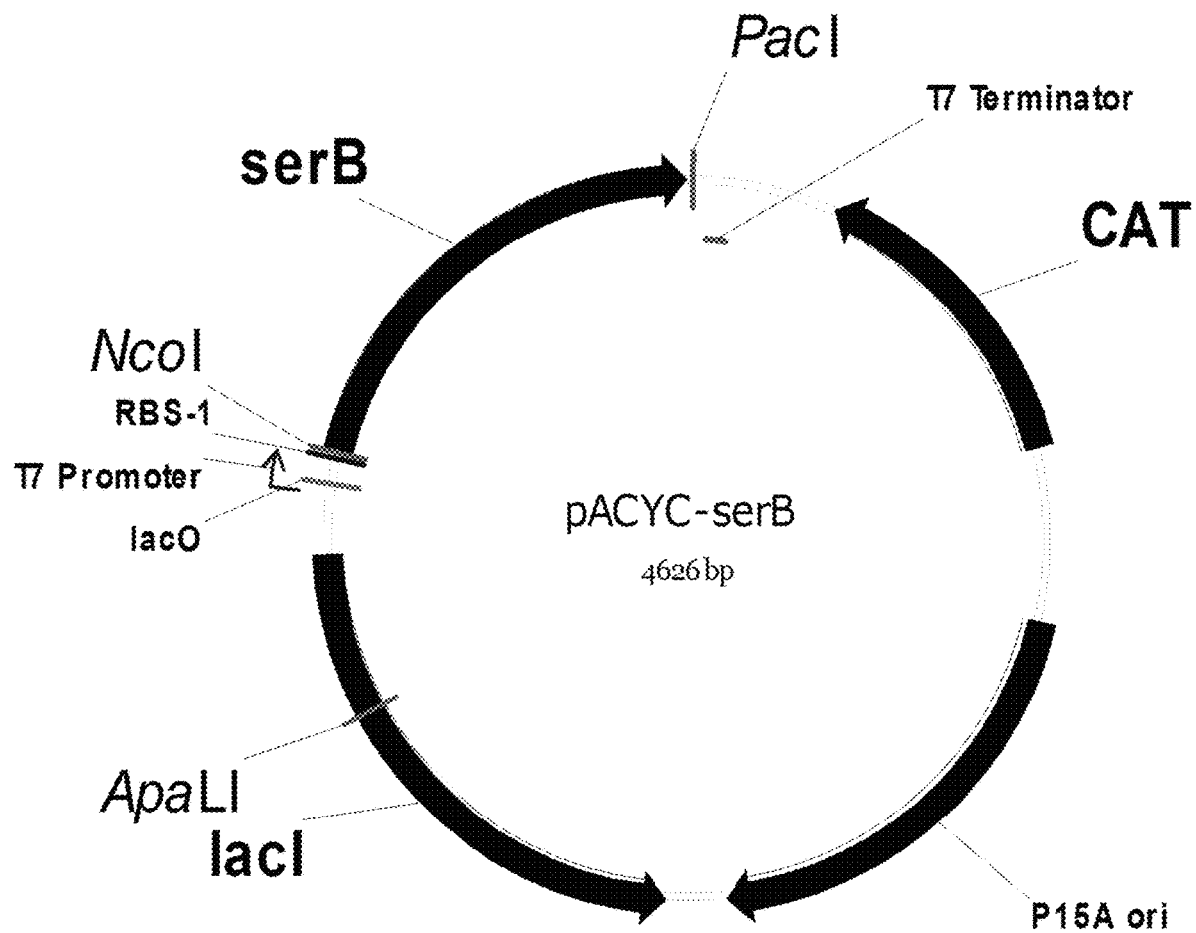
Figure 2:
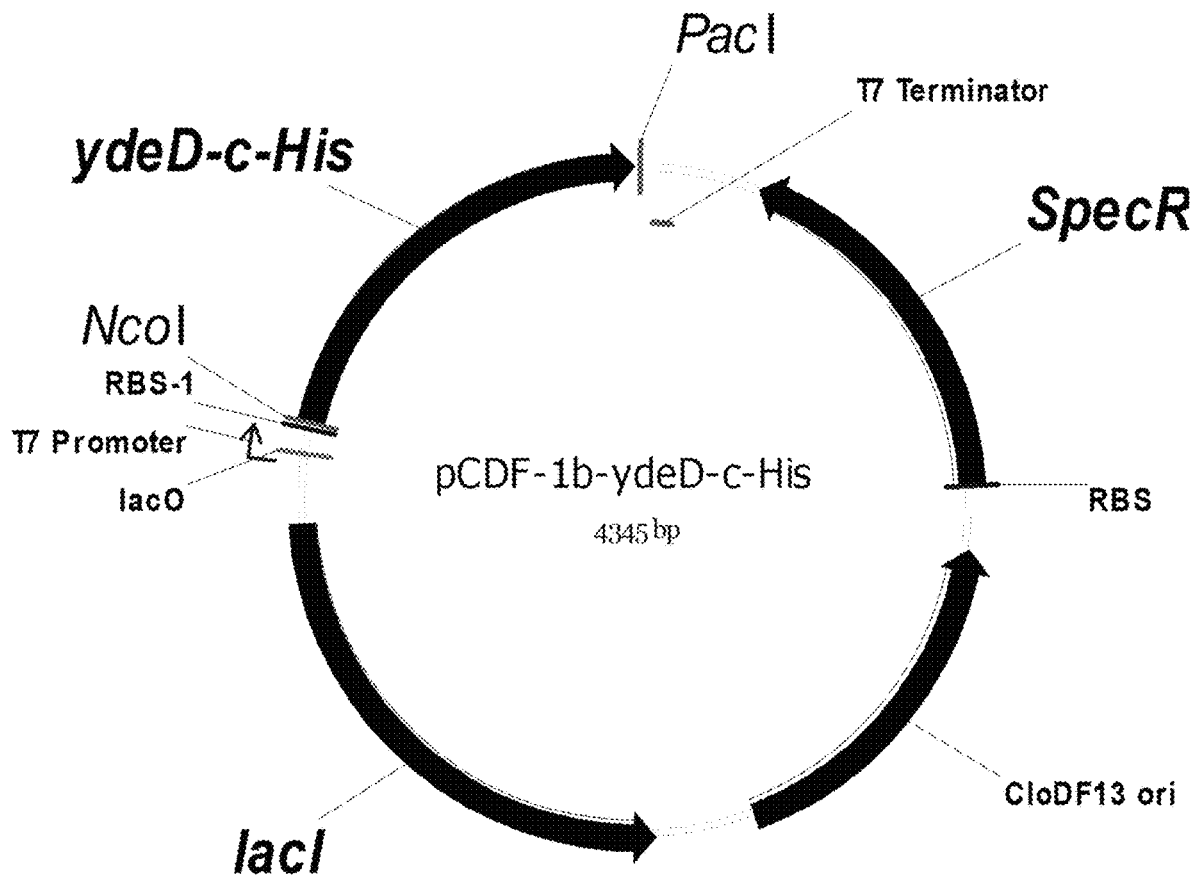

FIG. 2 shows the vector maps of the plasmid constructs.

TABLE S3

Primers used for amplification and cloning of serine production pathway

| Primer name | Sequence |
|---|---|
| serA-NcoI | GGCCCATGGCAAAG GTATCGCTGGAG |
| serA NotI_R | ATTGCGGCCGCTTAGTA CAGCAGACGGGCGCGA |
| serB_NcoI_F | GGCCCATGGCTAACATT ACCTGGTGCG |
| serB_R_HindIII | GCCAAGCTTTTATTACTT CTGATTCAGGCTGCC |
| serB_PacI_R | GCCTTAATTAATTATTAC TTCTGATTCAGGCTGCC |

TABLE S3-continued

Primers used for amplification and cloning of serine production pathway

| Primer name | Sequence |
| --- | --- |
| serC_F_NdeI | GGCCATATGATGGCTCAAA TCTTCAATTTTAGTTCTGG |
| serC_R_PacI | GCCTTAATTAATCATTAA CCGTGACGGCGTTCGAAC |
| ydeD_F_NdeI | CCGCATATGTCGCGAAAAGATGGGGTG |
| ydeD_cHis_R-PacI | GCCTTAATTAATGATGATGATGATGATGA CTTCCCACCT TTACCGCTT TACGCC |
| ydeD_NcoI_F1 | CCGCCATGGCGCGAAAAGATGGGGTG |

TABLE S4

Primers used for site directed mutagenesis of serine production pathway

| Primer name | Sequence |
| --- | --- |
| serA N364A_F | CGAGCAGGGCGTCGCTATCGCCGCGCAATA |
| serA N364A_R | TATTGCGCGGCGATAGCGACGCCCTGCTCG |
| serA H344AN 346A_F | CTGAT CACATCGCTGAAGCT CGTCCG GGCGTGC |
| serA H344AN 346A_R | GCACGCCCGGACGLAGCTTCAGCGATGTG CATCAG |
| serC_NcoIc_F | CAAGGTATTATTCTGTCATGGCGGTGGTCGCG |
| serC_NcoIc_R | CGCGACCACCGCCATGACAGAATAATACCTTG |

DE3 Integration and Serine Production During Batch Fermentation

The serine production was checked in M9 minimal media. Glucose M9 minimal media consisted of 2 g/L glucose, 0.1 mM CaCl$_2$, 2.0 mM MgSO$_4$, 1× trace element solution, and 1×M9 salts. The 4,000× trace element stock solution consisted of 27 g/L FeCl$_3$*6H$_2$O, 2 g/L ZnCl$_2$*4H$_2$O, 2 g/L CoCl$_2$*6H$_2$O, 2 g/L NaMoO$_4$*2H$_2$O, 1 g/L CaCl$_2$*H$_2$O, 1.3 g/L CuCl$_2$*6H$_2$O, 0.5 g/L H$_3$BO$_3$, and Concentrated HCl dissolved in ddH$_2$O and sterile filtered. The 10× M9 salts stock solution consisted of 68 g/L Na$_2$HPO$_4$ anhydrous, 30 g/L KH$_2$PO$_4$, 5 g/L NaCl, and 10 g/L NH$_4$Cl dissolved in ddH$_2$O and autoclaved.

To use pET vectors as expression system, a DE3 cassette containing T7 polymerase was integrated into the genome of each deletion mutant using a Lambda DE3 lysogenization kit (Millipore, Damstadt Germany). Subsequently, strains (MG1655 (DE3)) carrying single (ΔsdaA), triple (ΔsdaA, ΔtdcG, ΔsdaB), and quadruple deletions (ΔsdaA, ΔtdcG, ΔsdaB and ΔglyA) were transformed with pCDF-Duet1-serAmut-serC and pACYC-serB. The resulting glycerol stocks were grown overnight in 2YT medium containing 0.1% glucose and supplemented with required antibiotics (Spectinomycin and chloramphenicol). Overnight cultures were inoculated in triplicates into flasks containing M9 medium supplemented with 0.2% glucose, 1 mM threonine, required antibiotics (For the quadruple deletion strain, 2 mM glycine was also supplemented). Flasks were incubated at 37° C. at 250 rpm. Serine production was induced by addition of 40 µM IPTG after the cultures reached an optical density of 0.55 to 0.65. O.D. measurements and sampling were done at regular time intervals for following 60 hr. Samples were filtered and subjected to HPLC for glucose and byproduct analysis using a method described previously (Kildegaard et al., 2014) with the only exception that the column temperature was kept at 30° C. Serine concentrations were determined using LCMS. The LC-MS/MS system consisted of a CTC autosampler module, a high pressure mixing pump and a column module (Advance, Bruker, Fremont, Calif., USA). The injection volume was 1 The chromatography was performed on a ZIC-cHILIC column, 150 mm×2.1 mm, 3 µm pore size, (SeQuant, Merck Millipore). In front of the separation column was a 0.5µ depth filter and guard column, the filter (KrudKatcher Classic, phenomenex) and guard column ZIC-cHILIC, 20×2.1 mm(SeQuant, Merck). Eluent A: 20 mM ammonium acetate pH adjusted to 3.5 with formic acid in milliQ water. Eluent B: Acetonitrile. The total flow rate of eluent A and B was 0.4 ml/min. The isocratic elution 35%, and the total run time was 5 minutes. Retention time was 2.8 minutes for serine. The MS-MS detection was performed on a EVOQ triple quadrupole instrument (Bruker, Calif., USA) equipped with an atmospheric pressure ionization (API) interface. The mass spectrometer was operated with electrospray in the positive ion mode (ESI+). The spray voltage was set to 4500 V. The con gas flow was 20 l/h, and the cone temperature was set at 350° C. The heated probe gas flow was set at 50 l/h with a temperature of 350° C. Nebulizer flow was set at 50 l/h, and the exhaust gas was turned on. Argon was used as collision gas at a pressure of 1.5 mTorr. Detection was performed in multiple reacting monitoring (MRM) mode. The quantitative transition was 106→60, and the qualitative transition was 106→70. The collision energy was optimized to 7 eV for both transitions. Calibration standards of serine were prepared in media used for serine production and diluted 50:50 with 0.2% Formic acid in Acetonitrile. The concentration of the calibration standards was in the range from 0.001 to 0.5 g/L.

The experiment demonstrates that the deletion of all four genes involved in serine degradation in E. coli, referred to as Q1(DE3), results in the highest specific productivity and the highest yield from glucose as shown on FIG. 3.

Example 3: Reducing Product Toxicity by Overexpression of Transporter

Deletion of the main serine degradation pathways in E. coli results in significant decreased tolerance towards serine. In order to increase the tolerance, a transporter with a potential specificity for serine (ydeD) was overexpressed and tested during growth in high concentrations of serine. ydeD was cloned in pCDF-1b at NcoI and PacI site by amplification with primers mentioned in Table 53 and the protocol given in Example 1.

Q1(DE3) was transformed with the pCDF-1b empty vector and the pCDF-ydeD-c-His plasmid (FIG. 4). Transformants were selected on LB-spectinomycin plates. Overnight cultures of these transformants were inoculated in M9 media supplemented with 2 mM glycine, 2 g/L glucose and spectinomycin in 1:50 ratio. Cultures were incubated at 37° C. and 250 rpm at an optical density of 0.4 to 0.5, after which 800 µl was added to a 48-well biolector plate (M2P labs, Baeswieler, Germany) containing 800 µl M9 media with varying serine concentration (12.5, 25 and 50 g/L) and 2 mM glycine. The expression of ydeD was induced with 100 µM IPTG. The growth was then monitored in the Biolector instrument (M2P labs, Baeswieler, Germany) at 37° C. and 70% humidity with continuous shaking. Gain was set to 20% and scattering intensity was measured every 5 min for next 40 h.

The experiment demonstrates that the growth of *E. coli* lacking the main serine degradation pathways are severely growth inhibited in the presence of even low concentrations of serine. Upon overexpression of ydeD, the tolerance towards serine is increased substantially (FIG. 4), suggesting that YdeD may potentially transport serine out of the cell.

Example 4—Random Mutagenesis for Serine Tolerant Strain

Inactivation of the main serine degradation pathways in *E. coli* results in significant decreased tolerance towards serine. In order to increase the tolerance, the Q1 strain (obtained in Example 1) was grown in M9 media supplemented with 2 mM glycine and 3 g/L serine overnight. 1 ml of culture was spread in 6 well petri plate and exposed to UV irradiation (CBS Scientific, San Diego, Calif., USA) for 30 min. The culture was then added to 5 ml M9 media supplemented with 2 mM glycine, 2 g/L glucose and 50 g/L serine for enrichment of the tolerant mutants. The culture was incubated at 37° C. and 250 rpm for 3 days and then plated on M9 plate supplemented with 50 g/L serine for the selection of the tolerant clones. Colonies were isolated and the growth rates and tolerance was estimated using the following method:

Cultures were grown overnight in 2×YT media. They were then inoculated in 96 well flat bottom micro titer plates with 150 μL of M9 media containing 0.2% glucose and various concentration of Serine (in triplicates). For strains containing the glyA deletion, 2 mM glycine was also supplemented to the media. A total of 1.5 μL of cells (1:100) was used as inoculum. If required minor changes is volume were done to ensure equal amount of cells. Plates were sealed with Microamp clear adhesive film (Applied Biosystems, Warrington, UK) and were incubated in Microtiter plate reader (Biotek, Winooski Vt., USA). The reader was set at 37° C. with continuous shaking, and the O.D was monitored every 5 to 10 minutes at 630 nm for 32 hours.

Figure 5:
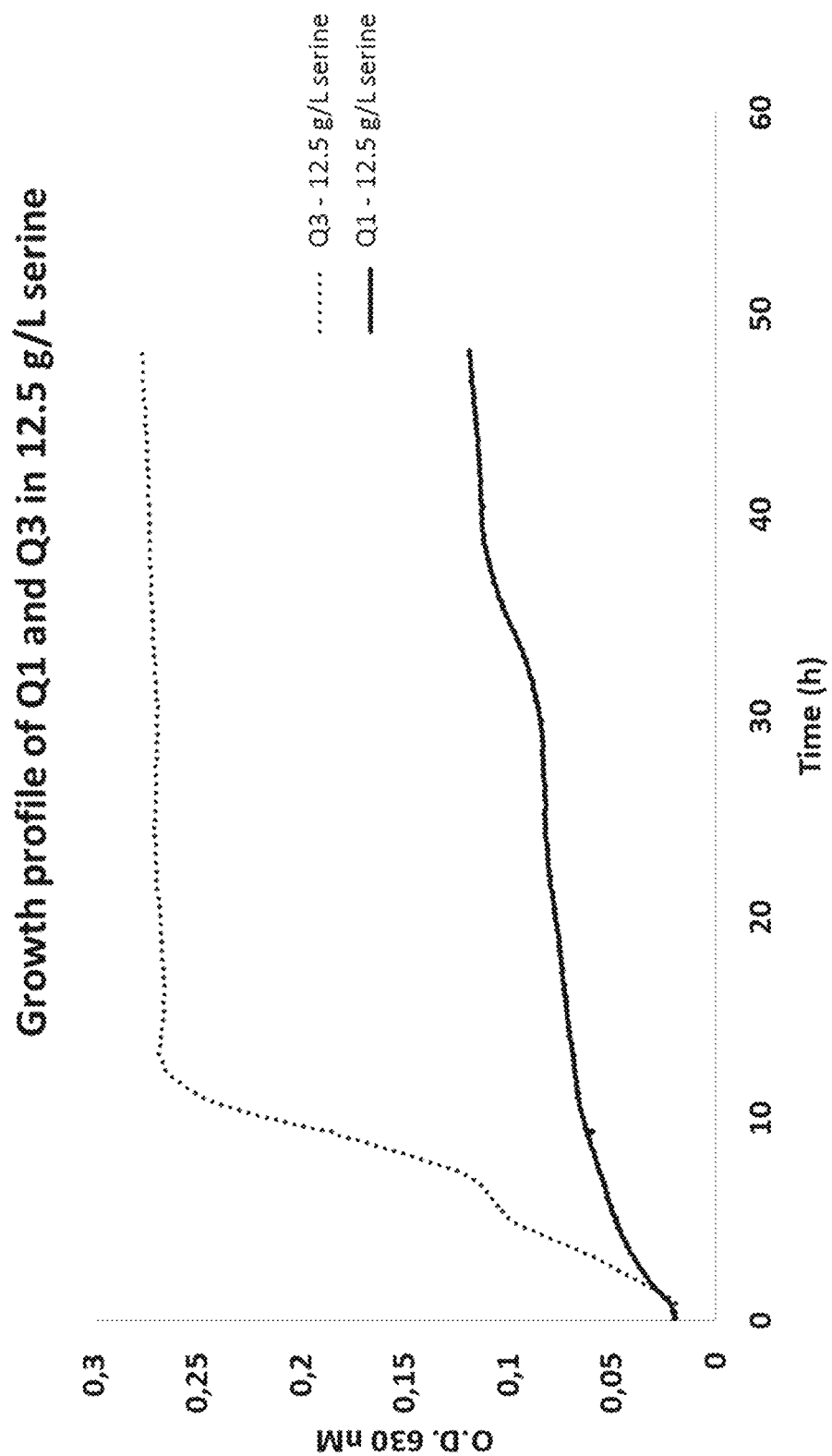
FIG. 5: Increased tolerance towards serine can be achieved by random mutagenesis. Growth rates of the parent strain (01) and evolved strains are shown at different serine concentrations.

The experiment demonstrates that random mutagenesis can be used to increase the tolerance towards serine significantly (FIG. 5). The resulting strain is referred to as Q3 below.

Example 5—Adaptive Evolution for L-Serine Tolerance

Apart from random mutagenesis, serine tolerance of a strain having the main serine degradation pathways inactivated was also increased by Adaptive evolution. Seven independent populations of the Q1 strain were adaptively evolved in M9 minimal media supplemented with 2 mM glycine and increasing concentrations of the amino acid L-Serine at 37° C. along 60 days.

Figure 6A:
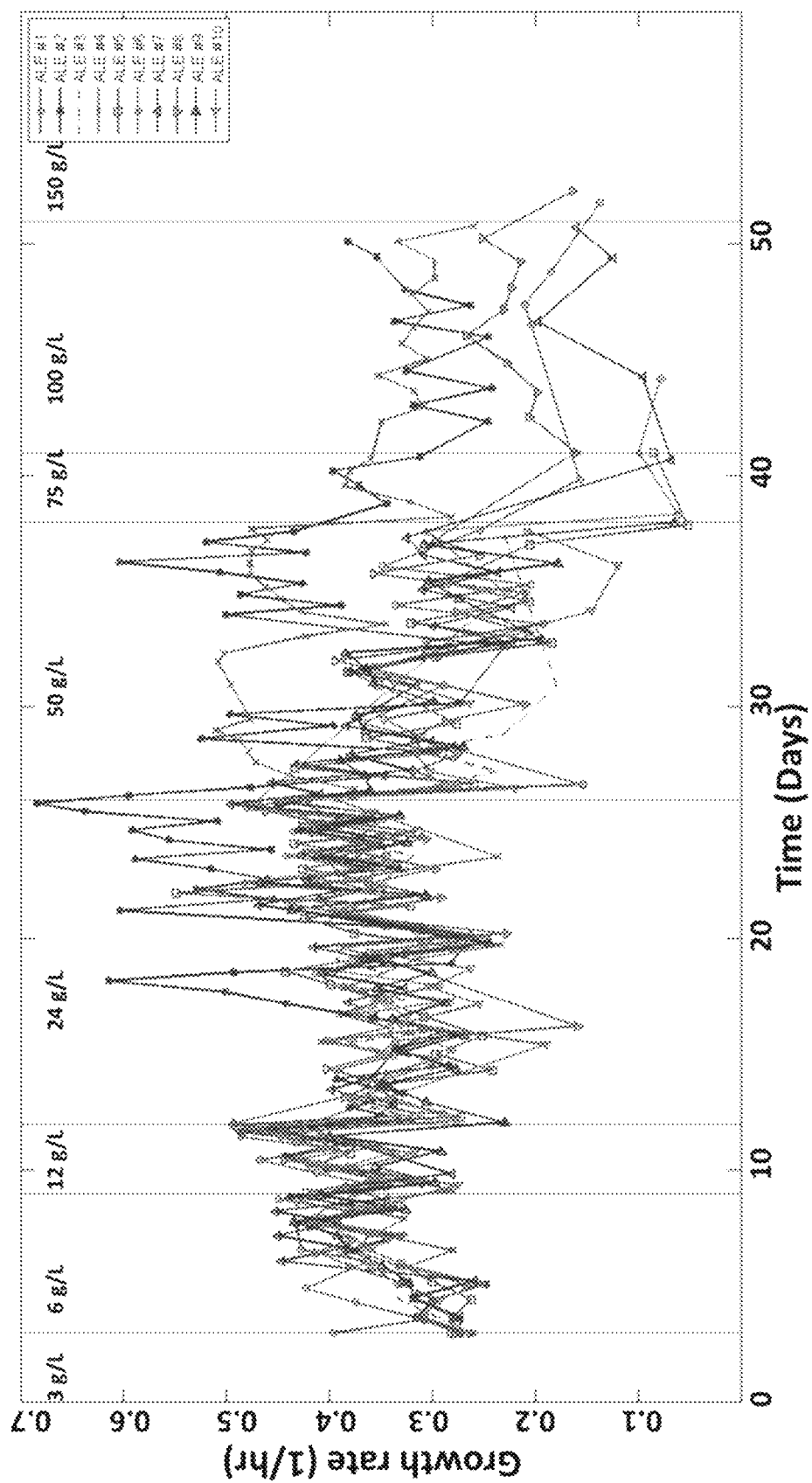
FIG. 6A-C: Adaptive Laboratory Evolution (ALE) experiment for improving tolerance towards serine.
Figure 6B:
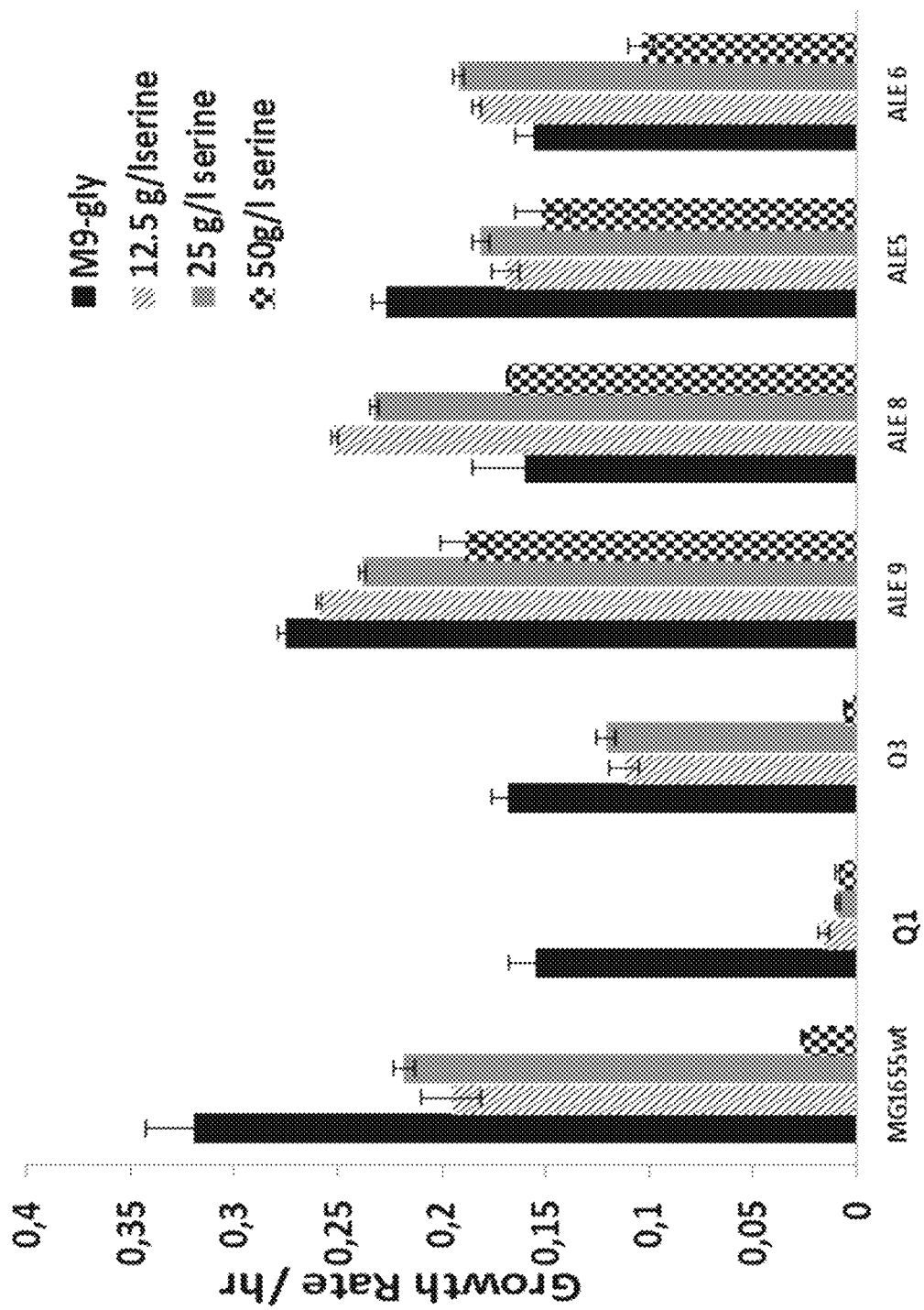
Figure 6C:
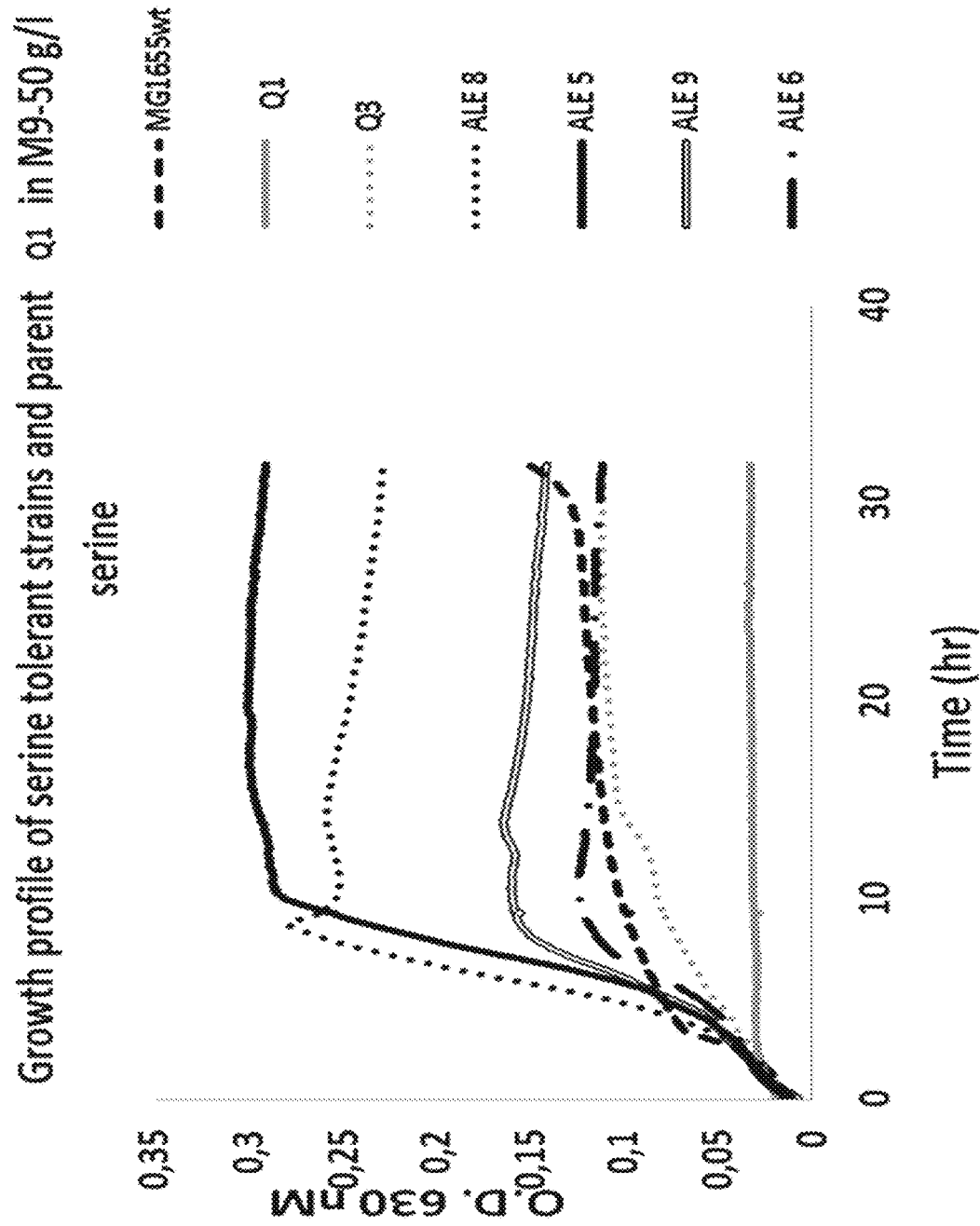

An Adaptive Laboratory Evolution (ALE) experiment was achieved by using an automated system, which enables the propagation of evolving populations over the course of many days while monitoring their growth rates. Prior to the start of the experiment, the system filled the required tubes with 25 ml of culture media and kept them at 37° C. in a heat block. Controlled aeration was obtained using magnetic tumble stirrers placed inside the tubes and spinning at 1,800 rpm. At the start of the experiment, a single colony was grown overnight in one of the tubes placed inside the system, and 100 μL aliquots were used by the robotics platform to inoculate seven independent flasks. As the bacteria grew, the automated system performed multiple OD measurements at 600 nm for each flask. Growth rates were automatically calculated by taking the slope of a least-square linear regression line fit to the logarithm of the OD measurements (FIG. 6). Once reaching a target OD of 0.4, 100 μl of culture was used to inoculate a new flask. This way, cultures were serially passed (~2-3 times per day) to flasks with fresh media after reaching a targeted cell density such that stationary phase was never reached. The populations were initially incubated with 3 g/L serine after desired growth rate was reached culture was supplemented with 6 g/L of L-Serine. When populations achieved a stable phenotype (i.e. growth rate), the L-Serine concentration was increased to 12 g/L. This process was repeated iteratively using 24, 50, 75, and 100 g/L of L-serine. The final population was plated on the LB-agar and 2 clones of each of the populations selected. The evolved strains had significantly increased tolerance when tested for growth in the presence of high concentrations of serine by using the MTP based assay described in Example 5, above. The results are shown in FIG. 6.

Genomic DNA Extraction, Library Sequencing and Analysis

Two clones of each evolved cultures as well as the strain evolved by random UV-mutagenesis (Example 5) were genome sequenced. Genomic DNA was extracted from 1.5 ml of overnight cultures of *E. coli* strains using QIAamp DNA Mini Kit (QIAGEN, Germany). The genomic libraries were generated using the TruSeq® Nano DNA LT Sample Preparation Kit (Illumina Inc., San Diego Calif., USA). Briefly, 100 ng of genomic DNA diluted in 52.5 ul TE buffer was fragmented in Covaris Crimp Cap microtubes on a Covaris E220 ultrasonicator (Covaris, Brighton, UK) with 5% duty factor, 175 W peak incident power, 200 cycles/burst, and 50-s duration under frequency sweeping mode at 5.5 to 6° C. (Illumina recommendations for a 350-bp average fragment size). The ends of fragmented DNA were repaired by T4 DNA polymerase, Klenow DNA polymerase, and T4 polynucleotide kinase. The Klenow exo minus enzyme was then used to add an 'A' base to the 3' end of the DNA fragments. After the ligation of the adapters to the ends of the DNA fragments, DNA fragments ranging from 300-400 bp were recovered by beads purification. Finally, the adapter-modified DNA fragments were enriched by 3-cycle-PCR. Final concentration of each library was measured by Qubit® 2.0 Florometer and Qubit DNA Broad range assay (Life Technologies, Paisley, UK). Average dsDNA library size was determined using the Agilent DNA 7500 kit on an Agilent 2100 Bioanalyzer. Libraries were normalized and pooled in 10 mM Tris-Cl, pH 8.0, plus 0.05% Tween 20 to the final concentration of 10 nM. Denaturated in 0.2N NaOH, 10 pM pool of 20 libraries in 600 μl ice-cold HT1 buffer was loaded onto the flow cell provided in the MiSeq Reagent kit v2 300 cycles and sequenced on a MiSeq (Illumina Inc., San Diego, Calif., USA) platform with a paired-end protocol and read lengths of 151 nt.

The breseq pipeline (Deatherage and Barrick, 2014) version 0.23 with bowtie2 (Langmead and Salzberg) was used to map sequencing reads and identify sequence variants relative to the *E. coli* K12 MG1655 reference genome (NCBI accession number NC_000913.2). Gene deletions present in the strains were verified manually based on missing coverage regions in the genome. Common variants found in MG1655 stock cultures (Freddolino et al., 2012) were excluded from further analysis. All sequencing samples had an average mapped coverage of at least 25×. The experiment identifies mutations that cause increased tolerance towards high concentrations of serine as shown in Table S5.

TABLE S5

Mutations found in the strains evolved for increased serine tolerance.
The reference number for the genome sequence is NC_000913.

| Gene Name | Change | Annotation | Q1 | Q3 | ALE5-4 | ALE5-8 | ALE6-1 | ALE6-2 |
|---|---|---|---|---|---|---|---|---|
| thrA | A -> G | Y356C | 0 | 0 | 0 | 0 | 0 | 0 |
| thrA | A -> C | S357R | 0 | 0 | 1 | 1 | 0 | 0 |
| thrA | T -> A | S359R | 0 | 0 | 0 | 0 | 1 | 1 |
| trxA/rho | IS1 -1 9 bp | Insertion[1] | 0 | 0 | 0 | 0 | 0 | 0 |
| rho | G -> T | R87L | 0 | 0 | 0 | 0 | 1 | 1 |
| gcvA/ygdI | 1 bp | Insertion[2] | 0 | 0 | 0 | 0 | 1 | 1 |
| gcvA/ygdI | IS4 1 13 bp | Insertion[3] | 0 | 0 | 1 | 1 | 0 | 0 |
| dapA/gcvR | 1 bp | Insertion[4] | 0 | 0 | 1 | 0 | 1 | 1 |
| lrp | A -> G | D143G | 0 | 0 | 0 | 0 | 0 | 0 |
| trxB/lrp | C -> T | Intergenic[9] (−271/−274) | 0 | 0 | 0 | 0 | 1 | 1 |
| frc | IS1 -1 9 bp | Insertion[5] | 0 | 0 | 0 | 0 | 0 | 0 |
| eno | C -> G | V164L | 0 | 0 | 0 | 0 | 0 | 0 |
| argP | C -> A | Q132K | 0 | 0 | 0 | 0 | 0 | 0 |
| tufA | C -> A | G19V | 0 | 0 | 0 | 0 | 0 | 0 |
| cycA | A -> G | I220V | 0 | 0 | 0 | 0 | 0 | 0 |
| rhtA/ompX/ybiP/mntS | 2854 bp | Deletion[6] | 0 | 1 | 0 | 0 | 0 | 0 |
| rpe | A -> G | I202T | 0 | 0 | 0 | 0 | 1 | 1 |
| ytfB/fklB | T -> C | Intergenic[10] (−154/−64) | 0 | 0 | 0 | 0 | 1 | 1 |
| yojL | G-->C | D334H | 0 | 0 | 0 | 0 | 1 | 0 |
| aroP | IS5 1 4 bp | Insertion[7] | 0 | 0 | 1 | 1 | 0 | 0 |
| hyaF | T -> G | V120G | 0 | 0 | 1 | 1 | 0 | 0 |
| mdtJ/tqsA | IS1 -1 9 bp | Insertion[8] | 0 | 0 | 0 | 0 | 0 | 0 |
| pykF | G -> T | E250* | 0 | 0 | 1 | 1 | 0 | 0 |
| malT | C -> T | Q420* | 0 | 0 | 1 | 1 | 0 | 0 |
| rpoB | C -> T | P520L | 0 | 0 | 1 | 1 | 0 | 0 |
| fumB | T -> G | T218P | 0 | 0 | 0 | 0 | 0 | 0 |
| gshA | G-->A | A178V | 0 | 0 | 0 | 1 | 0 | 0 |
| lamB | C-->T | Q112* | 0 | 0 | 0 | 1 | 0 | 0 |

| Gene Name | Change | Annotation | Q1 | ALE8-3 | ALE8-8 | ALE9-3 | ALE9-8 |
|---|---|---|---|---|---|---|---|
| thrA | A -> G | Y356C | 0 | 1 | 1 | 1 | 1 |
| thrA | A -> C | S357R | 0 | 0 | 0 | 0 | 0 |
| thrA | T -> A | S359R | 0 | 0 | 0 | 0 | 0 |
| trxA/rho | IS1 -1 9 bp | Insertion[1] | 0 | 1 | 1 | 1 | 1 |
| rho | G -> T | R87L | 0 | 0 | 0 | 0 | 0 |
| gcvA/ygdI | 1 bp | Insertion[2] | 0 | 0 | 0 | 0 | 0 |
| gcvA/ygdI | IS4 1 13 bp | Insertion[3] | 0 | 0 | 0 | 0 | 0 |
| dapA/gcvR | 1 bp | Insertion[4] | 0 | 0 | 0 | 0 | 0 |
| lrp | A -> G | D143G | 0 | 1 | 1 | 1 | 1 |
| trxB/lrp | C -> T | Intergenic[9] (−271/−274) | 0 | 0 | 0 | 0 | 0 |
| frc | IS1 -1 9 bp | Insertion[5] | 0 | 1 | 1 | 1 | 1 |
| eno | C -> G | V164L | 0 | 1 | 1 | 1 | 1 |
| argP | C -> A | Q132K | 0 | 1 | 1 | 1 | 1 |
| tufA | C -> A | G19V | 0 | 1 | 1 | 1 | 1 |
| cycA | A -> G | I220V | 0 | 1 | 1 | 1 | 1 |
| rhtA/ompX/ybiP/mntS | 2854 bp | Deletion[6] | 0 | 0 | 0 | 0 | 0 |
| rpe | A -> G | I202T | 0 | 0 | 0 | 0 | 0 |
| ytfB/fklB | T -> C | Intergenic[10] (−154/−64) | 0 | 0 | 0 | 0 | 0 |
| yojL | G-->C | D334H | 0 | 0 | 0 | 0 | 0 |
| aroP | IS5 1 4 bp | Insertion[7] | 0 | 0 | 0 | 0 | 0 |
| hyaF | T -> G | V120G | 0 | 0 | 0 | 0 | 0 |
| mdtJ/tqsA | IS1 -1 9 bp | Insertion[8] | 0 | 0 | 0 | 0 | 1 |
| pykF | G -> T | E250* | 0 | 0 | 0 | 0 | 0 |
| malT | C -> T | Q420* | 0 | 0 | 0 | 0 | 0 |
| rpoB | C -> T | P520L | 0 | 0 | 0 | 0 | 0 |

TABLE S5-continued

Mutations found in the strains evolved for increased serine tolerance.
The reference number for the genome sequence is NC_000913.

| fumB | T –> G | T218P | 0 | 0 | 0 | 1 | 0 |
| gshA | G-->A | A178V | 0 | 0 | 0 | 0 | 0 |
| lamB | C-->T | Q112* | 0 | 0 | 0 | 0 | 0 |

*designates a stop codon

Insertion[1]Insertion of a 768 bp long insertion sequence element IS1 in the lagging strand at the location 3966174, which is an intergenic region between genes trxA and rho. Duplication of 9 bp upstream and downstream of insertion sequence is observed.
Insertion[2]Insertion of 1 bp at location 2942629, which is an intergenic region between genes genes gcvA and ygdI.
Insertion[3]Insertion of 1342 bp long insertion sequence element IS4 at the location 2942878, which is an intergenic region between genes gcvA and ygdI. Duplication of around 13 bp upstream and downstream of insertion sequence is observed.
Insertion[4]Insertion of 1 bp at location 2599854, which is an intergenic region between genes genes dapA and gcvR.
Insertion[5]Insertion of 768 bp long insertion sequence element IS1 in the lagging strand at location 2492323, which leads to a truncation of gene frc. Duplication of 9 bp upstream and downstream of insertion sequence is observed.
Deletion[6]Deletion of 2854 bp from location 850092, resulting in deletion of the first 5 bp of rhtA, complete deletion of genes ompX and ybiP, deletion of 239 bp of sRNA rybA and 77 bp deletion of mntS gene.
Insertion[7]Insertion of 1195 bp long insertion sequence element IS5 at location 121518 which leads to deletion of the majority of aroP. Duplication of 4 bp upstream and downstream of insertion sequence is observed.
Insertion[8]Insertion of 768 bp long insertion sequence element IS1 in the lagging strand at location 1673670, which is an intergenic region between genes mdtJ and tgsA. Duplication of 9 bp upstream and downstream of insertion sequence is observed.
Intergenic[9]C –> T mutation at location 923321 which is an intergenic region between trxB and lrp. The mutation is 271 bp upstream of of trxB and 274 bp upstream of lrp.
Intergenic[10]T –> C mutation at the location 4428871 which is an intergenic region between yftB and fklB. The mutation is 154 bp upstream of yftB and 64 bp upstream of fklB.

Example 6—Reverse Engineering of ALE Mutations by Cam-sacB System and Multiplex Genome Engineering In order to identify mutations that cause increased tolerance towards serine, the mutations identified in Example 5 were introduced into the Q1(DE3) strain using two different methods as described below.

A. Introduction of thrA Mutations

Mutations in thrA were introduced into the genome of the Q1(DE3) strain using a cam-sacB based selection system. Cam-sacB was inserted using pKD46 plasmid harboring exo, beta and gamma genes for recombination. Positive selection for cassette insertion was done by selecting clones for chloramphenicol resistance. The loss of cassette was selected by replica plating clones on LB-chloramphenicol and LB-sucrose plate containing 15% sucrose (no NaCl). The Cam-sacB cassette was amplified using thrA_camsacB_F and R (Table 56) primers respectively. Apart from template and extention time, the reaction mixture and PCR program was the same as described in example 1. The extension time was 2 min and 30 sec, while template was 1 µl of overnight culture of the E. coli culture containing cam-sacB cassette. Competent Q1(DE3) cells were then transformed with 200 ng of thrA-cam-sacB cassette, and were plated on LB-chloramphenicol-ampicillin plates after two hour and incubated overnight at 30° C. A single colony was picked and made electrocompetent after 1 h of induction (Example 1) and transformed with thrA alleles. After 2 hours of recovery, cells were plated on LB-sucrose plates and incubated at 37° C. to cure pKD46 plasmid. 24 clones of each experiment were replica plated on LB-chloramphenicol and LB plates. Clones that did not grow on chloramphenicol plates were checked for the loss of the cassette by colony PCR and were subsequently sequenced by Sanger sequencing.

All three strains containing thrA mutations (Y356C, S357R or S359R) were grown in M9 media supplemented with 2 mM glycine, 2 g/L glucose and 6.25 g/L L-serine. In this experiment, the background was not subtracted from the measurements, resulting in apparent increase in the OD for the Q1 strain. However, under these conditions, the 01 strain did not show significant growth. On the other hand, each of the thrA mutations resulted in a similar and very significant increase in tolerance towards L-serine (FIG. 7), allowing them to grow at a L-serine concentration of at least 6.25 g/L opposed to the parent Q1 strain. Since all thrA mutants had same growth profile, S357R mutant was chosen as the parent strain (referred to as strain Q1(DE3)-thrAS357R) for the multiplex genome engineering described below.

TABLE S6

Primers used for genome integration of thrA mutations in the genome.

| Primer name | Sequence |
| --- | --- |
| thrA_gF | ATGCGAGTGTTGAAGTTCGGCG |
| thrA_gR | TCAGACTCCTAACTTCCATGAGAGGG |
| thrA_camsacB_F | ATGCGAGTGTTGAAGTTCGGCGGTACA TCAGTGGCAAATGCAGAACGTTTAAAAT GAGACGTTGATCGGCACG |
| thrA_camsacB_R | TCAGACTCCTAACTTCCATGAGAGGGTA CGTAGCAGATCAGCAAAGACACCAAAG GGAAAACTGTCCATATGCAC |

Figure 8:
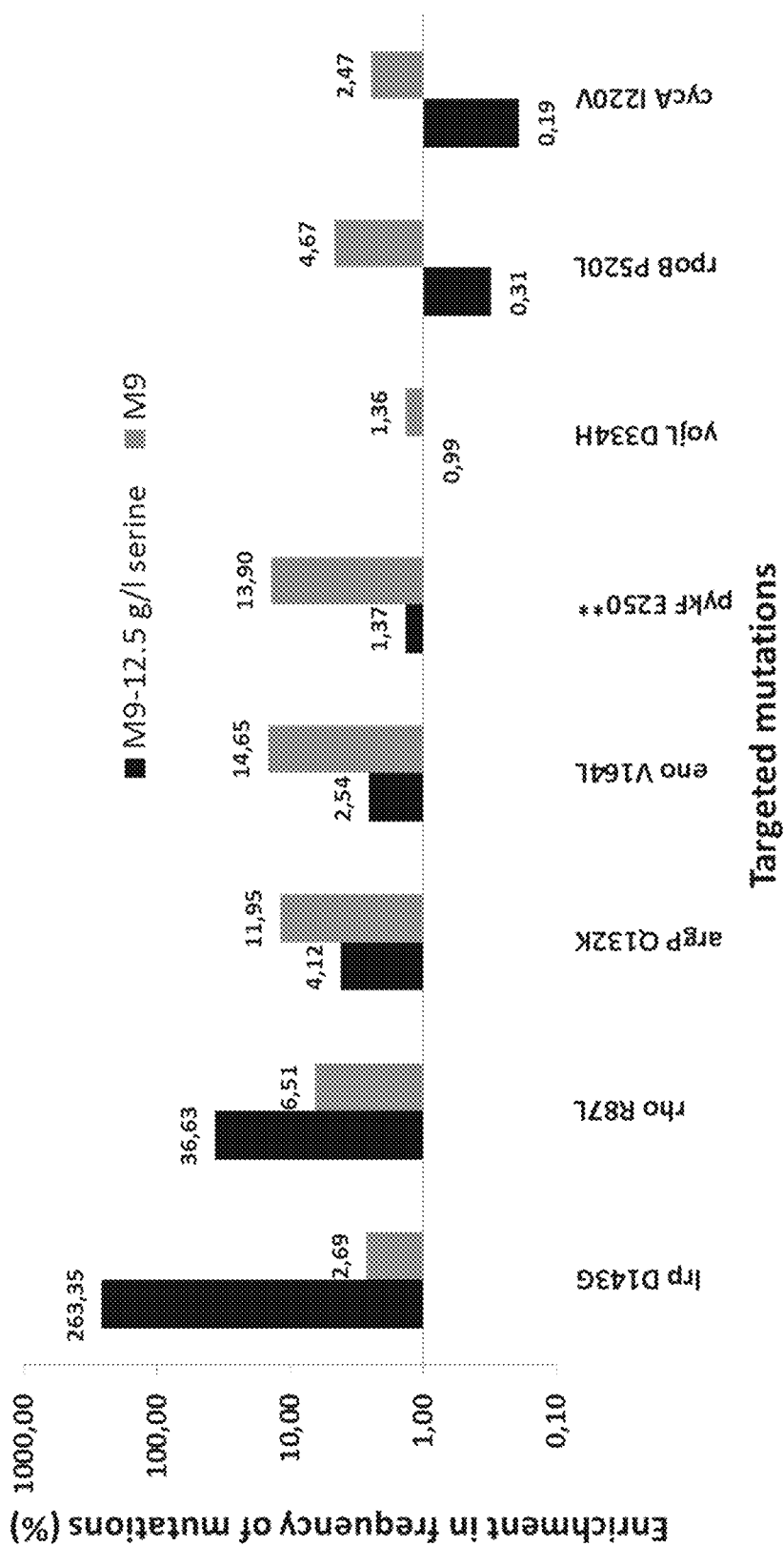
FIG. 8: Identification of mutations that cause increased tolerance towards serine. Amplicon sequencing analysis was used to analyze the effect of ALE mutations after introduction into the Q1 (DE3) strain by MAGE.

B. Multiplex Genome Engineering, Screening and Amplicon Sequencing of Selected ALE Mutations In order to identify mutations that cause increased tolerance towards serine, selected mutations identified in Example 5 were introduced into the Q1(DE3)-thrAS357R strain using multiplex genome engineering (Wang et al., 2011). The protocol applied for multiplex genome engineering was similar to the method published by Wang and Church, 2011. Strain Q1(DE3)-thrAS357R was transformed with plasmid pMA1 (containing only beta protein under control by the arabinose inducible promoter). Clones were plated on LB-ampicillin plates and incubated at 37° C. Colonies were cultured overnight in TY-amp-gly media at 37° C. and re-inoculated in 25 ml fresh TY-gly media the following day. After reaching an O.D. of 0.4 at 37° C., arabinose was added to a final concentration of 0.2%. Cells were re-incubated at 37° C. and 250 rpm for additional 15 min and were then made electro-competent by washing twice with 10% glycerol (ice cold). Final volume of electro competent cells was adjusted to 200 µl using 10% glycerol. The primers targeting the loci (lrp D143G, eno V164L, argP Q132K, cycA I220V, pykF E250*, rpoB520L, gcvA*, yojL D334H, rho R87L) are given in Table S7. All primers were pooled and adjusted to a final concentration of 10 pmol/µl. To 50 µl of cells, 1 µl of this mix was added and transformed by electroporation. The transformed cells were directly added to 25 ml TY-gly media and were incubated at 37° C., 250 rpm for two hours to reach O.D. of 0.4, followed by arabinose induction and transformation as above for second round of multiplex engineering. The process was repeated six times. After the 6th round of multiplex genome engineering, the cells were incubated overnight. The resulting library of mutants was subsequently grown in M9 minimal media with and without serine. This way, mutations resulting in increased growth rates in minimal media or increased tolerance towards serine were enriched: A total of 1.5 µl of overnight culture was added in triplicates to wells in micro titer plates containing 150 µl triplicates of M9 media supplemented with 2 mM glycine and 2 g/L glucose (minimal media) or M9 media with 2 mM glycine, 2 g/L glucose and 25 g/L serine (minimal media with serine). Growth profiles were monitored at 37° C. with continuous fast shaking in a microtiter plate reader for 40 hr. Optical density was measured at 630 nm every 5 min. Triplicates were pooled and used as template for amplicon generation. The PCR program and reaction composition was as described in Example 1. Illumina protocol was followed for amplicon processing and next gen sequencing was as described in Example 5. Sequencing results were analyzed computationally, and the enrichment of the various mutations was calculated as the frequency of the mutations in either minimal media or minimal media with serine, divided by the frequency of the mutations in the unselected library (FIG. 8). This experiment shows that the mutations in lrp, rho, argP and eno results in increased tolerance towards serine.

TABLE S7

Primers used for Multiplex genome engineering

| Primer name | Sequence |
| --- | --- |
| lrpD143G | GCTTGACTTCTTCCATAACAAC GTAAGTGCGCGTCCCGTTAACC CCAGGCAGACGCAGCAGGGTTTC |
| enoV164L | CCAACCGGCTGAATCATGAATTCTTGA ATGTCGAGATTATTATCAGCGTGCTCA CCACCGTTGATGATG |
| argPQ132K | CTCAACTTGCAGGTAGAAGATGAAACGA GGAAAGAGAGGCTCCGCCGCGGCGAAGT GGTCGGC |
| cycAI220V | CAGCTCAATCCCCACGAAAGCTAATACG GCAACTTGAAAACCGGCAAAGAAGCCAC TTAAACCTTTC |
| pykFE250*** | GCATCATGGTTGCGCGTGGCGAC CTCGGCGTTTAGTGACCCTAAAT CTTCGCCCAGAAGATGATGA |
| rpoBP520L | GATACGACGTTTGTGCGTAATTTCTGA GAGGAGATTATTTTGGTCCATAAACTG AGACAGCTG |
| gcvA*** | CTCGTAAGGCATTTAGCGGTGGTA ATG GTTATCATTAGGCTATTAAACTTTGATG TTAAATG |
| yojLD334H | GGTGAGATTAATCGGACCAACGGAGAAG GCATTGTGTTGGTATGCAAACGTCACGT TACGCAGCTCCAGC |

TABLE S7-continued

Primers used for Multiplex genome engineering

| Primer name | Sequence |
| --- | --- |
| rhoR87L | GAGATGGTATCACCAGTGCGGAGATTAA ATCTTAGTATCTGAGAAGGGGAAACGTA GATGTCATCAG |

TABLE S8

Primers used for amplicon sequencing

| Primer name | Sequence |
| --- | --- |
| lrp_F | TCGTCGGCAGCGTCAGATGTGTATAAGAGACAGCG GTGATTTCGACTACCTGTTG |
| lrp_R | GTCTCGTGGGCTCGGAGATGTGTATAAGAGACAGG CGCGTCTTAATAACCAGACGAT |
| enoV164_F | TCGTCGGCAGCGTCAGATGTGTATAAGAGACAGGC TGTACGAGCACATCGCTGAAC |
| enoV164_R | GTCTCGTGGGCTCGGAGATGTGTATAAGAGACAGC CCATGCGGATGGCTTCTTTCAC |
| argP_F | TCGTCGGCAGCGTCAGATGTGTATAAGAGACAGGA CAGTCTGGCGACGTGGTTGCT |
| argP_R | GTCTCGTGGGCTCGGAGATGTGTATAAGAGACAGT ATCGACAAGACAACTCGGCAGCG |
| cycA_F | TCGTCGGCAGCGTCAGATGTGTATAAGAGACAGGG AAGCGTCATTCGCGCATTTG |
| cycA_R | GTCTCGTGGGCTCGGAGATGTGTATAAGAGACAGG TTAATCGCGCGTGGCAGTG |
| pyfK_F | TCGTCGGCAGCGTCAGATGTGTATAAGAGACAGGG CCTCAACAACTTCGACGA |
| pyfK_R | GTCTCGTGGGCTCGGAGATGTGTATAAGAGACAGG AATCCAGCATCTGGGTCGC |
| rpoB_F | TCGTCGGCAGCGTCAGATGTGTATAAGAGACAGCA ACGCCAAGCCGATTTCCG |
| rpoB_R | GTCTCGTGGGCTCGGAGATGTGTATAAGAGACAGG TCTCGAACTTCGAAGCCTGC |
| gcvA_F | TCGTCGGCAGCGTCAGATGTGTATAAGAGACAGGC TGGTAGAAGCTCAACGGAC |
| gcvA_R | GTCTCGTGGGCTCGGAGATGTGTATAAGAGACAGT GCTGCGGCATCAAAAACTCG |
| yojI_F | TCGTCGGCAGCGTCAGATGTGTATAAGAGACAGGC CTTTCAAAGCAGAGTTTCCGC |
| yojI_R | GTCTCGTGGGCTCGGAGATGTGTATAAGAGACAGC TACCGTTGCCGCCAATCAG |
| rho_F | TCGTCGGCAGCGTCAGATGTGTATAAGAGACAGGC AGGATGGATTTGGTTTCCTCC |
| rho_R | GTCTCGTGGGCTCGGAGATGTGTATAAGAGACAGG CAGCGCAAAATAGCGTTCACC |

Example 7—Serine Production by Tolerant and Susceptible *E. coli* During Fed Batch Fermentation A new vector was constructed in order to upregulate expression of exporter along with serine pathway in the pACYC-Duet vector by following the same above strategy as mentioned in Example 2. serB was cloned using NcoI and HindIII double digestion followed by ligation. The resulting vector (pACYC-Duet-serB) was then subjected to double digestion by NdeI and PacI for cloning of ydeD-c-His. Both strains 01 (DE3) and Q3 (DE3) were made electrocompetent by growing cells in 30 ml 2×YT media supplemented with 0.2% glucose (37° C., 250 rpm) to mid log phase. Cells were harvested by centrifugation at 6500 rpm for 5 min at 4° C., and were washed twice by ice cold 10% glycerol. Cells were finally resuspended in 500 µL of 10% glycerol and 50 µL of cells were transformed with plasmids pCDF-Duet1-serAmut-serC and pACYC-serB-ydeD-c-His for serine production.

Serine production was demonstrated during fed batch fermentation in 1 L fermenters (Sartorius, Gottingen, Germany). The media contained 2 g/L MGSO4*7H2O, 2 g/L KH2PO4, 5 g/L (NH4)2SO4, 7.5 g/L Glucose, 2 g/L Yeast extract, 0.6 g/L glycine, 0.12 g/L threonine, 4× trace element (as mentioned in Example 2), 50 mg/L spectinomycin and 25 mg/L chloramphenicol. For the *E. coli* Q1(DE3) strain, the initial glucose concentration was 10 g/L in order to enhance the growth before induction. The feed generally contained 140 g/L glucose, 24 g/L Ammonium sulfate, 2 g/L glycine, 0.12 g/L threonine, 2.5 g/L each of MGSO4*7H2O and KH2PO4, 1× trace elements 50 mg/L spectinomycin and 25 mg/L chloramphenicol, while the feed for the Q1(DE3) strain contained 120 g/L of glucose.

A log phase culture was used to inoculate 500 ml media by 1:50 inoculum ratio. The cultures were allowed to grow over night in the fermenter at 37° C., 1000 rpm baffle speed and 20% air saturation. Feed at the rate of 8 g/h was started after glucose concentration was below 250 mg/L in the media. Production was induced at late log phase (O.D. 7.5 to 9.5) by the addition of 40 µM IPTG and feed rate was reduced to 6 g/h. Samples were taken at regular intervals and were subjected to HPLC and LCMS analysis as mentioned before.

Figure 9A:
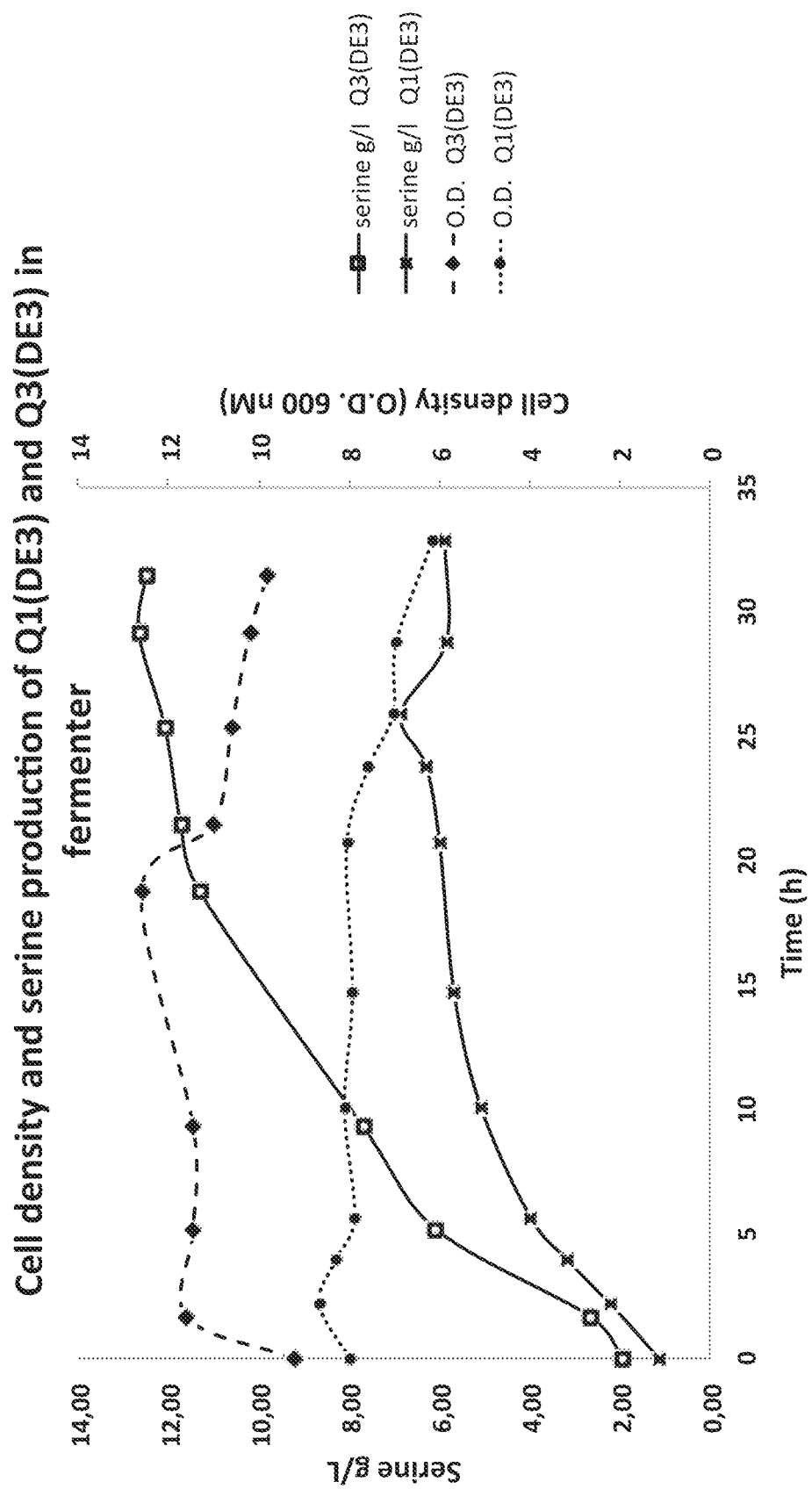
FIG. 9A-B.
Figure 9B:
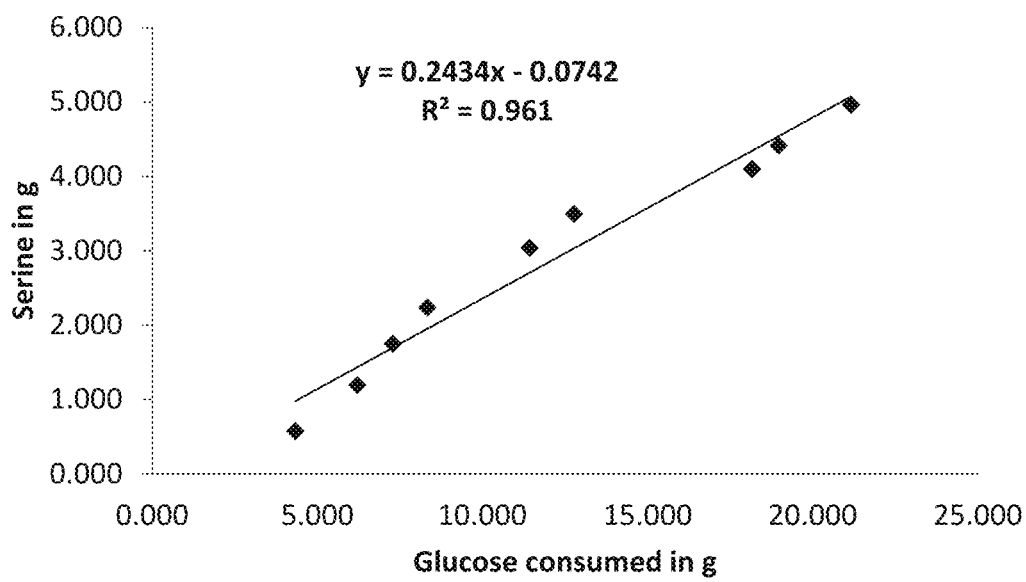
Figure 9B:
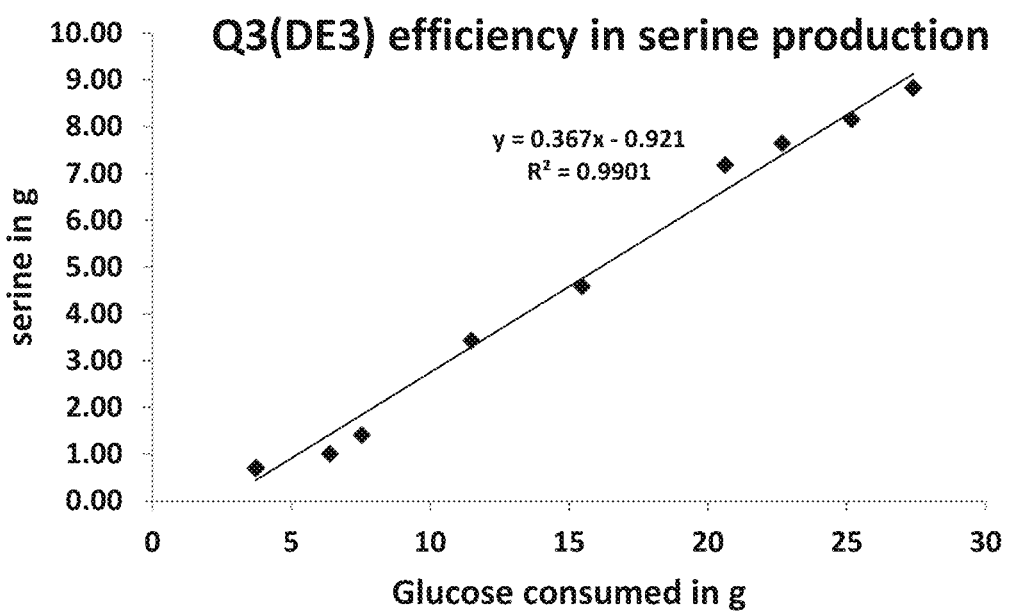

The experiment demonstrates that serine can be produced at high titer and with a high yield in *E. coli* using fed batch fermentation (FIG. 9). The titers were 6.8 g/L and 12.5 g/L for the Q1(DE3) and the Q3(DE3) strain, respectively. The fermentations resulted in a surprisingly high mass yield of 36.7% from glucose in the Q3(DE3) strain when compared to 24.3% in the Q1(DE3) strain (FIG. 9B). This shows that a higher titer and yield can be achieved using the production strain that is tolerant towards serine.

Example 8—Reverse Engineered Strains Showing Increased Serine Production

Strains reverse engineered in Example 6 were checked for serine tolerance as mentioned in Example 3. The best serine tolerant strain (F7) was checked for serine production and was also genome sequenced as described in Example 5. Plasmids for overexpression of the serine production pathway were introduced as described in Example 7. Shake flask experiments were carried out as described in Example 2, with the only difference being that the concentration of glucose was 2.5 g/L. The O.D. measurements and sampling were done at regular intervals, and the samples were analyzed using methods described in Example 2. Surprisingly, said strain resulted in a significantly increased production and yield of serine from glucose as shown in Table S9. The genome sequence revealed a deletion of zwf, which encodes the first enzyme in the pentose phosphate pathway. Additionally the strain carried the thrAS357R and rhoR87L mutations. Furthermore the strain also had a truncation of the branched chain amino acid exporter brnQ (105 bp was deleted starting at location 419986. The 439 amino acid protein was truncated after 308 amino acids).

TABLE S9

Effect of Δzwf on production of serine

| | Serine concentration in g/L (+/−standard diviation) | Yield from glucose (g serine/g glucose) |
|---|---|---|
| ΔsdaA ΔsdaB ΔtdcG ΔglyA (Q1) | 0.925 (+/−0.048) | 0.37 |
| ΔsdaA ΔsdaB ΔtdcG ΔglyA Δzwf ΔbrnQ thrA S357R rho R87L | 1.323 (+/−0.06) | 0.53 |

Example 9—Production by ALE 8

To use pET vectors as expression system, a DE3 cassette containing T7 polymerase was integrated into the genome of the ALE 8-8 mutant (Example 5) using a Lambda DE3 lysogenization kit (Millipore, Damstadt Germany) resulting in the strain ALE 8-8(DE3). Subsequently, the ALE 8-8 (DE3) was made electrocompetent by growing cells in 30 ml 2×YT media supplemented with 0.2% glucose (37° C., 250 rpm) to mid log phase. Cells were harvested by centrifugation at 6500 rpm for 5 min at 4° C., and were washed twice by ice cold 10% glycerol. Cells were finally resuspended in 500 µL of 10% glycerol and 50 µl of cells were transformed with plasmids pCDF-Duet1-serAmut-serC and pACYC-serB for serine production.

Serine production was demonstrated during fed batch fermentation in 1 L fermenters (Sartorius, Gottingen, Germany) as mentioned in Example 7. The media contained 2 g/L MGSO4*7H2O, 2 g/L KH2PO4, 5 g/L (NH4)2SO4, 10 g/L Glucose, 2 g/L Yeast extract, 0.6 g/L glycine, 4× trace elements (as mentioned in Example 2), 50 mg/L spectinomycin and 25 mg/L chloramphenicol. The 375 g of feed contained 400 g/L glucose, 24 g/L Ammonium sulfate, 2 g/L glycine, 2.5 g/L of MGSO4*7H$_2$O and 5 g/L of KH2PO4, 1× trace elements 50 mg/L spectinomycin and 25 mg/L chloramphenicol. A log phase culture was used to inoculate 500 ml media by 1:50 inoculum ratio. The cultures were allowed to grow overnight in the fermenter at 37° C., 1000 rpm baffle speed and 20% air saturation. Production was induced at late log phase (O.D. 8.5 to 9.5) by the addition of 80 µM IPTG and feed at the rate of 8 g/h was started. Samples were taken at regular intervals and were subjected to HPLC and LCMS analysis as mentioned before.

Figure 10:
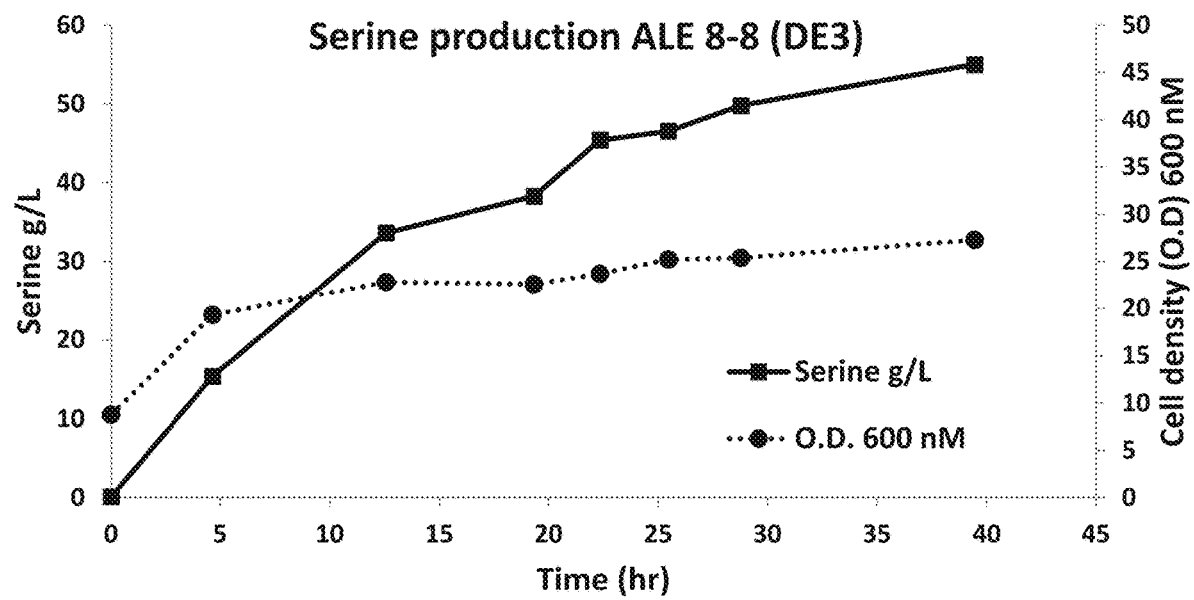
FIG. 10: (A) Cell density and serine titer of ALE 8-8 (DE3) strain. (B) Mass yield from glucose.
Figure 10:
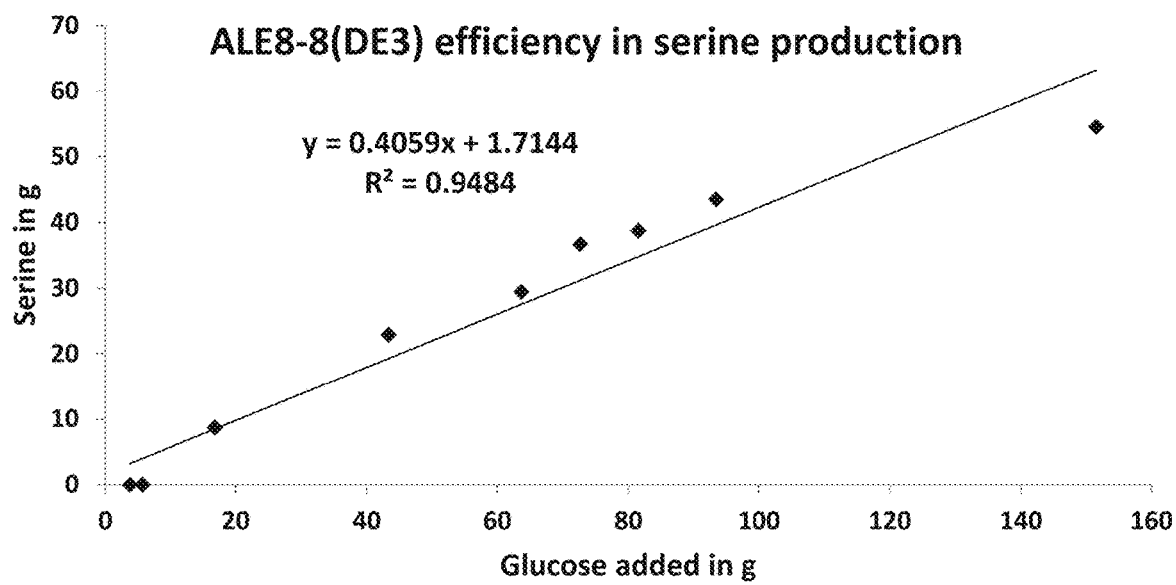

The experiment shows that both a high cell density and a high serine titer (55.0 g/L) can be obtained in ALE 8-8 (DE3) strain (FIG. 10A) with a mass yield from glucose of 36.0% (FIG. 10B).

Example 10—Over Expression and Site Saturation Mutagenesis of thrA at Site Y356, S357 and S359

Using site saturation mutagenesis (SSM), the selected amino acid residue/s can be mutated to all other 20 amino acids. This makes it possible to investigate the effect of amino acid substitutions on the enzyme activity and in turn on phenotype. The thrA gene was amplified from MG-1655 wt strain using primers thrA_NcoI_F and thrA_HindIII (primer sequences in Table 510) and cloned in pACYC-Duet1 plasmid using NcoI and HindIII enzyme. The protocol of cloning was same as for cloning serB in Example 2. The vector constructed was pACYC-thrA. This plasmid was used as a template for SSM. SSM for observed thrA mutations in ALE strains (Y356, S357 and S359) was performed using primers given in Table S10. The SSM protocol was similar to SDM protocol applied in Example 2 for mutagenesis of feedback insensitive serA. PCR product was DpnI digested and transformed in 01 (DE3) strain, which carries the wild type thrA gene in its genome, and plated on LB-chloramphenicol plates supplemented with 0.1% glucose and 4 mM glycine. Chloramphenicol was supplemented in all following media for plasmid stability.

Individual colonies were picked and inoculated into 96 well MTP plate containing 2× TY media supplemented with 0.1% glucose and 2 mM glycine. 90 clones (1 microtiter plate (MTP)) from each SSM library was picked (in total 3 plates). The Q1(DE3) strain harboring pACYC-Duet empty vector and pACYC-thrAwt was inoculated as a control strain in each plate. The plate was incubated at 37° C. and 300 rpm overnight. This pre-culture plate was used as inoculum from which 1 µL was added to a new 96 well MTP plate containing 100 µL of M9 media supplemented with 0.2% glucose, 2 mM glycine. The culture was incubated for 4 h after which 25 uL of 1 mM IPTG was added to induce the expression. The plate was subsequently incubated for 2 h and then M9 media containing 0.2% glucose, 2 mM glycine and 12.5 g/L L-serine was added thus reaching final serine concentration of 6.25 g/L. The plate was then incubated with shaking in an MTP reader for growth analysis as described before. Selected clones showing tolerance from each plate were collected in 1 plate and the tolerance studies were repeated for these strains. The plasmids from the tolerant cloned were sequenced and the growth rates were estimated from the log phase of culture. This way, a number of amino acid substitutions that result in tolerance towards serine were identified (FIG. 11). FIG. 11 (A-C) shows the growth rate of mutant strains having different amino acid substitutions observed at positions 356, 357 and 359 of ThrA, respectively (denoted by the respective one-letter code). The growth rate of E. coli carrying the wild type thrA gene is denoted "wt".

The experiment demonstrates that amino acid substitutions at position 356, 357 and/or 359 in the native ThrA protein confer increased tolerance of modified strains towards L-serine. The data further demonstrates that overexpression of mutants of ThrA can increase the tolerance towards L-serine even in strains having a native thrA gene present in their genome.

TABLE S10

Primers used for cloning and site saturation mutagenesis (SSM) of thrA.

| | |
|---|---|
| thrA_NcoI_F | GCGCCATGGGAGTGT TGAAGTTCGGCG |
| thrA_HindIII_R | GCCAAGCTTTCAGACTCCT AACTTCCATGAGAGGG |
| thrA_Y356NNK_F | CGCAGAAACTGATGCTMN NTTCGGAAGATGATTGCG |
| thrA_Y356NNK_R | CGCAGAAACTGATGCTMN NTTCGGAAGATGATTGCG |
| thrA_S357NNK_F | CAATCATCTTCCGAATACNN KATCAGTTTCTGCGTTCC |
| thrA_S357NNK_R | GGAACGCAGAAACTGATMN NGTATTCGGAAGATGATTG |
| thrA_S359NNK_F | CCGAATACAGCATCNNK TTCTGCGTTCCAC |

TABLE S10-continued

Primers used for cloning and site saturation mutagenesis (SSM) of thrA.

| | |
|---|---|
| thrA_S359NNK_R | GTGGAACGCAGAAMNN GATGCTGTATTCGG |

Example 11: Deletion of Serine Deaminase Encoded by sdaA

Deletion of sdaA was done using the lambda red mediated gene replacement method (Datsenko and Wanner, 2000). The protocol applied for deleting these genes is similar to the protocol described by Sawitzke et al. (2013). Primers used for amplification of the kanamycin cassette are shown in Table 1. The PCR reaction contained 250 nM each of KF and KR primer of the given gene, 250 µM of dNTP mix, 4 Units of Phusion polymerase (Thermoscientific, Waltham, Mass., USA), 40 µl of HF buffer and 10 ng of pKD4 plasmid. The following two-step PCR protocol was used for the PCR amplification: An initial denaturation step at 98° C. for 40 seconds, followed by 5 cycles of denaturation at 98° C. for 10 seconds, annealing at 55° C. for 30 seconds, extension at 72° C. for 90 seconds the cycle, followed by 20 cycles, where the annealing temperature was increased from 55° C. to 65° C. The PCR products were column purified (Macherey Nagel, Durn, Germany) and concentration was measured using a Nanodrop instrument (Thermoscientific, Waltham, Mass., USA) and subjected to overnight DpnI digestion. E. coli MG1655 was used as parent strain to make sequential knock outs. The parent strain was transformed with pKD46 were grown in 2YT-amp media at 30° C. and 250 rpm. The expression of exo, beta and gamma proteins were induced by addition of 20 mM arabinose at mid log phase (O.D. 0.4 to 0.5) and the cells were harvested after additional 1 h incubation. Culture was then transferred to 50 ml ice cold falcon tubes and centrifuged at 6500 rpm for 5 min at 4° C. Supernatant was discarded and cells were washed twice with ice cold 10% glycerol. These electro-competent cells were transformed with 200 ng of kanamycin cassette, and transfomants were plated on LB-kan plates. The kanamycin cassette was removed using the plasmid pcp20 encoding flippase gene. Primers for checking the loop out are shown in Table 2. To use pET vectors as expression system, a DE3 cassette containing T7 polymerase was integrated into the genome of each deletion mutant using a Lambda DE3 lysogenization kit (Millipore, Damstadt Germany).

As a result, a strain is provided wherein the sdaA gene is deleted. This strain has been used in subsequent examples.

TABLE S11

Primers used for amplification of kanamycin cassette

| Primer name | Sequence |
|---|---|
| sdaA_KF | GCGCTGTTATTAGTTCGTTACTGGAAGTCCAGT CACCTTGTCAGGAGTATTATCGTGGTGTAGGCT GGAGCTGCTTCG |
| sdaA_KR | CGCCCATCCGTTGCAGATGGGCGAGTAAGAAGT ATTAGTCACACTGGACCATATGAATATCCTCCT TAGTTCC |

TABLE S12

Primers used for checking
the deletion of given genes

| Primer name | Sequence |
|---|---|
| sdaA_cF | GCGCTGTTATTAGTTCGTTACTGGAAGTCC |
| sdaA_cR | CGCCCATCCGTTGCAGATGGGC |

Example 12—Overexpression and Site Saturation Mutagenesis of thrA at Site Y356, S357 and S359

Over expression of thrA was achieved using the plasmid pACYC-Duet. The thrA gene was amplified from MG-1655 wt strain using primers thrA_NcoI_F and thrA_HindIII (primer sequences in Table S10) and cloned in pACYC-Duet1 plasmid using NcoI and HindIII enzyme. The 100 µl PCR mixture contained 250 nM each of forward and reverse primer, 250 µM of dNTP, 2 U of Phusion polymerase, 1× HF buffer, 1 µl of overnight culture. The following two-step PCR protocol was used for the PCR amplification: An initial denaturation step at 98° C. for 40, followed by 5 cycles of denaturation at 98° C. for 10 seconds, annealing at 55° C. for 30 seconds, extension at 72° C. for 120 seconds the cycle, followed by 20 cycles, where the annealing temperature was increased from 55° C. to 65° C. After column purification, the gene products and plasmids were digested using Fast digest enzymes (Thermoscientific, Waltham, Mass., USA). About 500 ng of PCR product or 1 µg of plasmids were subjected to digestion by 1 µl each of the restriction enzymes in 1× fast digest buffer. The reaction was incubated for 3h and then column purified again. Ligation reaction included 1× T4 ligase buffer, 50 ng of plasmid DNA and 100 ng of insert and 0.3 µl per 10 µl of T4DNA ligase (Thermoscientific, Waltham, Mass., USA). The ligation mixture was transformed in chemically competent DH5a cells and plated on Lb-chloramphenicol plates. The plasmid was isolated using plasmid prep kit (Macherey Nagel, Durn, Germany).

Using site saturation mutagenesis (SSM), the selected amino acid residue/s can be mutated to all other 20 amino acids. This makes it possible to investigate the effect of amino acid substitutions on the enzyme activity and in turn on phenotype. SSM for thrA sites Y356, S357 and S359 was performed using primers shown in Table S10. The master mix was used as mentioned above with the only modification that the master mix was divided in two equal aliquots, after which forward and reverse primers were added to each aliquot. A total of 100 ng of pACYC-Duet-thrA plasmid was used as a template. The two step PCR program: initial denaturation at 98° C. for 40 sec, denaturation at 98° C. for 10 sec, annealing 60° C. for 30 sec, extension 72° C. for 5 min the cycle was repeated 5 times and then the two aliquots were mixed and subjected to an additional 15 cycles. PCR product was DpnI digested and transformed in the sdaAΔ (DE3) strain (Example 11), which carries the wild type thrA gene in its genome, and plated on LB-chloramphenicol plates supplemented with 0.1% glucose. Chloramphenicol was supplemented in all following media for plasmid stability.

Figure 12:
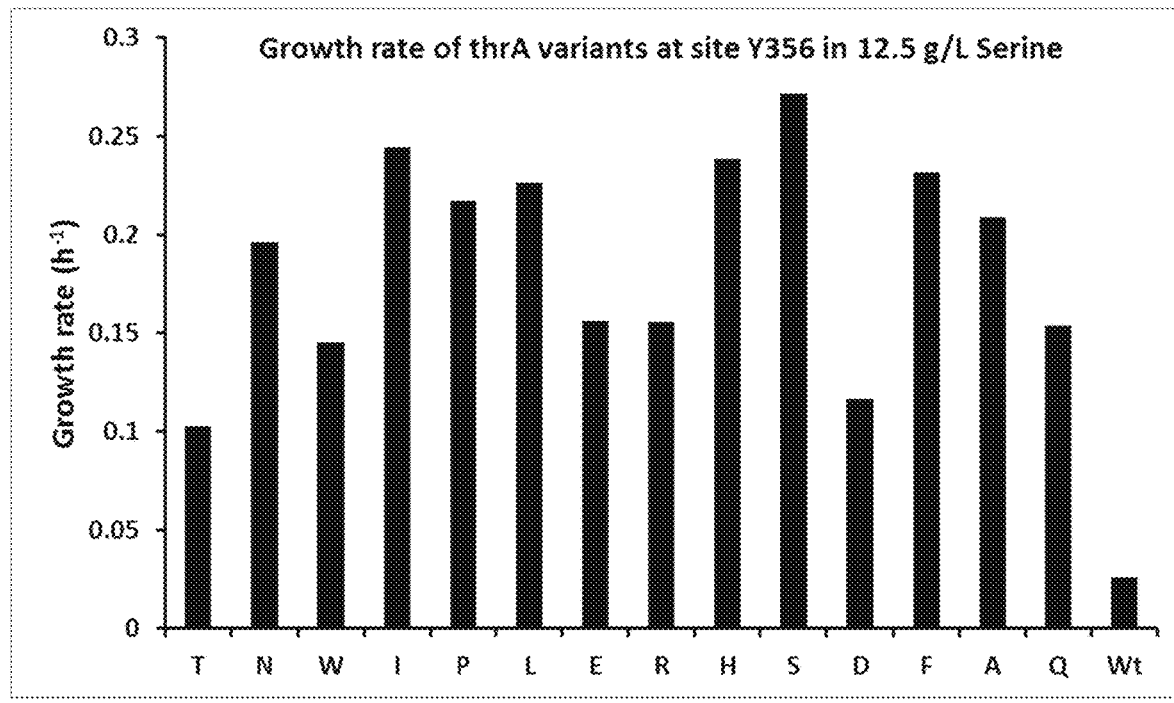
FIG. 12: Growth rate of mutant ΔsdaA *E. coli* strains having different amino acid substitutions observed at positions 356 (11A), 357 (11B) and 359 (11C) of ThrA, respectively (the amino acid substitution is denoted by the respective one-letter code). The growth rate of *E. coli* carrying the wild type thrA gene is denoted "wt".
Figure 12:
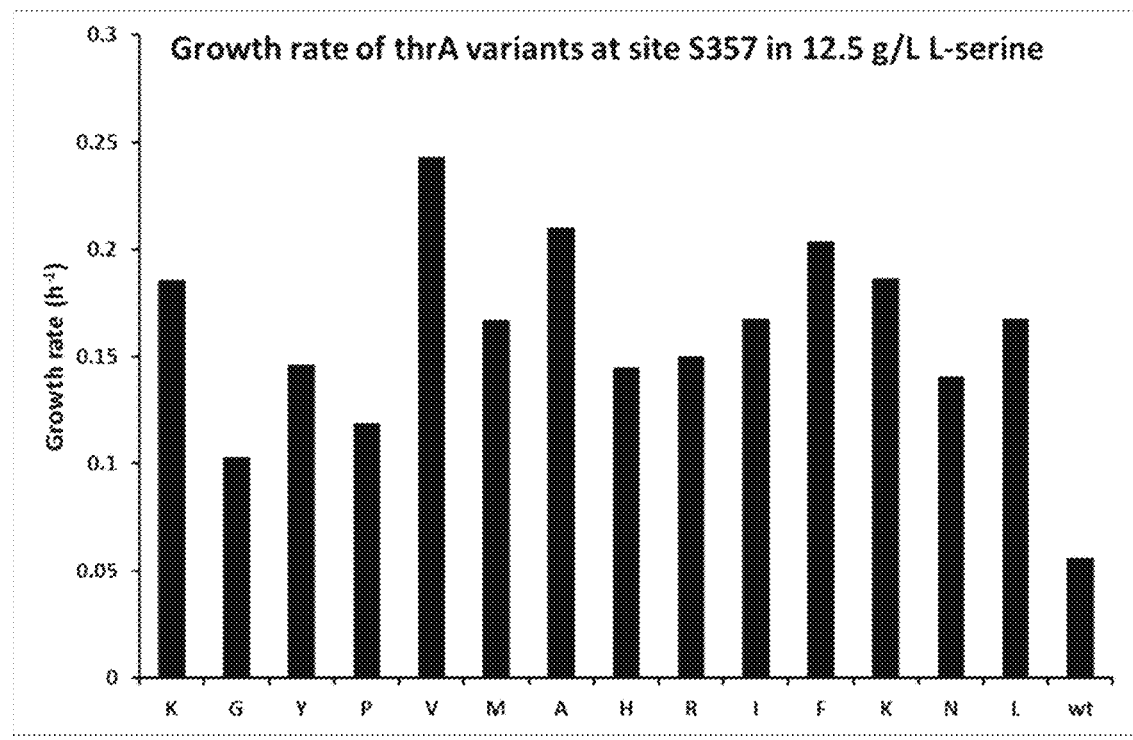
Figure 12:
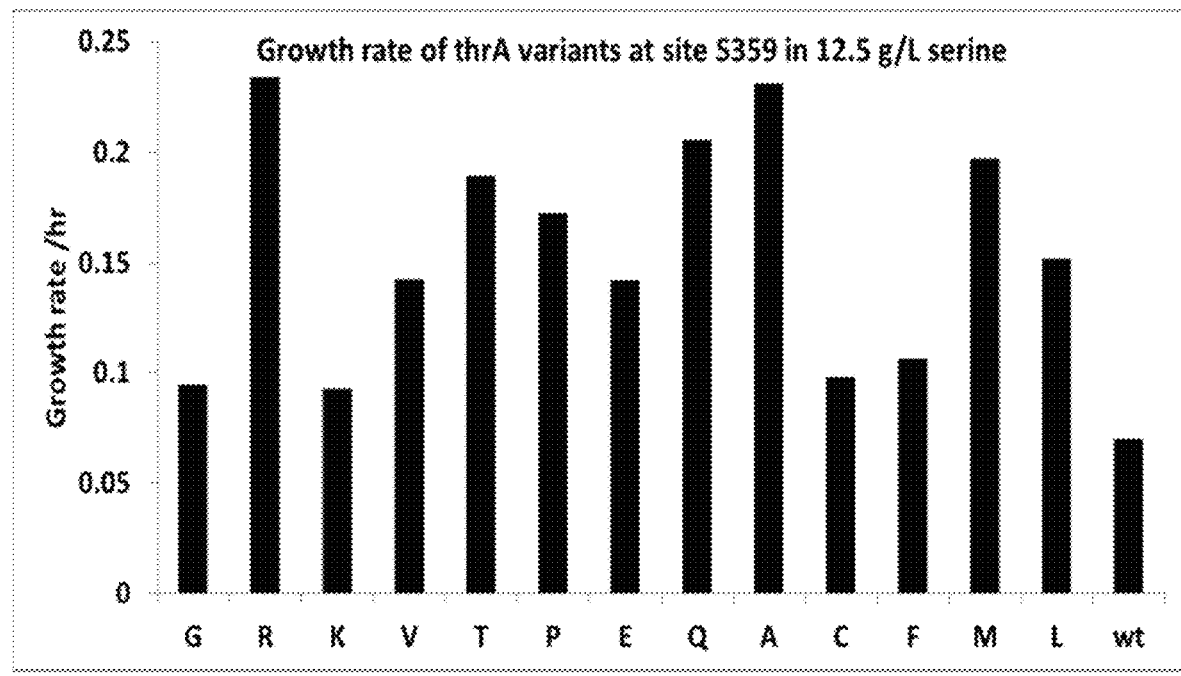

Individual colonies were picked and inoculated into 96 well micro titer plates (MTP) containing 2× TY media supplemented with 0.1% glucose and 2 mM Glycine. 240 clones from each SSM library was picked (in total 3 plates). The sdaAΔ (DE3) strain harboring pACYC-Duet empty vector and pACYC-thrAwt was inoculated as a control strain in each plate. The plate was incubated at 37° C. and 300 rpm overnight. This pre-culture plate was used as inoculum from which 1 µL was added to a new 96 well MTP plate containing 100 µL of M9 media supplemented with 0.2% glucose. The culture was incubated for 4 h after which 25 uL of 1 mM IPTG was added to induce the expression. The plate was subsequently incubated for 2 h and then M9 media containing 0.2% glucose and 25 g/L L-serine was added thus reaching final serine concentration of 12.5 g/L. The plates were incubated in Microtiter plate reader (Biotek, Winooski Vt., USA). The reader was set at 37° C. with continuous shaking, and the O.D was monitored every 5 minutes at 630 nm for 18 hours. The plasmids from the tolerant clones were sequenced and the growth rates were estimated from the log phase of culture. This way, a number of amino acid substitutions that result in tolerance towards serine were identified. FIGS. 12 (A-C) shows the growth rate of mutant strains having different amino acid substitutions observed at positions 356 (12A), 357 (12B) and 359 (12C) of ThrA, respectively (denoted by the respective one-letter code). The growth rate of *E. coli* carrying the wild type thrA gene is denoted "wt".

In conclusion, the experiment demonstrates that overexpression of mutants of thrA can increase the tolerance towards L-serine of strains having a native thrA gene present in its genome. This works for example in a strain carrying a single genomic deletion of sdaA. This way, the experiment identifies mutants that confer L-serine tolerance.

Example 13: Multiplex Genome Engineering of Beneficial Mutations Enhancing Serine Tolerance In order to investigate if genome integration of beneficial mutations identified in the Q1 strain may also cause increased tolerance towards serine in other strains, the mutations were genome integrated into the sdaAΔ (DE3) strain (Example 11) using multiplex genome engineering (Wang et al., 2011). The protocol applied for multiplex genome engineering was similar to the method published by Wang and Church, 2011. Strain sdaAΔ (DE3) (Example 11) was transformed with plasmid pMA7-sacB plasmid (Lennen et al. 2015). Clones were plated on LB-ampicillin plates and incubated at 37° C. Colonies were cultured overnight in TY-amp-gly media at 37° C. and re-inoculated in 25 ml fresh TY-gly media the following day. After reaching an O.D. of 0.4 at 37° C., arabinose was added to a final concentration of 0.2%. Cells were re-incubated at 37° C. and 250 rpm for additional 15 min and were then made electro-competent by washing twice with 10% glycerol (ice cold). Final volume of electro competent cells was adjusted to 200 µl using 10% glycerol. The primers targeting the loci (lrp D143G, thrA S357R) are shown in Table S13. The primers were pooled and adjusted to a final concentration of 10 pmol/µl. A total of 1.5 µl of this mix was added to 50 µl of cells and transformed by electroporation. The transformed cells were directly added to 25 ml TY-gly media and were incubated at 37° C., 250 rpm for two hours to reach O.D. of 0.4, followed by arabinose induction and transformation as above for second round of multiplex engineering. The process was repeated three times. After the $3^{rd}$ round of multiplex genome engineering, the cells were resuspended in 2 ml TY media. 1 ml was centrifuged at 16000 rpm for 1 min to centrifuge the cells and remove the supernatant cells were then suspended in minimal M9 media and plated on M9-agar plate containing 12.5 g/L L-serine and was incubated for 40 h in 37° C. incubator. A similar protocol was followed for the parental strain. More than 400 clones were observed on the plate containing genome engineered cells while only few spontaneous mutants were observed on the control plate. This shows that by employing such genome engineering approach, beneficial mutations can be easily engineered and selected for in these cells.

Figure 13:
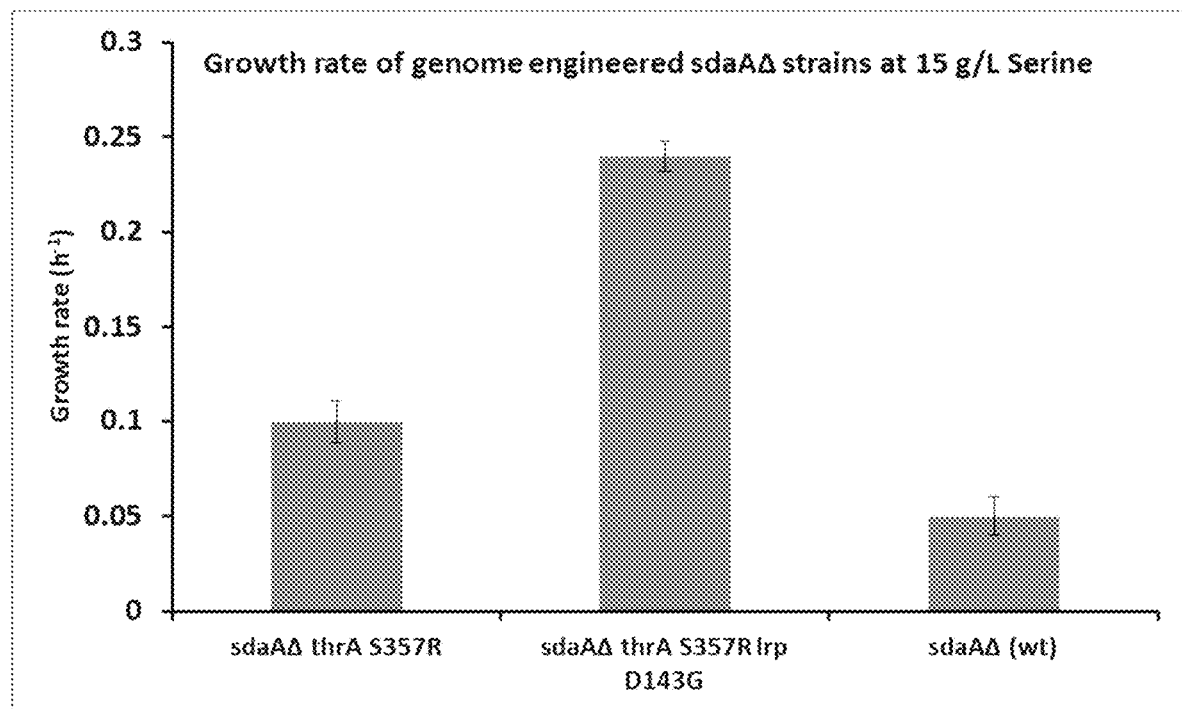
FIG. 13: Growth profile of multiplex genome engineered strains.

To investigate if these clones were serine tolerant, they were pre-cultured in a 96 well plate as described in Example 12. After 8 h of incubation, 3 µL of cells were inoculated in 150 µl. M9 media containing 15 g/L L-Serine and subjected for growth profile studies in a micro titer plate reader as described in Example 12. FIG. 13 shows the difference between the control (wt) and the genome engineered strains. Thirty random clones from this plate were sequenced for targeted sites. In this small sample size, 5 lrp mutants and more than 15 thrA mutants were found. All lrp mutants were found to also contain thrA mutation. The growth rates were estimated from the logarithmic growth phase. Average growth rates and deviations were determined from at least 4 samples as shown in FIG. 13.

In conclusion, it was demonstrated that the genomic mutation of lrp-D143G and thrA-S357R significantly increases the L-serine tolerance in a strain carrying for example a single deletion of sdaA.

TABLE S13

Primers used for Multiplex genome engineering

| Primer name | Sequence (5' to 3') |
| --- | --- |
| lrpD143G | GCTTGACTTCTTCCATAACAACGTAA GTGCGCGTCCCGTTAACCCCAGGCAG ACGCAGCAGGGTTTC |
| thrAS357R | CACACAGTCGCTTTGTGGAACGCAGAA ACTAATCCGATACTCCGAAGATGATTGC GTAATCAGCACC |

Figure 14:
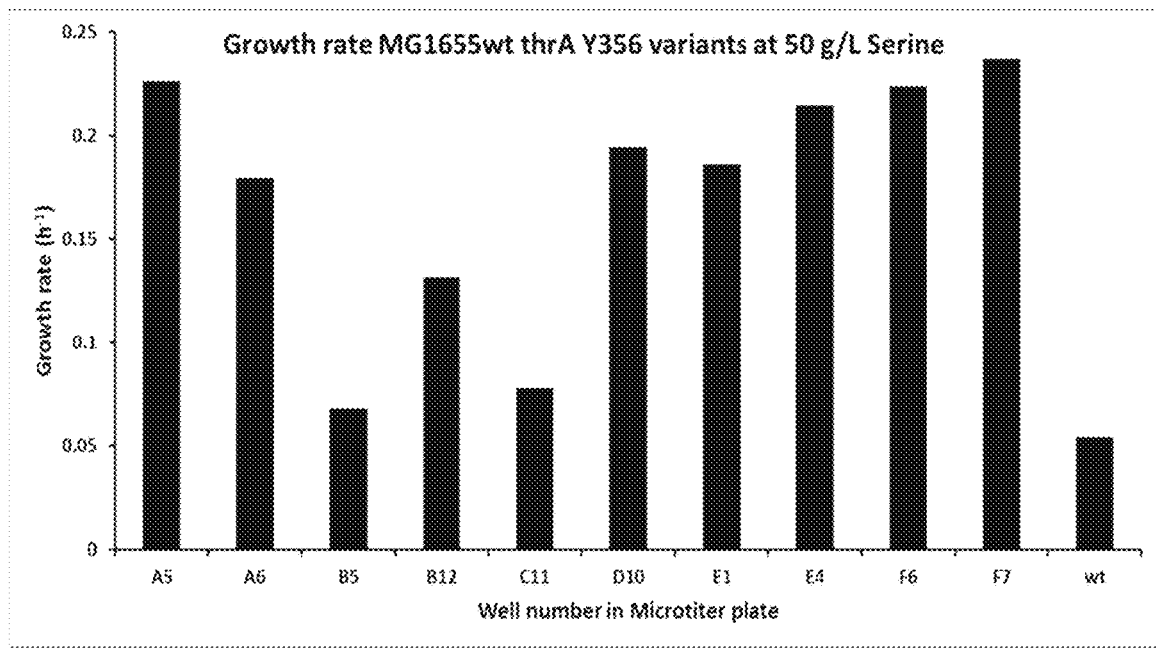
FIG. 14: Growth rate of *E coli* MG1655 expressing wild type thrA or mutant variants of thrA.
Figure 14:
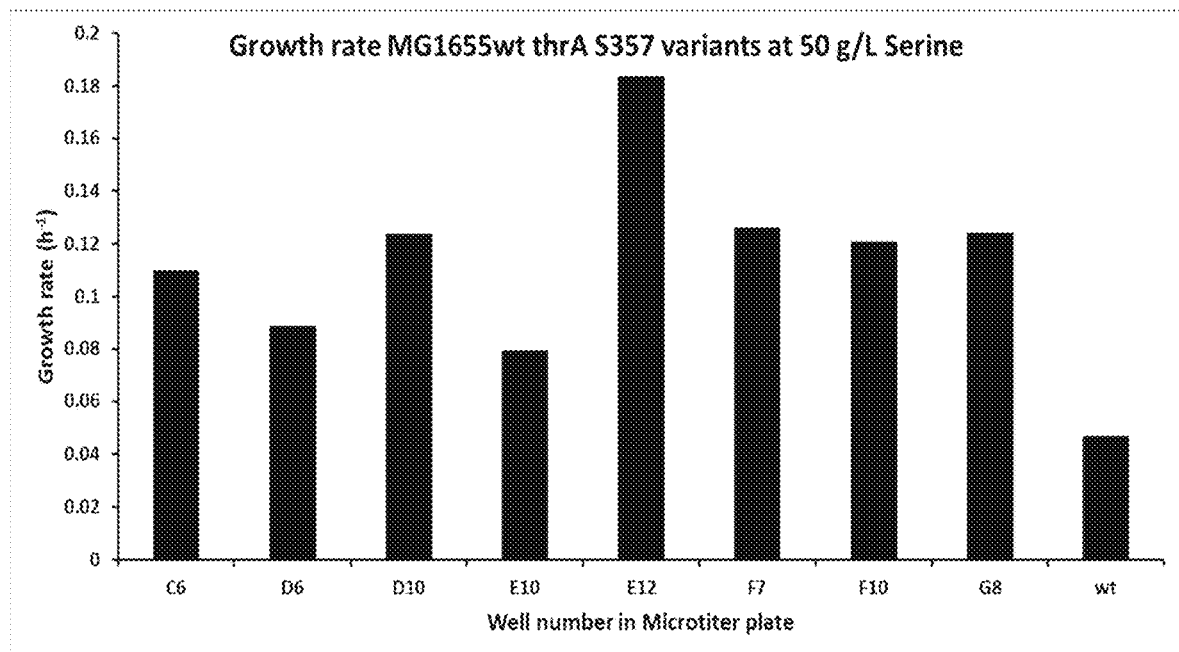
Figure 14:
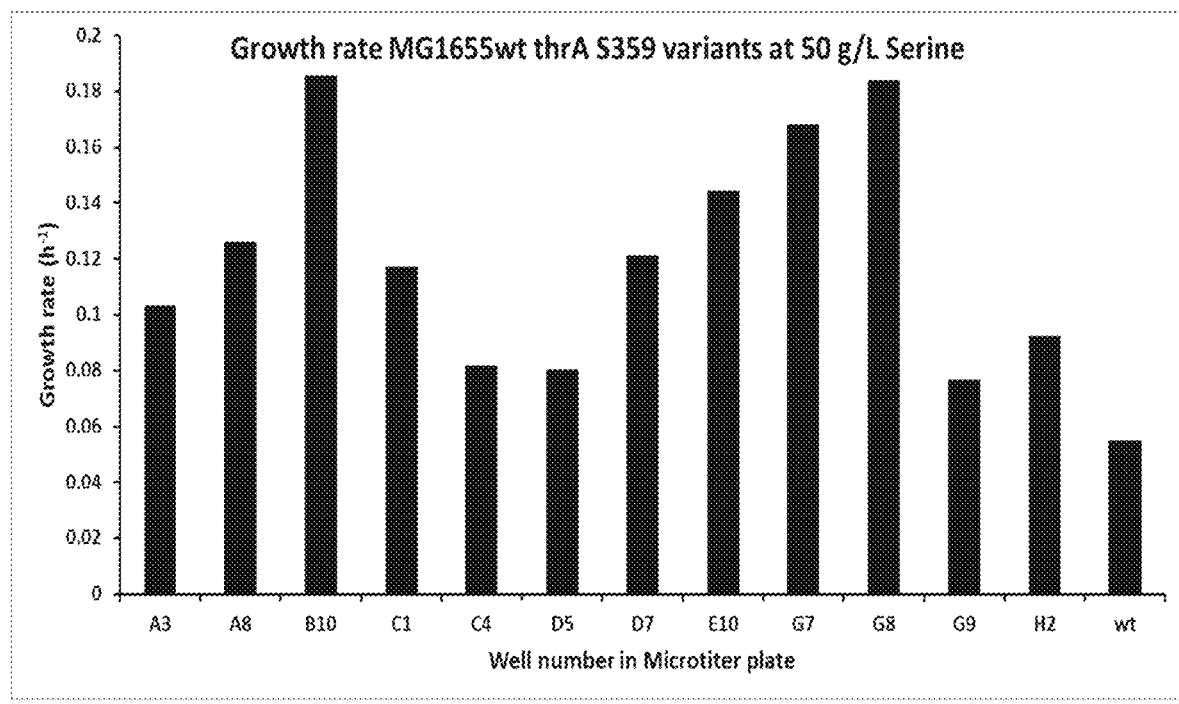

Example 14: Over Expression of thrA and Site Saturation Mutagenesis of thrA at Site Y356, S357 and S359 in a Wild Type *E. coli* Strain Wild type *E. coli* is naturally more tolerant towards L-serine due to presence of serine deaminases and serine hydroxymethyltransferase. At high serine concentrations, such as 50 g/L, serine does affect the growth rate of the wild type strain. In this example we show that the serine tolerance can be increased in the wild type strain by introduction of mutations that were found to confer serine tolerance in the Q1 strain (Example 5 and 6). As an example mutant variants of thrA were overexpressed in wild type *E. coli* MG1655. All the methods and materials were as described in Example 12, except that the strain used for transformation was *E. coli* MG1655 (DE3). Additionally, after IPTG induction of thrA expression, the cells were grown in M9 media containing 0.2% glucose, and 100 g/L L-serine was added to make a final concentration of 50 g/L L-serine. Growth profiles were monitored using a microtiter plate reader, and growth rate of *E coli* MG1655 expressing wild type thrA or mutant variants of thrA are shown in FIG. 14.

In conclusion, the experiment demonstrates that overexpression of mutant variants of thrA can increase the tolerance towards L-serine of wild type *E. coli* having a native thrA gene present in its genome. This demonstrates the positive effect of mutants of thrA even in an *E. coli* wild type strain that does not have attenuated activity of serine deaminases or serine hydroxymethyltransferase.

LIST OF REFERENCES CITED IN THE DESCRIPTION

Leuchtenberger W, Huthmacher K, Drauz K: Biotechnological production of amino acids and derivatives: current status and prospects. Appl Microbiol Biotechnol 2005, 69:1-8.

Sawers G. 1998. The anaerobic degradation of L-serine and L-threonine in enterobacteria: networks of pathways and regulatory signals. Arch Microbiol 171(1):1-5.

Pereira B, Zhang H, De Mey M, Lim C G, Li Z J, Stephanopoulos G. 2016. Engineering a novel biosynthetic pathway in *Escherichia coli* for production of renewable ethylene glycol. Biotechnol Bioeng 113(2): 376-83.

Akio Iwashima, Yoshitsugi Nose, Incorporation of glycine in pyrimidine and thiazole moieties of thiamine in *Escherichia coli*, Biochimica et Biophysica Acta (BBA)—General Subjects, Volume 252, Issue 2, 1971, Pages 235-238, ISSN 0304-4165

Hagishita T, Yoshida T, Izumi Y, Mitsunaga T: Efficient L-serine production from methanol and glycine by resting cells of *Methylobacterium* sp. strain M N43. Biosci Biotechnol Biochem 1996, 60:1604-1607.

Burgard A P, Maranas C D: Probing the performance limits of the *Escherichia coli* metabolic network subject to gene additions or deletions. Biotechnol Bioeng 2001, 74:364-375.

Li Y, Chen G K, Tong X W, Zhang H T, Liu X G, Liu Y H, Lu F P: Construction of *Escherichia coli* strains producing L-serine from glucose. Biotechnol Lett 2012, 34:1525-1530.

Peters-Wendisch P, Stolz M, Etterich H, Kennerknecht N, Sahm H, Eggeling L: Metabolic engineering of *Corynebacterium glutamicum* for L-serine production. Appl Environ Microbiol 2005, 71:7139-7144.

Gu P, Yang F, Su T, Li F, Li Y, Qi Q: Construction of an L-serine producing *Escherichia coli* via metabolic engineering. J Ind Microbiol Biotechnol 2014, 41:1443-1450.

Stolz M, Peters-Wendisch P, Etterich H, Gerharz T, Faurie R, Sahm H, Fersterra H, Eggeling L: Reduced folate supply as a key to enhanced L-serine production by *Corynebacterium glutamicum*. Appl Environ Microbiol 2007, 73:750-755.

Zhang X, Newman E: Deficiency in 1-serine deaminase results in abnormal growth and cell division of *Escherichia coli* K-12. Mol Microbiol 2008, 69:870-881.

Hama H, Sumita Y, Kakutani Y, Tsuda M, Tsuchiya T: Target of serine inhibition in *Escherichia coli*. Biochem Biophys Res Commun 1990, 168:1211-1216.

de Lorenzo V, Sekowska A, Danchin A: Chemical reactivity drives spatiotemporal organisation of bacterial metabolism. FEMS Microbiol Rev 2014.

Chowdhury A, Zomorrodi A R, Maranas C D: k-OptForce: integrating kinetics with flux balance analysis for strain design. PLoS Comput Biol 2014, 10:e1003487.

von Kamp A, Klamt S: Enumeration of smallest intervention strategies in genome-scale metabolic networks. PLoS Comput Biol 2014, 10:e1003378.

Qui Z and Goodman M F: The *Escherichia coli* polB locus is identical to dinA, the structural gene for DNA polymerase II. Characterization of Pol II purified from a polB mutant. J Biol Chem. 1997, 272(13): 8611-8617.

Kwon D H, Peña J A, Osato M S, Fox J G, Graham D Y, Versalovic J: Frameshift mutations in rdxA and metronidazole resistance in North American *Helicobacter pylori* isolates. J Antimicrob Chemother 2000, 46(5): 793-796

Yu D, Ellis H M, Lee E, Jenkins N A, Copeland N G, and Court D L: An efficient recombination system for chromosome engineering in *Escherichia coli*. Proc Natl Acad Sci USA 2000, 97: 5978-5983.

Datsenko K A, Wanner B L: One-step inactivation of chromosomal genes in *Escherichia coli* K-12 using PCR products. Proc Natl Acad Sci USA 2000, 97:6640-6645.

Sawitzke J A, Thomason L C, Bubunenko M, Li X, Costantino N, Court D L: Recombineering: using drug cassettes to knock out genes in vivo. Methods Enzymol 2013, 533:79-102.

Thomason L C, Costantino N, Court D L: *E. coli* genome manipulation by P1 transduction. Curr Protoc Mol Biol 2007, Chapter 1:Unit 1 17.

Baba T, Ara T, Hasegawa M, Takai Y, Okumura Y, Baba M, Datsenko K A, Tomita M, Wanner B L, Mori H: Construction of *Escherichia coli* K-12 in-frame, single-gene knockout mutants: the Keio collection. Mol Syst Biol 2006, 2:2006 0008.

Al-Rabiee R, Zhang Y, Grant G A: The mechanism of velocity modulated allosteric regulation in D-3-phosphoglycerate dehydrogenase. Site-directed mutagenesis of effector binding site residues. J Biol Chem 1996, 271: 23235-23238.

Kildegaard K R, Hallstrom B M, Blicher T H, Sonnenschein N, Jensen N B, Sherstyk 5, Harrison S J, Maury J, Herrgard M J, Juncker A S, et al.: Evolution reveals a glutathione-dependent mechanism of 3-hydroxypropionic acid tolerance. Metab Eng 2014, 26C:57-66.

Deatherage D E, Barrick J E: Identification of mutations in laboratory-evolved microbes from next-generation sequencing data using breseq. Methods Mol Biol 2014, 1151:165-188.

Langmead B, Salzberg S L: Fast gapped-read alignment with Bowtie 2. Nat Methods 2012, 9:357-359.

Freddolino P L, Amini S, Tavazoie S: Newly identified genetic variations in common *Escherichia coli* MG1655 stock cultures. J Bacteriol 2012, 194:303-306.

Wang H H, Isaacs F J, Carr P A, Sun Z Z, Xu G, Forest C R, Church G M: Programming cells by multiplex genome engineering and accelerated evolution. Nature 2009, 460: 894-898.

Wang H H, Church G M: Multiplexed genome engineering and genotyping methods applications for synthetic biology and metabolic engineering. Methods Enzymol 2011, 498:409-426.

Mertens N, Remaut E, Fiers W. 1995. Tight transcriptional control mechanism ensures stable high-level expression from T7 promoter-based expression plasmids. Biotechnology (N Y) 13(2):175-9.

St-Pierre F, Cui L, Priest D G, Endy D, Dodd I B, Shearwin K E. 2013. One-step cloning and chromosomal integration of DNA. ACS Synth Biol 2(9):537-41.

Lennen R M, Nilsson Wallin A I, Pedersen M, Bonde M, Luo H, Herrgard M J, Sommer M O. 2015. Transient overexpression of DNA adenine methylase enables efficient and mobile genome engineering with reduced off-target effects. Nucleic Acids Res.

---

The invention claimed is:

1. An *Escherichia coli* bacterium which expresses a polypeptide having an amino acid sequence, which has at least 95% sequence identity to the amino acid sequence set forth in SEQ ID NO: 12, wherein said polypeptide comprises an amino acid sequence in which position 143 D is replaced by another amino acid.

2. The bacterium according to claim 1 which expresses a polypeptide having an amino acid sequence, which has at least 95% sequence identity to the amino acid sequence set forth in SEQ ID NO: 12, wherein said polypeptide comprises an amino acid sequence in which position 143 D is replaced by G.

3. The bacterium according to claim 1, wherein said bacterium comprises within the lrp gene one or more nucleotide substitutions resulting in an amino acid substitution in the encoded polypeptide at position 143.

4. The bacterium according to claim 1, wherein at least one gene selected from sdaA, sdaB, tdcG or glyA is inactivated.

5. The bacterium according to claim 1, wherein at least two genes selected from sdaA, sdaB, tdcG or glyA are inactivated.

6. The bacterium according to claim 1, wherein at least three genes selected from sdaA, sdaB, tdcG or glyA are inactivated.

7. The bacterium according to claim 1, wherein at least one gene selected from sdaA, sdaB or tdcG is inactivated.

8. The bacterium according to claim 1, wherein at least two genes selected from sdaA, sdaB or tdcG are inactivated.

9. The bacterium according to claim 1, wherein the genes sdaA, sdaB or tdcG are inactivated.

10. The bacterium according to claim 1, wherein at least the gene glyA is inactivated.

11. The bacterium according to claim 1, wherein the genes sdaA, sdaB, tdcG and glyA are inactivated.

12. A method for producing L-serine or a L-serine derivative, the method comprising cultivating the bacterium according to claim 1 in a culture medium.

13. The method according to claim 12, wherein the L-serine derivative is selected from the group consisting of L-cysteine, L-methionine, L-glycine, O-acetylserine, L-tryptophan, thiamine ethanolamine and ethylene glycol.

* * * * *

UNITED STATES PATENT AND TRADEMARK OFFICE
CERTIFICATE OF CORRECTION

| | |
|---|---|
| PATENT NO. | : 11,407,976 B2 |
| APPLICATION NO. | : 17/064203 |
| DATED | : August 9, 2022 |
| INVENTOR(S) | : Hemanshu Mundhada |

It is certified that error appears in the above-identified patent and that said Letters Patent is hereby corrected as shown below:

In the Drawings

On Sheet 3 of 23, Figure 2 (cont.), Line 5, delete "Hin dIII" and insert --HindIII--.

In the Specification

In Column 1, Line 67, delete "thimine" and insert --thiamine--.

In Column 2, Line 46, delete "Hama" and insert --(Hama--.

In Column 9, Line 50, delete "0-acetylserine." and insert --O-acetylserine.--.

In Column 10, Line 38, delete "5357" and insert --S357--.

In Column 11, Line 66, delete "S3591, 5359P," and insert --S359T, S359P,--.

In Column 12, Line 16 (Approx.), delete "Y356A, Y356G," and insert --Y356Q, Y356G,--.

In Column 12, Line 65, delete "2)" and insert --2).--.

In Column 13, Line 7, delete "(01)" and insert --(Q1)--.

In Column 13, Line 25, delete "FIG." and insert --FIGS.--.

In Column 18, Line 64, delete "N-n itrosoguanidine)," and insert --N-nitrosoguanidine),--.

In Column 24, Line 36, delete "0-acetylserine" and insert --O-acetylserine--.

In Column 24, Line 59, delete "0-acetylserine" and insert --O-acetylserine--.

Signed and Sealed this
Twenty-fifth Day of April, 2023

Katherine Kelly Vidal
*Director of the United States Patent and Trademark Office*

In Column 24, Line 60, delete "0-acetylserine" and insert --O-acetylserine--.

In Column 25, Line 1, delete "0-acetylserine" and insert --O-acetylserine--.

In Column 25, Lines 2-3, delete "0-acetylserine" and insert --O-acetylserine--.

In Column 25, Line 19, delete "0-acetylserine" and insert --O-acetylserine--.

In Column 25, Line 20, delete "0-acetylserine" and insert --O-acetylserine--.

In Column 25, Line 29, delete "0-acetylserine" and insert --O-acetylserine--.

In Column 25, Line 30, delete "0-acetylserine" and insert --O-acetylserine--.

In Column 25, Line 41, delete "0-acetylserine" and insert --O-acetylserine--.

In Column 25, Line 43, delete "0-acetylserine" and insert --O-acetylserine--.

In Column 25, Line 50-51, delete "0-acetylserine" and insert --O-acetylserine--.

In Column 25, Line 52, delete "0-acetylserine" and insert --O-acetylserine--.

In Column 26, Line 34, delete "55." and insert --S5.--.

In Column 26, Line 59, delete "kinase/homoserine" and insert --kinase I/homoserine--.

In Column 30, Line 33, delete "S3591," and insert --S359T,--.

In Column 30, Line 40, delete "S3591," and insert --S359T,--.

In Column 32, Line 1, delete "Y356I," and insert --Y356T,--.

In Column 32, Line 19, delete "Y3560," and insert --Y356Q,--.

In Column 32, Line 33, delete "Y356G, Y356G," and insert --Y356Q, Y356G,--.

In Column 32, Line 33, delete "Y3560," and insert --Y356D,--.

In Column 32, Line 62, delete "Y3560," and insert --Y356Q,--.

In Column 33, Line 12, delete "Y356A," and insert --Y356Q,--.

In Column 33, Line 42, delete "S3591," and insert --S359T,--.

In Column 34, Line 42, delete "S359A, S359A," and insert --S359Q, S359A,--.

CERTIFICATE OF CORRECTION (continued)
U.S. Pat. No. 11,407,976 B2

In Column 37, Line 55, delete "such at" and insert --such as at--.

In Column 37, Line 63, delete "Y3S6A," and insert --Y356A,--.

In Column 38, Line 2, delete "S359A," and insert --S359Q,--.

In Column 38, Line 33, delete "S359A, S359A," and insert --S359Q, S359A,--.

In Column 38, Line 47, delete "S3591," and insert --S359T,--.

In Column 38, Line 51, delete "such at" and insert --such as at--.

In Column 40, Line 57, delete "S359A, S359A," and insert --S359Q, S359A,--.

In Column 44, Line 17, delete "such at" and insert --such as at--.

In Column 44, Line 25, delete "such at" and insert --such as at--.

In Column 44, Line 32, delete "Y356I," and insert --Y356T,--.

In Column 49, Line 14, delete "1220V" and insert --I220V--.

In Column 49, Line 20, delete "220 1" and insert --220 I--.

In Column 49, Line 39, delete "1220." and insert --I220.--.

In Column 49, Line 52, delete "1202T" and insert --I202T--.

In Column 50, Line 10, delete "2021." and insert --202I.--.

In Column 51, Line 49, delete "least," and insert --least--.

In Column 54, Line 12, delete "polypetide" and insert --polypeptide--.

In Column 56, Line 35, delete "151" and insert --IS1--.

In Column 56, Line 39, delete "151" and insert --IS1--.

In Column 57, Line 42, delete "151" and insert --IS1--.

In Column 57, Line 46, delete "151" and insert --IS1--.

In Column 57, Line 60, delete "trx8" and insert --trxB--.

In Column 58, Line 2, delete "of of" and insert --of--.

CERTIFICATE OF CORRECTION (continued)
U.S. Pat. No. 11,407,976 B2

In Column 60, Line 20, delete "c1857" and insert --cI857--.

In Column 63, Line 48, delete "casaminoacids" and insert --casamino acids--.

In Column 66, Line 32, delete "myristilation," and insert --myristoylation,--.

In Columns 67-68, Line 61, delete "5" and insert --6--.

In Columns 67-68, Line 63, delete "8" and insert --5--.

In Columns 67-68, Line 64, delete "6" and insert --5--.

In Columns 69-70, Line 5, delete "8" and insert --5--.

In Columns 69-70, Line 7, delete "-3" and insert -- -1--.

In Columns 69-70, Line 9, delete "6" and insert --5--.

In Column 70, Line 43, delete "Durn," and insert --Duren,--.

In Column 70, Line 57, delete "transfomants" and insert --transformants--.

In Column 70, Line 65, delete "CaCl2)" and insert --CaCl2--.

In Column 72, Line 7, delete "53)." and insert --S3).--.

In Column 72, Line 7, delete "μI" and insert --μl--.

In Column 72, Line 28, delete "ser8." and insert --serB.--.

In Column 73, Line 30 (Approx.), delete "GLAG" and insert --GAG--.

In Column 73, Line 42 (Approx.), delete "1×M9" and insert --1× M9--.

In Column 73, Line 53, delete "Damstadt" and insert --Darmstadt--.

In Column 74, Line 9 (Approx.), delete "1" and insert --μl.--.

In Column 74, Line 26, delete "I/h," and insert --l/h,--.

In Column 74, Line 28, delete "I/h" and insert --l/h--.

In Column 74, Line 53, delete "53" and insert --S3--.

In Column 74, Line 62, delete "μI" and insert --μl--.

CERTIFICATE OF CORRECTION (continued)
U.S. Pat. No. 11,407,976 B2

In Column 74, Line 63, delete "Baeswieler," and insert --Baesweiler,--.

In Column 74, Line 67, delete "Baeswieler," and insert --Baesweiler,--.

In Column 76, Line 44, delete "Florometer" and insert -- Fluorometer--.

In Column 76, Line 49, delete "Denaturated" and insert --Denatured--.

In Columns 77-78, Line 10, delete "gcvA/ygdI" and insert --gcvA/ygdl--.

In Columns 77-78, Line 11, delete "gcvA/ygdI" and insert --gcvA/ygdl--.

In Columns 77-78, Line 41, delete "gcvA/ygdI" and insert --gcvA/ygdl--.

In Columns 77-78, Line 42, delete "gcvA/ygdI" and insert --gcvA/ygdl--.

In Columns 79-80, Line 8, delete "Insertion[1]Insertion" and insert --Insertion[1]: Insertion--.

In Columns 79-80, Line 11, delete "Insertion[2]Insertion" and insert --Insertion[2]: Insertion--.

In Columns 79-80, Line 11, delete "genes genes" and insert --genes--.

In Columns 79-80, Line 11, delete "ygdI." and insert --ygdl.--.

In Columns 79-80, Line 12, delete "Insertion[3]Insertion" and insert --Insertion[3]: Insertion--.

In Columns 79-80, Line 13, delete "ygdI." and insert --ygdl.--.

In Columns 79-80, Line 14, delete "Insertion[4]Insertion" and insert --Insertion[4]: Insertion--.

In Columns 79-80, Line 14, delete "genes genes" and insert --genes--.

In Columns 79-80, Line 15, delete "Insertion[5]Insertion" and insert --Insertion[5]: Insertion--.

In Columns 79-80, Line 17, delete "Deletion[6]Deletion" and insert --Deletion[6]: Deletion--.

In Columns 79-80, Line 19, delete "Insertion[7]Insertion" and insert --Insertion[7]: Insertion--.

In Columns 79-80, Line 21, delete "Insertion[8]Insertion" and insert --Insertion[8]: Insertion--.

In Columns 79-80, Line 22, delete "tgsA." and insert --tqsA.--.

In Columns 79-80, Line 24, delete "Intergenic[9]C" and insert --Intergenic[9]: C--.

In Columns 79-80, Line 25, delete "of of" and insert --of--.

CERTIFICATE OF CORRECTION (continued)
U.S. Pat. No. 11,407,976 B2

In Columns 79-80, Line 25, delete "Irp." and insert --lrp.--.

In Columns 79-80, Line 26, delete "Intergenic$^{10}$T" and insert --Intergenic$^{10}$: T--.

In Column 79, Line 42, delete "56)" and insert --S6)--.

In Column 79, Line 43, delete "extention" and insert --extension--.

In Column 79, Line 65, delete "01" and insert --Q1--.

In Column 80, Line 66, delete "µI" and insert --µl--.

In Column 81, Line 41 (Approx.), delete "IrpD143G" and insert --lrpD143G--.

In Column 82, Line 15 (Approx.), delete "Irp_F" and insert --lrp_F--.

In Column 82, Line 18 (Approx.), delete "Irp_R" and insert --lrp_R--.

In Column 83, Line 4, delete "01" and insert --Q1--.

In Column 84, Line 8, delete "diviation)" and insert --deviation)--.

In Column 84, Line 21, delete "Damstadt" and insert --Darmstadt--.

In Column 84, Line 63, delete "510)" and insert --S10)--.

In Column 85, Line 5, delete "01" and insert --Q1--.

In Column 86, Line 21, delete "µI" and insert --µl--.

In Column 86, Line 29 (Approx.), delete "Durn," and insert --Duren,--.

In Column 86, Lines 43-44, delete "transfomants" and insert --transformants--.

In Column 86, Line 50, delete "Damstadt" and insert --Darmstadt--.

In Column 87, Line 22, delete "µI" and insert --µl--.

In Column 87, Line 32, delete "µI" and insert --µl--.

In Column 87, Line 38, delete "DH5a" and insert --DH5α--.

In Column 87, Line 40, delete "Durn," and insert --Duren,--.

In Column 88, Line 50, delete "µI" and insert --µl--.

CERTIFICATE OF CORRECTION (continued)
U.S. Pat. No. 11,407,976 B2

In Column 88, Line 53, delete "pmol/µl." and insert --pmol/µl.--.

In Column 88, Line 54, delete "1.5 µI" and insert --1.5 µl--.

In Column 89, Line 9 (Approx.), delete "µl." and insert --µL.--.

In Column 89, Line 31 (Approx.), delete "IrpD143G" and insert --lrpD143G--.

In Column 90, Line 24, delete "4165" and insert --4165.--.

In Column 90, Line 27, delete "M N43." and insert --MN43.--.

In Column 90, Line 49, delete "1-serine" and insert --l-serine--.

In Column 91, Line 4, delete "796" and insert --796.--.

In Column 91, Line 30, delete "5," and insert --S,--.

SEQUENCE LISTING

```
<160> NUMBER OF SEQ ID NOS: 104

<210> SEQ ID NO 1
<211> LENGTH: 1365
<212> TYPE: DNA
<213> ORGANISM: Escherichia coli

<400> SEQUENCE: 1
gtgattagtc tattcgacat gtttaaggtg gggattggtc cctcatcttc ccataccgta     60
gggcctatga aggcaggtaa acagttcgtc gatgatctgg tcgaaaaagg cttactggat    120
agcgttactc gcgttgccgt ggacgtttat ggttcactgt cgctgacggg taaaggccac    180
cacaccgata tcgccattat tatgggtctt gcaggtaacg aacctgccac cgtggatatc    240
gacagtattc ccggttttat tcgcgacgta gaagagcgcg aacgtctgct gctggcacag    300
ggacggcatg aagtggattt cccgcgcgac aacgggatgc gttttcataa cggcaacctg    360
ccgctgcatg aaaacggtat gcaaatccac gcctataacg gcgatgaagt cgtctacagc    420
aaaacttatt attccatcgg cggcggtttt atcgtcgatg aagaacactt tggtcaggat    480
gctgccaacg aagtaagcgt gccgtatccg ttcaaatctg ccaccgaact gctcgcgtac    540
tgtaatgaaa ccggctattc gctgtctggt ctcgctatgc agaacgaact ggcgctgcac    600
agcaagaaag agatcgacga gtatttcgcg catgtctggc aaaccatgca ggcatgtatc    660
gatcgcggga tgaacaccga aggtgtactg ccaggcccgc tgcgcgtgcc acgtcgtgcg    720
tctgccctgc gccggatgct ggtttccagc gataaactgt ctaacgatcc gatgaatgtc    780
attgactggg taaacatgtt tgcgctggca gttaacgaag aaaacgccgc cggtggtcgt    840
gtggtaactg cgccaaccaa cggtgcctgc ggtatcgttc cggcagtgct ggcttactat    900
```

```
gaccacttta ttgaatcggt cagcccggac atctataccc gttactttat ggcagcgggc    960
gcgattggtg cattgtataa aatgaacgcc tctatttccg gtgcggaagt tggttgccag   1020
ggcgaagtgg gtgttgcctg ttcaatggct gctgcgggtc ttgcagaact gctgggcggt   1080
agcccggaac aggtttgcgt ggcggcgaaa attggcatgg aacacaacct tggtttaacc   1140
tgcgacccgg ttgcagggca ggttcaggtg ccgtgcattg agcgtaatgc cattgcctct   1200
gtgaaggcga ttaacgccgc gcggatggct ctgcgccgca ccagtgcacc gcgcgtctcg   1260
ctggataagg tcatcgaaac gatgtacgaa accggtaagg acatgaacgc caaataccgc   1320
gaaacctcac gcggtggtct ggcaatcaaa gtccagtgtg actaa                  1365
```

<210> SEQ ID NO 2
<211> LENGTH: 1368
<212> TYPE: DNA
<213> ORGANISM: Escherichia coli

<400> SEQUENCE: 2

```
atgattagcg tattcgatat tttcaaaatc ggcattggcc cttccagttc tcataccgtt     60
ggaccaatga aagcgggtaa acaatttacc gacgatctga ttgcccgtaa cctgcttaaa    120
gacgtgaccc gcgtggtggt tgacgtgtac ggctcgctct ctctgaccgg taaaggccac    180
cacactgata tcgccattat tatgggcctg gcgggtaacc tgccggatac cgtggatatc    240
gattccatcc ccagttttat tcaggatgtg aatactcatg gtcgcctgat gctggcaaac    300
ggtcagcatg aagtggagtt cccggttgat cagtgcatga acttccacgc cgacaacctt    360
tctctgcatg aaaacggtat gcgcattacc gcgctggcgg gcgataaagt cgtttacagc    420
cagacttact actctattgg cggtggcttt atcgttgatg aagagcattt tggccagcag    480
gatagcgcac cggttgaagt tccttatccg tacagttcag cagccgatct gcaaaaacat    540
tgtcaggaaa ccgggctgtc actctctggc ctgatgatga aaacgagct ggcgctgcac    600 agcaaagaag agctggaaca gcacctggcg aacgtctggg aagtcatgcg cggcggtatt    660
gagcgcggta tttccaccga aggcgtgttg cctggcaaac tgcgcgttcc acgccgtgct    720
gcggcactac gccggatgct ggtcagccag gataaaacca ccactgaccc gatggcggtt    780
gttgactgga tcaacatgtt tgcactggca gtgaacgaag agaacgctgc tggcggtcgc    840
gtggtgactg cgccgactaa cggtgcgtgc gggattatcc cggcagttct ggcgtactac    900
gacaagttta ccgcgaagt gaacgctaac tcactggctc gttacctgct ggtagccagc    960
gccattggtt ctctttataa gatgaacgcg tcgatttctg gtgctgaagt gggttgccag   1020
ggtgaagttg gcgtggcgtg ctcaatggcg gcggctggtc tggcagaact attaggcgca   1080
agcccggcgc aggtgtgcat cgcggcgaa atcgccatgg agcacaacct cggtctgacg   1140
tgtgacccgg tcgccggaca ggtacaggtg ccatgcatcg agcgtaacgc cattgcggca   1200
gtaaaagcgg tgaacgccgc acgtatggcg ctgcgccgta ccagcgagcc gcgcgtctgc   1260
ctcgataaag ttatcgaaac catgtacgaa acaggtaaag atatgaacgc caagtaccgc   1320
gaaacctctc gcggcggcct ggcaatgaag atcgttgcct gcgattaa               1368
```

<210> SEQ ID NO 3
<211> LENGTH: 1365
<212> TYPE: DNA
<213> ORGANISM: Escherichia coli

<400> SEQUENCE: 3

```
atgattagtg cattcgatat tttcaaaatt gggattggtc cctccagttc gcataccgtg      60
gggccaatga atgccggaaa aagttttatt gatcggctgg aaagtagcgg cttattaacc     120
gcgacgagcc atattgtggt cgatctgtac gggtcgttgt cactgacggg caaaggccat     180
gccacggatg tcgccatcat catgggactg gcaggaaaca gtccgcagga tgttgtcatt     240
gatgagatcc ctgcatttat agagttagta acgcgcagcg ggcggctgcc agtggcatct     300
ggtgcgcata ttgttgattt tcctgtagca aagaacatta tcttccatcc cgaaatgttg     360
cctcgccatg agaacggaat gcggatcact gcctggaagg acaggaaga gctattaagt     420
aaaacctatt actctgtcgg cggcgggttt attgtcgaag aagaacactt cggcctgtcg     480
cacgatgtcg aaacgtccgt accttacgat ttccactcag caggtgaact gctgaaaatg     540
tgtgattaca acggcctgtc tatatctggt ctgatgatgc acaacgagct agcgctgcgc     600
agcaaagcgg aaattgacgc cggttttgcc cgtatctggc aagtgatgca tgacggtatt     660
gaacgtggga tgaacactga aggcgtgctg cctggtccgc tcaatgtgcc gcgccgtgcc     720
gtagcgctgc gtcgtcagct ggtttccagc gataacatct ctaacgatcc gatgaatgtc     780
atcgactgga tcaacatgta cgcgctggcg gttagtgaag aaaacgcagc tggcgggcgc     840
gtggtaacgg caccgactaa cggtgcgtgc ggcattattc cggcagtact ggcttattac     900
gataagttcc gtcgtccggt aaacgagcgg tcaattgccc gctattttct ggccgcgggg     960
gctattggcg cgctgtataa aatgaacgcc tccatctctg gcgcggaagt cggctgtcag    1020
ggggagattg gcgtggcctg ttcaatggcg gcggcagggt taactgaact actgggcggc    1080
agtccggcgc aggtatgcaa tgcggcggaa atcgcgatgg agcataacct tgggctgacc    1140
tgcgatccgg ttgccggaca ggtacaaatc ccgtgcattg aacgtaatgc cattaatgcc    1200
gtgaaagcag taaacgccgc gcggatggcg atgcgccgca cctcggcacc gcgtgtttca    1260
ctcgataaag tgatcgagac gatgtatgaa accggcaaag atatgaacga taaataccgc    1320
gaaacatcac gcggaggact ggccattaaa gtggtctgcg gctga                    1365
```

<210> SEQ ID NO 4
<211> LENGTH: 1254
<212> TYPE: DNA
<213> ORGANISM: Escherichia coli

<400> SEQUENCE: 4

```
atgttaaagc gtgaaatgaa cattgccgat tatgatgccg aactgtggca ggctatggag      60
caggaaaaag tacgtcagga agagcacatc gaactgatcg cctccgaaaa ctacaccagc     120
ccgcgcgtaa tgcaggcgca gggttctcag ctgaccaaca aatatgctga aggttatccg     180
ggcaaacgct actacggcgg ttgcgagtat gttgatatcg ttgaacaact ggcgatcgat     240
cgtgcgaaag aactgttcgg cgctgactac gctaacgtcc agccgcactc cggctcccag     300
gctaactttg cggtctacac cgcgctgctg aaccaggtg ataccgttct gggtatgaac     360
ctggcgcatg gcggtcacct gactcacggt tctccggtta acttctccgg taaactgtac     420
aacatcgttc cttacggtat cgatgctacc ggtcatatcg actacgccga tctggaaaaa     480
caagccaaag aacacaagcc gaaaatgatt atcggtggtt tctctgcata ttccggcgtg     540
gtggactggg cgaaaatgcg tgaaatcgct gacagcatcg gtgcttacct gttcgttgat     600
atggcgcacg ttgcgggcct ggttgctgct ggcgtctacc cgaacccggt tcctcatgct     660
cacgttgtta ctaccaccac tcacaaaacc ctggcgggtc cgcgcggcgg cctgatcctg     720
gcgaaaggtg gtagcgaaga gctgtacaaa aaactgaact ctgccgtttt ccctggtggt     780
```

```
caggggcggtc cgttgatgca cgtaatcgcc ggtaaagcgg ttgctctgaa agaagcgatg    840
gagcctgagt tcaaaactta ccagcagcag gtcgctaaaa acgctaaagc gatggtagaa    900
gtgttcctcg agcgcggcta caaagtggtt tccggcggca ctgataacca cctgttcctg    960
gttgatctgg ttgataaaaa cctgaccggt aaagaagcag acgccgctct gggccgtgct   1020
aacatcaccg tcaacaaaaa cagcgtaccg aacgatccga agagcccgtt tgtgacctcc   1080
ggtattcgtg taggtactcc ggcgattacc cgtcgcggct ttaaagaagc cgaagcgaaa   1140
gaactggctg gctggatgtg tgacgtgctg gacagcatca atgatgaagc cgttatcgag   1200
cgcatcaaag gtaaagttct cgacatctgc gcacgttacc cggtttacgc ataa         1254
```

<210> SEQ ID NO 5
<211> LENGTH: 410
<212> TYPE: PRT
<213> ORGANISM: Escherichia coli

<400> SEQUENCE: 5

```
Met Ala Lys Val Ser Leu Glu Lys Asp Lys Ile Lys Phe Leu Leu Val
1               5                   10                  15

Glu Gly Val His Gln Lys Ala Leu Glu Ser Leu Arg Ala Ala Gly Tyr
            20                  25                  30

Thr Asn Ile Glu Phe His Lys Gly Ala Leu Asp Asp Glu Gln Leu Lys
        35                  40                  45

Glu Ser Ile Arg Asp Ala His Phe Ile Gly Leu Arg Ser Arg Thr His
    50                  55                  60

Leu Thr Glu Asp Val Ile Asn Ala Ala Glu Lys Leu Val Ala Ile Gly
65                  70                  75                  80

Cys Phe Cys Ile Gly Thr Asn Gln Val Asp Leu Asp Ala Ala Ala Lys
                85                  90                  95

Arg Gly Ile Pro Val Phe Asn Ala Pro Phe Ser Asn Thr Arg Ser Val
            100                 105                 110

Ala Glu Leu Val Ile Gly Glu Leu Leu Leu Leu Arg Gly Val Pro
        115                 120                 125

Glu Ala Asn Ala Lys Ala His Arg Gly Val Trp Asn Lys Leu Ala Ala
    130                 135                 140

Gly Ser Phe Glu Ala Arg Gly Lys Lys Leu Gly Ile Ile Gly Tyr Gly
145                 150                 155                 160

His Ile Gly Thr Gln Leu Gly Ile Leu Ala Glu Ser Leu Gly Met Tyr
                165                 170                 175

Val Tyr Phe Tyr Asp Ile Glu Asn Lys Leu Pro Leu Gly Asn Ala Thr
            180                 185                 190

Gln Val Gln His Leu Ser Asp Leu Leu Asn Met Ser Asp Val Val Ser
        195                 200                 205

Leu His Val Pro Glu Asn Pro Ser Thr Lys Asn Met Met Gly Ala Lys
    210                 215                 220

Glu Ile Ser Leu Met Lys Pro Gly Ser Leu Leu Ile Asn Ala Ser Arg
225                 230                 235                 240

Gly Thr Val Val Asp Ile Pro Ala Leu Cys Asp Ala Leu Ala Ser Lys
                245                 250                 255

His Leu Ala Gly Ala Ala Ile Asp Val Phe Pro Thr Glu Pro Ala Thr
            260                 265                 270

Asn Ser Asp Pro Phe Thr Ser Pro Leu Cys Glu Phe Asp Asn Val Leu
        275                 280                 285
```

```
Leu Thr Pro His Ile Gly Gly Ser Thr Gln Glu Ala Gln Glu Asn Ile
    290                 295                 300
Gly Leu Glu Val Ala Gly Lys Leu Ile Lys Tyr Ser Asp Asn Gly Ser
305                 310                 315                 320
Thr Leu Ser Ala Val Asn Phe Pro Glu Val Ser Leu Pro Leu His Gly
                325                 330                 335
Gly Arg Arg Leu Met His Ile His Glu Asn Arg Pro Gly Val Leu Thr
            340                 345                 350
Ala Leu Asn Lys Ile Phe Ala Glu Gln Gly Val Asn Ile Ala Ala Gln
        355                 360                 365
Tyr Leu Gln Thr Ser Ala Gln Met Gly Tyr Val Val Ile Asp Ile Glu
370                 375                 380
Ala Asp Glu Asp Val Ala Glu Lys Ala Leu Gln Ala Met Lys Ala Ile
385                 390                 395                 400
Pro Gly Thr Ile Arg Ala Arg Leu Leu Tyr
                405                 410

<210> SEQ ID NO 6
<211> LENGTH: 410
<212> TYPE: PRT
<213> ORGANISM: Artificial Sequence
<220> FEATURE:
<223> OTHER INFORMATION: Mutant SerA

<400> SEQUENCE: 6

Met Ala Lys Val Ser Leu Glu Lys Asp Lys Ile Lys Phe Leu Leu Val
1               5                   10                  15
Glu Gly Val His Gln Lys Ala Leu Glu Ser Leu Arg Ala Ala Gly Tyr
            20                  25                  30
Thr Asn Ile Glu Phe His Lys Gly Ala Leu Asp Asp Glu Gln Leu Lys
        35                  40                  45
Glu Ser Ile Arg Asp Ala His Phe Ile Gly Leu Arg Ser Arg Thr His
    50                  55                  60
Leu Thr Glu Asp Val Ile Asn Ala Ala Glu Lys Leu Val Ala Ile Gly
65                  70                  75                  80
Cys Phe Cys Ile Gly Thr Asn Gln Val Asp Leu Asp Ala Ala Ala Lys
                85                  90                  95
Arg Gly Ile Pro Val Phe Asn Ala Pro Phe Ser Asn Thr Arg Ser Val
            100                 105                 110
Ala Glu Leu Val Ile Gly Glu Leu Leu Leu Leu Arg Gly Val Pro
        115                 120                 125
Glu Ala Asn Ala Lys Ala His Arg Gly Val Trp Asn Lys Leu Ala Ala
    130                 135                 140
Gly Ser Phe Glu Ala Arg Gly Lys Lys Leu Gly Ile Ile Gly Tyr Gly
145                 150                 155                 160
His Ile Gly Thr Gln Leu Gly Ile Leu Ala Glu Ser Leu Gly Met Tyr
                165                 170                 175
Val Tyr Phe Tyr Asp Ile Glu Asn Lys Leu Pro Leu Gly Asn Ala Thr
            180                 185                 190
Gln Val Gln His Leu Ser Asp Leu Leu Asn Met Ser Asp Val Val Ser
        195                 200                 205
Leu His Val Pro Glu Asn Pro Ser Thr Lys Asn Met Met Gly Ala Lys
    210                 215                 220
Glu Ile Ser Leu Met Lys Pro Gly Ser Leu Leu Ile Asn Ala Ser Arg
225                 230                 235                 240
```

Gly Thr Val Val Asp Ile Pro Ala Leu Cys Asp Ala Leu Ala Ser Lys
            245                 250                 255

His Leu Ala Gly Ala Ala Ile Asp Val Phe Pro Thr Glu Pro Ala Thr
        260                 265                 270

Asn Ser Asp Pro Phe Thr Ser Pro Leu Cys Glu Phe Asp Asn Val Leu
        275                 280                 285

Leu Thr Pro His Ile Gly Gly Ser Thr Gln Glu Ala Gln Glu Asn Ile
        290                 295                 300

Gly Leu Glu Val Ala Gly Lys Leu Ile Lys Tyr Ser Asp Asn Gly Ser
305                 310                 315                 320

Thr Leu Ser Ala Val Asn Phe Pro Glu Val Ser Leu Pro Leu His Gly
                325                 330                 335

Gly Arg Arg Leu Met His Ile Ala Glu Ala Arg Pro Gly Val Leu Thr
                340                 345                 350

Ala Leu Asn Lys Ile Phe Ala Glu Gln Gly Val Ala Ile Ala Ala Gln
            355                 360                 365

Tyr Leu Gln Thr Ser Ala Gln Met Gly Tyr Val Val Ile Asp Ile Glu
        370                 375                 380

Ala Asp Glu Asp Val Ala Glu Lys Ala Leu Gln Ala Met Lys Ala Ile
385                 390                 395                 400

Pro Gly Thr Ile Arg Ala Arg Leu Leu Tyr
                405                 410

<210> SEQ ID NO 7
<211> LENGTH: 322
<212> TYPE: PRT
<213> ORGANISM: Escherichia coli

<400> SEQUENCE: 7

Met Pro Asn Ile Thr Trp Cys Asp Leu Pro Glu Asp Val Ser Leu Trp
1               5                   10                  15

Pro Gly Leu Pro Leu Ser Leu Ser Gly Asp Glu Val Met Pro Leu Asp
            20                  25                  30

Tyr His Ala Gly Arg Ser Gly Trp Leu Leu Tyr Gly Arg Gly Leu Asp
        35                  40                  45

Lys Gln Arg Leu Thr Gln Tyr Gln Ser Lys Leu Gly Ala Ala Met Val
    50                  55                  60

Ile Val Ala Ala Trp Cys Val Glu Asp Tyr Gln Val Ile Arg Leu Ala
65                  70                  75                  80

Gly Ser Leu Thr Ala Arg Ala Thr Arg Leu Ala His Glu Ala Gln Leu
                85                  90                  95

Asp Val Ala Pro Leu Gly Lys Ile Pro His Leu Arg Thr Pro Gly Leu
            100                 105                 110

Leu Val Met Asp Met Asp Ser Thr Ala Ile Gln Ile Glu Cys Ile Asp
        115                 120                 125

Glu Ile Ala Lys Leu Ala Gly Thr Gly Glu Met Val Ala Glu Val Thr
    130                 135                 140

Glu Arg Ala Met Arg Gly Glu Leu Asp Phe Thr Ala Ser Leu Arg Ser
145                 150                 155                 160

Arg Val Ala Thr Leu Lys Gly Ala Asp Ala Asn Ile Leu Gln Gln Val
                165                 170                 175

Arg Glu Asn Leu Pro Leu Met Pro Gly Leu Thr Gln Leu Val Leu Lys
            180                 185                 190

Leu Glu Thr Leu Gly Trp Lys Val Ala Ile Ala Ser Gly Gly Phe Thr
        195                 200                 205

```
Phe Phe Ala Glu Tyr Leu Arg Asp Lys Leu Arg Leu Thr Ala Val Val
    210                 215                 220

Ala Asn Glu Leu Glu Ile Met Asp Gly Lys Phe Thr Gly Asn Val Ile
225                 230                 235                 240

Gly Asp Ile Val Asp Ala Gln Tyr Lys Ala Lys Thr Leu Thr Arg Leu
                245                 250                 255

Ala Gln Glu Tyr Glu Ile Pro Leu Ala Gln Thr Val Ala Ile Gly Asp
            260                 265                 270

Gly Ala Asn Asp Leu Pro Met Ile Lys Ala Ala Gly Leu Gly Ile Ala
        275                 280                 285

Tyr His Ala Lys Pro Lys Val Asn Glu Lys Ala Glu Val Thr Ile Arg
    290                 295                 300

His Ala Asp Leu Met Gly Val Phe Cys Ile Leu Ser Gly Ser Leu Asn
305                 310                 315                 320

Gln Lys

<210> SEQ ID NO 8
<211> LENGTH: 362
<212> TYPE: PRT
<213> ORGANISM: Escherichia coli

<400> SEQUENCE: 8

Met Ala Gln Ile Phe Asn Phe Ser Ser Gly Pro Ala Met Leu Pro Ala
1               5                   10                  15

Glu Val Leu Lys Gln Ala Gln Gln Glu Leu Arg Asp Trp Asn Gly Leu
            20                  25                  30

Gly Thr Ser Val Met Glu Val Ser His Arg Gly Lys Glu Phe Ile Gln
        35                  40                  45

Val Ala Glu Glu Ala Glu Lys Asp Phe Arg Asp Leu Leu Asn Val Pro
    50                  55                  60

Ser Asn Tyr Lys Val Leu Phe Cys His Gly Gly Gly Arg Gly Gln Phe
65                  70                  75                  80

Ala Ala Val Pro Leu Asn Ile Leu Gly Asp Lys Thr Thr Ala Asp Tyr
                85                  90                  95

Val Asp Ala Gly Tyr Trp Ala Ala Ser Ala Ile Lys Glu Ala Lys Lys
            100                 105                 110

Tyr Cys Thr Pro Asn Val Phe Asp Ala Lys Val Thr Val Asp Gly Leu
        115                 120                 125

Arg Ala Val Lys Pro Met Arg Glu Trp Gln Leu Ser Asp Asn Ala Ala
    130                 135                 140

Tyr Met His Tyr Cys Pro Asn Glu Thr Ile Asp Gly Ile Ala Ile Asp
145                 150                 155                 160

Glu Thr Pro Asp Phe Gly Ala Asp Val Val Val Ala Ala Asp Phe Ser
                165                 170                 175

Ser Thr Ile Leu Ser Arg Pro Ile Asp Val Ser Arg Tyr Gly Val Ile
            180                 185                 190

Tyr Ala Gly Ala Gln Lys Asn Ile Gly Pro Ala Gly Leu Thr Ile Val
        195                 200                 205

Ile Val Arg Glu Asp Leu Leu Gly Lys Ala Asn Ile Ala Cys Pro Ser
    210                 215                 220

Ile Leu Asp Tyr Ser Ile Leu Asn Asp Asn Gly Ser Met Phe Asn Thr
225                 230                 235                 240

Pro Pro Thr Phe Ala Trp Tyr Leu Ser Gly Leu Val Phe Lys Trp Leu
                245                 250                 255
```

```
Lys Ala Asn Gly Gly Val Ala Glu Met Asp Lys Ile Asn Gln Gln Lys
            260                 265                 270

Ala Glu Leu Leu Tyr Gly Val Ile Asp Asn Ser Asp Phe Tyr Arg Asn
        275                 280                 285

Asp Val Ala Lys Ala Asn Arg Ser Arg Met Asn Val Pro Phe Gln Leu
    290                 295                 300

Ala Asp Ser Ala Leu Asp Lys Leu Phe Leu Glu Glu Ser Phe Ala Ala
305                 310                 315                 320

Gly Leu His Ala Leu Lys Gly His Arg Val Val Gly Met Arg Ala
                325                 330                 335

Ser Ile Tyr Asn Ala Met Pro Leu Glu Gly Val Lys Ala Leu Thr Asp
                340                 345                 350

Phe Met Val Glu Phe Glu Arg Arg His Gly
            355                 360

<210> SEQ ID NO 9
<211> LENGTH: 299
<212> TYPE: PRT
<213> ORGANISM: Escherichia coli

<400> SEQUENCE: 9

Met Ser Arg Lys Asp Gly Val Leu Ala Leu Leu Val Val Val Val Trp
1               5                   10                  15

Gly Leu Asn Phe Val Val Ile Lys Val Gly Leu His Asn Met Pro Pro
            20                  25                  30

Leu Met Leu Ala Gly Leu Arg Phe Met Leu Val Ala Phe Pro Ala Ile
        35                  40                  45

Phe Phe Val Ala Arg Pro Lys Val Pro Leu Asn Leu Leu Leu Gly Tyr
    50                  55                  60

Gly Leu Thr Ile Ser Phe Ala Gln Phe Ala Phe Leu Phe Cys Ala Ile
65                  70                  75                  80

Asn Phe Gly Met Pro Ala Gly Leu Ala Ser Leu Val Leu Gln Ala Gln
                85                  90                  95

Ala Phe Phe Thr Ile Met Leu Gly Ala Phe Thr Phe Gly Glu Arg Leu
            100                 105                 110

His Gly Lys Gln Leu Ala Gly Ile Ala Leu Ala Ile Phe Gly Val Leu
        115                 120                 125

Val Leu Ile Glu Asp Ser Leu Asn Gly Gln His Val Ala Met Leu Gly
    130                 135                 140

Phe Met Leu Thr Leu Ala Ala Ala Phe Ser Trp Ala Cys Gly Asn Ile
145                 150                 155                 160

Phe Asn Lys Lys Ile Met Ser His Ser Thr Arg Pro Ala Val Met Ser
                165                 170                 175

Leu Val Ile Trp Ser Ala Leu Ile Pro Ile Ile Pro Phe Phe Val Ala
            180                 185                 190

Ser Leu Ile Leu Asp Gly Ser Ala Thr Met Ile His Ser Leu Val Thr
        195                 200                 205

Ile Asp Met Thr Thr Ile Leu Ser Leu Met Tyr Leu Ala Phe Val Ala
    210                 215                 220

Thr Ile Val Gly Tyr Gly Ile Trp Gly Thr Leu Leu Gly Arg Tyr Glu
225                 230                 235                 240

Thr Trp Arg Val Ala Pro Leu Ser Leu Leu Val Pro Val Val Gly Leu
                245                 250                 255

Ala Ser Ala Ala Leu Leu Leu Asp Glu Arg Leu Thr Gly Leu Gln Phe
```

```
                260             265             270
Leu Gly Ala Val Leu Ile Met Thr Gly Leu Tyr Ile Asn Val Phe Gly
        275             280             285

Leu Arg Trp Arg Lys Ala Val Lys Val Gly Ser
        290             295

<210> SEQ ID NO 10
<211> LENGTH: 305
<212> TYPE: PRT
<213> ORGANISM: Artificial Sequence
<220> FEATURE:
<223> OTHER INFORMATION: YdeD containing His-tag at C-terminus

<400> SEQUENCE: 10

Met Ser Arg Lys Asp Gly Val Leu Ala Leu Val Val Val Val Val Trp
1               5                   10                  15

Gly Leu Asn Phe Val Val Ile Lys Val Gly Leu His Asn Met Pro Pro
            20                  25                  30

Leu Met Leu Ala Gly Leu Arg Phe Met Leu Val Ala Phe Pro Ala Ile
        35                  40                  45

Phe Phe Val Ala Arg Pro Lys Val Pro Leu Asn Leu Leu Leu Gly Tyr
    50                  55                  60

Gly Leu Thr Ile Ser Phe Ala Gln Phe Ala Phe Leu Phe Cys Ala Ile
65                  70                  75                  80

Asn Phe Gly Met Pro Ala Gly Leu Ala Ser Leu Val Leu Gln Ala Gln
                85                  90                  95

Ala Phe Phe Thr Ile Met Leu Gly Ala Phe Thr Phe Gly Glu Arg Leu
            100                 105                 110

His Gly Lys Gln Leu Ala Gly Ile Ala Leu Ala Ile Phe Gly Val Leu
        115                 120                 125

Val Leu Ile Glu Asp Ser Leu Asn Gly Gln His Val Ala Met Leu Gly
    130                 135                 140

Phe Met Leu Thr Leu Ala Ala Ala Phe Ser Trp Ala Cys Gly Asn Ile
145                 150                 155                 160

Phe Asn Lys Lys Ile Met Ser His Ser Thr Arg Pro Ala Val Met Ser
                165                 170                 175

Leu Val Ile Trp Ser Ala Leu Ile Pro Ile Ile Pro Phe Phe Val Ala
            180                 185                 190

Ser Leu Ile Leu Asp Gly Ser Ala Thr Met Ile His Ser Leu Val Thr
        195                 200                 205

Ile Asp Met Thr Thr Ile Leu Ser Leu Met Tyr Leu Ala Phe Val Ala
    210                 215                 220

Thr Ile Val Gly Tyr Gly Ile Trp Gly Thr Leu Leu Gly Arg Tyr Glu
225                 230                 235                 240

Thr Trp Arg Val Ala Pro Leu Ser Leu Leu Val Pro Val Val Gly Leu
                245                 250                 255

Ala Ser Ala Ala Leu Leu Leu Asp Glu Arg Leu Thr Gly Leu Gln Phe
            260                 265                 270

Leu Gly Ala Val Leu Ile Met Thr Gly Leu Tyr Ile Asn Val Phe Gly
        275                 280                 285

Leu Arg Trp Arg Lys Ala Val Lys Val Gly Ser His His His His
    290                 295                 300

His
305
```

```
<210> SEQ ID NO 11
<211> LENGTH: 820
<212> TYPE: PRT
<213> ORGANISM: Escherichia coli

<400> SEQUENCE: 11
```

| | | | | | | | | | | | | | | |
|---|---|---|---|---|---|---|---|---|---|---|---|---|---|---|
| Met | Arg | Val | Leu | Lys | Phe | Gly | Gly | Thr | Ser | Val | Ala | Asn | Ala | Glu | Arg |
| 1 | | | | 5 | | | | | 10 | | | | | 15 | |
| Phe | Leu | Arg | Val | Ala | Asp | Ile | Leu | Glu | Ser | Asn | Ala | Arg | Gln | Gly | Gln |
| | | | 20 | | | | | 25 | | | | | 30 | | |
| Val | Ala | Thr | Val | Leu | Ser | Ala | Pro | Ala | Lys | Ile | Thr | Asn | His | Leu | Val |
| | | 35 | | | | | 40 | | | | | 45 | | | |
| Ala | Met | Ile | Glu | Lys | Thr | Ile | Ser | Gly | Gln | Asp | Ala | Leu | Pro | Asn | Ile |
| | 50 | | | | | 55 | | | | | 60 | | | | |
| Ser | Asp | Ala | Glu | Arg | Ile | Phe | Ala | Glu | Leu | Leu | Thr | Gly | Leu | Ala | Ala |
| 65 | | | | | 70 | | | | | 75 | | | | | 80 |
| Ala | Gln | Pro | Gly | Phe | Pro | Leu | Ala | Gln | Leu | Lys | Thr | Phe | Val | Asp | Gln |
| | | | | 85 | | | | | 90 | | | | | 95 | |
| Glu | Phe | Ala | Gln | Ile | Lys | His | Val | Leu | His | Gly | Ile | Ser | Leu | Leu | Gly |
| | | | 100 | | | | | 105 | | | | | 110 | | |
| Gln | Cys | Pro | Asp | Ser | Ile | Asn | Ala | Ala | Leu | Ile | Cys | Arg | Gly | Glu | Lys |
| | | | 115 | | | | | 120 | | | | | 125 | | |
| Met | Ser | Ile | Ala | Ile | Met | Ala | Gly | Val | Leu | Glu | Ala | Arg | Gly | His | Asn |
| | 130 | | | | | 135 | | | | | 140 | | | | |
| Val | Thr | Val | Ile | Asp | Pro | Val | Glu | Lys | Leu | Leu | Ala | Val | Gly | His | Tyr |
| 145 | | | | | 150 | | | | | 155 | | | | | 160 |
| Leu | Glu | Ser | Thr | Val | Asp | Ile | Ala | Glu | Ser | Thr | Arg | Arg | Ile | Ala | Ala |
| | | | | 165 | | | | | 170 | | | | | 175 | |
| Ser | Arg | Ile | Pro | Ala | Asp | His | Met | Val | Leu | Met | Ala | Gly | Phe | Thr | Ala |
| | | | 180 | | | | | 185 | | | | | 190 | | |
| Gly | Asn | Glu | Lys | Gly | Glu | Leu | Val | Val | Leu | Gly | Arg | Asn | Gly | Ser | Asp |
| | | | 195 | | | | | 200 | | | | | 205 | | |
| Tyr | Ser | Ala | Ala | Val | Leu | Ala | Ala | Cys | Leu | Arg | Ala | Asp | Cys | Cys | Glu |
| | 210 | | | | | 215 | | | | | 220 | | | | |
| Ile | Trp | Thr | Asp | Val | Asp | Gly | Val | Tyr | Thr | Cys | Asp | Pro | Arg | Gln | Val |
| 225 | | | | | 230 | | | | | 235 | | | | | 240 |
| Pro | Asp | Ala | Arg | Leu | Leu | Lys | Ser | Met | Ser | Tyr | Gln | Glu | Ala | Met | Glu |
| | | | | 245 | | | | | 250 | | | | | 255 | |
| Leu | Ser | Tyr | Phe | Gly | Ala | Lys | Val | Leu | His | Pro | Arg | Thr | Ile | Thr | Pro |
| | | | 260 | | | | | 265 | | | | | 270 | | |
| Ile | Ala | Gln | Phe | Gln | Ile | Pro | Cys | Leu | Ile | Lys | Asn | Thr | Gly | Asn | Pro |
| | | | 275 | | | | | 280 | | | | | 285 | | |
| Gln | Ala | Pro | Gly | Thr | Leu | Ile | Gly | Ala | Ser | Arg | Asp | Glu | Asp | Glu | Leu |
| | 290 | | | | | 295 | | | | | 300 | | | | |
| Pro | Val | Lys | Gly | Ile | Ser | Asn | Leu | Asn | Asn | Met | Ala | Met | Phe | Ser | Val |
| 305 | | | | | 310 | | | | | 315 | | | | | 320 |
| Ser | Gly | Pro | Gly | Met | Lys | Gly | Met | Val | Gly | Met | Ala | Ala | Arg | Val | Phe |
| | | | | 325 | | | | | 330 | | | | | 335 | |
| Ala | Ala | Met | Ser | Arg | Ala | Arg | Ile | Ser | Val | Val | Leu | Ile | Thr | Gln | Ser |
| | | | 340 | | | | | 345 | | | | | 350 | | |
| Ser | Ser | Glu | Tyr | Ser | Ile | Ser | Phe | Cys | Val | Pro | Gln | Ser | Asp | Cys | Val |
| | | | 355 | | | | | 360 | | | | | 365 | | |
| Arg | Ala | Glu | Arg | Ala | Met | Gln | Glu | Glu | Phe | Tyr | Leu | Glu | Leu | Lys | Glu |
| | 370 | | | | | 375 | | | | | 380 | | | | |

```
Gly Leu Leu Glu Pro Leu Ala Val Thr Glu Arg Leu Ala Ile Ile Ser
385                 390                 395                 400

Val Val Gly Asp Gly Met Arg Thr Leu Arg Gly Ile Ser Ala Lys Phe
            405                 410                 415

Phe Ala Leu Ala Arg Ala Asn Ile Asn Ile Val Ala Ile Ala Gln
            420                 425                 430

Gly Ser Ser Glu Arg Ser Ile Ser Val Val Asn Asn Asp Asp Ala
            435                 440                 445

Thr Thr Gly Val Arg Val Thr His Gln Met Leu Phe Asn Thr Asp Gln
    450                 455                 460

Val Ile Glu Val Phe Val Ile Gly Val Gly Val Gly Ala Leu
465             470                 475                 480

Leu Glu Gln Leu Lys Arg Gln Gln Ser Trp Leu Lys Asn Lys His Ile
            485                 490                 495

Asp Leu Arg Val Cys Gly Val Ala Asn Ser Lys Ala Leu Leu Thr Asn
            500                 505                 510

Val His Gly Leu Asn Leu Glu Asn Trp Gln Glu Glu Leu Ala Gln Ala
    515                 520                 525

Lys Glu Pro Phe Asn Leu Gly Arg Leu Ile Arg Leu Val Lys Glu Tyr
    530                 535                 540

His Leu Leu Asn Pro Val Ile Val Asp Cys Thr Ser Ser Gln Ala Val
545                 550                 555                 560

Ala Asp Gln Tyr Ala Asp Phe Leu Arg Glu Gly Phe His Val Val Thr
            565                 570                 575

Pro Asn Lys Lys Ala Asn Thr Ser Ser Met Asp Tyr Tyr His Gln Leu
            580                 585                 590

Arg Tyr Ala Ala Glu Lys Ser Arg Arg Lys Phe Leu Tyr Asp Thr Asn
            595                 600                 605

Val Gly Ala Gly Leu Pro Val Ile Glu Asn Leu Gln Asn Leu Leu Asn
            610                 615                 620

Ala Gly Asp Glu Leu Met Lys Phe Ser Gly Ile Leu Ser Gly Ser Leu
625                 630                 635                 640

Ser Tyr Ile Phe Gly Lys Leu Asp Glu Gly Met Ser Phe Ser Glu Ala
            645                 650                 655

Thr Thr Leu Ala Arg Glu Met Gly Tyr Thr Glu Pro Asp Pro Arg Asp
            660                 665                 670

Asp Leu Ser Gly Met Asp Val Ala Arg Lys Leu Leu Ile Leu Ala Arg
            675                 680                 685

Glu Thr Gly Arg Glu Leu Glu Leu Ala Asp Ile Glu Ile Glu Pro Val
    690                 695                 700

Leu Pro Ala Glu Phe Asn Ala Glu Gly Asp Val Ala Ala Phe Met Ala
705                 710                 715                 720

Asn Leu Ser Gln Leu Asp Asp Leu Phe Ala Ala Arg Val Ala Lys Ala
            725                 730                 735

Arg Asp Glu Gly Lys Val Leu Arg Tyr Val Gly Asn Ile Asp Glu Asp
            740                 745                 750

Gly Val Cys Arg Val Lys Ile Ala Glu Val Asp Gly Asn Asp Pro Leu
            755                 760                 765

Phe Lys Val Lys Asn Gly Glu Asn Ala Leu Ala Phe Tyr Ser His Tyr
            770                 775                 780

Tyr Gln Pro Leu Pro Leu Val Leu Arg Gly Tyr Gly Ala Gly Asn Asp
785                 790                 795                 800

Val Thr Ala Ala Gly Val Phe Ala Asp Leu Leu Arg Thr Leu Ser Trp
```

-continued

```
                   805                 810                 815

Lys Leu Gly Val
            820

<210> SEQ ID NO 12
<211> LENGTH: 164
<212> TYPE: PRT
<213> ORGANISM: Escherichia coli

<400> SEQUENCE: 12

Met Val Asp Ser Lys Lys Arg Pro Gly Lys Asp Leu Asp Arg Ile Asp
1               5                   10                  15

Arg Asn Ile Leu Asn Glu Leu Gln Lys Asp Gly Arg Ile Ser Asn Val
            20                  25                  30

Glu Leu Ser Lys Arg Val Gly Leu Ser Pro Thr Pro Cys Leu Glu Arg
        35                  40                  45

Val Arg Arg Leu Glu Arg Gln Gly Phe Ile Gln Gly Tyr Thr Ala Leu
    50                  55                  60

Leu Asn Pro His Tyr Leu Asp Ala Ser Leu Leu Val Phe Val Glu Ile
65                  70                  75                  80

Thr Leu Asn Arg Gly Ala Pro Asp Val Phe Glu Gln Phe Asn Thr Ala
                85                  90                  95

Val Gln Lys Leu Glu Glu Ile Gln Glu Cys His Leu Val Ser Gly Asp
            100                 105                 110

Phe Asp Tyr Leu Leu Lys Thr Arg Val Pro Asp Met Ser Ala Tyr Arg
        115                 120                 125

Lys Leu Leu Gly Glu Thr Leu Arg Leu Pro Gly Val Asn Asp Thr
    130                 135                 140

Arg Thr Tyr Val Val Met Glu Glu Val Lys Gln Ser Asn Arg Leu Val
145                 150                 155                 160

Ile Lys Thr Arg

<210> SEQ ID NO 13
<211> LENGTH: 419
<212> TYPE: PRT
<213> ORGANISM: Escherichia coli

<400> SEQUENCE: 13

Met Asn Leu Thr Glu Leu Lys Asn Thr Pro Val Ser Glu Leu Ile Thr
1               5                   10                  15

Leu Gly Glu Asn Met Gly Leu Glu Asn Leu Ala Arg Met Arg Lys Gln
            20                  25                  30

Asp Ile Ile Phe Ala Ile Leu Lys Gln His Ala Lys Ser Gly Glu Asp
        35                  40                  45

Ile Phe Gly Asp Gly Val Leu Glu Ile Leu Gln Asp Gly Phe Gly Phe
    50                  55                  60

Leu Arg Ser Ala Asp Ser Ser Tyr Leu Ala Gly Pro Asp Asp Ile Tyr
65                  70                  75                  80

Val Ser Pro Ser Gln Ile Arg Arg Phe Asn Leu Arg Thr Gly Asp Thr
                85                  90                  95

Ile Ser Gly Lys Ile Arg Pro Pro Lys Glu Gly Glu Arg Tyr Phe Ala
            100                 105                 110

Leu Leu Lys Val Asn Glu Val Asn Phe Asp Lys Pro Glu Asn Ala Arg
        115                 120                 125

Asn Lys Ile Leu Phe Glu Asn Leu Thr Pro Leu His Ala Asn Ser Arg
    130                 135                 140
```

-continued

```
Leu Arg Met Glu Arg Gly Asn Gly Ser Thr Glu Asp Leu Thr Ala Arg
145                 150                 155                 160

Val Leu Asp Leu Ala Ser Pro Ile Gly Arg Gly Gln Arg Gly Leu Ile
                165                 170                 175

Val Ala Pro Pro Lys Ala Gly Lys Thr Met Leu Leu Gln Asn Ile Ala
            180                 185                 190

Gln Ser Ile Ala Tyr Asn His Pro Asp Cys Val Leu Met Val Leu Leu
        195                 200                 205

Ile Asp Glu Arg Pro Glu Glu Val Thr Glu Met Gln Arg Leu Val Lys
210                 215                 220

Gly Glu Val Val Ala Ser Thr Phe Asp Glu Pro Ala Ser Arg His Val
225                 230                 235                 240

Gln Val Ala Glu Met Val Ile Glu Lys Ala Lys Arg Leu Val Glu His
                245                 250                 255

Lys Lys Asp Val Ile Ile Leu Leu Asp Ser Ile Thr Arg Leu Ala Arg
            260                 265                 270

Ala Tyr Asn Thr Val Val Pro Ala Ser Gly Lys Val Leu Thr Gly Gly
        275                 280                 285

Val Asp Ala Asn Ala Leu His Arg Pro Lys Arg Phe Phe Gly Ala Ala
290                 295                 300

Arg Asn Val Glu Glu Gly Gly Ser Leu Thr Ile Ile Ala Thr Ala Leu
305                 310                 315                 320

Ile Asp Thr Gly Ser Lys Met Asp Glu Val Ile Tyr Glu Glu Phe Lys
                325                 330                 335

Gly Thr Gly Asn Met Glu Leu His Leu Ser Arg Lys Ile Ala Glu Lys
            340                 345                 350

Arg Val Phe Pro Ala Ile Asp Tyr Asn Arg Ser Gly Thr Arg Lys Glu
        355                 360                 365

Glu Leu Leu Thr Thr Gln Glu Glu Leu Gln Lys Met Trp Ile Leu Arg
370                 375                 380

Lys Ile Ile His Pro Met Gly Glu Ile Asp Ala Met Glu Phe Leu Ile
385                 390                 395                 400

Asn Lys Leu Ala Met Thr Lys Thr Asn Asp Asp Phe Phe Glu Met Met
                405                 410                 415

Lys Arg Ser

<210> SEQ ID NO 14
<211> LENGTH: 432
<212> TYPE: PRT
<213> ORGANISM: Escherichia coli

<400> SEQUENCE: 14

Met Ser Lys Ile Val Lys Ile Ile Gly Arg Glu Ile Ile Asp Ser Arg
1               5                   10                  15

Gly Asn Pro Thr Val Glu Ala Glu Val His Leu Glu Gly Gly Phe Val
                20                  25                  30

Gly Met Ala Ala Ala Pro Ser Gly Ala Ser Thr Gly Ser Arg Glu Ala
            35                  40                  45

Leu Glu Leu Arg Asp Gly Asp Lys Ser Arg Phe Leu Gly Lys Gly Val
        50                  55                  60

Thr Lys Ala Val Ala Ala Val Asn Gly Pro Ile Ala Gln Ala Leu Ile
65                  70                  75                  80

Gly Lys Asp Ala Lys Asp Gln Ala Gly Ile Asp Lys Ile Met Ile Asp
                85                  90                  95
```

Leu Asp Gly Thr Glu Asn Lys Ser Lys Phe Gly Ala Asn Ala Ile Leu
            100                 105                 110

Ala Val Ser Leu Ala Asn Ala Lys Ala Ala Ala Ala Lys Gly Met
        115                 120                 125

Pro Leu Tyr Glu His Ile Ala Glu Leu Asn Gly Thr Pro Gly Lys Tyr
        130                 135                 140

Ser Met Pro Val Pro Met Met Asn Ile Ile Asn Gly Gly Glu His Ala
145                 150                 155                 160

Asp Asn Asn Val Asp Ile Gln Glu Phe Met Ile Gln Pro Val Gly Ala
                165                 170                 175

Lys Thr Val Lys Glu Ala Ile Arg Met Gly Ser Glu Val Phe His His
        180                 185                 190

Leu Ala Lys Val Leu Lys Ala Lys Gly Met Asn Thr Ala Val Gly Asp
        195                 200                 205

Glu Gly Gly Tyr Ala Pro Asn Leu Gly Ser Asn Ala Glu Ala Leu Ala
        210                 215                 220

Val Ile Ala Glu Ala Val Lys Ala Ala Gly Tyr Glu Leu Gly Lys Asp
225                 230                 235                 240

Ile Thr Leu Ala Met Asp Cys Ala Ala Ser Glu Phe Tyr Lys Asp Gly
                245                 250                 255

Lys Tyr Val Leu Ala Gly Glu Gly Asn Lys Ala Phe Thr Ser Glu Glu
        260                 265                 270

Phe Thr His Phe Leu Glu Glu Leu Thr Lys Gln Tyr Pro Ile Val Ser
        275                 280                 285

Ile Glu Asp Gly Leu Asp Glu Ser Asp Trp Asp Gly Phe Ala Tyr Gln
        290                 295                 300

Thr Lys Val Leu Gly Asp Lys Ile Gln Leu Val Gly Asp Asp Leu Phe
305                 310                 315                 320

Val Thr Asn Thr Lys Ile Leu Lys Glu Gly Ile Glu Lys Gly Ile Ala
                325                 330                 335

Asn Ser Ile Leu Ile Lys Phe Asn Gln Ile Gly Ser Leu Thr Glu Thr
        340                 345                 350

Leu Ala Ala Ile Lys Met Ala Lys Asp Ala Gly Tyr Thr Ala Val Ile
        355                 360                 365

Ser His Arg Ser Gly Glu Thr Glu Asp Ala Thr Ile Ala Asp Leu Ala
        370                 375                 380

Val Gly Thr Ala Ala Gly Gln Ile Lys Thr Gly Ser Met Ser Arg Ser
385                 390                 395                 400

Asp Arg Val Ala Lys Tyr Asn Gln Leu Ile Arg Ile Glu Glu Ala Leu
                405                 410                 415

Gly Glu Lys Ala Pro Tyr Asn Gly Arg Lys Glu Ile Lys Gly Gln Ala
        420                 425                 430

<210> SEQ ID NO 15
<211> LENGTH: 297
<212> TYPE: PRT
<213> ORGANISM: Escherichia coli

<400> SEQUENCE: 15

Met Lys Arg Pro Asp Tyr Arg Thr Leu Gln Ala Leu Asp Ala Val Ile
1               5                   10                  15

Arg Glu Arg Gly Phe Glu Arg Ala Ala Gln Lys Leu Cys Ile Thr Gln
                20                  25                  30

Ser Ala Val Ser Gln Arg Ile Lys Gln Leu Glu Asn Met Phe Gly Gln

```
                35                   40                  45
Pro Leu Leu Val Arg Thr Val Pro Arg Pro Thr Glu Gln Gly Gln
 50                      55                  60

Lys Leu Leu Ala Leu Leu Arg Gln Val Glu Leu Leu Glu Glu Trp
 65                  70                  75                  80

Leu Gly Asp Glu Gln Thr Gly Ser Thr Pro Leu Leu Ser Leu Ala
                 85                  90                  95

Val Asn Ala Asp Ser Leu Ala Thr Trp Leu Pro Ala Leu Ala Pro
            100                 105                 110

Val Leu Ala Asp Ser Pro Ile Arg Leu Asn Leu Gln Val Asp Glu
        115                 120                 125

Thr Arg Thr Gln Glu Arg Leu Arg Arg Gly Glu Val Val Gly Ala Val
130                 135                 140

Ser Ile Gln His Gln Ala Leu Pro Ser Cys Leu Val Asp Lys Leu Gly
145                 150                 155                 160

Ala Leu Asp Tyr Leu Phe Val Ser Ser Lys Pro Phe Ala Glu Lys Tyr
                165                 170                 175

Phe Pro Asn Gly Val Thr Arg Ser Ala Leu Leu Lys Ala Pro Val Val
            180                 185                 190

Ala Phe Asp His Leu Asp Asp Met His Gln Ala Phe Leu Gln Gln Asn
        195                 200                 205

Phe Asp Leu Pro Pro Gly Ser Val Pro Cys His Ile Val Asn Ser Ser
210                 215                 220

Glu Ala Phe Val Gln Leu Ala Arg Gln Gly Thr Thr Cys Cys Met Ile
225                 230                 235                 240

Pro His Leu Gln Ile Glu Lys Glu Leu Ala Ser Gly Glu Leu Ile Asp
                245                 250                 255

Leu Thr Pro Gly Leu Phe Gln Arg Arg Met Leu Tyr Trp His Arg Phe
            260                 265                 270

Ala Pro Glu Ser Arg Met Met Arg Lys Val Thr Asp Ala Leu Leu Asp
        275                 280                 285

Tyr Gly His Lys Val Leu Arg Gln Asp
290                 295

<210> SEQ ID NO 16
<211> LENGTH: 394
<212> TYPE: PRT
<213> ORGANISM: Escherichia coli

<400> SEQUENCE: 16

Met Ser Lys Glu Lys Phe Glu Arg Thr Lys Pro His Val Asn Val Gly
 1               5                  10                  15

Thr Ile Gly His Val Asp His Gly Lys Thr Thr Leu Thr Ala Ala Ile
             20                  25                  30

Thr Thr Val Leu Ala Lys Thr Tyr Gly Gly Ala Ala Arg Ala Phe Asp
         35                  40                  45

Gln Ile Asp Asn Ala Pro Glu Glu Lys Ala Arg Gly Ile Thr Ile Asn
     50                  55                  60

Thr Ser His Val Glu Tyr Asp Thr Pro Thr Arg His Tyr Ala His Val
 65                  70                  75                  80

Asp Cys Pro Gly His Ala Asp Tyr Val Lys Asn Met Ile Thr Gly Ala
                 85                  90                  95

Ala Gln Met Asp Gly Ala Ile Leu Val Val Ala Ala Thr Asp Gly Pro
            100                 105                 110
```

```
Met Pro Gln Thr Arg Glu His Ile Leu Leu Gly Arg Gln Val Gly Val
            115                 120                 125

Pro Tyr Ile Ile Val Phe Leu Asn Lys Cys Asp Met Val Asp Asp Glu
        130                 135                 140

Glu Leu Leu Glu Leu Val Glu Met Glu Val Arg Glu Leu Leu Ser Gln
145                 150                 155                 160

Tyr Asp Phe Pro Gly Asp Thr Pro Ile Val Arg Gly Ser Ala Leu
                165                 170                 175

Lys Ala Leu Glu Gly Asp Ala Glu Trp Glu Ala Lys Ile Leu Glu Leu
                180                 185                 190

Ala Gly Phe Leu Asp Ser Tyr Ile Pro Glu Pro Glu Arg Ala Ile Asp
        195                 200                 205

Lys Pro Phe Leu Leu Pro Ile Glu Asp Val Phe Ser Ile Ser Gly Arg
        210                 215                 220

Gly Thr Val Val Thr Gly Arg Val Glu Arg Gly Ile Ile Lys Val Gly
225                 230                 235                 240

Glu Glu Val Glu Ile Val Gly Ile Lys Glu Thr Gln Lys Ser Thr Cys
                245                 250                 255

Thr Gly Val Glu Met Phe Arg Lys Leu Leu Asp Glu Gly Arg Ala Gly
                260                 265                 270

Glu Asn Val Gly Val Leu Leu Arg Gly Ile Lys Arg Glu Glu Ile Glu
        275                 280                 285

Arg Gly Gln Val Leu Ala Lys Pro Gly Thr Ile Lys Pro His Thr Lys
        290                 295                 300

Phe Glu Ser Glu Val Tyr Ile Leu Ser Lys Asp Glu Gly Gly Arg His
305                 310                 315                 320

Thr Pro Phe Phe Lys Gly Tyr Arg Pro Gln Phe Tyr Phe Arg Thr Thr
                325                 330                 335

Asp Val Thr Gly Thr Ile Glu Leu Pro Glu Gly Val Glu Met Val Met
                340                 345                 350

Pro Gly Asp Asn Ile Lys Met Val Val Thr Leu Ile His Pro Ile Ala
        355                 360                 365

Met Asp Asp Gly Leu Arg Phe Ala Ile Arg Glu Gly Gly Arg Thr Val
        370                 375                 380

Gly Ala Gly Val Val Ala Lys Val Leu Gly
385                 390

<210> SEQ ID NO 17
<211> LENGTH: 470
<212> TYPE: PRT
<213> ORGANISM: Escherichia coli

<400> SEQUENCE: 17

Met Val Asp Gln Val Lys Val Val Ala Asp Asp Gln Ala Pro Ala Glu
1               5                   10                  15

Gln Ser Leu Arg Arg Asn Leu Thr Asn Arg His Ile Gln Leu Ile Ala
                20                  25                  30

Ile Gly Gly Ala Ile Gly Thr Gly Leu Phe Met Gly Ser Gly Lys Thr
            35                  40                  45

Ile Ser Leu Ala Gly Pro Ser Ile Ile Phe Val Tyr Met Ile Ile Gly
        50                  55                  60

Phe Met Leu Phe Phe Val Met Arg Ala Met Gly Glu Leu Leu Leu Ser
65                  70                  75                  80

Asn Leu Glu Tyr Lys Ser Phe Ser Asp Phe Ala Ser Asp Leu Leu Gly
                85                  90                  95
```

Pro Trp Ala Gly Tyr Phe Thr Gly Trp Thr Tyr Trp Phe Cys Trp Val
            100                 105                 110

Val Thr Gly Met Ala Asp Val Ala Ile Thr Ala Tyr Ala Gln Phe
        115                 120                 125

Trp Phe Pro Asp Leu Ser Asp Trp Val Ala Ser Leu Ala Val Ile Val
130                 135                 140

Leu Leu Leu Thr Leu Asn Leu Ala Thr Val Lys Met Phe Gly Glu Met
145                 150                 155                 160

Glu Phe Trp Phe Ala Met Ile Lys Ile Val Ala Ile Val Ser Leu Ile
                165                 170                 175

Val Val Gly Leu Val Met Val Ala Met His Phe Gln Ser Pro Thr Gly
            180                 185                 190

Val Glu Ala Ser Phe Ala His Leu Trp Asn Asp Gly Gly Trp Phe Pro
        195                 200                 205

Lys Gly Leu Ser Gly Phe Phe Ala Gly Phe Gln Ile Ala Val Phe Ala
        210                 215                 220

Phe Val Gly Ile Glu Leu Val Gly Thr Thr Ala Ala Glu Thr Lys Asp
225                 230                 235                 240

Pro Glu Lys Ser Leu Pro Arg Ala Ile Asn Ser Ile Pro Ile Arg Ile
                245                 250                 255

Ile Met Phe Tyr Val Phe Ala Leu Ile Val Ile Met Ser Val Thr Pro
            260                 265                 270

Trp Ser Ser Val Val Pro Glu Lys Ser Pro Phe Val Glu Leu Phe Val
        275                 280                 285

Leu Val Gly Leu Pro Ala Ala Ala Ser Val Ile Asn Phe Val Val Leu
        290                 295                 300

Thr Ser Ala Ala Ser Ser Ala Asn Ser Gly Val Phe Ser Thr Ser Arg
305                 310                 315                 320

Met Leu Phe Gly Leu Ala Gln Glu Gly Val Ala Pro Lys Ala Phe Ala
                325                 330                 335

Lys Leu Ser Lys Arg Ala Val Pro Ala Lys Gly Leu Thr Phe Ser Cys
            340                 345                 350

Ile Cys Leu Leu Gly Gly Val Val Met Leu Tyr Val Asn Pro Ser Val
        355                 360                 365

Ile Gly Ala Phe Thr Met Ile Thr Thr Val Ser Ala Ile Leu Phe Met
        370                 375                 380

Phe Val Trp Thr Ile Ile Leu Cys Ser Tyr Leu Val Tyr Arg Lys Gln
385                 390                 395                 400

Arg Pro His Leu His Glu Lys Ser Ile Tyr Lys Met Pro Leu Gly Lys
                405                 410                 415

Leu Met Cys Trp Val Cys Met Ala Phe Phe Val Phe Val Val Leu
            420                 425                 430

Leu Thr Leu Glu Asp Asp Thr Arg Gln Ala Leu Leu Val Thr Pro Leu
        435                 440                 445

Trp Phe Ile Ala Leu Gly Leu Gly Trp Leu Phe Ile Gly Lys Lys Arg
        450                 455                 460

Ala Ala Glu Leu Arg Lys
465                 470

<210> SEQ ID NO 18
<211> LENGTH: 225
<212> TYPE: PRT
<213> ORGANISM: Escherichia coli

<400> SEQUENCE: 18

```
Met Lys Gln Tyr Leu Ile Ala Pro Ser Ile Leu Ser Ala Asp Phe Ala
1               5                   10                  15
Arg Leu Gly Glu Asp Thr Ala Lys Ala Leu Ala Ala Gly Ala Asp Val
            20                  25                  30
Val His Phe Asp Val Met Asp Asn His Tyr Val Pro Asn Leu Thr Ile
        35                  40                  45
Gly Pro Met Val Leu Lys Ser Leu Arg Asn Tyr Gly Ile Thr Ala Pro
    50                  55                  60
Ile Asp Val His Leu Met Val Lys Pro Val Arg Ile Val Pro Asp
65                  70                  75                  80
Phe Ala Ala Gly Ala Ser Ile Ile Thr Phe His Pro Glu Ala Ser
                85                  90                  95
Glu His Val Asp Arg Thr Leu Gln Leu Ile Lys Glu Asn Gly Cys Lys
            100                 105                 110
Ala Gly Leu Val Phe Asn Pro Ala Thr Pro Leu Ser Tyr Leu Asp Tyr
        115                 120                 125
Val Met Asp Lys Leu Asp Val Ile Leu Leu Met Ser Val Asn Pro Gly
    130                 135                 140
Phe Gly Gly Gln Ser Phe Ile Pro Gln Thr Leu Asp Lys Leu Arg Glu
145                 150                 155                 160
Val Arg Arg Arg Ile Asp Glu Ser Gly Phe Asp Ile Arg Leu Glu Val
                165                 170                 175
Asp Gly Gly Val Lys Val Asn Asn Ile Gly Glu Ile Ala Ala Ala Gly
            180                 185                 190
Ala Asp Met Phe Val Ala Gly Ser Ala Ile Phe Asp Gln Pro Asp Tyr
        195                 200                 205
Lys Lys Val Ile Asp Glu Met Arg Ser Glu Leu Ala Lys Val Ser His
    210                 215                 220
Glu
225
```

<210> SEQ ID NO 19
<211> LENGTH: 547
<212> TYPE: PRT
<213> ORGANISM: Escherichia coli

<400> SEQUENCE: 19

```
Met Glu Leu Leu Val Leu Val Trp Arg Gln Tyr Arg Trp Pro Phe Ile
1               5                   10                  15
Ser Val Met Ala Leu Ser Leu Ala Ser Ala Ala Leu Gly Ile Gly Leu
            20                  25                  30
Ile Ala Phe Ile Asn Gln Arg Leu Ile Glu Thr Ala Asp Thr Ser Leu
        35                  40                  45
Leu Val Leu Pro Glu Phe Leu Gly Leu Leu Leu Leu Met Ala Val
    50                  55                  60
Thr Leu Gly Ser Gln Leu Ala Leu Thr Thr Leu Gly His His Phe Val
65                  70                  75                  80
Tyr Arg Leu Arg Ser Glu Phe Ile Lys Arg Ile Leu Asp Thr His Val
                85                  90                  95
Glu Arg Ile Glu Gln Leu Gly Ser Ala Ser Leu Leu Ala Gly Leu Thr
            100                 105                 110
Ser Asp Val Arg Asn Ile Thr Ile Ala Phe Val Arg Leu Pro Glu Leu
        115                 120                 125
```

```
Val Gln Gly Ile Ile Leu Thr Ile Gly Ser Ala Ala Tyr Leu Trp Met
130                 135                 140

Leu Ser Gly Lys Met Leu Leu Val Thr Ala Ile Trp Met Ala Ile Thr
145                 150                 155                 160

Ile Trp Gly Gly Phe Val Leu Val Ala Arg Val Tyr Lys His Met Ala
                165                 170                 175

Thr Leu Arg Glu Thr Glu Asp Lys Leu Tyr Thr Asp Phe Gln Thr Val
            180                 185                 190

Leu Glu Gly Arg Lys Glu Leu Thr Leu Asn Arg Glu Arg Ala Glu Tyr
        195                 200                 205

Val Phe Asn Asn Leu Tyr Ile Pro Asp Ala Gln Glu Tyr Arg His His
210                 215                 220

Ile Ile Arg Ala Asp Thr Phe His Leu Ser Ala Val Asn Trp Ser Asn
225                 230                 235                 240

Ile Met Met Leu Gly Ala Ile Gly Leu Val Phe Trp Met Ala Asn Ser
                245                 250                 255

Leu Gly Trp Ala Asp Thr Asn Val Ala Ala Thr Tyr Ser Leu Thr Leu
            260                 265                 270

Leu Phe Leu Arg Thr Pro Leu Leu Ser Ala Val Gly Ala Leu Pro Thr
        275                 280                 285

Leu Leu Thr Ala Gln Val Ala Phe Asn Lys Leu Asn Lys Phe Ala Leu
290                 295                 300

Ala Pro Phe Lys Ala Glu Phe Pro Arg Pro Gln Ala Phe Pro Asn Trp
305                 310                 315                 320

Gln Thr Leu Glu Leu Arg Asn Val Thr Phe Ala Tyr Gln Asp Asn Ala
                325                 330                 335

Phe Ser Val Gly Pro Ile Asn Leu Thr Ile Lys Arg Gly Glu Leu Leu
            340                 345                 350

Phe Leu Ile Gly Gly Asn Gly Ser Gly Lys Ser Thr Leu Ala Met Leu
        355                 360                 365

Leu Thr Gly Leu Tyr Gln Pro Gln Ser Gly Glu Ile Leu Leu Asp Gly
370                 375                 380

Lys Pro Val Ser Gly Glu Gln Pro Glu Asp Tyr Arg Lys Leu Phe Ser
385                 390                 395                 400

Ala Val Phe Thr Asp Val Trp Leu Phe Asp Gln Leu Leu Gly Pro Glu
                405                 410                 415

Gly Lys Pro Ala Asn Pro Gln Leu Val Glu Lys Trp Leu Ala Gln Leu
            420                 425                 430

Lys Met Ala His Lys Leu Glu Leu Ser Asn Gly Arg Ile Val Asn Leu
        435                 440                 445

Lys Leu Ser Lys Gly Gln Lys Lys Arg Val Ala Leu Leu Ala Leu
450                 455                 460

Ala Glu Glu Arg Asp Ile Ile Leu Leu Asp Glu Trp Ala Ala Asp Gln
465                 470                 475                 480

Asp Pro His Phe Arg Arg Glu Phe Tyr Gln Val Leu Leu Pro Leu Met
                485                 490                 495

Gln Glu Met Gly Lys Thr Ile Phe Ala Ile Ser His Asp Asp His Tyr
            500                 505                 510

Phe Ile His Ala Asp Arg Leu Leu Glu Met Arg Asn Gly Gln Leu Ser
        515                 520                 525

Glu Leu Thr Gly Glu Glu Arg Asp Ala Ala Ser Arg Asp Ala Val Ala
530                 535                 540

Arg Thr Ala
```

<210> SEQ ID NO 20
<211> LENGTH: 285
<212> TYPE: PRT
<213> ORGANISM: Escherichia coli

<400> SEQUENCE: 20

```
Met Ser Glu Thr Phe Phe His Leu Leu Gly Pro Gly Thr Gln Pro Asn
1               5                   10                  15

Asp Asp Ser Phe Ser Met Asn Pro Leu Pro Ile Thr Cys Gln Val Asn
            20                  25                  30

Asp Glu Pro Ser Met Ala Ala Leu Glu Gln Cys Ala His Ser Pro Gln
        35                  40                  45

Val Ile Ala Leu Leu Asn Glu Leu Gln His Gln Leu Ser Glu Arg Gln
    50                  55                  60

Pro Pro Leu Gly Glu Val Leu Ala Val Asp Leu Leu Asn Leu Asn Ala
65                  70                  75                  80

Asp Asp Arg His Phe Ile Asn Thr Leu Leu Gly Gly Glu Val Ser
                85                  90                  95

Val Arg Ile Gln Gln Ala Asp Asp Ser Glu Ser Glu Ile Gln Glu Ala
                100                 105                 110

Ile Phe Cys Gly Leu Trp Arg Val Arg Arg Arg Gly Glu Lys Leu
            115                 120                 125

Leu Glu Asp Lys Leu Glu Ala Gly Cys Ala Pro Leu Ala Leu Trp Gln
130                 135                 140

Ala Ala Thr Gln Asn Leu Leu Pro Thr Asp Ser Leu Leu Pro Pro Pro
145                 150                 155                 160

Ile Asp Gly Leu Met Asn Gly Leu Pro Leu Ala His Glu Leu Leu Ala
                165                 170                 175

His Val Arg Asn Pro Asp Ala Gln Pro His Ser Ile Asn Leu Thr Gln
                180                 185                 190

Leu Pro Ile Ser Glu Ala Asp Arg Leu Phe Leu Ser Arg Leu Cys Gly
            195                 200                 205

Pro Gly Asn Ile Gln Ile Arg Thr Ile Gly Tyr Gly Glu Ser Tyr Ile
        210                 215                 220

Asn Ala Thr Gly Leu Arg His Val Trp His Leu Arg Cys Thr Asp Thr
225                 230                 235                 240

Leu Lys Gly Pro Leu Leu Glu Ser Tyr Glu Ile Cys Pro Ile Pro Glu
                245                 250                 255

Val Val Leu Ala Ala Pro Glu Asp Leu Val Asp Ser Ala Gln Arg Leu
                260                 265                 270

Ser Glu Val Cys Gln Trp Leu Ala Glu Ala Ala Pro Thr
            275                 280                 285
```

<210> SEQ ID NO 21
<211> LENGTH: 470
<212> TYPE: PRT
<213> ORGANISM: Escherichia coli

<400> SEQUENCE: 21

```
Met Lys Lys Thr Lys Ile Val Cys Thr Ile Gly Pro Lys Thr Glu Ser
1               5                   10                  15

Glu Glu Met Leu Ala Lys Met Leu Asp Ala Gly Met Asn Val Met Arg
            20                  25                  30

Leu Asn Phe Ser His Gly Asp Tyr Ala Glu His Gly Gln Arg Ile Gln
```

```
                35                  40                  45
Asn Leu Arg Asn Val Met Ser Lys Thr Gly Lys Thr Ala Ala Ile Leu
 50                  55                  60
Leu Asp Thr Lys Gly Pro Glu Ile Arg Thr Met Lys Leu Glu Gly Gly
 65                  70                  75                  80
Asn Asp Val Ser Leu Lys Ala Gly Gln Thr Phe Thr Phe Thr Thr Asp
                 85                  90                  95
Lys Ser Val Ile Gly Asn Ser Glu Met Val Ala Val Thr Tyr Glu Gly
                100                 105                 110
Phe Thr Thr Asp Leu Ser Val Gly Asn Thr Val Leu Val Asp Asp Gly
                115                 120                 125
Leu Ile Gly Met Glu Val Thr Ala Ile Glu Gly Asn Lys Val Ile Cys
    130                 135                 140
Lys Val Leu Asn Asn Gly Asp Leu Gly Glu Asn Lys Gly Val Asn Leu
145                 150                 155                 160
Pro Gly Val Ser Ile Ala Leu Pro Ala Leu Ala Glu Lys Asp Lys Gln
                165                 170                 175
Asp Leu Ile Phe Gly Cys Glu Gln Gly Val Asp Phe Val Ala Ala Ser
                180                 185                 190
Phe Ile Arg Lys Arg Ser Asp Val Ile Glu Ile Arg Glu His Leu Lys
                195                 200                 205
Ala His Gly Gly Glu Asn Ile His Ile Ile Ser Lys Ile Glu Asn Gln
    210                 215                 220
Glu Gly Leu Asn Asn Phe Asp Glu Ile Leu Glu Ala Ser Asp Gly Ile
225                 230                 235                 240
Met Val Ala Arg Gly Asp Leu Gly Val Glu Ile Pro Val Glu Glu Val
                245                 250                 255
Ile Phe Ala Gln Lys Met Met Ile Glu Lys Cys Ile Arg Ala Arg Lys
                260                 265                 270
Val Val Ile Thr Ala Thr Gln Met Leu Asp Ser Met Ile Lys Asn Pro
    275                 280                 285
Arg Pro Thr Arg Ala Glu Ala Gly Asp Val Ala Asn Ala Ile Leu Asp
290                 295                 300
Gly Thr Asp Ala Val Met Leu Ser Gly Glu Ser Ala Lys Gly Lys Tyr
305                 310                 315                 320
Pro Leu Glu Ala Val Ser Ile Met Ala Thr Ile Cys Glu Arg Thr Asp
                325                 330                 335
Arg Val Met Asn Ser Arg Leu Glu Phe Asn Asn Asp Asn Arg Lys Leu
                340                 345                 350
Arg Ile Thr Glu Ala Val Cys Arg Gly Ala Val Glu Thr Ala Glu Lys
    355                 360                 365
Leu Asp Ala Pro Leu Ile Val Ala Thr Gln Gly Gly Lys Ser Ala
370                 375                 380
Arg Ala Val Arg Lys Tyr Phe Pro Asp Ala Thr Ile Leu Ala Leu Thr
385                 390                 395                 400
Thr Asn Glu Lys Thr Ala His Gln Leu Val Leu Ser Lys Gly Val Val
                405                 410                 415
Pro Gln Leu Val Lys Glu Ile Thr Ser Thr Asp Asp Phe Tyr Arg Leu
                420                 425                 430
Gly Lys Glu Leu Ala Leu Gln Ser Gly Leu Ala His Lys Gly Asp Val
                435                 440                 445
Val Val Met Val Ser Gly Ala Leu Val Pro Ser Gly Thr Thr Asn Thr
    450                 455                 460
```

```
Ala Ser Val His Val Leu
465                 470
```

<210> SEQ ID NO 22
<211> LENGTH: 249
<212> TYPE: PRT
<213> ORGANISM: Escherichia coli

<400> SEQUENCE: 22

```
Met Lys Lys Thr Lys Ile Val Cys Thr Ile Gly Pro Lys Thr Glu Ser
1               5                   10                  15

Glu Glu Met Leu Ala Lys Met Leu Asp Ala Gly Met Asn Val Met Arg
            20                  25                  30

Leu Asn Phe Ser His Gly Asp Tyr Ala Glu His Gly Gln Arg Ile Gln
        35                  40                  45

Asn Leu Arg Asn Val Met Ser Lys Thr Gly Lys Thr Ala Ala Ile Leu
    50                  55                  60

Leu Asp Thr Lys Gly Pro Glu Ile Arg Thr Met Lys Leu Glu Gly Gly
65                  70                  75                  80

Asn Asp Val Ser Leu Lys Ala Gly Gln Thr Phe Thr Phe Thr Thr Asp
                85                  90                  95

Lys Ser Val Ile Gly Asn Ser Glu Met Val Ala Val Thr Tyr Glu Gly
            100                 105                 110

Phe Thr Thr Asp Leu Ser Val Gly Asn Thr Val Leu Val Asp Asp Gly
        115                 120                 125

Leu Ile Gly Met Glu Val Thr Ala Ile Glu Gly Asn Lys Val Ile Cys
    130                 135                 140

Lys Val Leu Asn Asn Gly Asp Leu Gly Glu Asn Lys Gly Val Asn Leu
145                 150                 155                 160

Pro Gly Val Ser Ile Ala Leu Pro Ala Leu Ala Glu Lys Asp Lys Gln
                165                 170                 175

Asp Leu Ile Phe Gly Cys Glu Gln Gly Val Asp Phe Val Ala Ala Ser
            180                 185                 190

Phe Ile Arg Lys Arg Ser Asp Val Ile Glu Ile Arg Glu His Leu Lys
        195                 200                 205

Ala His Gly Gly Glu Asn Ile His Ile Ile Ser Lys Ile Glu Asn Gln
    210                 215                 220

Glu Gly Leu Asn Asn Phe Asp Glu Ile Leu Glu Ala Ser Asp Gly Ile
225                 230                 235                 240

Met Val Ala Arg Gly Asp Leu Gly Val
                245
```

<210> SEQ ID NO 23
<211> LENGTH: 901
<212> TYPE: PRT
<213> ORGANISM: Escherichia coli

<400> SEQUENCE: 23

```
Met Leu Ile Pro Ser Lys Leu Ser Arg Pro Val Arg Leu Asp His Thr
1               5                   10                  15

Val Val Arg Glu Arg Leu Leu Ala Lys Leu Ser Gly Ala Asn Asn Phe
            20                  25                  30

Arg Leu Ala Leu Ile Thr Ser Pro Ala Gly Tyr Gly Lys Thr Thr Leu
        35                  40                  45

Ile Ser Gln Trp Ala Ala Gly Lys Asn Asp Ile Gly Trp Tyr Ser Leu
    50                  55                  60
```

```
Asp Glu Gly Asp Asn Gln Gln Glu Arg Phe Ala Ser Tyr Leu Ile Ala
 65                  70                  75                  80

Ala Val Gln Gln Ala Thr Asn Gly His Cys Ala Ile Cys Glu Thr Met
                 85                  90                  95

Ala Gln Lys Arg Gln Tyr Ala Ser Leu Thr Ser Leu Phe Ala Gln Leu
            100                 105                 110

Phe Ile Glu Leu Ala Glu Trp His Ser Pro Leu Tyr Leu Val Ile Asp
        115                 120                 125

Asp Tyr His Leu Ile Thr Asn Pro Val Ile His Glu Ser Met Arg Phe
    130                 135                 140

Phe Ile Arg His Gln Pro Glu Asn Leu Thr Leu Val Val Leu Ser Arg
145                 150                 155                 160

Asn Leu Pro Gln Leu Gly Ile Ala Asn Leu Arg Val Arg Asp Gln Leu
                165                 170                 175

Leu Glu Ile Gly Ser Gln Gln Leu Ala Phe Thr His Gln Glu Ala Lys
            180                 185                 190

Gln Phe Phe Asp Cys Arg Leu Ser Ser Pro Ile Glu Ala Ala Glu Ser
        195                 200                 205

Ser Arg Ile Cys Asp Asp Val Ser Gly Trp Ala Thr Ala Leu Gln Leu
    210                 215                 220

Ile Ala Leu Ser Ala Arg Gln Asn Thr His Ser Ala His Lys Ser Ala
225                 230                 235                 240

Arg Arg Leu Ala Gly Ile Asn Ala Ser His Leu Ser Asp Tyr Leu Val
                245                 250                 255

Asp Glu Val Leu Asp Asn Val Asp Leu Ala Thr Arg His Phe Leu Leu
            260                 265                 270

Lys Ser Ala Ile Leu Arg Ser Met Asn Asp Ala Leu Ile Thr Arg Val
        275                 280                 285

Thr Gly Glu Glu Asn Gly Gln Met Arg Leu Glu Glu Ile Glu Arg Gln
    290                 295                 300

Gly Leu Phe Leu Gln Arg Met Asp Asp Thr Gly Glu Trp Phe Cys Tyr
305                 310                 315                 320

His Pro Leu Phe Gly Asn Phe Leu Arg Gln Arg Cys Gln Trp Glu Leu
                325                 330                 335

Ala Ala Glu Leu Pro Glu Ile His Arg Ala Ala Glu Ser Trp Met
            340                 345                 350

Ala Gln Gly Phe Pro Ser Glu Ala Ile His His Ala Leu Ala Ala Gly
        355                 360                 365

Asp Ala Leu Met Leu Arg Asp Ile Leu Leu Asn His Ala Trp Ser Leu
    370                 375                 380

Phe Asn His Ser Glu Leu Ser Leu Leu Glu Glu Ser Leu Lys Ala Leu
385                 390                 395                 400

Pro Trp Asp Ser Leu Leu Glu Asn Pro Gln Leu Val Leu Leu Gln Ala
                405                 410                 415

Trp Leu Met Gln Ser Gln His Arg Tyr Gly Glu Val Asn Thr Leu Leu
            420                 425                 430

Ala Arg Ala Glu His Glu Ile Lys Asp Ile Arg Glu Asp Thr Met His
        435                 440                 445

Ala Glu Phe Asn Ala Leu Arg Ala Gln Val Ala Ile Asn Asp Gly Asn
    450                 455                 460

Pro Asp Glu Ala Glu Arg Leu Ala Lys Leu Ala Leu Glu Glu Leu Pro
465                 470                 475                 480
```

```
Pro Gly Trp Phe Tyr Ser Arg Ile Val Ala Thr Ser Val Leu Gly Glu
            485                 490                 495

Val Leu His Cys Lys Gly Glu Leu Thr Arg Ser Leu Ala Leu Met Gln
        500                 505                 510

Gln Thr Glu Gln Met Ala Arg Gln His Asp Val Trp His Tyr Ala Leu
    515                 520                 525

Trp Ser Leu Ile Gln Gln Ser Glu Ile Leu Phe Ala Gln Gly Phe Leu
530                 535                 540

Gln Thr Ala Trp Glu Thr Gln Glu Lys Ala Phe Gln Leu Ile Asn Glu
545                 550                 555                 560

Gln His Leu Glu Gln Leu Pro Met His Glu Phe Leu Val Arg Ile Arg
                565                 570                 575

Ala Gln Leu Leu Trp Ala Trp Ala Arg Leu Asp Glu Ala Glu Ala Ser
            580                 585                 590

Ala Arg Ser Gly Ile Glu Val Leu Ser Ser Tyr Gln Pro Gln Gln Gln
        595                 600                 605

Leu Gln Cys Leu Ala Met Leu Ile Gln Cys Ser Leu Ala Arg Gly Asp
    610                 615                 620

Leu Asp Asn Ala Arg Ser Gln Leu Asn Arg Leu Glu Asn Leu Leu Gly
625                 630                 635                 640

Asn Gly Lys Tyr His Ser Asp Trp Ile Ser Asn Ala Asn Lys Val Arg
                645                 650                 655

Val Ile Tyr Trp Gln Met Thr Gly Asp Lys Ala Ala Ala Asn Trp
            660                 665                 670

Leu Arg His Thr Ala Lys Pro Glu Phe Ala Asn Asn His Phe Leu Gln
        675                 680                 685

Gly Gln Trp Arg Asn Ile Ala Arg Ala Gln Ile Leu Leu Gly Glu Phe
    690                 695                 700

Glu Pro Ala Glu Ile Val Leu Glu Glu Leu Asn Glu Asn Ala Arg Ser
705                 710                 715                 720

Leu Arg Leu Met Ser Asp Leu Asn Arg Asn Leu Leu Leu Leu Asn Gln
                725                 730                 735

Leu Tyr Trp Gln Ala Gly Arg Lys Ser Asp Ala Gln Arg Val Leu Leu
            740                 745                 750

Asp Ala Leu Lys Leu Ala Asn Arg Thr Gly Phe Ile Ser His Phe Val
        755                 760                 765

Ile Glu Gly Glu Ala Met Ala Gln Gln Leu Arg Gln Leu Ile Gln Leu
    770                 775                 780

Asn Thr Leu Pro Glu Leu Glu Gln His Arg Ala Gln Arg Ile Leu Arg
785                 790                 795                 800

Glu Ile Asn Gln His His Arg His Lys Phe Ala His Phe Asp Glu Asn
                805                 810                 815

Phe Val Glu Arg Leu Leu Asn His Pro Glu Val Pro Glu Leu Ile Arg
            820                 825                 830

Thr Ser Pro Leu Thr Gln Arg Glu Trp Gln Val Leu Gly Leu Ile Tyr
        835                 840                 845

Ser Gly Tyr Ser Asn Glu Gln Ile Ala Gly Glu Leu Glu Val Ala Ala
    850                 855                 860

Thr Thr Ile Lys Thr His Ile Arg Asn Leu Tyr Gln Lys Leu Gly Val
865                 870                 875                 880

Ala His Arg Gln Asp Ala Val Gln His Ala Gln Gln Leu Leu Lys Met
                885                 890                 895

Met Gly Tyr Gly Val
```

<210> SEQ ID NO 24
<211> LENGTH: 779
<212> TYPE: PRT
<213> ORGANISM: Escherichia coli

<400> SEQUENCE: 24

```
Met Leu Ile Pro Ser Lys Leu Ser Arg Pro Val Arg Leu Asp His Thr
1               5                   10                  15

Val Val Arg Glu Arg Leu Leu Ala Lys Leu Ser Gly Ala Asn Asn Phe
            20                  25                  30

Arg Leu Ala Leu Ile Thr Ser Pro Ala Gly Tyr Gly Lys Thr Thr Leu
        35                  40                  45

Ile Ser Gln Trp Ala Ala Gly Lys Asn Asp Ile Gly Trp Tyr Ser Leu
    50                  55                  60

Asp Glu Gly Asp Asn Gln Gln Glu Arg Phe Ala Ser Tyr Leu Ile Ala
65                  70                  75                  80

Ala Val Gln Gln Ala Thr Asn Gly His Cys Ala Ile Cys Glu Thr Met
                85                  90                  95

Ala Gln Lys Arg Gln Tyr Ala Ser Leu Thr Ser Leu Phe Ala Gln Leu
            100                 105                 110

Phe Ile Glu Leu Ala Glu Trp His Ser Pro Leu Tyr Leu Val Ile Asp
        115                 120                 125

Asp Tyr His Leu Ile Thr Asn Pro Val Ile His Glu Ser Met Arg Phe
    130                 135                 140

Phe Ile Arg His Gln Pro Glu Asn Leu Thr Leu Val Val Leu Ser Arg
145                 150                 155                 160

Asn Leu Pro Gln Leu Gly Ile Ala Asn Leu Arg Val Arg Asp Gln Leu
                165                 170                 175

Leu Glu Ile Gly Ser Gln Gln Leu Ala Phe Thr His Gln Glu Ala Lys
            180                 185                 190

Gln Phe Phe Asp Cys Arg Leu Ser Ser Pro Ile Glu Ala Ala Glu Ser
        195                 200                 205

Ser Arg Ile Cys Asp Asp Val Ser Gly Trp Ala Thr Ala Leu Gln Leu
    210                 215                 220

Ile Ala Leu Ser Ala Arg Gln Asn Thr His Ser Ala His Lys Ser Ala
225                 230                 235                 240

Arg Arg Leu Ala Gly Ile Asn Ala Ser His Leu Ser Asp Tyr Leu Val
                245                 250                 255

Asp Glu Val Leu Asp Asn Val Asp Leu Ala Thr Arg His Phe Leu Leu
            260                 265                 270

Lys Ser Ala Ile Leu Arg Ser Met Asn Asp Ala Leu Ile Thr Arg Val
        275                 280                 285

Thr Gly Glu Glu Asn Gly Gln Met Arg Leu Glu Glu Ile Glu Arg Gln
    290                 295                 300

Gly Leu Phe Leu Gln Arg Met Asp Asp Thr Gly Glu Trp Phe Cys Tyr
305                 310                 315                 320

His Pro Leu Phe Gly Asn Phe Leu Arg Gln Arg Cys Gln Trp Glu Leu
                325                 330                 335

Ala Ala Glu Leu Pro Glu Ile His Arg Ala Ala Glu Ser Trp Met
            340                 345                 350

Ala Gln Gly Phe Pro Ser Glu Ala Ile His His Ala Leu Ala Ala Gly
        355                 360                 365
```

```
Asp Ala Leu Met Leu Arg Asp Ile Leu Leu Asn His Ala Trp Ser Leu
    370                 375                 380

Phe Asn His Ser Glu Leu Ser Leu Leu Glu Glu Ser Leu Lys Ala Leu
385                 390                 395                 400

Pro Trp Asp Ser Leu Leu Glu Asn Pro Gln Leu Val Leu Leu Gln Ala
                405                 410                 415

Trp Leu Met Gln Ser Gln His Arg Tyr Gly Glu Val Asn Thr Leu Leu
            420                 425                 430

Ala Arg Ala Glu His Glu Ile Lys Asp Ile Arg Glu Asp Thr Met His
        435                 440                 445

Ala Glu Phe Asn Ala Leu Arg Ala Gln Val Ala Ile Asn Asp Gly Asn
    450                 455                 460

Pro Asp Glu Ala Glu Arg Leu Ala Lys Leu Ala Leu Glu Glu Leu Pro
465                 470                 475                 480

Pro Gly Trp Phe Tyr Ser Arg Ile Val Ala Thr Ser Val Leu Gly Glu
                485                 490                 495

Val Leu His Cys Lys Gly Glu Leu Thr Arg Ser Leu Ala Leu Met Gln
                500                 505                 510

Gln Thr Glu Gln Met Ala Arg Gln His Asp Val Trp His Tyr Ala Leu
    515                 520                 525

Trp Ser Leu Ile Gln Gln Ser Glu Ile Leu Phe Ala Gln Gly Phe Leu
530                 535                 540

Gln Thr Ala Trp Glu Thr Gln Glu Lys Ala Phe Gln Leu Ile Asn Glu
545                 550                 555                 560

Gln His Leu Glu Gln Leu Pro Met His Glu Phe Leu Val Arg Ile Arg
                565                 570                 575

Ala Gln Leu Leu Trp Ala Trp Ala Arg Leu Asp Glu Ala Glu Ala Ser
            580                 585                 590

Ala Arg Ser Gly Ile Glu Val Leu Ser Ser Tyr Gln Pro Gln Gln Gln
        595                 600                 605

Leu Gln Cys Leu Ala Met Leu Ile Gln Cys Ser Leu Ala Arg Gly Asp
    610                 615                 620

Leu Asp Asn Ala Arg Ser Gln Leu Asn Arg Leu Glu Asn Leu Leu Gly
625                 630                 635                 640

Asn Gly Lys Tyr His Ser Asp Trp Ile Ser Asn Ala Asn Lys Val Arg
                645                 650                 655

Val Ile Tyr Trp Gln Met Thr Gly Asp Lys Ala Ala Ala Ala Asn Trp
            660                 665                 670

Leu Arg His Thr Ala Lys Pro Glu Phe Ala Asn Asn His Phe Leu Gln
        675                 680                 685

Gly Gln Trp Arg Asn Ile Ala Arg Ala Gln Ile Leu Leu Gly Glu Phe
    690                 695                 700

Glu Pro Ala Glu Ile Val Leu Glu Glu Leu Asn Glu Asn Ala Arg Ser
705                 710                 715                 720

Leu Arg Leu Met Ser Asp Leu Asn Arg Asn Leu Leu Leu Leu Asn Gln
                725                 730                 735

Leu Tyr Trp Gln Ala Gly Arg Lys Ser Asp Ala Gln Arg Val Leu Leu
            740                 745                 750

Asp Ala Leu Lys Leu Ala Asn Arg Thr Gly Phe Ile Ser His Phe Val
        755                 760                 765

Ile Glu Gly Glu Ala Met Ala Gln Gln Leu Arg
    770                 775
```

<210> SEQ ID NO 25
<211> LENGTH: 1342
<212> TYPE: PRT
<213> ORGANISM: Escherichia coli

<400> SEQUENCE: 25

```
Met Val Tyr Ser Tyr Thr Glu Lys Lys Arg Ile Arg Lys Asp Phe Gly
 1               5                  10                  15

Lys Arg Pro Gln Val Leu Asp Val Pro Tyr Leu Leu Ser Ile Gln Leu
            20                  25                  30

Asp Ser Phe Gln Lys Phe Ile Glu Gln Asp Pro Glu Gly Gln Tyr Gly
        35                  40                  45

Leu Glu Ala Ala Phe Arg Ser Val Phe Pro Ile Gln Ser Tyr Ser Gly
50                  55                  60

Asn Ser Glu Leu Gln Tyr Val Ser Tyr Arg Leu Gly Glu Pro Val Phe
65                  70                  75                  80

Asp Val Gln Glu Cys Gln Ile Arg Gly Val Thr Tyr Ser Ala Pro Leu
                85                  90                  95

Arg Val Lys Leu Arg Leu Val Ile Tyr Glu Arg Glu Ala Pro Glu Gly
            100                 105                 110

Thr Val Lys Asp Ile Lys Glu Gln Glu Val Tyr Met Gly Glu Ile Pro
        115                 120                 125

Leu Met Thr Asp Asn Gly Thr Phe Val Ile Asn Gly Thr Glu Arg Val
130                 135                 140

Ile Val Ser Gln Leu His Arg Ser Pro Gly Val Phe Phe Asp Ser Asp
145                 150                 155                 160

Lys Gly Lys Thr His Ser Ser Gly Lys Val Leu Tyr Asn Ala Arg Ile
                165                 170                 175

Ile Pro Tyr Arg Gly Ser Trp Leu Asp Phe Glu Phe Asp Pro Lys Asp
            180                 185                 190

Asn Leu Phe Val Arg Ile Asp Arg Arg Arg Lys Leu Pro Ala Thr Ile
        195                 200                 205

Ile Leu Arg Ala Leu Asn Tyr Thr Thr Glu Gln Ile Leu Asp Leu Phe
210                 215                 220

Phe Glu Lys Val Ile Phe Glu Ile Arg Asp Asn Lys Leu Gln Met Glu
225                 230                 235                 240

Leu Val Pro Glu Arg Leu Arg Gly Glu Thr Ala Ser Phe Asp Ile Glu
                245                 250                 255

Ala Asn Gly Lys Val Tyr Val Glu Lys Gly Arg Arg Ile Thr Ala Arg
            260                 265                 270

His Ile Arg Gln Leu Glu Lys Asp Asp Val Lys Leu Ile Glu Val Pro
        275                 280                 285

Val Glu Tyr Ile Ala Gly Lys Val Val Ala Lys Asp Tyr Ile Asp Glu
290                 295                 300

Ser Thr Gly Glu Leu Ile Cys Ala Ala Asn Met Glu Leu Ser Leu Asp
305                 310                 315                 320

Leu Leu Ala Lys Leu Ser Gln Ser Gly His Lys Arg Ile Glu Thr Leu
                325                 330                 335

Phe Thr Asn Asp Leu Asp His Gly Pro Tyr Ile Ser Glu Thr Leu Arg
            340                 345                 350

Val Asp Pro Thr Asn Asp Arg Leu Ser Ala Leu Val Glu Ile Tyr Arg
        355                 360                 365

Met Met Arg Pro Gly Glu Pro Pro Thr Arg Glu Ala Ala Glu Ser Leu
370                 375                 380
```

```
Phe Glu Asn Leu Phe Phe Ser Glu Asp Arg Tyr Asp Leu Ser Ala Val
385                 390                 395                 400

Gly Arg Met Lys Phe Asn Arg Ser Leu Leu Arg Glu Glu Ile Glu Gly
            405                 410                 415

Ser Gly Ile Leu Ser Lys Asp Asp Ile Ile Asp Val Met Lys Lys Leu
                420                 425                 430

Ile Asp Ile Arg Asn Gly Lys Gly Glu Val Asp Asp Ile Asp His Leu
            435                 440                 445

Gly Asn Arg Arg Ile Arg Ser Val Gly Glu Met Ala Glu Asn Gln Phe
    450                 455                 460

Arg Val Gly Leu Val Arg Val Glu Arg Ala Val Lys Glu Arg Leu Ser
465                 470                 475                 480

Leu Gly Asp Leu Asp Thr Leu Met Pro Gln Asp Met Ile Asn Ala Lys
                485                 490                 495

Pro Ile Ser Ala Ala Val Lys Glu Phe Phe Gly Ser Ser Gln Leu Ser
            500                 505                 510

Gln Phe Met Asp Gln Asn Asn Pro Leu Ser Glu Ile Thr His Lys Arg
        515                 520                 525

Arg Ile Ser Ala Leu Gly Pro Gly Gly Leu Thr Arg Glu Arg Ala Gly
    530                 535                 540

Phe Glu Val Arg Asp Val His Pro Thr His Tyr Gly Arg Val Cys Pro
545                 550                 555                 560

Ile Glu Thr Pro Glu Gly Pro Asn Ile Gly Leu Ile Asn Ser Leu Ser
                565                 570                 575

Val Tyr Ala Gln Thr Asn Glu Tyr Gly Phe Leu Glu Thr Pro Tyr Arg
            580                 585                 590

Lys Val Thr Asp Gly Val Val Thr Asp Glu Ile His Tyr Leu Ser Ala
        595                 600                 605

Ile Glu Glu Gly Asn Tyr Val Ile Ala Gln Ala Asn Ser Asn Leu Asp
    610                 615                 620

Glu Glu Gly His Phe Val Glu Asp Leu Val Thr Cys Arg Ser Lys Gly
625                 630                 635                 640

Glu Ser Ser Leu Phe Ser Arg Asp Gln Val Asp Tyr Met Asp Val Ser
                645                 650                 655

Thr Gln Gln Val Val Ser Val Gly Ala Ser Leu Ile Pro Phe Leu Glu
            660                 665                 670

His Asp Asp Ala Asn Arg Ala Leu Met Gly Ala Asn Met Gln Arg Gln
        675                 680                 685

Ala Val Pro Thr Leu Arg Ala Asp Lys Pro Leu Val Gly Thr Gly Met
    690                 695                 700

Glu Arg Ala Val Ala Val Asp Ser Gly Val Thr Ala Val Ala Lys Arg
705                 710                 715                 720

Gly Gly Val Val Gln Tyr Val Asp Ala Ser Arg Ile Val Ile Lys Val
                725                 730                 735

Asn Glu Asp Glu Met Tyr Pro Gly Glu Ala Gly Ile Asp Ile Tyr Asn
            740                 745                 750

Leu Thr Lys Tyr Thr Arg Ser Asn Gln Asn Thr Cys Ile Asn Gln Met
        755                 760                 765

Pro Cys Val Ser Leu Gly Glu Pro Val Glu Arg Gly Asp Val Leu Ala
    770                 775                 780

Asp Gly Pro Ser Thr Asp Leu Gly Glu Leu Ala Leu Gly Gln Asn Met
785                 790                 795                 800

Arg Val Ala Phe Met Pro Trp Asn Gly Tyr Asn Phe Glu Asp Ser Ile
```

```
              805                 810                 815
Leu Val Ser Glu Arg Val Val Gln Glu Asp Arg Phe Thr Thr Ile His
              820                 825                 830

Ile Gln Glu Leu Ala Cys Val Ser Arg Asp Thr Lys Leu Gly Pro Glu
              835                 840                 845

Glu Ile Thr Ala Asp Ile Pro Asn Val Gly Glu Ala Ala Leu Ser Lys
              850                 855                 860

Leu Asp Glu Ser Gly Ile Val Tyr Ile Gly Ala Glu Val Thr Gly Gly
865                     870                 875                 880

Asp Ile Leu Val Gly Lys Val Thr Pro Lys Gly Glu Thr Gln Leu Thr
                  885                 890                 895

Pro Glu Glu Lys Leu Leu Arg Ala Ile Phe Gly Glu Lys Ala Ser Asp
              900                 905                 910

Val Lys Asp Ser Ser Leu Arg Val Pro Asn Gly Val Ser Gly Thr Val
              915                 920                 925

Ile Asp Val Gln Val Phe Thr Arg Asp Gly Val Glu Lys Asp Lys Arg
              930                 935                 940

Ala Leu Glu Ile Glu Glu Met Gln Leu Lys Gln Ala Lys Lys Asp Leu
945                     950                 955                 960

Ser Glu Glu Leu Gln Ile Leu Glu Ala Gly Leu Phe Ser Arg Ile Arg
                  965                 970                 975

Ala Val Leu Val Ala Gly Gly Val Glu Ala Gly Lys Leu Asp Lys Leu
              980                 985                 990

Pro Arg Asp Arg Trp Leu Glu Leu Gly Leu Thr Asp Glu Glu Lys Gln
              995                 1000                1005

Asn Gln Leu Glu Gln Leu Ala Glu Gln Tyr Asp Glu Leu Lys His
    1010                1015                1020

Glu Phe Glu Lys Lys Leu Glu Ala Lys Arg Arg Lys Ile Thr Gln
    1025                1030                1035

Gly Asp Asp Leu Ala Pro Gly Val Leu Lys Ile Val Lys Val Tyr
    1040                1045                1050

Leu Ala Val Lys Arg Arg Ile Gln Pro Gly Asp Lys Met Ala Gly
    1055                1060                1065

Arg His Gly Asn Lys Gly Val Ile Ser Lys Ile Asn Pro Ile Glu
    1070                1075                1080

Asp Met Pro Tyr Asp Glu Asn Gly Thr Pro Val Asp Ile Val Leu
    1085                1090                1095

Asn Pro Leu Gly Val Pro Ser Arg Met Asn Ile Gly Gln Ile Leu
    1100                1105                1110

Glu Thr His Leu Gly Met Ala Ala Lys Gly Ile Gly Asp Lys Ile
    1115                1120                1125

Asn Ala Met Leu Lys Gln Gln Gln Glu Val Ala Lys Leu Arg Glu
    1130                1135                1140

Phe Ile Gln Arg Ala Tyr Asp Leu Gly Ala Asp Val Arg Gln Lys
    1145                1150                1155

Val Asp Leu Ser Thr Phe Ser Asp Glu Glu Val Met Arg Leu Ala
    1160                1165                1170

Glu Asn Leu Arg Lys Gly Met Pro Ile Ala Thr Pro Val Phe Asp
    1175                1180                1185

Gly Ala Lys Glu Ala Glu Ile Lys Glu Leu Leu Lys Leu Gly Asp
    1190                1195                1200

Leu Pro Thr Ser Gly Gln Ile Arg Leu Tyr Asp Gly Arg Thr Gly
    1205                1210                1215
```

-continued

```
Glu Gln Phe Glu Arg Pro Val Thr Val Gly Tyr Met Tyr Met Leu
    1220                1225                1230

Lys Leu Asn His Leu Val Asp Asp Lys Met His Ala Arg Ser Thr
    1235                1240                1245

Gly Ser Tyr Ser Leu Val Thr Gln Gln Pro Leu Gly Gly Lys Ala
    1250                1255                1260

Gln Phe Gly Gly Gln Arg Phe Gly Glu Met Glu Val Trp Ala Leu
    1265                1270                1275

Glu Ala Tyr Gly Ala Ala Tyr Thr Leu Gln Glu Met Leu Thr Val
    1280                1285                1290

Lys Ser Asp Asp Val Asn Gly Arg Thr Lys Met Tyr Lys Asn Ile
    1295                1300                1305

Val Asp Gly Asn His Gln Met Glu Pro Gly Met Pro Glu Ser Phe
    1310                1315                1320

Asn Val Leu Leu Lys Glu Ile Arg Ser Leu Gly Ile Asn Ile Glu
    1325                1330                1335

Leu Glu Asp Glu
    1340

<210> SEQ ID NO 26
<211> LENGTH: 548
<212> TYPE: PRT
<213> ORGANISM: Escherichia coli

<400> SEQUENCE: 26

Met Ser Asn Lys Pro Phe Ile Tyr Gln Ala Pro Phe Pro Met Gly Lys
1               5                   10                  15

Asp Asn Thr Glu Tyr Tyr Leu Leu Thr Ser Asp Tyr Val Ser Val Ala
            20                  25                  30

Asp Phe Asp Gly Glu Thr Ile Leu Lys Val Glu Pro Glu Ala Leu Thr
        35                  40                  45

Leu Leu Ala Gln Gln Ala Phe His Asp Ala Ser Phe Met Leu Arg Pro
    50                  55                  60

Ala His Gln Lys Gln Val Ala Ala Ile Leu His Asp Pro Glu Ala Ser
65                  70                  75                  80

Glu Asn Asp Lys Tyr Val Ala Leu Gln Phe Leu Arg Asn Ser Glu Ile
                85                  90                  95

Ala Ala Lys Gly Val Leu Pro Thr Cys Gln Asp Thr Gly Thr Ala Ile
            100                 105                 110

Ile Val Gly Lys Lys Gly Gln Arg Val Trp Thr Gly Gly Gly Asp Glu
        115                 120                 125

Glu Thr Leu Ser Lys Gly Val Tyr Asn Thr Tyr Ile Glu Asp Asn Leu
    130                 135                 140

Arg Tyr Ser Gln Asn Ala Ala Leu Asp Met Tyr Lys Glu Val Asn Thr
145                 150                 155                 160

Gly Thr Asn Leu Pro Ala Gln Ile Asp Leu Tyr Ala Val Asp Gly Asp
                165                 170                 175

Glu Tyr Lys Phe Leu Cys Val Ala Lys Gly Gly Gly Ser Ala Asn Lys
            180                 185                 190

Thr Tyr Leu Tyr Gln Glu Thr Lys Ala Leu Leu Thr Pro Gly Lys Leu
        195                 200                 205

Lys Asn Phe Leu Val Glu Lys Met Arg Thr Leu Gly Thr Ala Ala Cys
    210                 215                 220

Pro Pro Tyr His Ile Ala Phe Val Ile Gly Gly Thr Ser Ala Glu Thr
```

```
                225                 230                 235                 240
Asn Leu Lys Thr Val Lys Leu Ala Ser Ala His Tyr Tyr Asp Glu Leu
                245                 250                 255

Pro Thr Glu Gly Asn Glu His Gly Gln Ala Phe Arg Asp Val Gln Leu
                260                 265                 270

Glu Gln Glu Leu Leu Glu Ala Gln Lys Leu Gly Leu Gly Ala Gln
            275                 280                 285

Phe Gly Gly Lys Tyr Phe Ala His Asp Ile Arg Val Ile Arg Leu Pro
            290                 295                 300

Arg His Gly Ala Ser Cys Pro Val Gly Met Gly Val Ser Cys Ser Ala
305                 310                 315                 320

Asp Arg Asn Ile Lys Ala Lys Ile Asn Arg Glu Gly Ile Trp Ile Glu
                325                 330                 335

Lys Leu Glu His Asn Pro Gly Gln Tyr Ile Pro Gln Glu Leu Arg Gln
            340                 345                 350

Ala Gly Glu Gly Glu Ala Val Lys Val Asp Leu Asn Arg Pro Met Lys
            355                 360                 365

Glu Ile Leu Ala Gln Leu Ser Gln Tyr Pro Val Ser Thr Arg Leu Ser
            370                 375                 380

Leu Thr Gly Thr Ile Ile Val Gly Arg Asp Ile Ala His Ala Lys Leu
385                 390                 395                 400

Lys Glu Leu Ile Asp Ala Gly Lys Glu Leu Pro Gln Tyr Ile Lys Asp
                405                 410                 415

His Pro Ile Tyr Tyr Ala Gly Pro Ala Lys Thr Pro Ala Gly Tyr Pro
            420                 425                 430

Ser Gly Ser Leu Gly Pro Thr Thr Ala Gly Arg Met Asp Ser Tyr Val
            435                 440                 445

Asp Leu Leu Gln Ser His Gly Gly Ser Met Ile Met Leu Ala Lys Gly
            450                 455                 460

Asn Arg Ser Gln Gln Val Thr Asp Ala Cys His Lys His Gly Gly Phe
465                 470                 475                 480

Tyr Leu Gly Ser Ile Gly Gly Pro Ala Ala Val Leu Ala Gln Gln Ser
                485                 490                 495

Ile Lys His Leu Glu Cys Val Ala Tyr Pro Glu Leu Gly Met Glu Ala
            500                 505                 510

Ile Trp Lys Ile Glu Val Glu Asp Phe Pro Ala Phe Ile Leu Val Asp
            515                 520                 525

Asp Lys Gly Asn Asp Phe Phe Gln Gln Ile Val Asn Lys Gln Cys Ala
            530                 535                 540

Asn Cys Thr Lys
545

<210> SEQ ID NO 27
<211> LENGTH: 518
<212> TYPE: PRT
<213> ORGANISM: Escherichia coli

<400> SEQUENCE: 27

Met Ile Pro Asp Val Ser Gln Ala Leu Ala Trp Leu Glu Lys His Pro
1               5                   10                  15

Gln Ala Leu Lys Gly Ile Gln Arg Gly Leu Glu Arg Glu Thr Leu Arg
            20                  25                  30

Val Asn Ala Asp Gly Thr Leu Ala Thr Thr Gly His Pro Glu Ala Leu
        35                  40                  45
```

-continued

```
Gly Ser Ala Leu Thr His Lys Trp Ile Thr Thr Asp Phe Ala Glu Ala
    50                  55                  60

Leu Leu Glu Phe Ile Thr Pro Val Asp Gly Asp Ile Glu His Met Leu
 65                  70                  75                  80

Thr Phe Met Arg Asp Leu His Arg Tyr Thr Ala Arg Asn Met Gly Asp
                 85                  90                  95

Glu Arg Met Trp Pro Leu Ser Met Pro Cys Tyr Ile Ala Glu Gly Gln
            100                 105                 110

Asp Ile Glu Leu Ala Gln Tyr Gly Thr Ser Asn Thr Gly Arg Phe Lys
        115                 120                 125

Thr Leu Tyr Arg Glu Gly Leu Lys Asn Arg Tyr Gly Ala Leu Met Gln
130                 135                 140

Thr Ile Ser Gly Val His Tyr Asn Phe Ser Leu Pro Met Ala Phe Trp
145                 150                 155                 160

Gln Ala Lys Cys Gly Asp Ile Ser Gly Ala Asp Ala Lys Glu Lys Ile
                165                 170                 175

Ser Ala Gly Tyr Phe Arg Val Ile Arg Asn Tyr Tyr Arg Phe Gly Trp
            180                 185                 190

Val Ile Pro Tyr Leu Phe Gly Ala Ser Pro Ala Ile Cys Ser Ser Phe
        195                 200                 205

Leu Gln Gly Lys Pro Thr Ser Leu Pro Phe Glu Lys Thr Glu Cys Gly
210                 215                 220

Met Tyr Tyr Leu Pro Tyr Ala Thr Ser Leu Arg Leu Ser Asp Leu Gly
225                 230                 235                 240

Tyr Thr Asn Lys Ser Gln Ser Asn Leu Gly Ile Thr Phe Asn Asp Leu
                245                 250                 255

Tyr Glu Tyr Val Ala Gly Leu Lys Gln Ala Ile Lys Thr Pro Ser Glu
            260                 265                 270

Glu Tyr Ala Lys Ile Gly Ile Glu Lys Asp Gly Lys Arg Leu Gln Ile
        275                 280                 285

Asn Ser Asn Val Leu Gln Ile Glu Asn Glu Leu Tyr Ala Pro Ile Arg
290                 295                 300

Pro Lys Arg Val Thr Arg Ser Gly Glu Ser Pro Ser Asp Ala Leu Leu
305                 310                 315                 320

Arg Gly Gly Ile Glu Tyr Ile Glu Val Arg Ser Leu Asp Ile Asn Pro
                325                 330                 335

Phe Ser Pro Ile Gly Val Asp Glu Gln Val Arg Phe Leu Asp Leu
            340                 345                 350

Phe Met Val Trp Cys Ala Leu Ala Asp Ala Pro Glu Met Ser Ser Ser
        355                 360                 365

Glu Leu Ala Cys Thr Arg Val Asn Trp Asn Arg Val Ile Leu Glu Gly
370                 375                 380

Arg Lys Pro Gly Leu Thr Leu Gly Ile Gly Cys Glu Thr Ala Gln Phe
385                 390                 395                 400

Pro Leu Pro Gln Val Gly Lys Asp Leu Phe Arg Asp Leu Lys Arg Val
                405                 410                 415

Ala Gln Thr Leu Asp Ser Ile Asn Gly Gly Glu Ala Tyr Gln Lys Val
            420                 425                 430

Cys Asp Glu Leu Val Ala Cys Phe Asp Asn Pro Asp Leu Thr Phe Ser
        435                 440                 445

Ala Arg Ile Leu Arg Ser Met Ile Asp Thr Gly Ile Gly Gly Thr Gly
450                 455                 460

Lys Ala Phe Ala Glu Ala Tyr Arg Asn Leu Leu Arg Glu Glu Pro Leu
```

```
               465                 470                 475                 480
        Glu Ile Leu Arg Glu Glu Asp Phe Val Ala Glu Arg Glu Ala Ser Glu
                        485                 490                 495
        Arg Arg Gln Gln Glu Met Glu Ala Ala Asp Thr Glu Pro Phe Ala Val
                        500                 505                 510
        Trp Leu Glu Lys His Ala
                        515

<210> SEQ ID NO 28
<211> LENGTH: 446
<212> TYPE: PRT
<213> ORGANISM: Escherichia coli

<400> SEQUENCE: 28

Met Met Ile Thr Leu Arg Lys Leu Pro Leu Ala Val Ala Val Ala Ala
1               5                   10                  15

Gly Val Met Ser Ala Gln Ala Met Ala Val Asp Phe His Gly Tyr Ala
                20                  25                  30

Arg Ser Gly Ile Gly Trp Thr Gly Ser Gly Gly Glu Gln Gln Cys Phe
            35                  40                  45

Gln Thr Thr Gly Ala Gln Ser Lys Tyr Arg Leu Gly Asn Glu Cys Glu
    50                  55                  60

Thr Tyr Ala Glu Leu Lys Leu Gly Gln Glu Val Trp Lys Glu Gly Asp
65                  70                  75                  80

Lys Ser Phe Tyr Phe Asp Thr Asn Val Ala Tyr Ser Val Ala Gln Gln
                85                  90                  95

Asn Asp Trp Glu Ala Thr Asp Pro Ala Phe Arg Glu Ala Asn Val Gln
            100                 105                 110

Gly Lys Asn Leu Ile Glu Trp Leu Pro Gly Ser Thr Ile Trp Ala Gly
    115                 120                 125

Lys Arg Phe Tyr Gln Arg His Asp Val His Met Ile Asp Phe Tyr Tyr
130                 135                 140

Trp Asp Ile Ser Gly Pro Gly Ala Gly Leu Glu Asn Ile Asp Val Gly
145                 150                 155                 160

Phe Gly Lys Leu Ser Leu Ala Ala Thr Arg Ser Ser Glu Ala Gly Gly
                165                 170                 175

Ser Ser Ser Phe Ala Ser Asn Asn Ile Tyr Asp Tyr Thr Asn Glu Thr
            180                 185                 190

Ala Asn Asp Val Phe Asp Val Arg Leu Ala Gln Met Glu Ile Asn Pro
    195                 200                 205

Gly Gly Thr Leu Glu Leu Gly Val Asp Tyr Gly Arg Ala Asn Leu Arg
    210                 215                 220

Asp Asn Tyr Arg Leu Val Asp Gly Ala Ser Lys Asp Gly Trp Leu Phe
225                 230                 235                 240

Thr Ala Glu His Thr Gln Ser Val Leu Lys Gly Phe Asn Lys Phe Val
                245                 250                 255

Val Gln Tyr Ala Thr Asp Ser Met Thr Ser Gln Gly Lys Gly Leu Ser
            260                 265                 270

Gln Gly Ser Gly Val Ala Phe Asp Asn Glu Lys Phe Ala Tyr Asn Ile
    275                 280                 285

Asn Asn Asn Gly His Met Leu Arg Ile Leu Asp His Gly Ala Ile Ser
    290                 295                 300

Met Gly Asp Asn Trp Asp Met Met Tyr Val Gly Met Tyr Gln Asp Ile
305                 310                 315                 320
```

Asn Trp Asp Asn Asp Asn Gly Thr Lys Trp Trp Thr Val Gly Ile Arg
            325                 330                 335

Pro Met Tyr Lys Trp Thr Pro Ile Met Ser Thr Val Met Glu Ile Gly
            340                 345                 350

Tyr Asp Asn Val Glu Ser Gln Arg Thr Gly Asp Lys Asn Asn Gln Tyr
            355                 360                 365

Lys Ile Thr Leu Ala Gln Gln Trp Gln Ala Gly Asp Ser Ile Trp Ser
            370                 375                 380

Arg Pro Ala Ile Arg Val Phe Ala Thr Tyr Ala Lys Trp Asp Glu Lys
385                 390                 395                 400

Trp Gly Tyr Asp Tyr Thr Gly Asn Ala Asp Asn Asn Ala Asn Phe Gly
            405                 410                 415

Lys Ala Val Pro Ala Asp Phe Asn Gly Gly Ser Phe Gly Arg Gly Asp
            420                 425                 430

Ser Asp Glu Trp Thr Phe Gly Ala Gln Met Glu Ile Trp Trp
            435                 440                 445

<210> SEQ ID NO 29
<211> LENGTH: 111
<212> TYPE: PRT
<213> ORGANISM: Escherichia coli

<400> SEQUENCE: 29

Met Met Ile Thr Leu Arg Lys Leu Pro Leu Ala Val Ala Val Ala Ala
1               5                   10                  15

Gly Val Met Ser Ala Gln Ala Met Ala Val Asp Phe His Gly Tyr Ala
            20                  25                  30

Arg Ser Gly Ile Gly Trp Thr Gly Ser Gly Gly Glu Gln Gln Cys Phe
            35                  40                  45

Gln Thr Thr Gly Ala Gln Ser Lys Tyr Arg Leu Gly Asn Glu Cys Glu
        50                  55                  60

Thr Tyr Ala Glu Leu Lys Leu Gly Gln Glu Val Trp Lys Glu Gly Asp
65                  70                  75                  80

Lys Ser Phe Tyr Phe Asp Thr Asn Val Ala Tyr Ser Val Ala Gln Gln
                85                  90                  95

Asn Asp Trp Glu Ala Thr Asp Pro Ala Phe Arg Glu Ala Asn Val
            100                 105                 110

<210> SEQ ID NO 30
<211> LENGTH: 1476
<212> TYPE: DNA
<213> ORGANISM: Escherichia coli

<400> SEQUENCE: 30
atggcggtaa cgcaaacagc ccaggcctgt gacctggtca ttttcggcgc gaaaggcgac    60
cttgcgcgtc gtaaattgct gccttccctg tatcaactgg aaaaagccgg tcagctcaac   120
ccggacaccc ggattatcgg cgtagggcgt gctgactggg ataaagcggc atataccaaa   180
gttgtccgcg aggcgctcga aactttcatg aaagaaacca ttgatgaagg tttatgggac   240
accctgagtg cacgtctgga ttttttgtaat ctcgatgtca atgacactgc tgcattcagc   300
cgtctcggcg cgatgctgga tcaaaaaaat cgtatcacca ttaactactt tgccatgccg   360
cccagcactt ttggcgcaat ttgcaaaggg cttggcgagg caaaactgaa tgctaaaccg   420
gcacgcgtag tcatggagaa accgctgggg acgtcgctgg cgacctcgca ggaaatcaat   480
gatcaggttg gcgaatactt cgaggagtgc caggtttacc gtatcgacca ctatcttggt   540

```
aaagaaacgg tgctgaacct gttggcgctg cgttttgcta actccctgtt tgtgaataac     600
tgggacaatc gcaccattga tcatgttgag attaccgtgg cagaagaagt ggggatcgaa     660
gggcgctggg gctattttga taaagccggt cagatgcgcg acatgatcca gaaccacctg     720
ctgcaaattc tttgcatgat tgcgatgtct ccgccgtctg acctgagcgc agacagcatc     780
cgcgatgaaa aagtgaaagt actgaagtct ctgcgccgca tcgaccgctc caacgtacgc     840 gaaaaaccg tacgcgggca atatactgcg ggcttcgccc agggcaaaaa agtgccggga     900
tatctggaag aagagggcgc gaacaagagc agcaatacag aaactttcgt ggcgatccgc     960
gtcgacattg ataactggcg ctgggccggt gtgccattct acctgcgtac tggtaaacgt    1020
ctgccgacca aatgttctga agtcgtggtc tatttcaaaa cacctgaact gaatctgttt    1080
aaagaatcgt ggcaggatct gccgcagaat aaactgacta tccgtctgca acctgatgaa    1140
ggcgtggata tccaggtact gaataaagtt cctggccttg accacaaaca taacctgcaa    1200
atcaccaagc tggatctgag ctattcagaa acctttaatc agacgcatct ggcggatgcc    1260
tatgaacgtt tgctgctgga aaccatgcgt ggtattcagg cactgtttgt acgtcgcgac    1320
gaagtggaag aagcctggaa atgggtagac tccattactg aggcgtgggc gatggacaat    1380
gatgcgccga accgtatca ggccggaacc tggggacccg ttgcctcggt ggcgatgatt    1440
acccgtgatg gtcgttcctg gaatgagttt gagtaa                              1476
```

<210> SEQ ID NO 31
<211> LENGTH: 439
<212> TYPE: PRT
<213> ORGANISM: Escherichia coli

<400> SEQUENCE: 31

```
Met Thr His Gln Leu Arg Ser Arg Asp Ile Ile Ala Leu Gly Phe Met
1               5                   10                  15

Thr Phe Ala Leu Phe Val Gly Ala Gly Asn Ile Ile Phe Pro Pro Met
                20                  25                  30

Val Gly Leu Gln Ala Gly Glu His Val Trp Thr Ala Ala Phe Gly Phe
            35                  40                  45

Leu Ile Thr Ala Val Gly Leu Pro Val Leu Thr Val Ala Leu Ala
        50                  55                  60

Lys Val Gly Gly Gly Val Asp Ser Leu Ser Thr Pro Ile Gly Lys Val
65                  70                  75                  80

Ala Gly Val Leu Leu Ala Thr Val Cys Tyr Leu Ala Val Gly Pro Leu
                85                  90                  95

Phe Ala Thr Pro Arg Thr Ala Thr Val Ser Phe Glu Val Gly Ile Ala
                100                 105                 110

Pro Leu Thr Gly Asp Ser Ala Leu Pro Leu Phe Ile Tyr Ser Leu Val
            115                 120                 125

Tyr Phe Ala Ile Val Ile Leu Val Ser Leu Tyr Pro Gly Lys Leu Leu
        130                 135                 140

Asp Thr Val Gly Asn Phe Leu Ala Pro Leu Lys Ile Ile Ala Leu Val
145                 150                 155                 160

Ile Leu Ser Val Ala Ala Ile Val Trp Pro Ala Gly Ser Ile Ser Thr
                165                 170                 175

Ala Thr Glu Ala Tyr Gln Asn Ala Ala Phe Ser Asn Gly Phe Val Asn
            180                 185                 190

Gly Tyr Leu Thr Met Asp Thr Leu Gly Ala Met Val Phe Gly Ile Val
        195                 200                 205
```

```
Ile Val Asn Ala Ala Arg Ser Arg Gly Val Thr Glu Ala Arg Leu Leu
    210                 215                 220
Thr Arg Tyr Thr Val Trp Ala Gly Leu Met Ala Gly Val Gly Leu Thr
225                 230                 235                 240
Leu Leu Tyr Leu Ala Leu Phe Arg Leu Gly Ser Asp Ser Ala Ser Leu
                245                 250                 255
Val Asp Gln Ser Ala Asn Gly Ala Ala Ile Leu His Ala Tyr Val Gln
                260                 265                 270
His Thr Phe Gly Gly Gly Ser Phe Leu Leu Ala Ala Leu Ile Phe
            275                 280                 285
Ile Ala Cys Leu Val Thr Ala Val Gly Leu Thr Cys Ala Cys Ala Glu
    290                 295                 300
Phe Phe Ala Gln Tyr Val Pro Leu Ser Tyr Arg Thr Leu Val Phe Ile
305                 310                 315                 320
Leu Gly Gly Phe Ser Met Val Val Ser Asn Leu Gly Leu Ser Gln Leu
                325                 330                 335
Ile Gln Ile Ser Val Pro Val Leu Thr Ala Ile Tyr Pro Pro Cys Ile
                340                 345                 350
Ala Leu Val Val Leu Ser Phe Thr Arg Ser Trp Trp His Asn Ser Ser
                355                 360                 365
Arg Val Ile Ala Pro Pro Met Phe Ile Ser Leu Leu Phe Gly Ile Leu
    370                 375                 380
Asp Gly Ile Lys Ala Ser Ala Phe Ser Asp Ile Leu Pro Ser Trp Ala
385                 390                 395                 400
Gln Arg Leu Pro Leu Ala Glu Gln Gly Leu Ala Trp Leu Met Pro Thr
                405                 410                 415
Val Val Met Val Val Leu Ala Ile Ile Trp Asp Arg Ala Ala Gly Arg
                420                 425                 430
Gln Val Thr Ser Ser Ala His
            435

<210> SEQ ID NO 32
<211> LENGTH: 308
<212> TYPE: PRT
<213> ORGANISM: Escherichia coli

<400> SEQUENCE: 32

Met Thr His Gln Leu Arg Ser Arg Asp Ile Ile Ala Leu Gly Phe Met
1               5                   10                  15
Thr Phe Ala Leu Phe Val Gly Ala Gly Asn Ile Ile Phe Pro Pro Met
                20                  25                  30
Val Gly Leu Gln Ala Gly Glu His Val Trp Thr Ala Ala Phe Gly Phe
            35                  40                  45
Leu Ile Thr Ala Val Gly Leu Pro Val Leu Thr Val Val Ala Leu Ala
        50                  55                  60
Lys Val Gly Gly Gly Val Asp Ser Leu Ser Thr Pro Ile Gly Lys Val
65                  70                  75                  80
Ala Gly Val Leu Leu Ala Thr Val Cys Tyr Leu Ala Val Gly Pro Leu
                85                  90                  95
Phe Ala Thr Pro Arg Thr Ala Thr Val Ser Phe Glu Val Gly Ile Ala
                100                 105                 110
Pro Leu Thr Gly Asp Ser Ala Leu Pro Leu Phe Ile Tyr Ser Leu Val
            115                 120                 125
Tyr Phe Ala Ile Val Ile Leu Val Ser Leu Tyr Pro Gly Lys Leu Leu
        130                 135                 140
```

```
Asp Thr Val Gly Asn Phe Leu Ala Pro Leu Lys Ile Ile Ala Leu Val
145                 150                 155                 160

Ile Leu Ser Val Ala Ala Ile Val Trp Pro Ala Gly Ser Ile Ser Thr
            165                 170                 175

Ala Thr Glu Ala Tyr Gln Asn Ala Ala Phe Ser Asn Gly Phe Val Asn
        180                 185                 190

Gly Tyr Leu Thr Met Asp Thr Leu Gly Ala Met Val Phe Gly Ile Val
    195                 200                 205

Ile Val Asn Ala Ala Arg Ser Arg Gly Val Thr Glu Ala Arg Leu Leu
210                 215                 220

Thr Arg Tyr Thr Val Trp Ala Gly Leu Met Ala Gly Val Gly Leu Thr
225                 230                 235                 240

Leu Leu Tyr Leu Ala Leu Phe Arg Leu Gly Ser Asp Ser Ala Ser Leu
            245                 250                 255

Val Asp Gln Ser Ala Asn Gly Ala Ala Ile Leu His Ala Tyr Val Gln
        260                 265                 270

His Thr Phe Gly Gly Gly Ser Phe Leu Leu Ala Ala Leu Ile Phe
    275                 280                 285

Ile Ala Cys Leu Val Thr Ala Val Gly Leu Thr Cys Ala Cys Ala Glu
    290                 295                 300

Phe Phe Ala Gln
305
```

<210> SEQ ID NO 33
<211> LENGTH: 78
<212> TYPE: DNA
<213> ORGANISM: Artificial Sequence
<220> FEATURE:
<223> OTHER INFORMATION: Primer

<400> SEQUENCE: 33
gcgctgttat tagttcgtta ctggaagtcc agtcaccttg tcaggagtat tatcgtggtg    60
taggctggag ctgcttcg                                                 78

<210> SEQ ID NO 34
<211> LENGTH: 73
<212> TYPE: DNA
<213> ORGANISM: Artificial Sequence
<220> FEATURE:
<223> OTHER INFORMATION: Primer

<400> SEQUENCE: 34
cgcccatccg ttgcagatgg gcgagtaaga agtattagtc acactggacc atatgaatat    60
cctccttagt tcc                                                      73

<210> SEQ ID NO 35
<211> LENGTH: 69
<212> TYPE: DNA
<213> ORGANISM: Artificial Sequence
<220> FEATURE:
<223> OTHER INFORMATION: Primer

<400> SEQUENCE: 35
cgctttcggg cggcgcttcc tccgttttaa cgcgatgtat ttcctatggt gtaggctgga    60
gctgcttcg                                                           69

<210> SEQ ID NO 36
<211> LENGTH: 70

```
<212> TYPE: DNA
<213> ORGANISM: Artificial Sequence
<220> FEATURE:
<223> OTHER INFORMATION: Primer

<400> SEQUENCE: 36
ggcctcgcaa aacgaggcct ttggagagcg attaatcgca ggcaaccata tgaatatcct    60
ccttagttcc                                                            70

<210> SEQ ID NO 37
<211> LENGTH: 67
<212> TYPE: DNA
<213> ORGANISM: Artificial Sequence
<220> FEATURE:
<223> OTHER INFORMATION: Primer

<400> SEQUENCE: 37
cgttccgctc cacttcactg aacggcaatc cgagggtgtg gatatggtgt aggctggagc    60
tgcttcg                                                               67

<210> SEQ ID NO 38
<211> LENGTH: 70
<212> TYPE: DNA
<213> ORGANISM: Artificial Sequence
<220> FEATURE:
<223> OTHER INFORMATION: Primer

<400> SEQUENCE: 38
gtgcacccaa ggatgaaagc tgacagcaat gtcagccgca gaccaccata tgaatatcct    60
ccttagttcc                                                            70

<210> SEQ ID NO 39
<211> LENGTH: 71
<212> TYPE: DNA
<213> ORGANISM: Artificial Sequence
<220> FEATURE:
<223> OTHER INFORMATION: Primer

<400> SEQUENCE: 39
gttagctgag tcaggagatg cggatgttaa agcgtgaaat gaacattgcc gtgtaggctg    60
gagctgcttc g                                                          71

<210> SEQ ID NO 40
<211> LENGTH: 73
<212> TYPE: DNA
<213> ORGANISM: Artificial Sequence
<220> FEATURE:
<223> OTHER INFORMATION: Primer

<400> SEQUENCE: 40
caacgagcac attgacagca aatcaccgtt tcgcttatgc gtaaaccggc atatgaatat    60
cctccttagt tcc                                                        73

<210> SEQ ID NO 41
<211> LENGTH: 30
<212> TYPE: DNA
<213> ORGANISM: Artificial Sequence
<220> FEATURE:
<223> OTHER INFORMATION: primer

<400> SEQUENCE: 41
gcgctgttat tagttcgtta ctggaagtcc                                      30
```

<210> SEQ ID NO 42
<211> LENGTH: 22
<212> TYPE: DNA
<213> ORGANISM: Artificial Sequence
<220> FEATURE:
<223> OTHER INFORMATION: Primer

<400> SEQUENCE: 42
cgcccatccg ttgcagatgg gc                                              22

<210> SEQ ID NO 43
<211> LENGTH: 22
<212> TYPE: DNA
<213> ORGANISM: Artificial Sequence
<220> FEATURE:
<223> OTHER INFORMATION: Primer

<400> SEQUENCE: 43
cgctttcggg cggcgcttcc tc                                              22

<210> SEQ ID NO 44
<211> LENGTH: 24
<212> TYPE: DNA
<213> ORGANISM: Artificial Sequence
<220> FEATURE:
<223> OTHER INFORMATION: Primer

<400> SEQUENCE: 44
ggcctcgcaa aacgaggcct ttgg                                            24

<210> SEQ ID NO 45
<211> LENGTH: 25
<212> TYPE: DNA
<213> ORGANISM: Artificial Sequence
<220> FEATURE:
<223> OTHER INFORMATION: Primer

<400> SEQUENCE: 45
cgttccgctc cacttcactg aacgg                                           25

<210> SEQ ID NO 46
<211> LENGTH: 27
<212> TYPE: DNA
<213> ORGANISM: Artificial Sequence
<220> FEATURE:
<223> OTHER INFORMATION: Primer

<400> SEQUENCE: 46
gtgcacccaa ggatgaaagc tgacagc                                         27

<210> SEQ ID NO 47
<211> LENGTH: 28
<212> TYPE: DNA
<213> ORGANISM: Artificial Sequence
<220> FEATURE:
<223> OTHER INFORMATION: Primer

<400> SEQUENCE: 47
gttagctgag tcaggagatg cggatgtt                                        28

<210> SEQ ID NO 48
<211> LENGTH: 28
<212> TYPE: DNA
<213> ORGANISM: Artificial Sequence
<220> FEATURE:
<223> OTHER INFORMATION: Primer

<400> SEQUENCE: 48
caacgagcac attgacagca aatcaccg                                    28

<210> SEQ ID NO 49
<211> LENGTH: 26
<212> TYPE: DNA
<213> ORGANISM: Artificial Sequence
<220> FEATURE:
<223> OTHER INFORMATION: Primer

<400> SEQUENCE: 49
ggcccatggc aaaggtatcg ctggag                                      26

<210> SEQ ID NO 50
<211> LENGTH: 33
<212> TYPE: DNA
<213> ORGANISM: Artificial Sequence
<220> FEATURE:
<223> OTHER INFORMATION: Primer

<400> SEQUENCE: 50
attgcggccg cttagtacag cagacgggcg cga                              33

<210> SEQ ID NO 51
<211> LENGTH: 27
<212> TYPE: DNA
<213> ORGANISM: Artificial Sequence
<220> FEATURE:
<223> OTHER INFORMATION: Primer

<400> SEQUENCE: 51
ggcccatggc taacattacc tggtgcg                                     27

<210> SEQ ID NO 52
<211> LENGTH: 33
<212> TYPE: DNA
<213> ORGANISM: Artificial Sequence
<220> FEATURE:
<223> OTHER INFORMATION: Primer

<400> SEQUENCE: 52
gccaagcttt tattacttct gattcaggct gcc                              33

<210> SEQ ID NO 53
<211> LENGTH: 35
<212> TYPE: DNA
<213> ORGANISM: Artificial Sequence
<220> FEATURE:
<223> OTHER INFORMATION: Primer

<400> SEQUENCE: 53
gccttaatta attattactt ctgattcagg ctgcc                            35

<210> SEQ ID NO 54
<211> LENGTH: 38
<212> TYPE: DNA
<213> ORGANISM: Artificial Sequence
<220> FEATURE:
<223> OTHER INFORMATION: Primer

<400> SEQUENCE: 54
ggccatatga tggctcaaat cttcaatttt agttctgg                         38

<210> SEQ ID NO 55

```
<211> LENGTH: 36
<212> TYPE: DNA
<213> ORGANISM: Artificial Sequence
<220> FEATURE:
<223> OTHER INFORMATION: Primer

<400> SEQUENCE: 55
gccttaatta atcattaacc gtgacggcgt tcgaac                              36

<210> SEQ ID NO 56
<211> LENGTH: 27
<212> TYPE: DNA
<213> ORGANISM: Artificial Sequence
<220> FEATURE:
<223> OTHER INFORMATION: Primer

<400> SEQUENCE: 56
ccgcatatgt cgcgaaaaga tggggtg                                        27

<210> SEQ ID NO 57
<211> LENGTH: 54
<212> TYPE: DNA
<213> ORGANISM: Artificial Sequence
<220> FEATURE:
<223> OTHER INFORMATION: Primer

<400> SEQUENCE: 57
gccttaatta atgatgatga tgatgatgac ttcccacctt taccgcttta cgcc          54

<210> SEQ ID NO 58
<211> LENGTH: 26
<212> TYPE: DNA
<213> ORGANISM: Artificial Sequence
<220> FEATURE:
<223> OTHER INFORMATION: Primer

<400> SEQUENCE: 58
ccgccatggc gcgaaaagat ggggtg                                         26

<210> SEQ ID NO 59
<211> LENGTH: 30
<212> TYPE: DNA
<213> ORGANISM: Artificial Sequence
<220> FEATURE:
<223> OTHER INFORMATION: Primer

<400> SEQUENCE: 59
cgagcagggc gtcgctatcg ccgcgcaata                                     30

<210> SEQ ID NO 60
<211> LENGTH: 30
<212> TYPE: DNA
<213> ORGANISM: Artificial Sequence
<220> FEATURE:
<223> OTHER INFORMATION: Primer

<400> SEQUENCE: 60
tattgcgcgg cgatagcgac gccctgctcg                                     30

<210> SEQ ID NO 61
<211> LENGTH: 33
<212> TYPE: DNA
<213> ORGANISM: Artificial Sequence
<220> FEATURE:
<223> OTHER INFORMATION: Primer

<400> SEQUENCE: 61
```
ctgatcacat cgctgaagct cgtccgggcg tgc 33

<210> SEQ ID NO 62
<211> LENGTH: 34
<212> TYPE: DNA
<213> ORGANISM: Artificial Sequence
<220> FEATURE:
<223> OTHER INFORMATION: Primer

<400> SEQUENCE: 62
gcacgcccgg acgagcttca gcgatgtgca tcag 34

<210> SEQ ID NO 63
<211> LENGTH: 32
<212> TYPE: DNA
<213> ORGANISM: Artificial Sequence
<220> FEATURE:
<223> OTHER INFORMATION: Primer

<400> SEQUENCE: 63
caaggtatta ttctgtcatg gcggtggtcg cg 32

<210> SEQ ID NO 64
<211> LENGTH: 32
<212> TYPE: DNA
<213> ORGANISM: Artificial Sequence
<220> FEATURE:
<223> OTHER INFORMATION: Primer

<400> SEQUENCE: 64
cgcgaccacc gccatgacag aataatacct tg 32

<210> SEQ ID NO 65
<211> LENGTH: 22
<212> TYPE: DNA
<213> ORGANISM: Artificial Sequence
<220> FEATURE:
<223> OTHER INFORMATION: Primer

<400> SEQUENCE: 65
atgcgagtgt tgaagttcgg cg 22

<210> SEQ ID NO 66
<211> LENGTH: 26
<212> TYPE: DNA
<213> ORGANISM: Artificial Sequence
<220> FEATURE:
<223> OTHER INFORMATION: Primer

<400> SEQUENCE: 66
tcagactcct aacttccatg agaggg 26

<210> SEQ ID NO 67
<211> LENGTH: 73
<212> TYPE: DNA
<213> ORGANISM: Artificial Sequence
<220> FEATURE:
<223> OTHER INFORMATION: Primer

<400> SEQUENCE: 67
atgcgagtgt tgaagttcgg cggtacatca gtggcaaatg cagaacgttt aaaatgagac 60
gttgatcggc acg 73

<210> SEQ ID NO 68

```
<211> LENGTH: 75
<212> TYPE: DNA
<213> ORGANISM: Artificial Sequence
<220> FEATURE:
<223> OTHER INFORMATION: Primer

<400> SEQUENCE: 68
tcagactcct aacttccatg agagggtacg tagcagatca gcaaagacac caaagggaaa    60
actgtccata tgcac                                                     75

<210> SEQ ID NO 69
<211> LENGTH: 67
<212> TYPE: DNA
<213> ORGANISM: Artificial Sequence
<220> FEATURE:
<223> OTHER INFORMATION: Primer

<400> SEQUENCE: 69
gcttgacttc ttccataaca acgtaagtgc gcgtcccgtt aacccaggc agacgcagca     60 gggtttc                                                              67

<210> SEQ ID NO 70
<211> LENGTH: 69
<212> TYPE: DNA
<213> ORGANISM: Artificial Sequence
<220> FEATURE:
<223> OTHER INFORMATION: Primer

<400> SEQUENCE: 70
ccaaccggct gaatcatgaa ttcttgaatg tcgagattat tatcagcgtg ctcaccaccg    60
ttgatgatg                                                            69

<210> SEQ ID NO 71
<211> LENGTH: 63
<212> TYPE: DNA
<213> ORGANISM: Artificial Sequence
<220> FEATURE:
<223> OTHER INFORMATION: Primer

<400> SEQUENCE: 71
ctcaacttgc aggtagaaga tgaaacgagg aaagagaggc tccgccgcgg cgaagtggtc    60
ggc                                                                  63

<210> SEQ ID NO 72
<211> LENGTH: 67
<212> TYPE: DNA
<213> ORGANISM: Artificial Sequence
<220> FEATURE:
<223> OTHER INFORMATION: Primer

<400> SEQUENCE: 72
cagctcaatc cccacgaaag ctaatacggc aacttgaaaa ccggcaaaga agccacttaa    60
acctttc                                                              67

<210> SEQ ID NO 73
<211> LENGTH: 66
<212> TYPE: DNA
<213> ORGANISM: Artificial Sequence
<220> FEATURE:
<223> OTHER INFORMATION: Primer

<400> SEQUENCE: 73
gcatcatggt tgcgcgtggc gacctcggcg tttagtgacc ctaaatcttc gcccagaaga    60
``` tgatga 66

<210> SEQ ID NO 74
<211> LENGTH: 63
<212> TYPE: DNA
<213> ORGANISM: Artificial Sequence
<220> FEATURE:
<223> OTHER INFORMATION: Primer

<400> SEQUENCE: 74
gatacgacgt tgtgcgtaa tttctgagag gagattattt tggtccataa actgagacag  60
ctg  63

<210> SEQ ID NO 75
<211> LENGTH: 62
<212> TYPE: DNA
<213> ORGANISM: Artificial Sequence
<220> FEATURE:
<223> OTHER INFORMATION: Primer

<400> SEQUENCE: 75
ctcgtaaggc atttagcggt ggtaatggtt atcattaggc tattaaactt tgatgttaaa  60
tg  62

<210> SEQ ID NO 76
<211> LENGTH: 70
<212> TYPE: DNA
<213> ORGANISM: Artificial Sequence
<220> FEATURE:
<223> OTHER INFORMATION: Primer

<400> SEQUENCE: 76
ggtgagatta atcggaccaa cggagaaggc attgtgttgg tatgcaaacg tcacgttacg  60
cagctccagc  70

<210> SEQ ID NO 77
<211> LENGTH: 67
<212> TYPE: DNA
<213> ORGANISM: Artificial Sequence
<220> FEATURE:
<223> OTHER INFORMATION: Primer

<400> SEQUENCE: 77
gagatggtat caccagtgcg gagattaaat cttagtatct gagaagggga aacgtagatg  60
tcatcag  67

<210> SEQ ID NO 78
<211> LENGTH: 55
<212> TYPE: DNA
<213> ORGANISM: Artificial Sequence
<220> FEATURE:
<223> OTHER INFORMATION: Primer

<400> SEQUENCE: 78
tcgtcggcag cgtcagatgt gtataagaga cagcggtgat ttcgactacc tgttg  55

<210> SEQ ID NO 79
<211> LENGTH: 57
<212> TYPE: DNA
<213> ORGANISM: Artificial Sequence
<220> FEATURE:
<223> OTHER INFORMATION: Primer

<400> SEQUENCE: 79
gtctcgtggg ctcggagatg tgtataagag acaggcgcgt cttaataacc agacgat    57

<210> SEQ ID NO 80
<211> LENGTH: 56
<212> TYPE: DNA
<213> ORGANISM: Artificial Sequence
<220> FEATURE:
<223> OTHER INFORMATION: Primer

<400> SEQUENCE: 80
tcgtcggcag cgtcagatgt gtataagaga caggctgtac gagcacatcg ctgaac    56

<210> SEQ ID NO 81
<211> LENGTH: 57
<212> TYPE: DNA
<213> ORGANISM: Artificial Sequence
<220> FEATURE:
<223> OTHER INFORMATION: Primer

<400> SEQUENCE: 81
gtctcgtggg ctcggagatg tgtataagag acagcccatg cggatggctt ctttcac    57

<210> SEQ ID NO 82
<211> LENGTH: 56
<212> TYPE: DNA
<213> ORGANISM: Artificial Sequence
<220> FEATURE:
<223> OTHER INFORMATION: Primer

<400> SEQUENCE: 82
tcgtcggcag cgtcagatgt gtataagaga caggacagtc tggcgacgtg gttgct    56

<210> SEQ ID NO 83
<211> LENGTH: 58
<212> TYPE: DNA
<213> ORGANISM: Artificial Sequence
<220> FEATURE:
<223> OTHER INFORMATION: Primer

<400> SEQUENCE: 83
gtctcgtggg ctcggagatg tgtataagag acagtatcga caagacaact cggcagcg    58

<210> SEQ ID NO 84
<211> LENGTH: 55
<212> TYPE: DNA
<213> ORGANISM: Artificial Sequence
<220> FEATURE:
<223> OTHER INFORMATION: Primer

<400> SEQUENCE: 84
tcgtcggcag cgtcagatgt gtataagaga cagggaagcg tcattcgcgc atttg    55

<210> SEQ ID NO 85
<211> LENGTH: 54
<212> TYPE: DNA
<213> ORGANISM: Artificial Sequence
<220> FEATURE:
<223> OTHER INFORMATION: Primer

<400> SEQUENCE: 85
gtctcgtggg ctcggagatg tgtataagag acaggttaat cgcgcgtggc agtg    54

<210> SEQ ID NO 86
<211> LENGTH: 53

```
<212> TYPE: DNA
<213> ORGANISM: Artificial Sequence
<220> FEATURE:
<223> OTHER INFORMATION: Primer

<400> SEQUENCE: 86
tcgtcggcag cgtcagatgt gtataagaga cagggcctca acaacttcga cga        53

<210> SEQ ID NO 87
<211> LENGTH: 54
<212> TYPE: DNA
<213> ORGANISM: Artificial Sequence
<220> FEATURE:
<223> OTHER INFORMATION: Primer

<400> SEQUENCE: 87
gtctcgtggg ctcggagatg tgtataagag acaggaatcc agcatctggg tcgc       54

<210> SEQ ID NO 88
<211> LENGTH: 53
<212> TYPE: DNA
<213> ORGANISM: Artificial Sequence
<220> FEATURE:
<223> OTHER INFORMATION: Primer

<400> SEQUENCE: 88
tcgtcggcag cgtcagatgt gtataagaga cagcaacgcc aagccgattt ccg        53

<210> SEQ ID NO 89
<211> LENGTH: 55
<212> TYPE: DNA
<213> ORGANISM: Artificial Sequence
<220> FEATURE:
<223> OTHER INFORMATION: Primer

<400> SEQUENCE: 89
gtctcgtggg ctcggagatg tgtataagag acaggtctcg aacttcgaag cctgc      55

<210> SEQ ID NO 90
<211> LENGTH: 54
<212> TYPE: DNA
<213> ORGANISM: Artificial Sequence
<220> FEATURE:
<223> OTHER INFORMATION: Primer

<400> SEQUENCE: 90
tcgtcggcag cgtcagatgt gtataagaga caggctggta gaagctcaac ggac       54

<210> SEQ ID NO 91
<211> LENGTH: 55
<212> TYPE: DNA
<213> ORGANISM: Artificial Sequence
<220> FEATURE:
<223> OTHER INFORMATION: Primer

<400> SEQUENCE: 91
gtctcgtggg ctcggagatg tgtataagag acagtgctgc ggcatcaaaa actcg      55

<210> SEQ ID NO 92
<211> LENGTH: 56
<212> TYPE: DNA
<213> ORGANISM: Artificial Sequence
<220> FEATURE:
<223> OTHER INFORMATION: Primer

<400> SEQUENCE: 92
```
tcgtcggcag cgtcagatgt gtataagaga caggcctttc aaagcagagt ttccgc                56

<210> SEQ ID NO 93
<211> LENGTH: 54
<212> TYPE: DNA
<213> ORGANISM: Artificial Sequence
<220> FEATURE:
<223> OTHER INFORMATION: Primer

<400> SEQUENCE: 93
gtctcgtggg ctcggagatg tgtataagag acagctaccg ttgccgccaa tcag              54

<210> SEQ ID NO 94
<211> LENGTH: 56
<212> TYPE: DNA
<213> ORGANISM: Artificial Sequence
<220> FEATURE:
<223> OTHER INFORMATION: Primer

<400> SEQUENCE: 94
tcgtcggcag cgtcagatgt gtataagaga caggcaggat ggatttggtt tcctcc            56

<210> SEQ ID NO 95
<211> LENGTH: 56
<212> TYPE: DNA
<213> ORGANISM: Artificial Sequence
<220> FEATURE:
<223> OTHER INFORMATION: Primer

<400> SEQUENCE: 95
gtctcgtggg ctcggagatg tgtataagag acaggcagcg caaaatagcg ttcacc            56

<210> SEQ ID NO 96
<211> LENGTH: 27
<212> TYPE: DNA
<213> ORGANISM: Artificial Sequence
<220> FEATURE:
<223> OTHER INFORMATION: Primer

<400> SEQUENCE: 96
gcgccatggg agtgttgaag ttcggcg                                             27

<210> SEQ ID NO 97
<211> LENGTH: 35
<212> TYPE: DNA
<213> ORGANISM: Artificial Sequence
<220> FEATURE:
<223> OTHER INFORMATION: Primer

<400> SEQUENCE: 97
gccaagcttt cagactccta acttccatga gaggg                                    35

<210> SEQ ID NO 98
<211> LENGTH: 36
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(17)
<223> OTHER INFORMATION: m is a or c
<220> FEATURE:
<221> NAME/KEY: misc_feature
<222> LOCATION: (18)..(19)
<223> OTHER INFORMATION: n is a, c, g, or t

<400> SEQUENCE: 98
cgcagaaact gatgctmnnt tcggaagatg attgcg                                36

<210> SEQ ID NO 99
<211> LENGTH: 36
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(17)
<223> OTHER INFORMATION: m is a or c
<220> FEATURE:
<221> NAME/KEY: misc_feature
<222> LOCATION: (18)..(19)
<223> OTHER INFORMATION: n is a, c, g, or t

<400> SEQUENCE: 99
cgcagaaact gatgctmnnt tcggaagatg attgcg                                36

<210> SEQ ID NO 100
<211> LENGTH: 38
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (19)..(20)
<223> OTHER INFORMATION: n is a, c, g, or t

<400> SEQUENCE: 100
caatcatctt ccgaatacnn katcagtttc tgcgttcc                              38

<210> SEQ ID NO 101
<211> LENGTH: 38
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (18)..(18)
<223> OTHER INFORMATION: m is a or c
<220> FEATURE:
<221> NAME/KEY: misc_feature
<222> LOCATION: (19)..(20)
<223> OTHER INFORMATION: n is a, c, g, or t

<400> SEQUENCE: 101
ggaacgcaga aactgatmnn gtattcggaa gatgattg                              38

<210> SEQ ID NO 102
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (15)..(16)
<223> OTHER INFORMATION: n is a, c, g, or t

<400> SEQUENCE: 102
ccgaatacag catcnnkttc tgcgttccac                                       30

<210> SEQ ID NO 103
<211> LENGTH: 30
<212> TYPE: DNA

```
<213> ORGANISM: Artificial Sequence
<220> FEATURE:
<223> OTHER INFORMATION: Primer
<220> FEATURE:
<221> NAME/KEY: misc_feature
<222> LOCATION: (14)..(14)
<223> OTHER INFORMATION: m is a or c
<220> FEATURE:
<221> NAME/KEY: misc_feature
<222> LOCATION: (15)..(16)
<223> OTHER INFORMATION: n is a, c, g, or t

<400> SEQUENCE: 103
gtggaacgca gaamnngatg ctgtattcgg                              30

<210> SEQ ID NO 104
<211> LENGTH: 67
<212> TYPE: DNA
<213> ORGANISM: Artificial Sequence
<220> FEATURE:
<223> OTHER INFORMATION: Primer

<400> SEQUENCE: 104
cacacagtcg ctttgtggaa cgcagaaact aatccgatac tccgaagatg attgcgtaat    60
cagcacc                                                              67
```